United States Patent
Barton et al.

(10) Patent No.: US 10,487,316 B2
(45) Date of Patent: Nov. 26, 2019

(54) PHOSPHOLIPASES, NUCLEIC ACIDS ENCODING THEM AND METHODS FOR MAKING AND USING THEM

(71) Applicant: DSM IP ASSETS B.V., Heerlen (NL)

(72) Inventors: Nelson R. Barton, San Diego, CA (US); Tim S. Hitchman, Carlsbad, CA (US); Jonathan D. Lyon, San Diego, CA (US); Eileen O'Donoghue, San Diego, CA (US); Mark A. Wall, San Diego, CA (US)

(73) Assignee: DSM IP ASSETS B.V., Heerlen (NL)

( * ) Notice: Subject to any disclaimer, the term of this patent is extended or adjusted under 35 U.S.C. 154(b) by 375 days.

(21) Appl. No.: 15/163,795

(22) Filed: May 25, 2016

(65) Prior Publication Data

US 2016/0326503 A1   Nov. 10, 2016

Related U.S. Application Data

(62) Division of application No. 13/502,069, filed as application No. PCT/US2010/051903 on Oct. 8, 2010, now Pat. No. 9,394,529.

(60) Provisional application No. 61/252,313, filed on Oct. 16, 2009.

(51) Int. Cl.
| | |
|---|---|
| *C12N 9/16* | (2006.01) |
| *C12Q 1/44* | (2006.01) |
| *C07K 16/40* | (2006.01) |
| *C11D 3/386* | (2006.01) |
| *A61K 38/46* | (2006.01) |

(52) U.S. Cl.
CPC ............ *C12N 9/16* (2013.01); *A61K 38/465* (2013.01); *C11D 3/38627* (2013.01); *C12Q 1/44* (2013.01); *C12Y 301/04011* (2013.01); *G01N 2333/916* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,049,686 A | 9/1977 | Ringers et al. | |
| 4,698,185 A | 10/1987 | Dijkstra et al. | |
| 5,239,096 A | 8/1993 | Rohdenburg et al. | |
| 5,264,367 A | 11/1993 | Aalrust et al. | |
| 5,286,886 A | 2/1994 | Van de Sande et al. | |
| 5,532,163 A | 7/1996 | Yagi et al. | |
| 6,001,640 A | 12/1999 | Loeffler et al. | |
| 6,103,505 A | 8/2000 | Clausen et al. | |
| 6,127,137 A | 10/2000 | Hasida et al. | |
| 6,143,545 A | 11/2000 | Clausen et al. | |
| 6,172,248 B1 | 1/2001 | Copeland et al. | |
| 6,548,633 B1 | 4/2003 | Edwards et al. | |
| 7,226,771 B2 | 6/2007 | Gramatikova et al. | |
| 7,494,676 B2 | 2/2009 | Chakrabrti et al. | |
| 7,977,080 B2 | 7/2011 | Gramatikova et al. | |
| 2003/0190651 A1 | 10/2003 | Kossida | |
| 2005/0059130 A1 | 3/2005 | Bojsen et al. | |
| 2005/0108789 A1* | 5/2005 | Gramatikova | C12N 9/16 800/281 |
| 2007/0134777 A1 | 6/2007 | Dayton et al. | |
| 2007/0218530 A1* | 9/2007 | Duck | C12P 19/14 435/101 |
| 2008/0182322 A1 | 7/2008 | Dayton et al. | |
| 2009/0069587 A1 | 3/2009 | Dayton et al. | |

OTHER PUBLICATIONS

International Search Report for PCT/US10/51903, dated Feb. 28, 2011.
Rolfs et al. (2006) Genbank EF040341).

* cited by examiner

*Primary Examiner* — Matthew R Keogh
(74) *Attorney, Agent, or Firm* — McBee Moore Woodward & Vanik IP, LLC

(57) ABSTRACT

In alternative embodiments, the invention provides phosphatidylinositol-specific phospholipase C (PI-PLC) enzymes, nucleic acids encoding them, antibodies that bind specifically to them, and methods for making and using them. Industrial methods and products comprising use of these phospholipases are also provided. In certain embodiments, provided herein are methods for hydration of non hydratable phospholipids (NHPs) within a lipid matrix. The methods enable migration of NHPs to an oil-water interface thereby allowing the NHPs to be reacted and/or removed from the lipids. In certain embodiments, provided is a method for removing NHPs, hydratable phospholipids, and lecithins from vegetable oils to produce a degummed oil or fat product that can be used for food production and/or non-food applications. In certain embodiments, provided herein are methods for hydration of NHPs followed by enzymatic treatment and removal of various phospholipids and lecithins. The methods provided herein can be practiced on either crude or water-degummed oils.

22 Claims, 19 Drawing Sheets

Specification includes a Sequence Listing.

FIGURE 6 – PLC Biodegumming (Crude soy): 2 centrifugation step process (Crude soy): 3 centrifugation step process (Crude soy oil): centrifugation step process with acid treatment

| Mutation | Original codon | Mutated codon | weight-fraction of total PL after reaction | | | | PA (uM) | PI (uM) | PI/PA (uM) | (TIP/P)/ (PA/TIP) | DAG released (rel. by HPLC) |
|---|---|---|---|---|---|---|---|---|---|---|---|
| | | | PA | PE | PI | PC | | | | | |
| E41A | GAG | GCA | 0.083 | 0.000 | 0.337 | 0.000 | 234 | 985 | 4.209 | 7.445 | 1.407 |
| E41W | GAG | TGG | 0.061 | 0.000 | 0.301 | 0.000 | 173 | 878 | 5.075 | 10.973 | 1.339 |
| E41F | GAG | TTC | | | | | | | | | |
| E41Y | GAG | TAC | | | | | | | | | |
| E41R | GAG | CGT | | | | | | | | | |
| E94R | GAG | CGG | 0.056 | 0.000 | 0.294 | 0.000 | 158 | 859 | 5.437 | 12.015 | 1.354 |
| D100L | GAT | TTG | 0.000 | 0.000 | 0.276 | 0.000 | 0 | 806 | #DIV/0! | #DIV/0! | 1.358 |
| D100M | GAT | ATG | 0.000 | 0.000 | 0.293 | 0.000 | 0 | 854 | #DIV/0! | #DIV/0! | 1.350 |
| D100Y | GAT | TAT | 0.044 | 0.000 | 0.359 | 0.000 | 124 | 1043 | 8.411 | 12.023 | 1.343 |
| D100F | GAT | TTT | 0.030 | 0.000 | 0.396 | 0.000 | 84 | 1150 | 13.690 | 17.307 | 1.338 |
| D100W | GAT | TGG | 0.034 | 0.000 | 0.270 | 0.000 | 97 | 792 | 8.165 | 21.728 | 1.226 |
| A104L | GCT | CTT | 0.069 | 0.000 | 0.318 | 0.000 | 195 | 926 | 4.749 | 9.388 | 1.273 |
| D111R | GAT | AGG | 0.096 | 0.000 | 0.374 | 0.000 | 268 | 1087 | 4.056 | 5.476 | 1.304 |
| T112R | ACT | CGG | 0.057 | 0.000 | 0.330 | 0.000 | 162 | 971 | 5.994 | 10.530 | 1.302 |
| Y116W | TAT | TGG | 0.086 | 0.000 | 0.428 | 0.000 | 245 | 1256 | 5.127 | 5.450 | 1.300 |
| I117W | ATT | TGG | 0.093 | 0.000 | 0.347 | 0.000 | 264 | 1018 | 3.856 | 6.288 | 1.288 |
| P118W | CCT | TGG | 0.051 | 0.000 | 0.292 | 0.000 | 143 | 851 | 5.951 | 14.102 | 1.376 |
| E125K | GAA | AAG | 0.067 | 0.000 | 0.301 | 0.000 | 189 | 875 | 4.630 | 9.938 | 1.352 |
| D171V | GAT | GTG | 0.052 | 0.000 | 0.338 | 0.000 | 145 | 986 | 6.800 | 12.003 | 1.430 |
| D171E | GAT | GAG | 0.074 | 0.000 | 0.317 | 0.000 | 209 | 927 | 4.435 | 8.391 | 1.463 |
| M176W | ATG | TGG | 0.021 | 0.000 | 0.359 | 0.000 | 59 | 1055 | 17.881 | 26.363 | 1.481 |
| D230H | GAT | CAT | 0.048 | 0.000 | 0.308 | 0.000 | 135 | 893 | 6.615 | 13.569 | 1.366 |
| D230R | GAT | CGT | 0.053 | 0.000 | 0.308 | 0.000 | 148 | 896 | 6.054 | 13.100 | 1.339 |
| D234W | GAT | TGG | 0.045 | 0.000 | 0.302 | 0.000 | 127 | 881 | 6.937 | 14.552 | 1.382 |
| D234V | GAT | GTG | 0.051 | 0.000 | 0.312 | 0.000 | 145 | 915 | 6.310 | 13.574 | 1.349 |
| D234G | GAT | GGT | 0.057 | 0.000 | 0.297 | 0.000 | 162 | 873 | 5.389 | 12.320 | 1.377 |
| D234R | GAT | CGG | 0.043 | 0.000 | 0.310 | 0.000 | 120 | 897 | 7.475 | 16.582 | 1.344 |
| D234K | GAT | AAG | 0.045 | 0.000 | 0.280 | 0.000 | 126 | 809 | 6.421 | 15.011 | 1.336 |
| Q265R | CAG | CGT | 0.074 | 0.000 | 0.000 | 0.000 | 209 | 0 | 0.000 | #DIV/0! | 1.441 |
| parent (SEQ ID NO:175) | | | 0.072 | 0.000 | 0.278 | 0.000 | 205 | 816 | 3.980 | 9.948 | 1.338 |
| parent (SEQ ID NO:175) | | | 0.082 | 0.000 | 0.280 | 0.000 | 230 | 811 | 3.526 | 9.186 | 1.428 |
| Positive control (E41A) | | | 0.021 | 0.000 | 0.340 | 0.000 | 59 | 985 | 16.690 | 28.320 | 1.470 |
| Negative control | | | 0.119 | 0.450 | 0.357 | 0.643 | 338 | 1049 | 3.104 | 4.672 | 0.466 |
| Negative control | | | 0.096 | 0.346 | 0.234 | 0.517 | 270 | 681 | 2.522 | 9.093 | 0.417 |

FIGURE 10

(1) Test 4; rerun 2, Monday, August 17, 2009 11:55:14 AM
(2) Test Emulsion 2, Thursday, August 13, 2009 4:26:10 PM
(3) Test 5, Monday, August 17, 2009 1:14:14 PM
(4) In-line Shear Mixing with PLA2 3, Monday, August 24, 2009 1:37:52 PM

PHOSPHOLIPASES, NUCLEIC ACIDS ENCODING THEM AND METHODS FOR MAKING AND USING THEM

CROSS REFERENCE TO RELATED APPLICATIONS

This application is a divisional of U.S. Ser. No. 13/502,069, filed Apr. 13, 2012, which claims priority from PCT/US2010/051903, filed Oct. 8, 2010, which claims priority from U.S. 61/252,313, filed Oct. 16, 2009, the contents of which are incorporated herein by reference in their entireties.

REFERENCE TO SEQUENCE LISTING SUBMITTED AS A COMPLIANT ASCII TEXT FILE (.txt)

A Sequence Listing is submitted herewith as an ASCII compliant text file named "2919208_175001_ST25"), created on May 24, 2016, and having a size of 18,691 KB kilobytes as permitted under 37 C.F.R. § 1.821(c). The material in the aforementioned file is hereby incorporated by reference in its entirety.

FIELD OF THE INVENTION

This invention relates generally to phospholipase enzymes, polynucleotides encoding the enzymes, methods of making and using these polynucleotides and polypeptides. In alternative embodiments, the invention provides phosphatidylinositol-specific phospholipase C (PI-PLC) enzymes, nucleic acids encoding them, antibodies that bind specifically to them, and methods for making and using them. Industrial methods and products comprising use of these phospholipases are provided. Also provided herein are methods for hydration of non hydratable phospholipids (NHPs) within a lipid matrix. The methods enable migration of NHPs to an oil-water interface thereby allowing the NHPs to be reacted and/or removed from the lipids. In certain embodiments, provided are methods for removing NHPs, hydratable phospholipids, and lecithins (known collectively as "gums") from vegetable oils to produce a degummed oil or fat product that can be used for food production and/or non-food applications. In certain embodiments, provided herein are methods for hydration of NHPs followed by enzymatic treatment and removal of various phospholipids and lecithins. The methods provided herein can be practiced on either crude or water-degummed oils. In certain embodiment, provided herein are methods for obtaining phospholipids from an edible oil.

BACKGROUND

Crude vegetable oils obtained from either pressing or solvent extraction methods are a complex mixture of triacylglycerols, phospholipids, sterols, tocopherols, free fatty acids, trace metals, and other minor compounds. It is desirable to remove the phospholipids, free fatty acids and trace metals in order to produce a quality salad oil with a bland taste, light color, and a long shelf life or oil suitable for transformation into a feedstock ready for chemical or enzymatic conversion into a biofuel (methyl- or ethyl-esters), bio-plastic (epoxidized oil), and other traditional petroleum based materials.

The removal of phospholipids generates almost all of the losses associated with the refining of vegetable oils. Most phospholipid molecules possess both a hydrophilic functional group and lipophilic fatty acid chains, they tend to be excellent natural emulsifiers. The functional group in phospholipids may be any of several of a variety of known types, a few of which are illustrated in scheme 1 below.

Scheme 1: Functional groups in phospholipids

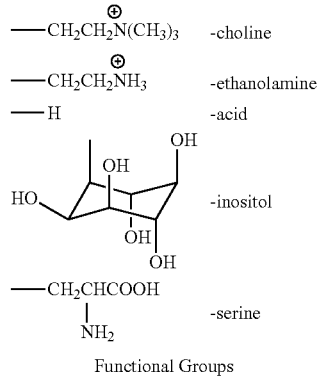

Functional Groups

Phospholipids containing the functional groups -choline, -inositol and -ethanolamine have the greatest affinity for water, while the acids, acid salts (Calcium (Ca), Magnesium (Mg), and Iron (Fe)), and -ethanolamine salts (Ca, Mg, and Fe) have much lower affinities for water. Phosphatidic acid and the salts of phosphatidic acid are commonly known as "non hydratable phospholipids" or NHPs. Table 1 contains relative rates of hydration of different phospholipids as reported by Sen Gupta, A. K., *Fette Seifen Anstrichmittel* 88 pages 79-86 (1986). and later by Segers, J. C., et al., "Degumming—Theory and Practice" published by American Oil Chemists's Society in "Edible fats and Oils processing: basic principals and modern practices: World conference proceedings"/edited by David Erickson, (1990) pages 88-93.

TABLE 1

Relative Rates of Hydration

| Phospholipids | Relative Rate of Hydration |
| --- | --- |
| Phosphatidyl Choline (PC) | 100 |
| Phosphatidyl Inositol (PI) | 44 |
| Calcium Salt of Phosphatidyl Inositol | 24 |
| Phosphatidyl Ethanolamine (PE) | 16 |
| Phosphatidic Acid (PA) | 8.5 |
| Calcium Salt of Phosphatidyl Ethanolamine | 0.9 |
| Calcium Salt of Phosphatidic Acid | 0.6 |

Calcium, magnesium, and iron salts of phospholipids are formed by an enzyme present in oilseeds, phospholipase D (PLD). The enzyme remains dormant within the mature seed until the protective coating of the seed has been damaged during storage or seed "preparations" prior to removal of the oil. The reaction of PLD within the seed will cleave the -choline, -inositol, -serine or -ethanolamine from the phosphate group yielding the Phosphatidic Acid (PA). Additionally, since the cleavage occurs in the presence of an abundance of divalent metals (Ca, Mg, and Fe), the NHPs are formed. The phosphatidic acid calcium ion complex is shown below:

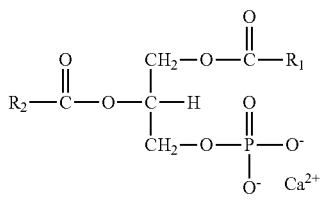

Calcium Salt of Phosphatidic Acid

Phospholipids are commonly measured in oil as "phosphorus content" in parts per million. Table 2 sets forth the typical amounts of phospholipids present in the major oilseed crops, and the distribution of the various functional groups as a percentage of the phospholipids present in the oil.

TABLE 2

Typical levels and phospholipid distributions for common oilseeds

|  | Soy Oil | Canola Oil | Sunflower Oil |
|---|---|---|---|
| Phosphorus (ppm) | 400-1500 | 200-900 | 300-700 |
| PC (%) | 12-46 | 25-40 | 29-52 |
| PE (%) | 8-34 | 15-25 | 17-26 |
| PA (%) | 2-21 | 10-20 | 15-30 |
| PS (%) | <0.5 | <0.5 | <0.5 |
| PI (%) | 2-15 | 2-25 | 11-22 |

Table 3 below provides typical phospholipid amounts and distributions for soybean gums. In Table 3, "as is" means the typical phospholipid composition removed from vegetable oil with the entrained oil (2 molecules of phospholipids and 1 molecule of oil), yielding an Acetone Insoluble content of 67%. "Normalized" means the phospholipid composition without any oil present, yielding an Acetone Insoluble content of 100%.

TABLE 3

Typical phospholipid amounts and distributions for soybean gums

|  | Percentage "As-Is" | Percentage "Normalized" |
|---|---|---|
| Phosphatidyl Choline (PC) | 33.9 | 47.2 |
| Phosphatidyl Ethanolamine (PE) | 14.3 | 19.9 |
| Phosphatidyl Serine (PS) | 0.4 | 0.6 |
| Phosphatidic Acid (PA) | 6.4 | 8.9 |
| Phosphatidyl Inositol (PI) | 16.8 | 23.4 |
| Total | 71.8 | 100.0 |

The conversion of phosphatidylcholine, phosphatidylethanolamine, phosphatidylserine, phosphatidylinositol, and phosphatidic acid into either their lyso- or phospho-forms greatly changes the economics of the degumming in a modern industrial refining operation. The conversion of all of the phospholipids into their lyso-forms eliminating the neutral oil loss represents an increase in oil yield of up to 1.4%, while converting all the phospholipids into their phospho-forms represents an oil yield increase up to 3.0% for a crude oil over water degumming containing 1000 ppm of phosphorus.

Phospholipids can be partially or totally removed from vegetable oils through several different known means. The most commonly used processes in the industry are water degumming, acid degumming, caustic refining and enzymatic degumming. Exemplary processes are described in U.S. Pat. Nos. 4,049,686; 4,698,185; 5,239,096; 5,264,367; 5,286,886; 5,532,163; 6,001,640; 6,103,505; U.S. Pat. Nos. 6,127,137; 6,143,545; 6,172,248; 6,548,633; 7,494,676; and 7,226,771, and U.S. publication nos. 2007/0134777, 2005/0059130, 2008/0182322, and 2009/0069587.

The existing methods are not sufficient to remove or react non-hydratable phospholipids present in the oil because the NHPs are not available to be hydrated or reacted to enable their removal.

There is a need for cost effective and efficient methods for removing NHPs, hydratable phospholipids, and lecithins (known collectively as "gums") from vegetable oils to produce a degummed oil or fat product that can be used for food production and/or non-food applications.

Phospholipases are enzymes that hydrolyze the ester bonds of phospholipids. Corresponding to their importance in the metabolism of phospholipids, these enzymes are widespread among prokaryotes and eukaryotes. The phospholipases affect the metabolism, construction and reorganization of biological membranes and are involved in signal cascades. Several types of phospholipases are known which differ in their specificity according to the position of the bond attacked in the phospholipid molecule.

Phosphatidylinositol-specific phospholipase C (PI-PLC) enzymes are a family of eukaryotic intracellular enzymes that play an important role in signal transduction processes. The PI-PLC catalyzed reaction is:

1-phosphatidyl-1D-myo-inositol 4,5-bisphosphate (also called $PIP_2$, phosphatidylinositol bisphosphate)+$H_2O$↔1 D-myo-inositol 1,4,5-trisphosphate (also called $IP_3$, inositol triphosphate)+ diacylglycerol Families of phospholipase C (PLC) enzymes have been identified in bacteria and in eukaryotic trypanosomes. PLC enzymes belong to the family of hydrolases and phosphodiesterases. PLC participate in phosphatidylinositol 4,5-bisphosphate ($PIP_2$) metabolism and lipid signaling pathways in a calcium-dependent manner. PLC isoforms can differ in their mode of activation, expression levels, catalytic regulation, cellular localization, membrane binding avidity and tissue distribution. All are capable of catalyzing the hydrolysis of $PIP_2$ into two important second messenger molecules, which go on to alter cell responses such as proliferation, differentiation, apoptosis, cytoskeleton remodeling, vesicular trafficking, ion channel conductance, endocrine function and neurotransmission. PLCs are described in, for example, Carmen, G., *J. Biol. Chem.* 270 (1995) 18711-18714, Jianag, Y., *J. Biol. Chem*, 271 (1996) 29528-29532, Waggoner, D., *J. Biol. Chem.* 270 (1995) 19422-19429, Molecular Probes Product Sheet 2001, and Sano et al., *Am. J. Physiol. Lung Cell Mol. Physiol.* 281:844-851, 2001.

Phospholipase A1 (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and 1-acyl-2-lysophospholipid. PLA1 and PLA2 enzymes can be intra- or extra-cellular, membrane-bound or soluble. Intracellular PLA2 is found in almost every mammalian cell. Phospholipase C (PLC) enzymes remove the phosphate moiety to produce 1,2 diacylglycerol and a phosphate ester. Phospholipase D (PLD) enzymes produce 1,2-diacylglycerophosphate and base group.

SUMMARY OF THE INVENTION

Provided herein are polypeptides and polynucleotides encoding polypeptides having a phosphatidylinositol-specific phospholipase C (PI-PLC) or equivalent enzyme activity, and/or another phospholipase activity, including a phospholipases A, B, C, D, patatin, phosphatidic acid phosphatases (PAP) and/or lipid acyl hydrolase (LAH) or equivalent enzyme activity, and methods of making and using these polynucleotides and polypeptides. In one aspect, provided herein are polypeptides, e.g., enzymes, having a phospholipase activity, e.g., phospholipase A, B, D or C activity, e.g. phosphatidylinositol-specific phospholipase C (PI-PLC) activity. The enzymatic activities of the polypeptides and peptides as provided herein include (comprise or consist of) a phospholipase activity, a phospholipase C activity, or a phosphatidylinositol-specific phospholipase C (PI-PLC) activity, including hydrolysis of lipids, acidolysis reactions (e.g., to replace an esterified fatty acid with a free fatty acid), transesterification reactions (e.g., exchange of fatty acids between triacylglycerides), ester synthesis, ester interchange reactions and lipid acyl hydrolase (LAH) activity. In another aspect, the polypeptides as provided herein are used to synthesize enantiomerically pure chiral products. The polypeptides as provided herein can be used in a variety of pharmaceutical, agricultural and industrial contexts, including the manufacture of cosmetics and nutraceuticals. Additionally, the polypeptides as provided herein can be used in food processing, brewing, bath additives, alcohol production, peptide synthesis, enantioselectivity, hide preparation in the leather industry, waste management and animal waste degradation, silver recovery in the photographic industry, medical treatment, silk degumming, biofilm degradation, biomass conversion to ethanol, biodefense, antimicrobial agents and disinfectants, personal care and cosmetics, biotech reagents, in increasing starch yield from corn wet milling, and as pharmaceuticals such as digestive aids and anti-inflammatory (antiphlogistic) agents.

In certain embodiments, provided herein are compositions (e.g., phospholipase, phospholipase C, phosphatidylinositol-specific phospholipase C (PI-PLC)) and methods for producing low phospholipid oils, e.g., oils with a lower phosphatidylcholine, phosphatidylethanolamine, phosphatidylserine, phosphatidylinositol, and/or phosphatidic acid content. Any oil, e.g. vegetable oil, e.g. canola oil, soybean oil, or animal oil or fat, e.g., tallow, can be treated with a composition, or by a method, as provided herein. Any foods, edible items, or baking, frying or cooking products (e.g., sauces, marinades, condiments, spray oils, margarines, baking oils, mayonnaise, cooking oils, salad oils, spoonable and pourable dressings, and the like, and products made therewith) can comprise a vegetable oil or animal fat that has been treated with a composition or by a method as provided herein. Vegetable oils modified to be lower phospholipid oils can be used in any foods, edible items or baking or cooking products, e.g., sauces, marinades, condiments, spray oils, margarines, baking oils, mayonnaise, cooking oils, salad oils, spoonable and pourable dressings and the like. In one embodiment, provided herein are oils, such as vegetable oils, e.g., canola oil or soybean oil, and foods or baking or cooking products, including sauces, marinades, condiments, spray oils, margarines, mayonnaise, baking oils, cooking oils, frying oils, salad oils, spoonable and pourable dressings, and the like, wherein the oil or food, baking or cooking product has been modified using an enzyme as provided herein. In one aspect, these vegetable oils, e.g. canola oil, castor oil, coconut oil, coriander oil, corn oil, cottonseed oil, hazelnut oil, hempseed oil, linseed oil, meadowfoam oil, olive oil, palm oil, palm kernel oil, peanut oil, rapeseed oil, rice bran oil, safflower oil, sasanqua oil, soybean oil, sunflower seed oil, tall oil, tsubaki oil, varieties of "natural" oils having altered fatty acid compositions via Genetically Modified Organisms (GMO) or traditional "breeding" such as high oleic, low linolenic, or low saturate oils (high oleic canola oil, low linolenic soybean oil or high stearic sunflower oils), animal fats (tallow, lard, butter fat, and chicken fat), fish oils (candlefish oil, cod-liver oil, orange roughy oil, sardine oil, herring oil, and menhaden oil), or blends of any of the above, and foods or baking, frying or cooking products, comprise oils with a lower saturated fatty acid content, including oils low in palmitic acid, myristic acid, lauric acid, stearic acid, caprylic acid (octanoic acid) etc., processed by using a composition or method as provided herein.

In one aspect, provided herein are polypeptides, for example, enzymes and catalytic antibodies, having a phospholipase activity, e.g., phospholipase C, e.g. phosphatidylinositol-specific phospholipase C (PI-PLC), including thermostable and thermotolerant enzymatic activities, and fatty acid specific or fatty acid selective activities, and low or high pH tolerant enzymatic activities, and polynucleotides encoding these polypeptides, including vectors, host cells, transgenic plants and non-human animals, and methods for making and using these polynucleotides and polypeptides.

In another aspect, provided herein are isolated, synthetic or recombinant nucleic acids (a) encoding a polypeptide having a phospholipase, e.g. a phospholipase C, e.g. a phosphatidylinositol-specific phospholipase C (PI-PLC) enzyme activity, and (i) having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or 100% sequence identity to SEQ ID NO:5 and encoding a polypeptide having at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine or thirty or more, or all, of the amino acid changes (mutations) consisting of those described in Table 12, Table 13, Table 14 and/or Table 15, or equivalent amino acid substitutions or mutations, or any combination thereof, and optionally the sequence identities are determined by analysis with a sequence comparison algorithm or by a visual inspection, and optionally the sequence comparison algorithm is a BLAST version 2.2.2 algorithm where a filtering setting is set to blastall-p blastp-d "nr pataa"-F F, and all other options are set to default;

(ii) encoding a polypeptide have an amino acid sequence as set forth in SEQ ID NO:6 and having at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine or thirty or more, or all, of the amino acid changes or substitutions (mutations) consisting of those described in Table 12, Table 13, Table 14 and/or Table 15, or equivalent amino acid changes or substitutions (mutations), or any combination thereof; or (iii) hybridizes under stringent conditions to a nucleic acid comprising SEQ ID NO:5 and encoding a polypeptide having at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine or thirty or more, or all, of the amino acid changes (mutations) consisting of those described in Table 12, Table 13, Table 14 and/or Table 15, or equivalent amino acid changes or substitutions (mutations), or any combination thereof, wherein the stringent conditions comprise a wash step comprising a wash in 0.2×SSC at a temperature of about 65° C. for about 15 minutes;

(iv) a nucleic acid comprising or consisting of the sequence SEQ ID NO:7, SEQ ID NO:9 or SEQ ID NO:10; or (v) having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or 100% sequence identity to SEQ ID NO:7, SEQ ID NO:9 or SEQ ID NO:10;

(b) the nucleic acid sequence of (a) encoding a polypeptide having the phospholipase, e.g. a phospholipase C, e.g. a phosphatidylinositol-specific phospholipase C (PI-PLC) enzyme activity but lacking a native signal sequence or proprotein amino acid sequence;

(c) the nucleic acid sequence of (a) or (b) encoding a polypeptide having the phospholipase, e.g. a phospholipase C, e.g. a phosphatidylinositol-specific phospholipase C (PI-PLC) enzyme activity but lacking a native promoter sequence;

(d) the nucleic acid of (c) further comprising a heterologous promoter sequence or other transcriptional regulatory sequence;

(e) the nucleic acid sequence of any of (a) to (d) further comprising nucleic acid encoding a heterologous amino acid sequence, or further comprising a heterologous nucleotide sequence;

(f) the nucleic acid of (e), wherein the nucleic acid encoding the heterologous amino acid sequence comprises, or consists of, a sequence encoding a heterologous (leader) signal sequence, or a tag or an epitope, or the heterologous nucleotide sequence comprises a heterologous promoter sequence;

(g) the nucleic acid of (d), (e) or (f), wherein the heterologous nucleotide sequence encodes a heterologous (leader) signal sequence comprising or consisting of an N-terminal and/or C-terminal extension for targeting to an endoplasmic reticulum (ER) or endomembrane, or to a plant endoplasmic reticulum (ER) or endomembrane system, or the heterologous sequence encodes a restriction site;

(h) the nucleic acid of (d), (e) or (f), wherein the heterologous promoter sequence comprises or consists of a constitutive or inducible promoter, or a cell type specific promoter, or a plant specific promoter, or a bacteria specific promoter;

(i) the nucleic acid of any of (a) to (h), wherein the phospholipase, e.g. a phospholipase C, e.g. a phosphatidylinositol-specific phospholipase C (PI-PLC) activity is thermostable;

(j) the nucleic acid of any of (a) to (h), wherein the phospholipase, e.g. a phospholipase C, e.g. a phosphatidylinositol-specific phospholipase C (PI-PLC) activity is thermotolerant;

(k) a nucleic acid sequence completely complementary to the nucleotide sequence of any of (a) to (j).

In one aspect, the isolated, synthetic or recombinant nucleic acid encodes a polypeptide or peptide having a phospholipase, e.g. a phospholipase C, e.g. a phosphatidylinositol-specific phospholipase C (PI-PLC) activity, which is thermostable. The polypeptides and peptides encoded by nucleic acids as provided herein, or any polypeptide or peptide as provided herein, can retain enzymatic or binding activity (e.g., substrate binding) under conditions comprising a temperature range of between about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., 5 about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. Provided herein are the thermostable polypeptides that retain a phospholipase, e.g. a phospholipase C, e.g. a phosphatidylinositol-specific phospholipase C (PI-PLC) activity, at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one aspect, polypeptides as provided herein can be thermotolerant and can retain a phospholipase, e.g. a phospholipase C, e.g. a phosphatidylinositol-specific phospholipase C (PI-PLC) activity after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more.

In some embodiments, the thermotolerant polypeptides retain a phospholipase, e.g. a phospholipase C, e.g. a phosphatidylinositol-specific phospholipase C (PI-PLC) activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In another aspect, provided herein are nucleic acid probes or amplification primers for isolating, making and/or identifying a nucleic acid encoding a polypeptide having a phospholiplase, e.g. phospholipase C, e.g. phosphatidylinositol-specific phospholipase C (PI-PLC) activity. In one embodiment, a nucleic acid probe, e.g., a probe for identifying a nucleic acid encoding a polypeptide having a phospholiplase, e.g. phospholipase C, e.g. phosphatidylinositol-specific phospholipase C (PI-PLC) activity, comprises a probe comprising or consisting of at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence as provided herein, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence as provided herein, or fragments or subsequences thereof. The probe can comprise an oligonucleotide comprising at least about 10 to 50, about 20 to 60, about 30 to 70, about 40 to 80, or about 60 to 100 consecutive bases of a nucleic acid sequence as provided herein, or a subsequence thereof.

In one embodiment, an amplification primer sequence pair for amplifying a nucleic acid encoding a polypeptide having a phospholiplase, e.g. phospholipase C, e.g. phosphatidylinositol-specific phospholipase C (PI-PLC) activity, comprises a primer pair comprising or consisting of a primer pair capable of amplifying a nucleic acid comprising a sequence as provided herein, or fragments or subsequences thereof. One or each member of the amplification primer sequence pair can comprise an oligonucleotide comprising at least about 10 to 50 consecutive bases of the sequence.

In one embodiment, methods of amplifying a nucleic acid encoding a polypeptide having a phospholiplase, e.g. phospholipase C, e.g. phosphatidylinositol-specific phospholipase C (PI-PLC) activity, comprise amplification of a template nucleic acid with an amplification primer sequence air capable of amplifying a nucleic acid sequence as provided herein, or fragments or subsequences thereof.

In one embodiment, vectors, expression cassettes, expression vectors, plasmids, or cloning vehicles comprise a nucleic acid as provided herein or subsequence thereof. In one aspect, the vector, expression cassette, expression vector, plasmid, or cloning vehicle can comprise or is contained in a viral vector, a phage, a phagemid, a cosmid, a fosmid, a bacteriophage, an artificial chromosome, an adenovirus vector, a retroviral vector or an adeno-associated viral vector; or, a bacterial artificial chromosome (BAC), a bacteriophage P1-derived vector (PAC), a yeast artificial chromosome (YAC), or a mammalian artificial chromosome (MAC).

In one embodiment, expression cassettes comprise a nucleic acid as provided herein or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

In one embodiment, a host cell or a transformed cell comprises a nucleic acid as provided herein. In one aspect, the host cell or a transformed cell can be a bacterial cell, a mammalian cell, a fungal cell, a yeast cell, an insect cell or a plant cell. In one aspect, the plant cell can be a potato, wheat, rice, corn, tobacco or barley cell. The transformed cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera Escherichia, Bacillus, Streptomyces, Salmonella, Pseudomonas and Staphylococcus, including, e.g., Escherichia coli, Lactococcus lactis, Bacillus subtilis, Bacillus cereus, Salmonella typhimurium, Pseudomonas fluorescens. Exemplary fungal cells include any species of Aspergillus. Exemplary yeast cells include any species of Pichia, Saccharomyces, Schizosaccharomyces, or Schwanniomyces, including Pichia pastoris, Saccharomyces cerevisiae, or Schizosaccharomyces pombe. Exemplary insect cells include any species of Spodoptera or Drosophila, including Drosophila S2 and Spodoptera Sf9. Exemplary animal cells include CHO, COS or Bowes melanoma or any mouse or human cell line.

In another embodiment, transgenic non-human animals comprise a nucleic acid as provided herein or a vector, expression cassette, expression vector, plasmid, or cloning vehicle as provided herein. The transgenic non-human animal can be a mouse, a rat, a goat, a rabbit, a sheep, a pig or a cow.

In one embodiment, a transgenic plant or seed comprises a nucleic acid as provided herein or a vector, expression cassette, expression vector, plasmid, or cloning vehicle as provided herein. In one embodiment, plant is a corn plant, a sorghum plant, a potato plant, a tomato plant, a wheat plant, an oilseed plant, a rapeseed plant, a soybean plant, a rice plant, a barley plant, a grass, a cottonseed, a palm, a sesame plant, a peanut plant, a sunflower plant or a tobacco plant; the transgenic seed. In one embodiment, the seed is a corn seed, a wheat kernel, an oilseed, a rapeseed, a soybean seed, a palm kernel, a sunflower seed, a sesame seed, a rice, a barley, a peanut, a cottonseed, a palm, a peanut, a sesame seed, a sunflower seed or a tobacco plant seed.

In one aspect, provided herein are an antisense oligonucleotide or inhibitory RNA comprising or consisting of a nucleic acid as provided herein.

In another aspect, provided herein is a method of inhibiting the translation of a phospholipase message (transcript, mRNA) in a cell comprising administering to the cell or expressing in the cell an antisense oligonucleotide or inhibitory RNA comprising or consisting of a nucleic acid sequence provided herein.

In one embodiment, isolated, synthetic or recombinant polypeptides have a phospholiplase, e.g. phospholipase C, e.g. phosphatidylinositol-specific phospholipase C (PI-PLC) activity, or polypeptides capable of generating an immune response specific for a phospholiplase, e.g. phospholipase C, e.g. phosphatidylinositol-specific phospholipase C (PI-PLC) (e.g., an epitope); and in alternative aspects peptides and polypeptides as provided herein comprise a sequence:

(a) comprising an amino acid sequence:
  (i) having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or 100% sequence identity to SEQ ID NO:6, and having at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine or thirty or more, or all, of the amino acid changes or substitutions (mutations) consisting of those described in Table 12, Table 13, Table 14 and/or Table 15, or equivalent amino acid changes or substitutions (mutations), or any combination thereof,
  wherein optionally the sequence identities are determined by analysis with a sequence comparison algorithm or by a visual inspection;

(ii) encoded by a nucleic acid as provided herein;

(iii) having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or 100% sequence identity to SEQ ID NO: 8;

(b) the polypeptide of (a) but lacking a native signal sequence and/or a proprotein sequence;

(c) the polypeptide of (a) or (b) further comprising a heterologous amino acid sequence or a heterologous moiety;

(d) the polypeptide of (c), wherein the heterologous amino acid sequence or heterologous moiety comprises, or consists of a heterologous (leader) signal sequence, a tag, a detectable label or an epitope;

(e) the polypeptide of (d), wherein the heterologous (leader) signal sequence comprises or consisting of an N-terminal and/or C-terminal extension for targeting to an endoplasmic reticulum (ER) or endomembrane, or to a plant endoplasmic reticulum (ER) or endomembrane system;

(f) the polypeptide of any of (a) to (e), wherein the phospholipase, e.g. phospholipase C, e.g. phosphatidylinositol-specific phospholipase C (PI-PLC) catalyzes a reaction comprising:

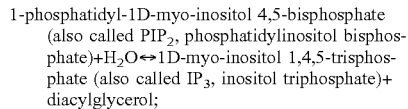

1-phosphatidyl-1D-myo-inositol 4,5-bisphosphate (also called PIP$_2$, phosphatidylinositol bisphosphate)+H$_2$O↔1D-myo-inositol 1,4,5-trisphosphate (also called IP$_3$, inositol triphosphate)+ diacylglycerol;

(g) the polypeptide of (a) to (f), wherein the phospholipase, e.g. phospholipase C, e.g. phosphatidylinositol-specific phospholipase C (PI-PLC) activity is thermostable;

(h) the polypeptide of (a) to (f), wherein the phospholipase, e.g. phospholipase C, e.g. phosphatidylinositol-specific phospholipase C (PI-PLC) activity is thermotolerant;

(i) the polypeptide of any one of (a) to (h), wherein: (i) the polypeptide is glycosylated, or the polypeptide comprises at least one glycosylation site, (ii) the polypeptide of (i) wherein the glycosylation is an N-linked glycosylation or an O-linked glycosylation; (iii) the polypeptide of (i) or (ii) wherein the polypeptide is glycosylated after being expressed in a yeast cell; or (iv) the polypeptide of (iii) wherein the yeast cell is a *P. pastoris* or a *S. pombe*;

(j) the polypeptide of any one of (a) to (i), further comprising or contained in a composition comprising at least one second enzyme, or at least one second phospholipase enzyme; or (k) the polypeptide of (j), wherein the at least one second phospholipase enzyme comprises a polypeptide having a sequence as set forth in SEQ ID N0:2 and/or SEQ ID NO:4, or at least one of their variant enzymes as described in Tables 8 and 9.

In one aspect, the isolated, synthetic or recombinant polypeptide can comprise the polypeptide as provided herein that lacks a signal (peptide) sequence, e.g., lacks its homologous signal sequence, and in one aspect, comprises a heterologous signal (peptide) sequence. In one aspect, the isolated, synthetic or recombinant polypeptide can comprise the polypeptide as provided herein comprising a heterologous signal sequence, such as a heterologous phospholipase or non-phospholipase (e.g., non-phospholipase, non-phospholipase C or non-phosphatidylinositol-specific phospholipase C (PI-PLC)) signal sequence. In one aspect, chimeric proteins comprise a first domain comprising a signal sequence as provided herein and at least a second domain. The protein can be a fusion protein. The second domain can comprise an enzyme. The enzyme can be a phospholipase, e.g. phospholipase C, e.g. phosphatidylinositol-specific phospholipase C (PI-PLC) as provided herein, or, another enzyme.

In one aspect, the phospholipase, e.g. phospholipase C, e.g. phosphatidylinositol-specific phospholipase C (PI-PLC) activity comprises a specific activity at about 37° C. in the range from about 100 to about 1000 units per milligram of protein. In another aspect, the phospholipase, e.g. phospholipase C, e.g. phosphatidylinositol-specific phospholipase C (PI-PLC) activity comprises a specific activity from about 500 to about 750 units per milligram of protein. Alternatively, the phospholipase activity comprises a specific activity at 37° C. in the range from about 500 to about 1200 units per milligram of protein. In one aspect, the phospholipase activity comprises a specific activity at 37° C. in the range from about 750 to about 1000 units per milligram of protein. In another aspect, the thermotolerance comprises retention of at least half of the specific activity of the phospholipase at 37° C. after being heated to an elevated temperature. Alternatively, the thermotolerance can comprise retention of specific activity at 37° C. in the range from about 500 to about 1200 units per milligram of protein after being heated to an elevated temperature.

In one embodiment, the isolated, synthetic or recombinant polypeptides as provided herein comprise at least one glycosylation site. In one aspect, glycosylation can be an N-linked glycosylation. In one aspect, the polypeptide can be glycosylated after being expressed in a *P. pastoris* or a *S. pombe* or in plants, such as oil producing plants e.g. soy bean, canola, rice, sunflower, or genetically-modified (GMO) variants of these plants.

In one aspect, the polypeptide can retain a phospholipase, e.g. phospholipase C, e.g. phosphatidylinositol-specific phospholipase C (PI-PLC) activity under conditions comprising about pH 6.5, pH 6, pH 5.5, pH 5, pH 4.5 or pH 4.0 or lower. In another aspect, the polypeptide can retain a phospholipase, e.g. phospholipase C, e.g. phosphatidylinositol-specific phospholipase C (PI-PLC) activity under conditions comprising about pH 7, pH 7.5, pH 8.0, pH 8.5, pH 9, pH 9.5, pH 10, pH 10.5, pH 11, pH 11.5, pH 12.0 or more.

In one embodiment, protein preparations comprise a polypeptide as provided herein, wherein the protein preparation comprises a liquid, a solid or a gel.

In one aspect, heterodimers as provided herein comprise a polypeptide and a second domain. In one aspect, the second domain can be a polypeptide and the heterodimer can be a fusion protein. In one aspect, the second domain can be an epitope or a tag. In one aspect, homodimers as provided herein comprise a polypeptide as provided herein.

In one embodiment, immobilized polypeptides as provided herein have a phospholipase, e.g. phospholipase C, e.g. phosphatidylinositol-specific phospholipase C (PI-PLC) activity, wherein the polypeptide comprises a polypeptide as provided herein, a polypeptide encoded by a nucleic acid as provided herein, or a polypeptide comprising a polypeptide as provided herein and a second domain. In one aspect, a polypeptide as provided herein can be immobilized on a cell, a vesicle, a liposome, a film, a membrane, a metal, a resin, a polymer, a ceramic, a glass, a microelectrode, a graphitic particle, a bead, a gel, a plate, a crystal, a tablet, a pill, a capsule, a powder, an agglomerate, a surface, a porous structure, an array or a capillary tube, or materials such as grains, husks, bark, skin, hair, enamel, bone, shell and materials deriving from them. Polynucleotides, polypeptides and enzymes as provided herein can be formulated in a solid form such as a powder, a lyophilized preparation, granules, a tablet, a bar, a crystal, a capsule, a pill, a pellet, or in a liquid form such as an aqueous solution, an aerosol, a gel, a paste, a slurry, an aqueous/oil emulsion, a cream, a capsule, or a vesicular or micellar suspension.

In one aspect, provided herein are isolated, synthetic or recombinant antibodies which specifically binds to a polypeptide as provided herein. In another aspect, the isolated, synthetic or recombinant antibodies are monoclonal or polyclonal antibodies, or are antigen binding fragments thereof. In one aspect, provided herein is an hybridoma comprising an antibody provided herein.

In one embodiment, provided herein is an array comprising an immobilized polypeptide, immobilized nucleic acid, or an antibody as provided herein, or a combination thereof.

In one embodiment, food supplements for an animal comprise a polypeptide as provided herein, e.g., a polypeptide encoded by the nucleic acid as provided herein. In one aspect, the polypeptide in the food supplement can be glycosylated. In one embodiment, edible enzyme delivery matrices comprise a polypeptide as provided herein, e.g., a polypeptide encoded by the nucleic acid as provided herein. In one aspect, the delivery matrix comprises a pellet. In one aspect, the polypeptide can be glycosylated. In one aspect, the phospholipase activity is thermotolerant. In another aspect, the phospholipase activity is thermostable.

In one embodiment, methods of isolating or identifying a polypeptide have a phospholipase, e.g. phospholipase C, e.g. phosphatidylinositol-specific phospholipase C (PI-PLC) activity comprising the steps of: (a) providing an antibody as provided herein; (b) providing a sample comprising polypeptides; and (c) contacting the sample of step (b) with the antibody of step (a) under conditions wherein the antibody can specifically bind to the polypeptide, thereby isolating or identifying a polypeptide having a phospholipase, e.g. phospholipase C, e.g. phosphatidylinositol-specific phospholipase C (PI-PLC) activity.

In one embodiment, methods of making an anti-phospholipase antibody comprise administering to a non-human animal a nucleic acid as provided herein or a polypeptide as provided herein or subsequences thereof in an amount sufficient to generate a humoral immune response, thereby making an anti-phospholipase antibody. Provided herein are methods of making an anti-phospholipase antibody comprising administering to a non-human animal a nucleic acid as provided herein or a polypeptide as provided herein or subsequences thereof in an amount sufficient to generate an immune response.

In one embodiment, methods of producing a recombinant polypeptide comprise the steps of: (A) (a) providing a nucleic acid as provided herein, wherein the nucleic acid is optionally linked to a promoter, wherein the nucleic acid comprises a nucleic acid as provided herein; and (b) expressing the nucleic acid of step (a) under conditions that allow expression of the polypeptide, thereby producing a recombinant polypeptide; or (B) the method of (A), further comprising transforming a host cell with the nucleic acid of step (a) followed by expressing the nucleic acid of step (a), thereby producing a recombinant polypeptide in a transformed cell.

In one embodiment, methods for identifying a polypeptide having a phospholipase activity comprise the steps of: (a) providing a polypeptide as provided herein; (b) providing a phospholipase substrate; and (c) contacting the polypeptide with the substrate of step (b) and detecting a decrease in the amount of substrate or an increase in the amount of a reaction product, wherein a decrease in the amount of the substrate or an increase in the amount of the reaction product detects a polypeptide having a phospholipase activity.

In another embodiment, methods for identifying a phospholipase substrate comprise the steps of: (a) providing a polypeptide as provided herein; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a phospholipase substrate.

In another aspect, methods of determining whether a test compound specifically binds to a polypeptide comprise the steps of: (a) expressing a nucleic acid or a vector comprising the nucleic acid under conditions permissive for translation of the nucleic acid to a polypeptide, wherein the nucleic acid comprises a nucleic acid as provided herein; (b) providing a test compound; (c) contacting the polypeptide with the test compound; and (d) determining whether the test compound of step (b) specifically binds to the polypeptide.

In another aspect, methods of determining whether a test compound specifically binds to a polypeptide comprise the steps of: (a) providing a polypeptide as provided herein; (b) providing a test compound; (c) contacting the polypeptide with the test compound; and (d) determining whether the test compound of step (b) specifically binds to the polypeptide.

In one embodiment, methods for identifying a modulator of a phospholipase activity comprise the steps of: (A) (a) providing a polypeptide as provided herein; (b) providing a test compound; (c) contacting the polypeptide of step (a) with the test compound of step (b) and measuring an activity of the phospholipase, wherein a change in the phospholipase activity measured in the presence of the test compound compared to the activity in the absence of the test compound provides a determination that the test compound modulates the phospholipase activity; (B) the method of (A), wherein the phospholipase activity is measured by providing a phospholipase substrate and detecting a decrease in the amount of the substrate or an increase in the amount of a reaction product, or, an increase in the amount of the substrate or a decrease in the amount of a reaction product; (c) the method of (B), wherein a decrease in the amount of the substrate or an increase in the amount of the reaction product with the test compound as compared to the amount of substrate or reaction product without the test compound identifies the test compound as an activator of phospholipase activity; or, (d) the method of (B), wherein an increase in the amount of the substrate or a decrease in the amount of the reaction product with the test compound as compared to the amount of substrate or reaction product without the test compound identifies the test compound as an inhibitor of phospholipase activity.

In one aspect, methods for isolating or recovering a nucleic acid encoding a polypeptide with a phospholipase activity from a sample comprise the steps of: (A) (a) providing a polynucleotide probe comprising a nucleic acid as provided herein; (b) isolating a nucleic acid from the sample or treating the sample such that nucleic acid in the sample is accessible for hybridization to a polynucleotide probe of step (a); (c) combining the isolated nucleic acid or the treated sample of step (b) with the polynucleotide probe of step (a); and (d) isolating a nucleic acid that specifically hybridizes with the polynucleotide probe of step (a), thereby isolating or recovering a nucleic acid encoding a polypeptide with a phospholipase activity from a sample; (B) the method of (A), wherein the sample is or comprises an environmental sample; (C) the method of (B), wherein the environmental sample is or comprises a water sample, a liquid sample, a soil sample, an air sample or a biological sample; or (D) the method of (C), wherein the biological sample is derived from a bacterial cell, a protozoan cell, an insect cell, a yeast cell, a plant cell, a fungal cell or a mammalian cell.

In one embodiment, methods for isolating or recovering a nucleic acid encoding a polypeptide having a phospholipase activity from a sample comprising the steps of: (a) providing an amplification primer sequence pair for amplifying a nucleic acid encoding a polypeptide having a phospholipase activity, wherein the primer pair is capable of amplifying a nucleic acid as provided herein; (b) isolating a nucleic acid from the sample or treating the sample such that nucleic acid in the sample is accessible for hybridization to the amplification primer pair; and, (c) combining the nucleic acid of step (b) with the amplification primer pair of step (a) and amplifying nucleic acid from the sample, thereby isolating or recovering a nucleic acid encoding a polypeptide having a phospholipase activity from a sample. In one embodiment, the sample is an environmental sample, e.g., a water sample, a liquid sample, a soil sample, an air sample or a biological sample, e.g. a bacterial cell, a protozoan cell, an insect cell, a yeast cell, a plant cell, a fungal cell or a mammalian cell. One or each member of the amplification primer sequence pair can comprise an oligonucleotide comprising at least about 10 to 50 or more consecutive bases of a sequence as provided herein.

In one embodiment, methods of increasing thermotolerance or thermostability of a phospholipase polypeptide comprise glycosylating a phospholipase polypeptide, wherein the polypeptide comprises at least thirty contiguous amino acids of a polypeptide as provided herein; or a polypeptide encoded by a nucleic acid sequence as provided herein, thereby increasing the thermotolerance or thermostability of the phospholipase polypeptide. In one aspect, the phospholipase specific activity can be thermostable or thermotolerant at a temperature in the range from greater than about 37° C. to about 95° C.

In one embodiment, methods for overexpressing a recombinant phospholipase, e.g. phospholipase C, e.g. phosphatidylinositol-specific phospholipase C (PI-PLC) polypeptide in a cell comprise expressing a vector comprising a nucleic acid as provided herein or a nucleic acid sequence as provided herein, wherein the sequence identities are determined by analysis with a sequence comparison algorithm or by visual inspection, wherein overexpression is effected by use of a high activity promoter, a dicistronic vector or by gene amplification of the vector.

In one embodiment, methods for generating a variant of a nucleic acid encoding a polypeptide with a phospholipase activity comprise the steps of: (A) (a) providing a template nucleic acid comprising a nucleic acid as provided herein; and (b) modifying, deleting or adding one or more nucleotides in the template sequence, or a combination thereof, to generate a variant of the template nucleic acid; (B) the method of (A), further comprising expressing the variant nucleic acid to generate a variant phospholipase polypeptide; (C) the method of (A) or (B), wherein the modifications, additions or deletions are introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR) and a combination thereof; (D) the method of any of (A) to (C), wherein the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof; (E) the method of any of (A) to (D), wherein the method is iteratively repeated until a (variant) phospholipase having an altered or different (variant) activity, or an altered or different (variant) stability from that of a polypeptide encoded by the template nucleic acid is produced, or an altered or different (variant) secondary structure from that of a polypeptide encoded by the template nucleic acid is produced, or an altered or different (variant) post-translational modification from that of a polypeptide encoded by the template nucleic acid is produced; (F) the method of (E), wherein the variant phospholipase polypeptide is thermotolerant, and retains some activity after being exposed to an elevated temperature; (G) the method of (E), wherein the variant phospholipase polypeptide has increased glycosylation as compared to the phospholipase encoded by a template nucleic acid; (H) the method of (E), wherein the variant phospholipase polypeptide has a phospholipase activity under a high temperature, wherein the phospholipase encoded by the template nucleic acid is not active under the high temperature; (I) the method of any of (A) to (H), wherein the method is iteratively repeated until a phospholipase coding sequence having an altered codon usage from that of the template nucleic acid is produced; or (J) the method of any of (A) to (H), wherein the method is iteratively repeated until a phospholipase gene having higher or lower level of message expression or stability from that of the template nucleic acid is produced.

In one aspect, methods for modifying codons in a nucleic acid encoding a phospholipase polypeptide, the method comprise the steps of: (a) providing a nucleic acid encoding a polypeptide with a phospholipase activity comprising a nucleic acid as provided herein; and, (b) identifying a codon in the nucleic acid of step (a) and replacing it with a different codon encoding the same amino acid as the replaced codon, thereby modifying codons in a nucleic acid encoding a phospholipase.

In one embodiment, methods for producing a library of nucleic acids encoding a plurality of modified phospholipase active sites or substrate binding sites, wherein the modified active sites or substrate binding sites are derived from a first nucleic acid comprising a sequence encoding a first active site or a first substrate binding site the method comprise the steps of: (A) (a) providing a first nucleic acid encoding a first active site or first substrate binding site, wherein the first nucleic acid sequence comprises a nucleic acid as provided herein, and the nucleic acid encodes a phospholipase active site or a phospholipase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified phospholipase active sites or substrate binding sites; (B) the method of (A), comprising mutagenizing the first nucleic acid of step (a) by a method comprising an optimized directed evolution system, Gene Site Saturation Mutagenesis (GSSM), or a synthetic ligation reassembly (SLR); (C)

the method of (A) or (B), comprising mutagenizing the first nucleic acid of step (a) or variants by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR) and a combination thereof; or (D) the method of (A) or (B), comprising mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, methods for making a small molecule comprise the steps of: (a) providing a plurality of biosynthetic enzymes capable of synthesizing or modifying a small molecule, wherein one of the enzymes comprises a phospholipase enzyme encoded by a nucleic acid as provided herein; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions.

In another aspect, methods for modifying a small molecule comprise the steps of: (A) (a) providing a phospholipase enzyme, wherein the enzyme comprises a polypeptide as provided herein, or a polypeptide encoded by a nucleic acid as provided herein; (b) providing a small molecule; and (c) reacting the enzyme of step (a) with the small molecule of step (b) under conditions that facilitate an enzymatic reaction catalyzed by the phospholipase enzyme, thereby modifying a small molecule by a phospholipase enzymatic reaction; (B) the method of (A), comprising a plurality of small molecule substrates for the enzyme of step (a), thereby generating a library of modified small molecules produced by at least one enzymatic reaction catalyzed by the phospholipase enzyme; (C) the method of (A) or (B), further comprising a plurality of additional enzymes under conditions that facilitate a plurality of biocatalytic reactions by the enzymes to form a library of modified small molecules produced by the plurality of enzymatic reactions; (D) the method of (C), further comprising the step of testing the library to determine if a particular modified small molecule which exhibits a desired activity is present within the library; or (E) the method of (D), wherein the step of testing the library further comprises the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

In another aspect, methods for determining a functional fragment of a phospholipase enzyme comprise the steps of: (A) (a) providing a phospholipase enzyme, wherein the enzyme comprises a polypeptide as provided herein, or a polypeptide encoded by a nucleic acid as provided herein; and (b) deleting a plurality of amino acid residues from the sequence of step (a) and testing the remaining subsequence for a phospholipase activity, thereby determining a functional fragment of a phospholipase enzyme; or, (B) the method of (A), wherein the phospholipase activity is measured by providing a phospholipase substrate and detecting a decrease in the amount of the substrate or an increase in the amount of a reaction product.

In one aspect, methods for whole cell engineering of new or modified phenotypes by using real-time metabolic flux analysis, the method comprise the steps of: (a) making a modified cell by modifying the genetic composition of a cell, wherein the genetic composition is modified by addition to the cell of a nucleic acid as provided herein; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis; (B) the method of (A), wherein the genetic composition of the cell is modified by a method comprising deletion of a sequence or modification of a sequence in the cell, or, knocking out the expression of a gene; (C) the method of (A) or (B), further comprising selecting a cell comprising a newly engineered phenotype; or (D) the method of (C), further comprising culturing the selected cell, thereby generating a new cell strain comprising a newly engineered phenotype.

In one embodiment, methods of making a transgenic plant comprise the following steps: (a) introducing a heterologous nucleic acid sequence into a plant cell, wherein the heterologous nucleic sequence comprises a nucleic acid sequence as provided herein, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

In one embodiment, methods of expressing a heterologous nucleic acid sequence in a plant cell comprise the following steps: (a) transforming the plant cell with a heterologous nucleic acid sequence operably linked to a promoter, wherein the heterologous nucleic sequence comprises a nucleic acid as provided herein; (b) growing the plant under conditions wherein the heterologous nucleic acid sequence is expressed in the plant cell.

In one aspect, provided herein are detergent compositions comprising the phospholipase polypeptide as provided herein, or a phospholipase polypeptide encoded by a nucleic acid as provided herein. In one aspect, the phospholipase is a nonsurface-active phospholipase or a surface-active phospholipase. In another aspect, the phospholipase is formulated in a non-aqueous liquid composition, a cast solid, a lyophilized powder, a granular form, a particulate form, a compressed tablet, a pellet, a gel form, a paste, an aerosol, or a slurry form.

In one aspect, methods for washing an object comprise the steps of: (a) providing a composition comprising a phospholipase polypeptide as provided herein, or a polypeptide encoded by a nucleic acid as provided herein; (b) providing an object; and (c) contacting the polypeptide of step (a) and the object of step (b) under conditions wherein the composition can wash the object.

In one embodiment, provided herein are compositions comprising a phospholipase polypeptide as provided herein, or a polypeptide encoded by a nucleic acid as provided herein.

In one aspect, methods for ameliorating, treating or preventing lipopolysaccharide (LPS)-mediated toxicity comprise administering to a patient a pharmaceutical composition comprising a polypeptide as provided herein, or a polypeptide encoded by a nucleic acid sequence as provided herein.

In another aspect, provided herein are pharmaceuticals, pharmaceutical precursors and pharmaceutical compositions comprising a polypeptide as provided herein or a polypeptide encoded by a nucleic acid as provided herein. In another aspect, provided herein are methods of manufacturing a pharmaceutical, a pharmaceutical precursor or a pharmaceutical composition comprising addition of a polypeptide encoded by a nucleic acid as provided herein to a pharmaceutical, a pharmaceutical precursor or a pharmaceutical composition. In one aspect, the pharmaceutical composition is used for preventing, treating or ameliorating lipopolysaccharide (LPS)-mediated toxicity, or to detoxify an endotoxin, or deacylating a 2' or a 3' fatty acid chain from a lipid A.

In one embodiment, methods for detoxifying an endotoxin comprise contacting the endotoxin with a polypeptide as provided herein or a polypeptide encoded by a nucleic acid as provided herein.

In another embodiment, methods for making a variant phospholipase coding sequence having increased expression in a host cell comprise modifying a nucleic acid as provided herein, such that one, several or all N-linked glycosylation site coding motifs are modified to a non-glycosylated motif.

In one embodiment, provided herein are compositions comprising a mixture of phospholipase enzymes comprising: (a)(i) a phospholipase polypeptide as provided herein or polypeptide encoded by a nucleic acid as provided herein, and (ii) at least one second enzyme; (b) the composition of (a), wherein the at least one enzyme is a phospholipase enzyme; or (c) the composition of (b), wherein the at least one second phospholipase enzyme comprises a polypeptide as set forth in SEQ ID NO:2 and/or SEQ ID NO:4, or at least one of the variant PLC enzymes as described in Tables 8 and 9.

In one aspect, methods for making a biofuel, e.g. a biodiesel, comprise the steps of: (A) (a) providing a phospholipase polypeptide as provided herein, or a phospholipase enzyme encoded by a nucleic acid as provided herein, or a composition comprising a polypeptide as provided herein; (b) providing a composition comprising a lipid or an alkyl ester; (c) contacting the phospholipase polypeptide of (a) with the composition of (b); (B) the method of (A), wherein the composition comprising a lipid or an alkyl ester is, or comprises, an oil and/or a fat; or (C) the method of (A) or (B), wherein the composition comprising a lipid or an alkyl ester is, or comprises, an algae, a vegetable oil, a straight vegetable oil, a virgin vegetable oil, a waste vegetable oil, an animal fat, a grease, a tallow, a lard or a yellow grease. In another aspect, provided herein are fuels, e.g. biofuels, e.g. biodiesel, made by methods that comprise the steps of: (A) (a) providing a phospholipase polypeptide as provided herein, or a phospholipase enzyme encoded by a nucleic acid as provided herein, or a composition comprising a polypeptide as provided herein; b) providing a composition comprising a lipid or an alkyl ester; (c) contacting the phospholipase polypeptide of (a) with the composition of (b); (B) the method of (A), wherein the composition comprising a lipid or an alkyl ester is, or comprises, an oil and/or a fat; or (C) the method of (A) or (B), wherein the composition comprising a lipid or an alkyl ester is, or comprises, an algae, a vegetable oil, a straight vegetable oil, a virgin vegetable oil, a waste vegetable oil, an animal fat, a grease, a tallow, a lard or a yellow grease.

In another aspect, a distillers dried soluble (DDS), a distillers dried grain (DDS), a condensed distillers soluble (CDS), a distillers wet grain (DWG) or a distillers dried grain with solubles (DDGS), comprises a polypeptide as provided herein, or a polypeptide encoded by a nucleic acid as provided herein, or a composition as provided herein.

In another embodiment, provided herein is a biomass comprising (a) a polypeptide as provided herein, or a polypeptide encoded by a nucleic acid as provided herein, or a composition as provided herein; (b) the biomass of (a), wherein the biomass is, or comprises, an animal, algae and/or plant biomass, or a lipid-comprising or lignocellulosic biomass, or a waste material.

In another embodiment, provided herein is a petroleum-based product comprising: (a) a polypeptide as provided herein, or a polypeptide encoded by a nucleic acid as provided herein, or a composition as provided herein; (b) made by a method comprising use of a polypeptide as provided herein, or a polypeptide encoded by a nucleic acid as provided herein, or a composition as provided herein; or (c) the petroleum-based product of (a) or (b) comprising an oil, a biodiesel or a gasoline, or a bioethanol, biobutanol, biopropanol or a biomethanol; or a mixture of bioethanol, biobutanol, biopropanol, biomethanol and/or biodiesel and gasoline.

In one embodiment, provided herein is a method for hydration of Non Hydratable Phospholipids (NHPs) within a lipid matrix by enabling them to migrate to an oil-water interface. The NHPs are then reacted and/or removed from the lipids. In one embodiment, the method comprises a) mixing an aqueous acid with an edible oil to obtain an acidic mixture having pH of less than about 4; and b) mixing a base with the acidic mixture to obtain a reacted mixture having pH of about 6-9. In certain embodiments, mixing in steps a) and/or b) creates an emulsion that comprises the aqueous phase in average droplet size between about 15 μm to about 45 μm. In certain embodiments, mixing in steps a) and/or b) creates an emulsion that comprises at least about 60% of the to aqueous phase by volume in droplet size between about 15 μm to about 45 μm in size, wherein percentage of the aqueous phase is based on the total volume of the aqueous phase. In certain embodiments, mixing in steps a) and/or b) creates an emulsion that comprises at least about 60, 70, 80, 90, 93, 95, 96, 97, 98, or 99% of the aqueous phase by volume in droplet size between about 20 μm to about 45 μm in size. In certain embodiments, the method further comprises degumming the reacted mixture with water or an enzyme to obtain a degummed oil. In certain embodiments, the mixing in steps a) and/or b) is carried out with a high shear mixer with a tip speed of at least about 1400 cm/s, 1600 cm/s, 1800 cm/s, 2000 cm/s, 2100 cm/s, 2300 cm/s, 2500 cm/s, 3000 cm/s, or 3500 cm/s.

Any acid deemed suitable by one of skill in the art can be used in the methods provided herein. In certain embodiments, the acid is selected from the group consisting of phosphoric acid, acetic acid, citric acid, tartaric acid, succinic acid, and a mixture thereof. Any acid deemed suitable by one of skill in the art can be sued in the methods provided herein. In certain embodiments, the base is selected from the group consisting of sodium hydroxide, potassium hydroxide, sodium silicate, sodium carbonate, calcium carbonate, and a combination thereof.

In certain embodiments, the method for hydration of non hydratable phospholipids in an edible oil further comprises a step of water or enzymatic degumming to obtain a degummed oil. In one embodiment, provided herein is a method wherein NHPs hydration is followed by enzymatic treatment and removal of various phospholipids and lecithins. Such methods can be practiced on either crude or water-degummed oils.

In certain embodiments, an oil degumming method provided herein comprises a) mixing an aqueous acid with an edible oil to obtain an acidic mixture having pH of about 1 to 4, b) mixing a base with the acidic mixture to obtain a reacted mixture having pH of about 6-9, and c) degumming the reacted mixture with water or an enzyme to obtain a degummed oil. In certain embodiments, mixing in steps a) and/or b) creates an emulsion that comprises an aqueous phase in average droplet size between about 15 µm to about 45 µm. In certain embodiments, mixing in steps a) and/or b) creates an emulsion that comprises at least about 60% of an aqueous phase by volume in droplet size between about 15 µm to about 45 µm in size, wherein percentage of the aqueous phase is based on the total volume of the aqueous phase.

In one embodiment, provided herein is a method for removing NHPs, hydratable phospholipids, and lecithins (known collectively as "gums") from vegetable oils to produce a degummed oil or fat product that can be used for food production and/or non-food applications. In certain embodiments, the degumming methods provided herein utilize water, various acids and/or various bases or a combination thereof.

In another aspect, provided herein is a method for enhancing the reaction rate of a phospholipase used in an enzymatic degumming method, such that the enzyme reaction has a duration of less than about one hour.

In yet another aspect, provided herein is a method for degumming an oil composition in which both hydratable and non-hydratable phospholipids can be treated in a single process, wherein an enzyme reaction is completed in less than about one hour.

In one embodiment, provided herein is a method for hydrolyzing, breaking up or disrupting a phospholipid-comprising composition comprising:
  (A) (a) providing a phospholipase polypeptide; (b) providing a composition comprising a phospholipid; and (c) contacting the polypeptide of step (a) with the composition of step (b) under conditions wherein the phospholipase hydrolyzes, breaks up or disrupts the phospholipid-comprising composition;
  (B) the method of (A), wherein the composition comprises a phospholipid-comprising lipid bilayer or membrane; or
  (C) the method of any of (A) or (B), wherein the composition comprises a plant cell, a bacterial cell, a yeast cell, an insect cell, or an animal cell.

In one embodiment, provided herein is a method for liquefying or removing a phospholipid-comprising composition comprising:
  (a) providing a phospholipase polypeptide;
  (b) providing a composition comprising a phospholipid; and
  (c) contacting the polypeptide of step (a) with the composition of step (b) under conditions wherein the phospholipase removes or liquefies the phospholipid-comprising composition.

In one embodiment, provided herein is a method for purification of a phytosterol or a triterpene comprising:
  AI) (AIa) providing a composition comprising a phospholipase polypeptide;
  (AIb) providing a composition comprising a phytosterol or a triterpene; and
  (AIc) contacting the polypeptide of step (a) with the composition of step (b) under conditions wherein the polypeptide can catalyze the hydrolysis of a phospholipid in the composition;
  (BI) the method of (AI), wherein the phytosterol or a triterpene comprises a plant sterol;
  (CI) the method of (BI), wherein the plant sterol is derived from a vegetable oil;
  (DI) the method of (CI), wherein the vegetable oil comprises a coconut oil, canola oil, cocoa butter oil, corn oil, cottonseed oil, linseed oil, olive oil, palm oil, peanut oil, oil derived from a rice bran, safflower oil, sesame oil, soybean oil or a sunflower oil;
  (EI) the method of any of (AI) to (DI), further comprising use of nonpolar solvents to quantitatively extract free phytosterols and phytosteryl fatty-acid esters; or
  (FI) the method of (EI), wherein the phytosterol or a triterpene comprises a☐ β-sitosterol, a campesterol, a stigmasterol, a stigmastanol, a β-sitostanol, a sitostanol, a desmosterol, a chalinasterol, a poriferasterol, a clionasterol or a brassicasterol.

In one embodiment, provided herein is a method for refining an oil or a fat comprising:
  (A1) (A1a) providing a composition comprising a phospholipase polypeptide;
  (A1b) providing a composition comprising an oil or a fat comprising a phospholipid; and
  (A1c) contacting the polypeptide of step (A1a) with the composition of step (A1b) under conditions wherein the polypeptide can catalyze the hydrolysis of a phospholipid in the composition;
  (B1) the method of (A1), wherein the polypeptide is in a water solution that is added to the composition;
  (C1) the method of (B1), wherein the water level is between about 0.5 to 5%;
  (D1) the method of any of (A1) to (C1), wherein the process time is less than about 2 hours;
  (E1) the method of any of (A1) to (C1), wherein the process time is less than about 60 minutes;
  (F1) the method of any of (A1) to (C1), wherein the process time is less than about 30 minutes, less than about 15 minutes, or less than about 5 minutes;
  (G1) the method of any of (A1) to (F1), wherein the hydrolysis conditions comprise a temperature of between about 25° C. to 70° C.;
  (H1) the method of any of (A1) to (G1), wherein the hydrolysis conditions comprise use of caustics;
  (I1) the method of any of (A1) to (H1), wherein the hydrolysis conditions comprise a pH of between about pH 3 and pH 10;
  (J1) the method of any of (A1) to (I1), wherein the hydrolysis conditions comprise addition of emulsifiers and/or mixing after the contacting of step (A1)(A1c);
  (K1) the method of any of (A1) to (J1), comprising addition of an emulsion-breaker and/or heat or cooling to promote separation of an aqueous phase;

(L1) the method of any of (A1) to (K1), comprising degumming before the contacting step to collect lecithin by centrifugation and then adding a PLC, a PLC and/or a PLA to remove non-hydratable phospholipids;

(M1) the method of any of (A1) to (L1), comprising water degumming of crude oil to less than 10 ppm phosphorus for edible oils and subsequent physical refining to less than about 50 ppm phosphorus for biodiesel oils; or (N1) the method of any of (A1) to (M1), comprising addition of acid to promote hydration of non-hydratable phospholipids.

In one embodiment, provided herein is a method for degumming an oil or a fat comprising
- (a1) providing a composition comprising a phospholipase polypeptide;
- (b1) providing a composition comprising an phospholipid-containing fat or oil; and
- (c1) contacting the polypeptide of step (a1) and the composition of step (b1) under conditions wherein the polypeptide can catalyze the hydrolysis of a phospholipid in the composition.

In one embodiment, provided herein is a method for physical refining of a phospholipid-containing composition comprising:
- (A-1) (A-1a) providing a composition comprising a phospholipase polypeptide;
  - (A-1b) providing a composition comprising a phospholipid; and
  - (A-1c) contacting the polypeptide of step (A-1a) with the composition of step (A-1b) before, during or after the physical refining;
- (B-1) the method of (A-1), wherein the polypeptide is added before physical refining and the composition comprising the phospholipid comprises a plant and the polypeptide is expressed transgenically in the plant, the polypeptide is added during crushing of a seed or other plant part, or, the polypeptide is added following crushing or prior to refining;
- (C-1) the method of (A-1), wherein the polypeptide is added during the physical refining;
- (D-1) the method of (A-1), wherein the polypeptide is added after physical refining: in an intense mixer or retention mixer prior to separation; following a heating step; in a centrifuge; in a soapstock; in a washwater; or, during a bleaching or a deodorizing step; or
- (E-1) the method of any of (A-1) to (D-1), further comprising adding a phospholipase A (PLA), a phospholipase B (PLB), phospholipase C (PLC), phospholipase D (PLD), or a phosphatase enzyme, or any combination thereof.

In one embodiment, provided herein is a method for caustic refining of a phospholipid-containing composition comprising:
- (A1) (A1a) providing a composition comprising a polypeptide having a phospholipase activity;
  - (A1b) providing a composition comprising a phospholipid; and
  - (A1c) contacting the polypeptide of step (A1a) with the composition of step (A1b) before, during or after the caustic refining;
- (B1) the method of (A1), wherein the polypeptide is added before addition of acid or caustic;
- (C1) the method of any of (A1) to (B1), wherein the polypeptide is added during caustic refining and varying levels of acid and caustic are added depending on levels of phosphorus and levels of free fatty acids; or
- (D1) the method of any of (A1) to (B1), wherein the polypeptide is added after caustic refining: in an intense mixer or retention mixer prior to separation; following a heating step; in a centrifuge; in a soapstock; in a washwater; or, during bleaching or deodorizing steps;
- (E1) the method of any of (A1) to (D1), wherein caustic refining conditions are generated by addition of a concentrated solution of caustic, or wherein caustic refining conditions comprise use of a concentrated solution of caustic more concentrated than the industrial standard of 11%, or wherein caustic refining conditions comprise use of a concentrated solution of caustic that is between about 12% and 50% concentrated;
- (F1) the method of any of (A1) to (E1), wherein the composition comprising the phospholipid comprises a plant;
- (G1) the method of any of (F1), wherein the polypeptide is expressed transgenically in the plant;
- (H1) the method of any of (A1) to (G1), wherein the polypeptide is added during crushing of a seed or other plant part, or, the polypeptide is added following crushing or prior to refining; or
- (I1) the method of any of (A1) to (H1), comprising a process as set forth in FIG. 10; or the process as set forth in FIG. 10, wherein sufficient acid is added to promote lowering of the calcium and magnesium metal content.

In one embodiment, provided herein is a method for deacylating a 2' or a 3' fatty acid chain from a lipid A comprising contacting the lipid A with a phospholipase polypeptide.

In one embodiment, provided herein is a process for reducing gum mass and increasing neutral oil (triglyceride) gain through reduced oil entrapment comprising:
- (A1) (A1a) providing a composition comprising a phospholipase polypeptide;
  - (A1b) providing a composition comprising an phospholipid-containing fat or oil; and
  - (A1c) contacting the polypeptide of step (A1a) and the composition of step (A1b) under conditions wherein the polypeptide can catalyze the hydrolysis of a phospholipid in the composition for a time sufficient to reduce gum mass and increase neutral oils;
- (B1) the protein preparation of (A1), wherein the protein preparation comprises a formulation comprising a non-aqueous liquid composition, a cast solid, a powder, a lyophilized powder, a granular form, a particulate form, a compressed tablet, a pellet, a pill, a gel form, a hydrogel, a paste, an aerosol, a spray, a lotion, a slurry formulation, an aqueous/oil emulsion, a cream, a capsule, a vesicle, or a micellar suspension; or,
- (C1) the method of (A1) or (B1), comprising use of high shear mixing of the composition, followed by no or low shear mixing with the at least one polypeptide of the invention having a phospholipase activity to allow adequate contacting of the phospholipid substrate with the phospholipase.

In one embodiment, provided herein is an oil or fat produced by the methods provided herein.

The enzymes for use in the methods provided herein include enzymes having phospholipase activity. The phospholipase activity comprises, for example, a phospholipase C (PLC) activity, a phospholipase A (PLA) activity, including a phospholipase A1 or phospholipase A2 activity, a phospholipase B (PLB) activity, including a phospholipase B1 or phospholipase B2 activity, a phospholipase D (PLD) activity, including a phospholipase D1 or a phospholipase D2 activity. In one embodiment, the enzymes for use herein comprise polypeptides having a phosphatidylinositol-specific phospholipase C (PI-PLC) or equivalent enzyme activity, and/or another phospholipase activity, including a phospholipase A, B, C, D, patatin, phosphatidic acid phosphatases (PAP) and/or lipid acyl hydrolase (LAH) or equivalent enzyme activity.

In certain embodiments, the enzyme for use in the methods provided herein is selected from a phospholipase A, phospholipase C, phosphatidyl-inositol specific phospholipase C, or a combination thereof. In certain embodiments, the enzyme for use in the methods provided herein is selected from a phospholipase C, phosphatidyl-inositol specific phospholipase C, or a combination thereof. In certain embodiments, the enzyme for use in the methods provided herein is phosphatidyl-inositol specific phospholipase C enzyme as described elsewhere herein. In certain embodiments, the enzyme for use in the methods provided herein is selected from phospholipase C, and an enzyme comprising SEQ ID NO:8. In certain embodiments, the enzyme for use in the methods provided herein is an enzyme comprising SEQ ID NO: 8.

In another embodiment, provided herein is a method for obtaining a phospholipid from an edible oil. In certain embodiment, the phospholipids obtained by the methods provided herein include a variety of phospholipids, including, but not limited to phosphatidylcholine (PC), phosphatidylethanolamine (PE), phosphatidylserine (PS), phosphatidylinositol (PI), phosphatidic acid (PA), lysophosphatidylcholine (LPC), lysophosphatidylethanolamine (LPE), lysophosphatidylserine (LPS), lysophosphatidylinositol (LPI), lysophosphatidic acid (LPA), choline (C), ethanolamine (E), serine (S), and inositol (I).

In another embodiment, provided herein is a method for obtaining choline (C), ethanolamine (E), serine (S), or inositol (I) from an edible oil.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of embodiments of the invention and are not meant to limit the scope of the invention as encompassed by the claims.

FIG. 10 illustrates the weight-fraction of individual phospholipid (PL) species phosphatidic acid (PA), phosphatidylethanolamine (PE), phosphatidylinositol (PI), phosphatidylcholine (PC) relative to the total PL remaining after treatment with the mutant phospholipases of the invention.

Like reference symbols in the various drawings indicate like elements.

DETAILED DESCRIPTION OF THE INVENTION

Figure 1:
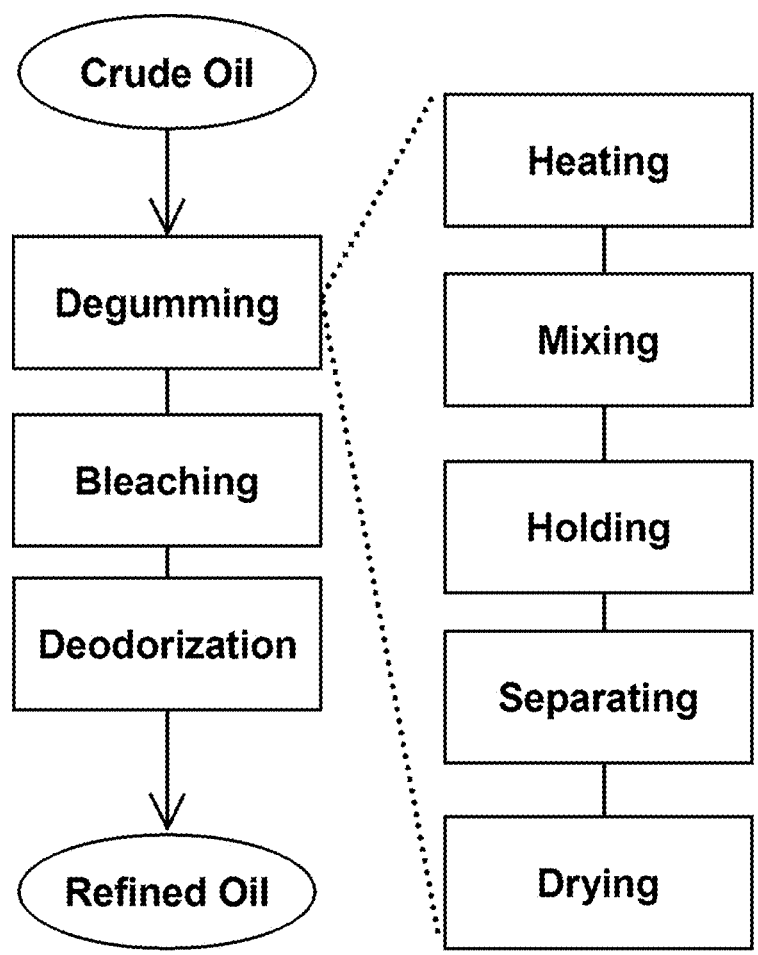
FIG. 1 schematically illustrates an exemplary vegetable oil refining process using the phospholipases of the invention.

The present invention provides polypeptides having a phosphatidylinositol-specific phospholipase C (PI-PLC) or equivalent enzyme activity, and/or another phospholipase activity, including a phospholipase A, B, C, D, patatin, phosphatidic acid phosphatases (PAP) and/or lipid acyl hydrolase (LAH) or equivalent enzyme activity, polynucleotides encoding them, antibodies that bind specifically to them, and methods for making and using them.

In one embodiment, the phosphatidylinositol-specific phospholipase C (PI-PLC) enzyme activity of polypeptides of this invention comprise:

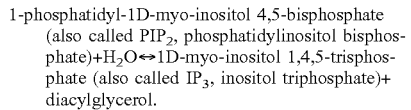

1-phosphatidyl-1D-myo-inositol 4,5-bisphosphate (also called $PIP_2$, phosphatidylinositol bisphosphate)+$H_2O$↔1D-myo-inositol 1,4,5-trisphosphate (also called $IP_3$, inositol triphosphate)+diacylglycerol.

In alternative embodiments, enzymes of the invention can efficiently cleave glycerolphosphate ester linkage in oils, such as vegetable oils, e.g., oilseed phospholipids, to generate a water extractable phosphorylated base and a diglyceride.

In alternative embodiments, phospholipases of the invention can have a lipid acyl hydrolase (LAH) activity; or can cleave glycerolphosphate ester linkages in phosphatidylcholine (PC), phosphatidylethanolamine (PE), phosphatidylserine (PS), phosphatidylinositol (PI), phosphatidic acid, and/or sphingomyelin, or a combination of these activities. For example, in one aspect a phospholipase of the invention is specific for one or more specific substrates, e.g., an enzyme of the invention can have a specificity of action for PE and PC; PE an PI; PE and PS; PS and PC; PS and PI; PI and PC; PS, PI and PC; PE, PI and PC; PC, PE and PS; PE, PS and PI; or, PE, PS, PI and PC.

In alternative embodiments, a phospholipase of the invention (e.g., a phosphatidylinositol-specific phospholipase C (PI-PLC) enzyme or equivalent activity) can be used for enzymatic degumming of oils, e.g. crude oils, because the phosphate moiety is soluble in water and easy to remove. The diglyceride product will remain in the oil and therefore will reduce losses. The PLCs of the invention can be used in addition to or in place of PLA1s and PLA2s in commercial oil degumming, such as in the ENZYMAX® process, where phospholipids are hydrolyzed by PLA1 and PLA2.

In alternative embodiments, the phospholipases of the invention are active at a high and/or at a low temperature, or, over a wide range of temperature, e.g., they can be active in the temperatures ranging between 20° C. to 90° C., between 30° C. to 80° C., or between 40° C. to 70° C. The invention also provides phospholipases of the invention having activity at alkaline pHs or at acidic pHs, e.g., low water acidity. In alternative aspects, the phospholipases of the invention can have activity in acidic pHs as low as pH 6.5, pH 6.0, pH 5.5, pH 5.0, pH 4.5, pH 4.0, pH 3.5, pH 3.0, pH 2.5, pH 2.0 or more acidic (i.e., <pH 2.0). In alternative aspects, the phospholipases of the invention can have activity in alkaline pHs as high as pH 7.5, pH 8.0, pH 8.5, pH 9.0, pH 9.5, pH 10.0 or more alkaline (i.e., >pH 10.0). In one aspect, the phospholipases of the invention are active in the temperature range of between about 40° C. to about 70° C., 75° C., or 80° C., or more, under conditions of low water activity (low water content).

The invention also provides methods for making PLCs and/or modifying the activity of exemplary phospholipases of the invention to generate enzymes with alternative desirable properties, e.g., phosphatidylinositol-specific phospholipase C (PI-PLC) enzyme activity having alternative substrates, or activities under various environmental conditions, e.g., of varying temperatures, pHs and the like. For example, phospholipases generated by the methods of the invention can have altered substrate specificities, substrate binding specificities, substrate cleavage patterns, thermal stability, pH/activity profile, pH/stability profile (such as increased stability at low, e.g. pH<6 or pH<5, or high, e.g. pH>9, pH values), stability towards oxidation, $Ca^{2+}$ dependency, specific activity and the like. The invention provides for altering any property of interest. For instance, the alteration may result in a variant which, as compared to a parent phospholipase, has altered pH and temperature activity profile.

In alternative embodiments, the phospholipases of the invention are used in various oil processing steps, such as in oil extraction, e.g., in the removal of "phospholipid gums" in a process called "oil degumming," as described herein. The invention provides compositions (e.g., comprising enzymes of the invention) and processes for the treatment of oils, e.g. crude oils, and for production of oils, e.g. vegetable oils, from various sources, such as oil from rice bran, soybeans, rapeseed, peanut, sesame, sunflower and corn. The phospholipase enzymes of the invention can be used in place of PLA, e.g., phospholipase A2, in any vegetable oil processing step.

In certain embodiments, suitable enzymes for use in the methods provided herein include, one or more phospholipase A (PLA) enzymes, phospholipase C (PLC), Phosphatidyl-Inositol specific phospholipase C (PI-PLC) enzymes, or a combination thereof. The PLA enzymes include phospholipase A1 (PLA1) and/or phospholipase A2 (PLA2).

As used herein, "crude oil" refers to (also called a non-degummed oil) a pressed or extracted oil or a mixture thereof from, e.g. vegetable sources, including but not limited to acai oil, almond oil, babassu oil, blackcurrent seed oil, borage seed oil, canola oil, cashew oil, castor oil, coconut oil, coriander oil, corn oil, cottonseed oil, crambe oil, flax seed oil, grape seed oil, hazelnut oil, hempseed oil, jatropha oil, jojoba oil, linseed oil, macadamia nut oil, mango kernel oil, meadowfoam oil, mustard oil, neat's foot oil, olive oil, palm oil, palm kernel oil, palm olein, peanut oil, pecan oil, pine nut oil, pistachio oil, poppy seed oil, rapeseed oil, rice bran oil, safflower oil, sasanqua oil, sesame oil, shea butter, soybean oil, sunflower seed oil, tall oil, tsubaki oil walnut oil, varieties of "natural" oils having altered fatty acid compositions via Genetically Modified Organisms (GMO) or traditional "breading" such as high oleic, low linolenic, or low saturated oils (high oleic canola oil, low linolenic soybean oil or high stearic sunflower Oils). Further exemplary oils suitable for use in the methods provided herein are described elsewhere herein. In certain embodiment, the total phosphatide content in a crude oil may vary from 0.5-3% w/w corresponding to a phosphorus content in the range of 200-1200 ppm or 250-1200 ppm.

As used herein, "degummed oil" refers to an oil obtained after removal of NHPs, hydratable phospholipids, and lecithins (known collectively as "gums") from the oil to produce a degummed oil or fat product that can be used for food production and/or non-food applications. Various degumming process are known in the art and are described above. In certain embodiments, the degummed oil has the phospholipids content of less than about 200 ppm phosphorus, less than about 150 ppm phosphorus, less than about 100 ppm phosphorus, less than about 50 ppm phosphorus, less than about 40 ppm phosphorus, less than about 30 ppm phosphorus, less than about 20 ppm phosphorus, less than about 15 ppm phosphorus, less than about 10 ppm phosphorus, less than about 7 ppm phosphorus, less than about 5 ppm phosphorus, less than about 3 ppm phosphorus or less than about 1 ppm phosphorus.

As used herein, the term "non hydratable phospholipids" or "NHPs" refers to phosphatidic acid and the salts of phosphatidic acid, for example, calcium, magnesium and iron salts of phosphatidic acid; and calcium, magnesium and iron salts of -ethanolamine.

As used herein, "water-degummed oil" refers to an oil obtained after water degumming process. In certain embodiments, water-degummed oil is obtained by mixing 1-3% w/w of hot water with warm (60-90° C.) crude oil for 30-60 minutes. In certain embodiments, the water-degumming step removes the phosphatides and mucilaginous gums which become insoluble in the oil when hydrated. The hydrated phosphatides and gums can be separated from the oil by settling, filtering or centrifuging.

Generating and Manipulating Nucleic Acids

The invention provides isolated, synthetic and recombinant nucleic acids (e.g., the exemplary SEQ ID NO:5 and nucleic acids encoding SEQ ID NO:6 comprising (and having) one or more amino acid residue changes (e.g., mutations) as set forth in Tables 12 to 15, including expression cassettes such as expression vectors, encoding the polypeptides and phospholipases of the invention. The invention also includes methods for discovering new phospholipase sequences using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

In alternative embodiments, gene sequences of the invention, or genes used to practice the invention, comprise the segment of DNA involved in producing a polypeptide chain, including, inter alia, regions preceding and following the coding region, such as leader and trailer, promoters and enhancers, as well as, where applicable, intervening sequences (introns) between individual coding segments (exons).

In alternative embodiments, nucleic acids or nucleic acid sequences of the invention, or used to practice the invention, can comprise an oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., double stranded iRNAs, e.g., iRNPs). The term encompasses nucleic acids, i.e., oligonucleotides, containing known analogues of natural nucleotides. In alternative embodiments, nucleic acids or nucleic acid sequences of the invention, or used to practice the invention, also encompass nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lad, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the E. coli lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Cassettes, Vectors and Cloning Vehicles

The invention provides expression vectors and cloning vehicles comprising nucleic acids of the invention, e.g., sequences encoding the phospholipases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as Bacillus, Aspergillus and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen, San Diego, Calif.), pBluescript plasmids (Stratagene, San Diego, Calif.), pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

In alternative embodiments, the term "expression cassette" comprises a nucleotide sequence which is capable of affecting expression of a structural gene (i.e., a protein coding sequence, such as a phospholipase of the invention) in a host compatible with such sequences. Expression cassettes can include at least a promoter operably linked with the polypeptide coding sequence; and, optionally, with other sequences, e.g., transcription termination signals. Additional factors necessary or helpful in effecting expression may also be used, e.g., enhancers. In alternative embodiments, "operably linked" refers to linkage of a promoter upstream from a DNA sequence such that the promoter mediates transcription of the DNA sequence. In alternative embodiments, expression cassettes include plasmids, expression vectors, recombinant viruses, any form of recombinant "naked DNA" vector, and the like.

In alternative embodiments, vectors of this invention comprise a nucleic acid which can infect, transfect, transiently or permanently transduce a cell. In alternative embodiments, a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors of this invention include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

In alternative embodiments, the invention provides plasmids, which can be designated by a lower case "p" preceded and/or followed by capital letters and/or numbers. In alternative embodiments, a "starting" plasmid is either commercially available, publicly available on an unrestricted basis, or can be constructed from available plasmids in accord with published procedures. In alternative embodiments, equivalent plasmids to those described herein are known in the art and will be apparent to the ordinarily skilled artisan.

In alternative embodiments, an expression vector may comprise a promoter, a ribosome-binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic acid sequence of the invention, e.g., a sequence encoding a phospholipase of the invention, a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Enzymes of the invention can be expressed in any host cell, e.g., any bacterial cell, any yeast cell, e.g., *Pichia pastoris, Saccharomyces cerevisiae* or *Schizosaccharomyces pombe*. Exemplary bacterial cells include any species within the genera *Escherichia, Bacillus, Streptomyces, Salmonella, Pseudomonas* and *Staphylococcus*, including, e.g., *Escherichia coli, Lactococcus lactis, Bacillus subtilis, Bacillus cereus, Salmonella typhimurium, Pseudomonas fluorescens*. Exemplary fungal cells include any species of *Aspergillus*. Exemplary yeast cells include any species of *Pichia, Saccharomyces, Schizosaccharomyces*, or *Schwanniomyces*, including *Pichia pastoris, Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

An exemplary PI-PLC enzyme (having a sequence as set forth in SEQ ID NO:6 comprising (and having) one or more amino acid residue changes (e.g., mutations) as set forth in Tables 12 to 15) has been over-expressed in active form in a variety of host systems including gram negative bacteria, such as *E. coli*, gram positive bacteria, such as any *Bacillus* sp. (e.g., *Bacillus subtilis, Bacillus cereus*), yeast host cells (including, e.g., *Pichia pastoris, Saccharomyces* sp., such as *S. cerevisiae* and *S. pombe*) and *Lactococcus lactis*, or mammalian, fungi, plant or insect cells. The active enzyme is expressed from a variety of constructs in each host system. These nucleic acid expression constructs can comprise nucleotides encoding the full-length open reading frame (composed of the signal sequence, the pro-sequence, and the mature protein coding sequence) or they can comprise a subset of these genetic elements either alone or in combination with heterologous genetic elements that serve as the signal sequence and/or the pro-sequence for the mature open reading frame. Each of these systems can serve as a commercial production host for the expression of PLC for use in the previously described enzymatic oil degumming processes.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides with a phospholipase activity. In one aspect, the primer pairs are capable of amplifying nucleic acid sequences of the invention. One of skill in the art can design amplification primer sequence pairs for any part of or the full length of these sequences.

The invention provides an amplification primer sequence pair for amplifying a nucleic acid encoding a polypeptide having a phospholipase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 12, 13, 14, 15, 16, 17, 18, 19, 20, 21, 22, 23, 24, or 25 consecutive bases of the sequence.

The invention provides amplification primer pairs, wherein the primer pair comprises a first member having a sequence as set forth by about the first (the 5') 12, 13, 14, 15, 16, 17, 18, 19, 20, 21, 22, 23, 24, or 25 residues of a nucleic acid of the invention, and a second member having a sequence as set forth by about the first (the 5') 12, 13, 14, 15, 16, 17, 18, 19, 20, 21, 22, 23, 24, or 25 residues of the complementary strand of the first member. The invention provides phospholipases generated by amplification, e.g., polymerase chain reaction (PCR), using an amplification primer pair of the invention. The invention provides methods of making a phospholipase by amplification, e.g., polymerase chain reaction (PCR), using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides isolated and recombinant nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention (e.g., SEQ ID NO:5 and encoding one or more mutations as set forth in Tables 12 to 15, as discussed in Example 3, or an enzymatically active fragment thereof, and nucleic acids encoding SEQ ID NO:6 and encoding one or more mutations as set forth in Tables 12 to 15, as discussed in Example 3, or an enzymatically active fragment thereof) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters. In alternative embodiments, the sequence identify can be over a region of at least about 5, 10, 20, 30, 40, 50, 100, 150, 200, 250, 300, 350, 400 consecutive residues, or the full length of the nucleic acid or polypeptide. The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous residues. For example, in alternative aspects of the invention, contiguous residues ranging anywhere from 20 to the full length of an exemplary sequence of the invention are compared to a reference sequence of the same number of contiguous positions after the two sequences are optimally aligned. If the reference sequence has the requisite sequence identity to an exemplary sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of the invention, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used. default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention, as discussed above, include:

"Filter for low complexity: ON
> Word Size: 3
> Matrix: Blosum62
> Gap Costs: Existence:11
>    Extension:1"

Other default settings are: filter for low complexity OFF, word size of 3 for protein, BLOSUM62 matrix, gap existence penalty of -11 and a gap extension penalty of -1.

An exemplary NCBI BLAST 2.2.2 program setting is set forth in Example 1, below. Note that the "-W" option defaults to 0. This means that, if not set, the word size defaults to 3 for proteins and 11 for nucleotides.

Hybridization of Nucleic Acids

The invention provides isolated, synthetic or recombinant nucleic acids that hybridize under stringent conditions to an exemplary sequence of the invention, e.g., a sequence as set forth in SEQ ID NO:5 and having one or more mutations as set forth in Tables 12 to 15, as described in Example 3, below, or a nucleic acid that encodes a polypeptide comprising a sequence as set forth in SEQ ID NO:6 and encoding one or more mutations as set forth in Tables 12 to 15, or an enzymatically active fragment thereof.

The stringent conditions can be highly stringent conditions, medium stringent conditions, low stringent conditions, including the high and reduced stringency conditions described herein. In alternative embodiments, nucleic acids of the invention as defined by their ability to hybridize under stringent conditions can be between about five residues and the full length of the molecule, e.g., an exemplary nucleic acid of the invention. For example, they can be at least 5, 10, 15, 20, 25, 30, 35, 40, 50, 55, 60, 65, 70, 75, 80, 90, 100, 150, 200, 250, 300, 350, 400 or more residues in length. Nucleic acids shorter than full length are also included. These nucleic acids are useful as, e.g., hybridization probes, labeling probes, PCR oligonucleotide probes, iRNA (single or double stranded), antisense or sequences encoding antibody binding peptides (epitopes), motifs, active sites, binding domains, regulatory domains and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 ug/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions can be used to practice the invention and are well known in the art. Hybridization conditions are discussed further, below.

Oligonucleotides Probes and Methods for Using them

The invention also provides nucleic acid probes for identifying and/or isolating a nucleic acid encoding a polypeptide having a phospholipase activity. In one aspect, the probe comprises or consists of a nucleic acid of the invention, e.g., a nucleic acid having a sequence as set forth in SEQ ID NO:5 and having one or more base changes (mutations) as set forth in Tables 12 to 15, as described in Example 3, below, or a nucleic acid that encodes a polypeptide comprising a sequence as set forth in SEQ ID NO:6 and encoding one or more amino acid residue changes (mutations) as set forth in Tables 12 to 15, or an enzymatically active fragment thereof. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 50, 55, 60, 65, 70, 75, 80, 85, 90, 95, 100, or 150, or more, or about 10 to 50, about 20 to 60 about 30 to 70, consecutive bases of a nucleic acid sequence of the invention.

The probes identify a nucleic acid by binding or hybridization. In alternative embodiments, hybridization comprises the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

The probes can be used in arrays of the invention, see discussion below, including, e.g., capillary arrays. The probes of the invention can also be used to isolate and/or identify other phospholipase-encoding nucleic acids or polypeptides having a phospholipase activity.

The probes of the invention can be used to determine whether a biological sample, such as a soil sample, contains an organism having a nucleic acid sequence of the invention. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. In alternative embodiments, a nucleic acid is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2 \times 10^7$ cpm (specific activity 4 to $9 \times 10^8$ cpm/ug) of $^{32}P$ end-labeled oligonucleotide probe can be added to the solution. In alternative embodiments, after about 12 to 16 hours of incubation, the membrane is washed for 30 minutes at room temperature (RT) in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligonucleotide probe. The membrane can be exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+ 0.41(fraction G+C)−(600/N) where N is the length of the probe. If the hybridization is carried out in a solution containing formamide, the melting temperature may be calculated using the equation: Tm=81.5+16.6(log [Na+])+ 0.41(fraction G+C)−(0.63% formamide)−(600/N) where N is the length of the probe. Prehybridization may be carried out in 6×SSC, 5×Denhardt's reagent, 0.5% SDS, 100 μg/ml denatured fragmented salmon sperm DNA or 6×SSC, 5×Denhardt's reagent, 0.5% SDS, 100 μg/ml denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes that can be used to practice this invention are: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to practice the invention, e.g., to wash filters or arrays. One of skill in the art would know that there are numerous recipes for different stringency washes, all of which can be used to practice the invention.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

In alternative embodiments, the hybridization is carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. In alternative embodiments, "moderate" conditions are above 25% formamide and "low" conditions are below 25% formamide. In alternative embodiments, "moderate" hybridization conditions is when the above hybridization is conducted at 30% formamide. In alternative embodiments, "low stringency" hybridization conditions is when the above hybridization is conducted at 10% formamide.

These probes and methods of the invention can be used to isolate nucleic acids having a sequence with at least about 99%, at least 98%, at least 97%, at least 96%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, or 500 consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to nucleic acids of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Inhibiting Expression of Phospholipases

The invention further provides nucleic acids complementary to (e.g., antisense sequences to) the nucleic acids of the invention, e.g., phospholipase-encoding nucleic acids. Antisense sequences are capable of inhibiting the transport, splicing or transcription of phospholipase-encoding genes. The inhibition can be effected through the targeting of genomic DNA or messenger RNA (mRNA, a transcript). The transcription or function of targeted nucleic acid can be inhibited, for example, by hybridization and/or cleavage. One particularly useful set of inhibitors provided by the present invention includes oligonucleotides which are able to either bind phospholipase gene or message, in either case preventing or inhibiting the production or function of phospholipase enzyme. The association can be though sequence specific hybridization. Another useful class of inhibitors includes oligonucleotides which cause inactivation or cleavage of phospholipase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Inhibition of phospholipase expression can have a variety of industrial applications. For example, inhibition of phospholipase expression can slow or prevent spoilage. Spoilage can occur when lipids or polypeptides, e.g., structural lipids or polypeptides, are enzymatically degraded. This can lead to the deterioration, or rot, of fruits and vegetables. In one aspect, use of compositions of the invention that inhibit the expression and/or activity of phospholipase, e.g., antibodies, antisense oligonucleotides, ribozymes and RNAi, are used to slow or prevent spoilage. Thus, in one aspect, the invention provides methods and compositions comprising application onto a plant or plant product (e.g., a fruit, seed, root, leaf, etc.) antibodies, antisense oligonucleotides, ribozymes and RNAi of the invention to slow or prevent spoilage. These compositions also can be expressed by the plant (e.g., a transgenic plant) or another organism (e.g., a bacterium or other microorganism transformed with a phospholipase gene of the invention).

The compositions of the invention for the inhibition of phospholipase expression (e.g., antisense, iRNA, ribozymes, antibodies) can be used as pharmaceutical compositions.

Antisense Oligonucleotides

The invention provides antisense oligonucleotides capable of binding phospholipase message which can inhibit phospholipase activity by targeting mRNA. Strategies for designing antisense oligonucleotides are well described in the scientific and patent literature, and the skilled artisan can design such phospholipase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl. Pharmacol. 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense phospholipase sequences of the invention (see, e.g., Gold (1995) J. of Biol. Chem. 270: 13581-13584).

Inhibitory Ribozymes

The invention provides for with ribozymes capable of binding phospholipase message which can inhibit phospholipase enzyme activity by targeting mRNA. Strategies for designing ribozymes and selecting the phospholipase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a phospholipase sequence of the invention. The RNAi molecule comprises a double-stranded RNA (dsRNA) molecule. The RNAi can inhibit expression of a phospholipase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding a phospholipase enzyme. In alternative embodiment, the invention provides methods for modifying an enzyme of the invention, e.g., by mutation of its coding sequence by random or stochastic methods, or, non-stochastic, or "directed evolution," such as Gene Site Saturation Mutagenesis™ (GSSM), to alter the enzymes pH range of activity or range of optimal activity, temperature range of activity or range of optimal activity, specificity, activity (kinetics); the enzyme's use of glycosylation, phosphorylation or metals (e.g., Ca, Mg, Zn, Fe, Na), e.g., to impact pH/temperature stability. The invention provides methods for modifying an enzyme of the invention, e.g., by mutation of its coding sequence, e.g., by GSSM, to increase its resistance to protease activity. The invention provides methods for modifying an enzyme of the invention, e.g., by mutation of its coding sequence, e.g., by GSSM, to modify the enzyme's use of metal chelators specific for Ca, Mg, Na that would not chelate Zn. The invention provides methods for modifying an enzyme of the invention, e.g., by mutation of its coding sequence, e.g., by GSSM, that would have a desired combination of activities, e.g., PI, PA and PC/PE specific PLCs.

In one embodiment, "Gene Site Saturation Mutagenesis" (GSSM) or "GSSM" comprises a method that uses degenerate oligonucleotide primers to introduce point mutations into a polynucleotide, as described in detail, below. In one embodiment, "optimized directed evolution system" or "optimized directed evolution" comprises a method for reassembling fragments of related nucleic acid sequences, e.g., related genes, and explained in detail, below. In one embodiment, "synthetic ligation reassembly" or "SLR" comprises a method of ligating oligonucleotide fragments in a non-stochastic fashion, and explained in detail, below.

In alternative embodiments, the invention provides "variants" of exemplary nucleic acids and polypeptides of the invention, including e.g., SEQ ID NO:8, encoded e.g., by SEQ ID NO:7, SEQ ID NO:8 or SEQ ID NO:9. In alternative embodiments variants of polynucleotides or polypeptides of the invention are nucleic acids or polypeptides that have been modified at one or more base pairs, codons, introns, exons, or amino acid residues (respectively) yet still retain the biological activity of a phospholipase. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant phospholipases having activity at a pH or temperature, for example, that is different from a wild-type phospholipase, are included herein.

These methods can be repeated or used in various combinations to generate phospholipase enzymes having an altered or different activity or an altered or different stability from that of a phospholipase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods.

Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154: 350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols used in the methods of the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

See also U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., saturation mutagenesis (e.g., GSSM), synthetic ligation reassembly (SLR), or a combination thereof are used to modify the nucleic acids of the invention to generate phospholipases with new or altered properties (e.g., activity under highly acidic or alkaline conditions, high temperatures, and the like). Polypeptides encoded by the modified nucleic acids can be screened for an activity before testing for a phospholipase or other activity. Any testing modality or protocol can be used, e.g., using a capillary array platform. See, e.g., U.S. Pat. Nos. 6,280,926; 5,939,250.

Saturation Mutagenesis, or, GSSM

In one aspect of the invention, non-stochastic gene modification, a "directed evolution process," is used to generate phospholipases with new or altered properties. Variations of this method have been termed "gene site mutagenesis," "site-saturation mutagenesis," "Gene Site Saturation Mutagenesis" or simply "GSSM." It can be used in combination with other mutagenization processes. See, e.g., U.S. Pat. Nos. 6,171,820; 6,238,884. In one aspect, GSSM comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

In one aspect, codon primers containing a degenerate N,N,G/T sequence are used to introduce point mutations into a polynucleotide, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position×100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., phospholipase) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased phospholipase activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process (es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate phospholipases with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled.

In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another embodiment, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate phospholipases with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found in U.S. Ser. No. 09/332,835. The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a 1/3 chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding an polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a 1/3 chance (assuming 3 parents) that a oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. One can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events.

Determining Crossover Events

Embodiments of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB® (The Mathworks, Natick, Mass.) a programming language and development environment for technical computing.

Iterative Processes

In practicing the invention, these processes can be iteratively repeated. For example a nucleic acid (or, the nucleic acid) responsible for an altered phospholipase phenotype is identified, re-isolated, again modified, re-tested for activity. This process can be iteratively repeated until a desired phenotype is engineered. For example, an entire biochemical anabolic or catabolic pathway can be engineered into a cell, including phospholipase activity.

Similarly, if it is determined that a particular oligonucleotide has no affect at all on the desired trait (e.g., a new phospholipase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, phospholipase enzymes, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides methods of making sequence variants of the nucleic acid and phospholipase sequences of the invention or isolating phospholipase enzyme, e.g., phospholipase, sequence variants using the nucleic acids and polypeptides of the invention. In one aspect, the invention provides for variants of a phospholipase gene of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/µl in a solution of 0.2 mM of each dNTP, 2.2 mM MgCl$_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an E. coli strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some embodiments, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250.

The invention also provides variants of polypeptides of the invention comprising sequences in which one or more of the amino acid residues (e.g., of an exemplary polypeptide of the invention) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., a phospholipase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying phospholipase-encoding nucleic acids to modify codon usage. In one aspect, the invention provides methods for modifying codons in a nucleic acid encoding a phospholipase to increase or decrease its expression in a host cell. The invention also provides nucleic acids encoding a phospholipase modified to increase its expression in a host cell, phospholipase enzymes so modified, and methods of making the modified phospholipase enzymes. The method comprises identifying a "non-preferred" or a "less preferred" codon in phospholipase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as any *Bacillus* (e.g., *B. cereus*) or *Streptomyces, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding a phospholipase isolated from a bacterial cell are modified such that the nucleic acid is optimally expressed in a bacterial cell different from the bacteria from which the phospholipase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study phospholipase activity, or, as models to screen for modulators of phospholipase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express a phospholipase.

Transgenic Plants and Seeds

The invention provides transgenic plants and seeds comprising a nucleic acid, a polypeptide (e.g., a phospholipase), an expression cassette or vector or a transfected or transformed cell of the invention. The invention also provides plant products, e.g., oils, seeds, leaves, extracts and the like, comprising a nucleic acid and/or a polypeptide (e.g., a phospholipase) of the invention. The transgenic plant can be dicotyledonous (a dicot) or monocotyledonous (a monocot). The invention also provides methods of making and using these transgenic plants and seeds. The transgenic plant or plant cell expressing a polypeptide of the invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's phospholipase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on oil-seed containing plants, such as rice, soybeans, rapeseed, sunflower seeds, sesame and peanuts. Nucleic acids of the invention can be used to manipulate metabolic pathways of a plant in order to optimize or alter host's expression of phospholipase. The can change phospholipase activity in a plant. Alternatively, a phospholipase of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot $1/100$th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a phospholipase) of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, Poa), forage grass such as festuca, lolium, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea.*

In alternative embodiments, the nucleic acids of the invention are expressed in plants (e.g., as transgenic plants), such as oil-seed containing plants, e.g., rice, soybeans, rapeseed, sunflower seeds, sesame and peanuts. The nucleic acids of the invention can be expressed in plants which contain fiber cells, including, e.g., cotton, silk cotton tree (Kapok, *Ceiba pentandra*), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides for transgenic plants to be used for producing large amounts of the polypeptides (e.g., a phospholipase or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

The invention provides isolated, synthetic or recombinant polypeptides having a sequence identity (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:6 having one or more sequence changes (e.g., mutations) as set forth in Tables 12 to 15, as discussed in Example 3, below, or an enzymatically active fragment thereof As discussed above, the identity can be over the full length of the polypeptide, or, the identity can be over a subsequence thereof, e.g., a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides. In alternative embodiment, the invention provides polypeptides (peptides, fragments) ranging in size between about 5 and the full length of a polypeptide, e.g., an enzyme, such as a phospholipase, e.g., phospholipase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400 or more residues, e.g., contiguous residues of the exemplary phospholipases. Peptides of the invention can be useful as, e.g., labeling probes, antigens, toleragens, motifs, phospholipase active sites, binding domains, regulatory domains, and the like.

In one aspect, the invention provides polypeptides having sequences as set forth in SEQ ID NO:6 comprising (and having) one or more amino acid residue changes (e.g., mutations) as set forth in Tables 12 to 15, and subsequences thereof, e.g., their active sites ("catalytic domains") having a phospholipase activity, e.g., a phospholipase C (PLC) activity, e.g., a PI-PLC activity. In one aspect, the polypeptide has a phospholipase activity but lacks neutral oil (triglyceride) hydrolysis activity. For example, in one aspect, the polypeptide has a phospholipase activity but lacks any activity that affects a neutral oil (triglyceride) fraction. In one aspect, the invention provides a degumming process comprising use of a polypeptide of the invention having a phospholipase activity, but not a lipase activity.

"Amino acid" or "amino acid sequence" as used herein refer to an oligopeptide, peptide, polypeptide, or protein sequence, or to a fragment, portion, or subunit of any of these, and to naturally occurring or synthetic molecules.

The terms "polypeptide" and "protein" as used herein, refer to amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a phospholipase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-di-isopropylcarbodiimide (DIC). Linking groups that can be an alternative to the traditional amide bond ("peptide bond") linkages include, e.g., ketomethylene (e.g., —C(═O)—CH2— for —C(═O)—NH—), aminomethylene (CH2-NH), ethylene, olefin (CH═CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxy-biphenylphenylalanine; D- or L-2-indole-(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N═C═N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form 0-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

Phospholipase Enzymes

The invention provides polypeptides having a phospholipase activity, nucleic acids encoding them, antibodies that bind them, peptides representing the enzyme's antigenic sites (epitopes) and active sites, regulatory and binding domains, and methods for making and using them. In one aspect, polypeptides of the invention have a phospholipase activity, or any combination of phospholipase activities, as described herein (e.g., a phosphatidylinositol-specific phospholipase C (PI-PLC) enzyme activity, etc.). In alternative aspects, the phospholipases of the invention have activities that have been modified from those of the exemplary phospholipases described herein.

As used herein, the term "phospholipase" encompasses enzymes having any phospholipase activity, for example, cleaving a glycerolphosphate ester linkage (catalyzing hydrolysis of a glycerolphosphate ester linkage), e.g., in an oil, such as a crude oil or a vegetable oil. The phospholipase activity of the invention can generate a water extractable phosphorylated base and a diglyceride. The term "a phospholipase activity" hydrolysis of glycerolphosphate ester linkages at high temperatures, low temperatures, alkaline pHs and at acidic pHs, cleaving a glycerolphosphate ester to generate a water extractable phosphorylated base and a diglyceride, cutting ester bonds of glycerin and phosphoric acid in phospholipids, and other activities, such as the ability to bind to and hydrolyze a substrate, such as an oil, e.g. a crude oil or a vegetable oil, substrate also including plant and animal phosphatidylcholines, phosphatidylethanolamines, phosphatidylserines and sphingomyelins. The phospholipase activity can comprise a phospholipase C (PLC) activity; a PI-PLC activity, a phospholipase A (PLA) activity, such as a phospholipase A1 or phospholipase A2 activity; a phospholipase B (PLB) activity, such as a phospholipase B1 or phospholipase B2 activity, including lysophospholipase (LPL) activity and/or lysophospholipase-transacylase (LPTA) activity; a phospholipase D (PLD) activity, such as a phospholipase D1 or a phospholipase D2 activity; and/or a patatin activity or any combination thereof. The phospholipase activity can comprise hydrolysis of a glycoprotein, e.g., as a glycoprotein found in a potato tuber or any plant of the genus *Solanum*, e.g., *Solanum tuberosum*. In alternative embodiments, the phospholipase activity can comprise a patatin enzymatic activity, such as a patatin esterase activity (see, e.g., Jimenez (2002) Biotechnol. Prog. 18:635-640). In certain embodiments, the phospholipase activity can comprise a lipid acyl hydrolase (LAH) activity.

In alternative embodiments, the PLC phospholipases of the invention utilize (e.g., catalyze hydrolysis of) a variety of phospholipid substrates including phosphatidylcholine (PC), phosphatidylethanolamine (PE), phosphatidylserine (PS), phosphatidylinositol (PI), and/or phosphatidic acid (PA) or a combination thereof. In addition, these enzymes can have varying degrees of activity on the lysophospholipid forms of these phospholipids. In various aspects, PLC enzymes of the invention may show a preference for phosphatidylcholine and phosphatidylethanolamine as substrates.

In alternative embodiments, the phosphatidylinositol PLC phospholipases of the invention utilize a variety of phospholipid substrates including phosphatidylcholine, phosphatidylethanolamine, phosphatidylserine, phosphatidylinositol, and phosphatidic acid, or a combination thereof. In alternative embodiments, these enzymes can have varying degrees of activity on the lysophospholipid forms of these phospholipids. In various aspects, phosphatidylinositol PLC enzymes of the invention may show a preference for phosphatidylinositol as a substrate.

In alternative embodiments, the phospholipase activity can comprise being specific for one or more specific substrates, e.g., an enzyme of the invention can have a specificity of action for PE and PC; PE an PI; PE and PS; PS and PC; PS and PI; PI and PC; PS, PI and PC; PE, PI and PC; PC, PE and PS; PE, PS and PI; or, PE, PS, PI and PC, or any combination thereof.

In alternative embodiments, a phospholipase of the invention can have multifunctional activity, e.g., a combination of one or more of the enzyme activities described herein. For example, in one aspect, a polypeptide of the invention is enzymatically active, but lacks a lipase activity or lacks any enzymatic activity that affects a neutral oil (triglyceride) fraction. It may be desirable to use such a polypeptide in a particular process, e.g., in a degumming process where it is important that the neutral oil fraction not be harmed (diminished, degraded, e.g., hydrolyzed). Thus, in one aspect, the invention provides a degumming process comprising use of a polypeptide of the invention having a phospholipase activity, but not a lipase activity.

In alternative embodiments, polypeptides of the invention having patatin enzyme activity can utilize a variety of phospholipid substrates including phosphatidylcholine, phosphatidylethanolamine, phosphatidylserine, phosphatidylinositol, and phosphatidic acid, or a combination thereof. In addition, these enzymes can have varying degrees of activity on the lysophospholipid forms of these phospholipids. In various aspects, patatins of the invention are based on a conservation of amino acid sequence similarity. In various aspects, these enzymes display a diverse set of biochemical properties and may perform reactions characteristic of PLA1, PLA2, PLC, or PLD enzyme classes.

In alternative embodiments, polypeptides of the invention having PLD phospholipases of the invention can utilize a variety of phospholipid substrates including phosphatidylcholine, phosphatidylethanolamine, phosphatidylserine, phosphatidylinositol, and phosphatidic acid, or a combination thereof. In addition, these enzymes can have varying degrees of activity on the lysophospholipid forms of these phospholipids. In one aspect, these enzymes are useful for carrying out transesterification reactions to produce structured phospholipids.

In alternative embodiments, polypeptides of the invention have an activity comprising cleavage of a glycerolphosphate ester linkage, the ability to hydrolyze phosphate ester bonds, including patatin, lipid acyl hydrolase (LAH), phospholipase A, B, C and/or phospholipase D activity, or any combination thereof.

As used herein, 1 enzyme unit is the quantity of an enzyme needed to cause a reaction to process 1 micromole of substance per minute under specified conditions.

In alternative embodiments, the invention provides polypeptides with and without signal sequences, and the signal sequences themselves (e.g., isolated signal sequence peptides). The invention includes fragments or subsequences of enzymes of the invention, e.g., peptides or polypeptides comprising or consisting of catalytic domains ("active sites"), binding sites, regulatory domains, epitopes, signal sequences, prepro domains, and the like. The invention also includes immobilized phospholipases, anti-phospholipase antibodies and fragments thereof. The invention includes heterocomplexes, e.g., fusion proteins, heterodimers, etc., comprising the phospholipases of the invention. Determining peptides representing the enzyme's antigenic sites (epitopes), active sites, binding sites, signal sequences, and the like can be done by routine screening protocols.

These enzymes and processes of the invention can be used to achieve a more complete degumming of high phosphorus oils, in particular, rice, soybean, corn, canola, and sunflower oils. For example, in one aspect, upon cleavage by PI-PLC, phosphatidylinositol is converted to diacylglycerol and phosphoinositol. The diacylglycerol partitions to the aqueous phase (improving oil yield) and the phosphoinositol partitions to the aqueous phase where it is removed as a component of the heavy phase during centrifugation. An enzyme of the invention, e.g., a PI-PLC of the invention, can be incorporated into either a chemical or physical oil refining process.

In alternative aspects, enzymes of the invention have phosphatidylinositol-specific phospholipase C (PI-PLC) activity, phosphatidylcholine-specific phospholipase C activity, phosphatidic acid phosphatase activity, phospholipase A activity and/or patatin-related phospholipase activity. These enzymes can be used alone or in combination each other or with other enzymes of the invention, or other enzymes. In one aspect, the invention provides methods wherein these enzymes (including phosphatidylinositol-specific phospholipase C (PIPLC), phosphatidylcholine-specific phospholipase C, and/or phospholipase D (in conjunction with a phosphatase), phosphatidic acid phosphatase, phospholipase A, patatin-related phospholipases of the invention) are used alone or in combination in the degumming of oils, e.g., vegetable oils, e.g., high phosphorus oils, such as soybean, corn, canola, rice bran and sunflower oils. These enzymes and processes of the invention can be used to achieve a more complete degumming of high phosphorus oils, in particular, soybean, corn, canola, rice bran and sunflower oils. Upon cleavage by PI-PLC, phosphatidylinositol is converted to diacylglycerol and phosphoinositol. The diacylglycerol partitions to the aqueous phase (improving oil yield) and the phosphoinositol partitions to the aqueous phase where it is removed as a component of the heavy phase during centrifugation. An enzyme of the invention, e.g., a PI-PLC of the invention, can be incorporated into either a chemical or physical oil refining process.

In one aspect, the invention provides compositions, e.g., solutions, comprising sodium citrate at neutral pH to hydrate non-hydratables. For example, the invention provides sodium citrate solutions in a pH range of between about 4 to 9, or, 5 to 8, or, 6 to 7, that can be used to hydrate non-hydratable phospholipids (including enzymes of the invention) in high phosphorus oils. In one aspect, the hydration of non-hydratable phospholipids is by chelating the calcium and magnesium associated with the phospholipids, thereby allowing the formerly insoluble phospholipid salts to more readily partition in the aqueous phase. In one aspect, once phospholipids move to the water/oil interface or into the aqueous phase, a phospholipase of the invention (e.g., a phospholipase-specific phosphohydrolase of the invention), or another phospholipase, will convert the phospholipid to diacylglycerol and a phosphate-ester. In one aspect, calcium and magnesium metal content are lowered upon addition of acid and caustic (see discussion on caustic processes).

The enzymes of the invention are highly selective catalysts. As with other enzymes, they catalyze reactions with exquisite stereo-, regio-, and chemo-selectivities that are unparalleled in conventional synthetic chemistry. Moreover, the enzymes of the invention are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates. Enzymes of the invention can be designed to be reactive toward a wide range of natural and unnatural substrates, thus enabling the modification of virtually any organic lead compound. Enzymes of the invention can also be designed to be highly enantio- and regio-selective. The high degree of functional group specificity exhibited by these enzymes enables one to keep track of each reaction in a synthetic sequence leading to a new active compound. Enzymes of the invention can also be designed to catalyze many diverse reactions unrelated to their native physiological function in nature.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound. The present invention uses selected biocatalysts, i.e., the enzymes of the invention, and reaction conditions that are specific for functional groups that are present in many starting compounds. Each biocatalyst is specific for one functional group, or several related functional groups, and can react with many starting compounds containing this functional group. The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

The invention provides methods for identifying a single active PLC enzyme within a library, where the library is characterized by the series of biocatalytic reactions used to produce it, a so-called "biosynthetic history". One embodiment comprises screening the library for biological activities and tracing the biosynthetic history identifies the specific reaction sequence producing the active compound. The reaction sequence cah be repeated and the structure of the synthesized compound determined. In this embodiment, for this mode of identification, an immobilization technology is not required; compounds can be synthesized and tested free in solution using virtually any type of screening assay. In this embodiment, the high degree of specificity of enzyme reactions on functional groups allows for the "tracking" of specific enzymatic reactions that make up the biocatalytically produced library.

The invention also provides methods of discovering new phospholipases using the nucleic acids, polypeptides and antibodies of the invention. In one aspect, lambda phage libraries are screened for expression-based discovery of phospholipases. Use of lambda phage libraries in screening allows detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. Screening in liquid phase gives greater flexibility in assay conditions; additional substrate flexibility; higher sensitivity for weak clones; and ease of automation over solid phase screening.

In alternative embodiments, procedural steps are performed using robotic automation; e.g., enabling the execution of many thousands of biocatalytic reactions and screening assays per day as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

Phospholipase Signal Sequences

The invention provides phospholipase signal sequences (e.g., signal peptides (SPs)), e.g., peptides comprising signal sequences and/or chimeric polypeptides, where the peptides or chimerics have a signal sequence as described herein. The invention provides nucleic acids encoding these signal sequences (SPs, e.g., a peptide having a sequence comprising/consisting of amino terminal residues of a polypeptide of the invention). In one aspect, the invention provides a signal sequence comprising a peptide comprising/consisting of a sequence as set forth in residues 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32 or 1 to 33 of a polypeptide of the invention, e.g., a polypeptide comprising a sequence as set forth in SEQ ID NO:6 and having one or more mutations as set forth in Tables 12 to 15, or an enzymatically active fragment thereof. Any of these peptides can be part of a chimeric protein, e.g., a recombinant protein. A signal sequence peptide can be matched with another enzyme of the invention (e.g., a phospholipase of the invention from which is was not derived), or, with another phospholipase, or with any polypeptide, as discussed further, below.

Exemplary signal sequences include residues 1 to 37 of SEQ ID NO:4 and residues 1 to 23 of SEQ ID NO:6.

In some aspects phospholipases of the invention do not have signal sequences. In one aspect, the invention provides the phospholipases of the invention lacking all or part of a signal sequence. In one aspect, the invention provides a nucleic acid sequence encoding a signal sequence from one phospholipase operably linked to a nucleic acid sequence of a different phospholipase or, optionally, a signal sequence from a non-phospholipase protein may be desired.

Phospholipase Prepro Domains, Binding Domains and Catalytic Domains

In addition to signal sequences (e.g., signal peptides (SPs)), as discussed above, the invention provides prepro domains, binding domains (e.g., substrate binding domain) and catalytic domains (CDs). The SP domains, binding domains, prepro domains and/or CDs of the invention can be isolated, synthetic or recombinant peptides or can be part of a fusion protein, e.g., as a heterologous domain in a chimeric protein. The invention provides nucleic acids encoding these catalytic domains (CDs) (e.g., "active sites"), prepro domains, binding domains and signal sequences (SPs, e.g., a peptide having a sequence comprising/consisting of amino terminal residues of a polypeptide of the invention).

The phospholipase signal sequences (SPs), binding domains, catalytic domains (CDs) and/or prepro sequences of the invention can be isolated peptides, or, sequences joined to another phospholipase or a non-phospholipase polypeptide, e.g., as a fusion (chimeric) protein. In one aspect, polypeptides comprising phospholipase signal sequences SPs and/or prepro of the invention comprise sequences heterologous to phospholipases of the invention (e.g., a fusion protein comprising an SP and/or prepro of the invention and sequences from another phospholipase or a non-phospholipase protein). In one aspect, the invention provides phospholipases of the invention with heterologous CDs, SPs and/or prepro sequences, e.g., sequences with a yeast signal sequence. A phospholipase of the invention can comprise a heterologous CD, SP and/or prepro in a vector, e.g., a pPIC series vector (Invitrogen, Carlsbad, Calif.).

In one aspect, SPs, CDs, and/or prepro sequences of the invention are identified following identification of novel phospholipase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from 13 to 45 or more amino acid residues. Various methods of recognition of signal sequences are known to those of skill in the art. For example, in one aspect, novel hydrolase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

In some aspects, a phospholipase of the invention may not have SPs and/or prepro sequences, and/or catalytic domains (CDs). In one aspect, the invention provides phospholipases lacking all or part of an SP, a CD and/or a prepro domain. In one aspect, the invention provides a nucleic acid sequence encoding a signal sequence (SP), a CD and/or prepro from one phospholipase operably linked to a nucleic acid sequence of a different phospholipase or, optionally, a signal sequence (SPs), a CD and/or prepro domain from a non-phospholipase protein may be desired.

The invention also provides isolated, synthetic or recombinant polypeptides comprising signal sequences (SPs), prepro domain and/or catalytic domains (CDs) of the invention and heterologous sequences. The heterologous sequences are sequences not naturally associated (e.g., to a phospholipase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated, synthetic or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., phospholipase sequence). Similarly in one aspect, the invention provides isolated, synthetic or recombinant nucleic acids encoding these polypeptides. Thus, in one aspect, the isolated, synthetic or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

The polypeptides of the invention include phospholipases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include phospholipases inactive for other reasons, e.g., before "activation" by a post-translational processing event, e.g., an endo- or exo-peptidase or proteinase action, a phosphorylation event, an amidation, a glycosylation, a deglycosylation, a sulfation, a dimerization event, and/or the like. Methods for identifying "prepro" domain sequences, CDs, binding domains and signal sequences are routine and well known in the art, see, e.g., Van de Ven (1993) Crit. Rev. Oncog. 4(2):115-136; yeast two-hybrid screenings for identifying protein-protein interactions, described e.g., by Miller (2004) Methods Mol. Biol. 261:247-62; Heyninck (2004) Methods Mol. Biol. 282:223-41, U.S. Pat. Nos. 6,617,122; 6,190,874. For example, to identify a prepro sequence, the protein is purified from the extracellular space and the N-terminal protein sequence is determined and compared to the unprocessed form.

The polypeptides of the invention can be formulated as a protein preparation into any liquid, solid, semi-solid or gel form. For example, a protein preparation of the invention can comprise a formulation comprising a non-aqueous liquid composition, a cast solid, a powder, a lyophilized powder, a granular form, a particulate form, a compressed tablet, a pellet, a pill, a gel form, a hydrogel, a paste, an aerosol, a spray, a lotion or a slurry formulation.

The polypeptides of the invention include all active forms, including active subsequences, e.g., catalytic domains (CDs) or active sites, of an enzyme of the invention. In one aspect, the invention provides catalytic domains or active sites as set forth below. In one aspect, the invention provides a peptide or polypeptide comprising or consisting of an active site domain as predicted through use of a database such as Pfam (which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent.

The invention provides fusion of N-terminal or C-terminal subsequences of enzymes of the invention (e.g., signal sequences, prepro sequences) with other polypeptides, active proteins or protein fragments. The production of an enzyme of the invention (e.g., a phospholipase C enzyme) may also be accomplished by expressing the enzyme as an inactive fusion protein that is later activated by a proteolytic cleavage event (using either an endogenous or exogenous protease activity, e.g. trypsin) that results in the separation of the fusion protein partner and the mature enzyme, e.g., phospholipase C enzyme. In one aspect, the fusion protein of the invention is expressed from a hybrid nucleotide construct that encodes a single open reading frame containing the following elements: the nucleotide sequence for the fusion protein, a linker sequence (defined as a nucleotide sequence that encodes a flexible amino acid sequence that joins two less flexible protein domains), protease cleavage recognition site, and the mature enzyme (e.g., any enzyme of the invention, e.g., a phospholipase) sequence. In alternative aspects, the fusion protein can comprise a pectate lyase sequence, a xylanase sequence, a phosphatidic acid phosphatase sequence, or another sequence, e.g., a sequence that has previously been shown to be over-expressed in a host system of interest.

Any host system can be used (see discussion, above), for example, any bacteria, e.g., a gram positive bacteria, such as *Bacillus*, or a gram negative bacteria, such as *E. coli*, or any yeast, e.g., *Pichia pastoris*. The arrangement of the nucleotide sequences in the chimeric nucleotide construction can be determined based on the protein expression levels achieved with each fusion construct. Proceeding from the 5' end of the nucleotide construct to the 3' prime end of the construct, in one aspect, the nucleotide sequences is assembled as follows: Signal sequence/fusion protein/linker sequence/protease cleavage recognition site/mature enzyme (e.g., any enzyme of the invention, e.g., a phospholipase) or Signal sequence/pro sequence/mature enzyme/linker sequence/fusion protein. The expression of enzyme (e.g., any enzyme of the invention, e.g., a phospholipase) as an inactive fusion protein may improve the overall expression of the enzyme's sequence, may reduce any potential toxicity associated with the overproduction of active enzyme and/or may increase the shelf life of enzyme prior to use because enzyme would be inactive until the fusion protein e.g. pectate lyase is separated from the enzyme, e.g., phospholipase protein.

In various aspects, the invention provides specific formulations for the activation of phospholipase of the invention expressed as a fusion protein. In one aspect, the activation of the phospholipase activity initially expressed as an inactive fusion protein is accomplished using a proteolytic activity or potentially a proteolytic activity in combination with an amino-terminal or carboxyl-terminal peptidase. This activation event may be accomplished in a variety of ways and at variety of points in the manufacturing/storage process prior to application in oil degumming. Exemplary processes of the invention include: Cleavage by an endogenous activity expressed by the manufacturing host upon secretion of the fusion construct into the fermentation media; Cleavage by an endogenous protease activity that is activated or comes in contact with intracellularly expressed fusion construct upon rupture of the host cells; Passage of the crude or purified fusion construct over a column of immobilized protease activity to accomplish cleavage and enzyme (e.g., phospholipase of the invention, e.g., a phospholipase C) activation prior to enzyme formulation; Treatment of the crude or purified fusion construct with a soluble source of proteolytic activity; Activation of a phospholipase (e.g., a phospholipase of the invention, e.g., a phospholipase C) at the oil refinery using either a soluble or insoluble source of proteolytic activity immediately prior to use in the process; and/or, Activation of the phospholipase (e.g., a phospholipase of the invention, e.g., a phospholipase C) activity by continuously circulating the fusion construct formulation through a column of immobilized protease activity at reduced temperature (for example, any between about 4° C. and 20° C.). This activation event may be accomplished prior to delivery to the site of use or it may occur on-site at the oil refinery.

Glycosylation

The peptides and polypeptides of the invention (e.g., hydrolases, antibodies) can also be glycosylated, for example, in one aspect, comprising at least one glycosylation site, e.g., an N-linked or O-linked glycosylation. In one aspect, the polypeptide can be glycosylated after being expressed in a *P. pastoris* or a *S. pombe*. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence.

Assays for Phospholipase Activity

The invention provides isolated, synthetic or recombinant polypeptides (e.g., enzymes, antibodies) having a phospholipase activity, or any combination of phospholipase activities, and nucleic acids encoding them. Any of the many phospholipase activity assays known in the art can be used to determine if a polypeptide has a phospholipase activity and is within the scope of the invention. Routine protocols for determining phospholipase A, B, D and C, patatin and lipid acyl hydrolase activities, or lipase activity, are well known in the art.

Exemplary activity assays include turbidity assays, methylumbelliferyl phosphocholine (fluorescent) assays, Amplex red (fluorescent) phospholipase assays, thin layer chromatography assays (TLC), cytolytic assays and p-nitrophenylphosphorylcholine assays. Using these assays polypeptides, peptides or antibodies can be quickly screened for a phospholipase activity.

The phospholipase activity can comprise a lipid acyl hydrolase (LAH) activity. See, e.g., Jimenez (2001) Lipids 36:1169-1174, describing an octaethylene glycol monododecyl ether-based mixed micellar assay for determining the lipid acyl hydrolase activity of a patatin. Pinsirodom (2000) J. Agric. Food Chem. 48:155-160, describes an exemplary lipid acyl hydrolase (LAH) patatin activity.

Turbidity assays to determine phospholipase activity are described, e.g., in Kauffmann (2001) "Conversion of *Bacillus thermocatenulatus* lipase into an efficient phospholipase with increased activity towards long-chain fatty acyl substrates by directed evolution and rational design," Protein Engineering 14:919-928; Ibrahim (1995) "Evidence implicating phospholipase as a virulence factor of *Candida albicans*," Infect. Immun. 63:1993-1998.

Methylumbelliferyl (fluorescent) phosphocholine assays to determine phospholipase activity are described, e.g., in Goode (1997) "Evidence for cell surface and internal phospholipase activity in ascidian eggs," Develop. Growth Differ. 39:655-660; Diaz (1999) "Direct fluorescence-based lipase activity assay," BioTechniques 27:696-700.

Amplex Red (fluorescent) Phospholipase Assays to determine phospholipase activity are available as kits, e.g., the detection of phosphatidylcholine-specific phospholipase using an Amplex Red phosphatidylcholine-specific phospholipase assay kit from Molecular Probes Inc. (Eugene, Oreg.), according to manufacturer's instructions. Fluorescence is measured in a fluorescence microplate reader using excitation at 560±10 nm and fluorescence detection at 590±10 nm. The assay is sensitive at very low enzyme concentrations.

Thin layer chromatography assays (TLC) to determine phospholipase activity are described, e.g., in Reynolds (1991) Methods in Enzymol. 197:3-13; Taguchi (1975) "Phospholipase from *Clostridium novyi* type A.I," Biochim. Biophys. Acta 409:75-85. Thin layer chromatography (TLC) is a widely used technique for detection of phospholipase activity. Various modifications of this method have been used to extract the phospholipids from the aqueous assay mixtures. In some PLC assays the hydrolysis is stopped by addition of chloroform/methanol (2:1) to the reaction mixture. The unreacted starting material and the diacylglycerol are extracted into the organic phase and may be fractionated by TLC, while the head group product remains in the aqueous phase. For more precise measurement of the phospholipid digestion, radiolabeled substrates can be used (see, e.g., Reynolds (1991) Methods in Enzymol. 197:3-13). The ratios of products and reactants can be used to calculate the actual number of moles of substrate hydrolyzed per unit time. If all the components are extracted equally, any losses in the extraction will affect all components equally. Separation of phospholipid digestion products can be achieved by silica gel TLC with chloroform/methanol/water (65:25:4) used as a solvent system (see, e.g., Taguchi (1975) Biochim. Biophys. Acta 409:75-85).

p-Nitrophenylphosphorylcholine assays to determine phospholipase activity are described, e.g., in Korbsrisate (1999) J. Clin. Microbiol. 37:3742-3745; Berka (1981) Infect. Immun. 34:1071-1074. This assay is based on enzymatic hydrolysis of the substrate analog p-nitrophenylphosphorylcholine to liberate a yellow chromogenic compound p-nitrophenol, detectable at 405 nm. This substrate is convenient for high-throughput screening.

A cytolytic assay can detect phospholipases with cytolytic activity based on lysis of erythrocytes. Toxic phospholipases can interact with eukaryotic cell membranes and hydrolyze phosphatidylcholine and sphingomyelin, leading to cell lysis. See, e.g., Titball (1993) Microbiol. Rev. 57:347-366.

Hybrid (Chimeric) Phospholipases and Peptide Libraries

In one aspect, the invention provides hybrid phospholipases and fusion proteins, including peptide libraries, comprising sequences of the invention. The peptide libraries of the invention can be used to isolate peptide modulators (e.g., activators or inhibitors) of targets, such as phospholipase substrates, receptors, enzymes. The peptide libraries of the invention can be used to identify formal binding partners of targets, such as ligands, e.g., cytokines, hormones and the like. In one aspect, the invention provides chimeric proteins comprising a signal sequence (SP) and/or catalytic domain (CD) of the invention and a heterologous sequence (see above).

The invention also provides methods for generating "improved" and hybrid phospholipases using the nucleic acids and polypeptides of the invention. For example, the invention provides methods for generating enzymes that have activity, e.g., phospholipase activity (such as, e.g., phospholipase A, B, C or D activity, patatin esterase activity, cleavage of a glycerolphosphate ester linkage, cleavage of an ester linkage in a phospholipid in a vegetable oil) at extreme alkaline pHs and/or acidic pHs, high and low temperatures, osmotic conditions and the like. The invention provides methods for generating hybrid enzymes (e.g., hybrid phospholipases).

In one aspect, the methods of the invention produce new hybrid polypeptides by utilizing cellular processes that integrate the sequence of a first polynucleotide such that resulting hybrid polynucleotides encode polypeptides demonstrating activities derived from the first biologically active polypeptides. For example, the first polynucleotides can be an exemplary nucleic acid sequence encoding an exemplary phospholipase of the invention. The first nucleic acid can encode an enzyme from one organism that functions effectively under a particular environmental condition, e.g. high salinity. It can be "integrated" with an enzyme encoded by a second polynucleotide from a different organism that functions effectively under a different environmental condition, such as extremely high temperatures. For example, when the two nucleic acids can produce a hybrid molecule by e.g., recombination and/or reductive reassortment. A hybrid polynucleotide containing sequences from the first and second original polynucleotides may encode an enzyme that exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Alternatively, a hybrid polypeptide resulting from this method of the invention may exhibit specialized enzyme activity not displayed in the original enzymes. For example, following recombination and/or reductive reassortment of polynucleotides encoding phospholipase activities, the resulting hybrid polypeptide encoded by a hybrid polynucleotide can be screened for specialized activities obtained from each of the original enzymes, i.e. the type of bond on which the phospholipase acts and the temperature at which the phospholipase functions. Thus, for example, the phospholipase may be screened to ascertain those chemical functionalities which distinguish the hybrid phospholipase from the original phospholipases, such as: (a) amide (peptide bonds), i.e., phospholipases; (b) ester bonds, i.e., phospholipases and lipases; (c) acetals, i.e., glycosidases and, for example, the temperature, pH or salt concentration at which the hybrid polypeptide functions.

Sources of the polynucleotides to be "integrated" with nucleic acids of the invention may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity. "Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample that may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions that promote recombination and/or reductive reassortment creating potentially active biomolecules with novel or enhanced activities.

The microorganisms from which hybrid polynucleotides may be prepared include prokaryotic microorganisms, such as Eubacteria and Archaebacteria, and lower eukaryotic microorganisms such as fungi, some algae and protozoa. Polynucleotides may be isolated from environmental samples. Nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. In one aspect, polynucleotides encoding phospholipase enzymes isolated from extremophilic microorganisms are used to make hybrid enzymes. Such enzymes may function at temperatures above 100° C. in, e.g., terrestrial hot springs and deep sea thermal vents, at temperatures below 0° C. in, e.g., arctic waters, in the saturated salt environment of, e.g., the Dead Sea, at pH values around 0 in, e.g., coal deposits and geothermal sulfur-rich springs, or at pH values greater than 11 in, e.g., sewage sludge. For example, phospholipases cloned and expressed from extremophilic organisms can show high activity throughout a wide range of temperatures and pHs.

Polynucleotides selected and isolated as described herein, including at least one nucleic acid of the invention, are introduced into a suitable host cell. A suitable host cell is any cell that is capable of promoting recombination and/or reductive reassortment. The selected polynucleotides can be in a vector that includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

Exemplary appropriate hosts may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia, Bacillus, Streptomyces, Salmonella, Pseudomonas* and *Staphylococcus*, including, e.g., *Escherichia coli, Lactococcus lactis, Bacillus subtilis, Bacillus cereus, Salmonella typhimurium, Pseudomonas fluorescens*. Exemplary fungal cells include any species of *Aspergillus*. Exemplary yeast cells include any species of *Pichia, Saccharomyces, Schizosaccharomyces*, or *Schwanniomyces*, including *Pichia pastoris, Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line. The selection of an appropriate host is within the abilities of those skilled in the art. The selection of an appropriate host for recombination and/or reductive reassortment or just for expression of recombinant protein is deemed to be within the scope of those skilled in the art from the teachings herein. Mammalian cell culture systems that can be employed for recombination and/or reductive reassortment or just for expression of recombinant protein include, e.g., the COS-7 lines of monkey kidney fibroblasts, described in "SV40-transformed simian cells support the replication of early SV40 mutants" (Gluzman, 1981), the C127, 3T3, CHO, HeLa and BHK cell lines. Mammalian expression vectors can comprise an origin of replication, a suitable promoter and enhancer, and necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

Host cells containing the polynucleotides of interest (for recombination and/or reductive reassortment or just for expression of recombinant protein) can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, the nucleic acids and methods of the present invention can be used to generate novel polynucleotides for biochemical pathways, e.g., pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of E. coli. This f-factor of E. coli is a plasmid which affects high-frequency transfer of itself during conjugation and is ideal to achieve and stably propagate large DNA fragments, such as gene clusters from mixed microbial samples. "Fosmids," cosmids or bacterial artificial chromosome (BAC) vectors can be used as cloning vectors. These are derived from E. coli f-factor which is able to stably integrate large segments of genomic DNA. When integrated with DNA from a mixed uncultured environmental sample, this makes it possible to achieve large genomic fragments in the form of a stable "environmental DNA library." Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Thus, in one aspect, the invention relates to a method for producing a biologically active hybrid polypeptide using a nucleic acid of the invention and screening the polypeptide for an activity (e.g., enhanced activity) by:

(1) introducing at least a first polynucleotide (e.g., a nucleic acid of the invention) in operable linkage and a second polynucleotide in operable linkage, said at least first polynucleotide and second polynucleotide sharing at least one region of partial sequence homology, into a suitable host cell;

(2) growing the host cell under conditions which promote sequence reorganization resulting in a hybrid polynucleotide in operable linkage;

(3) expressing a hybrid polypeptide encoded by the hybrid polynucleotide;

(4) screening the hybrid polypeptide under conditions which promote identification of the desired biological activity (e.g., enhanced phospholipase activity); and (5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

In vivo reassortment can be focused on "inter-molecular" processes collectively referred to as "recombination." In bacteria it is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. Thus, in one aspect of the invention, using the nucleic acids of the invention novel polynucleotides are generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species.

Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. "Quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units. When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, in one aspect of the invention, the sequences to be reassorted are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following: a) Primers that include a poly-A head and poly-T tail which when made single-stranded would provide orientation can be utilized. This is accomplished by having the first few bases of the primers made from RNA and hence easily removed RNase H. b) Primers that include unique restriction cleavage sites can be utilized. Multiple sites, a battery of unique sequences, and repeated synthesis and ligation steps would be required. c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by: 1) The use of vectors only stably maintained when the construct is reduced in complexity. 2) The physical recovery of shortened vectors by physical procedures. In this case, the cloning vector would be recovered using standard plasmid isolation procedures and size fractionated on either an agarose gel, or column with a low molecular weight cut off utilizing standard procedures. 3) The recovery of vectors containing interrupted genes which can be selected when insert size decreases. 4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, this process is not limited to such nearly identical repeats.

The following is an exemplary method of the invention. Encoding nucleic acid sequences (quasi-repeats) are derived from three (3) species, including a nucleic acid of the invention. Each sequence encodes a protein with a distinct set of properties, including an enzyme of the invention. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI). Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations. In one aspect, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure. The polypeptides, e.g., phospholipases, that are identified from such libraries can be used for various purposes, e.g., the industrial processes described herein and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acetylated or deacetylated 4'-fluro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl) phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

Screening Methodologies and "on-Line" Monitoring Devices

In practicing the methods of the invention, a variety of apparatus and methodologies can be used to in conjunction with the polypeptides and nucleic acids of the invention, e.g., to screen polypeptides for phospholipase activity, to screen compounds as potential modulators of activity (e.g., potentiation or inhibition of enzyme activity), for antibodies that bind to a polypeptide of the invention, for nucleic acids that hybridize to a nucleic acid of the invention, and the like.

Immobilized Enzyme Solid Supports

The phospholipase enzymes, fragments thereof and nucleic acids that encode the enzymes and fragments can be affixed to a solid support. This is often economical and efficient in the use of the phospholipases in industrial processes. For example, a consortium or cocktail of phospholipase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof.

Another type of solid support useful in the present invention is ceramic. Some examples include non-porous ceramic, porous ceramic, Sift, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support.

Other exemplary solid supports used to practice the invention comprise diatomaceous earth products and silicates. Some examples include CELITE® KENITE®, DIACTIV®, PRIMISIL®, DIAFIL® diatomites and MICRO-CEL®, CALFLO®, SILASORB™, and CELKATE® synthetic calcium and magnesium silicates. Another example of a solid support is a cell, such as a red blood cell.

Methods of Immobilization

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a microtiter plate having about 100,000 or more individual capillaries bound together.

Arrays, or "BioChips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a phospholipase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. "Polypeptide arrays" can also be used to simultaneously quantify a plurality of proteins.

In alternative embodiment, the invention provides "arrays" or "microarrays" or "biochips" or "chips" comprising a plurality of target elements, wherein each target element can comprise a defined amount of one or more polypeptides (including antibodies) or nucleic acids immobilized onto a defined area of a substrate surface, and at least one nucleic acid and/or polypeptide is a nucleic acid and/or polypeptide of this invention.

The present invention can be practiced with, or can comprise, any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated, synthetic or recombinant antibodies that specifically bind to a phospholipase of the invention. These antibodies can be used to isolate, identify or quantify the phospholipases of the invention or related polypeptides. These antibodies can be used to inhibit the activity of an enzyme of the invention. These antibodies can be used to isolated polypeptides related to those of the invention, e.g., related phospholipase enzymes.

An "antibody" of this invention can include a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention.

Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., a kit having at least one phospholipase of the invention) and/or antibodies (e.g., a kit having at least one antibody of the invention. The kits can contain enzymes for the processing (the making of) biofuels, detergents, or for treating or processing foods, feeds, biomass, food or feed additives or nutritional supplements, and the like. The kits also can contain instructional material teaching the methodologies and industrial uses of the invention, as described herein.

Industrial and Medical Uses of the Enzymes of the Invention

The invention provides many industrial uses and medical applications using polypeptides of the invention, e.g., a phospholipase and other enzymes of the invention, e.g., phospholipases A, B, C and D, patatins, including converting a non-hydratable phospholipid to a hydratable form, making biofuels and processing biomass, oil degumming, processing of oils from plants, fish, algae and the like, to name just a few applications. In any of these alternative industrial uses and medical applications, an enzymes can be added in a specific order, e.g., phospholipases with differing specificities are added in a specific order, for example, an enzyme with PC- and PE-hydrolyzing activity is added first (or two enzymes are added, one with PC-hydrolyzing activity and the other with PE-hydrolyzing activity), then an enzyme with PI-hydrolyzing activity (e.g., PLC or PI-PLC activity) is added, or any combination thereof.

Any or all of the methods of the invention can be used on a "process scale", e.g., an oil processes or refining on a scale from about 15,000; 25,000; 50,000; 75,000; or 100,000 lbs of refined oil/day up to about 1, 2, 3, 4, 5 or 6 or more million lbs refined oil/day.

Methods of using phospholipase enzymes in industrial applications are well known in the art. For example, the phospholipases and methods of the invention can be used for the processing of fats and oils as described, e.g., in JP Patent Application Publication H6-306386, describing converting phospholipids present in the oils and fats into water-soluble substances containing phosphoric acid groups.

Phospholipases of the invention can be used to process plant oils and phospholipids such as those derived from or isolated from rice bran, soy, canola, palm, cottonseed, corn, palm kernel, coconut, peanut, sesame, sunflower. Phospholipases of the invention can be used to process essential oils, e.g., those from fruit seed oils, e.g., grapeseed, apricot, borage, etc. Phospholipases of the invention can be used to process oils and phospholipids in different forms, including crude forms, degummed, gums, wash water, clay, silica, soapstock, and the like. The phospholipids of the invention can be used to process high phosphorus oils, fish oils, animal oils, plant oils, algae oils and the like. In any aspect of the invention, any time a phospholipase C can be used, an alternative comprises use of a phospholipase D of the invention and a phosphatase (e.g., using a PLD/phosphatase combination to improve yield in a high phosphorus oil, such as a soy bean oil).

Phospholipases of the invention can be used to process and make edible oils, biodiesel oils, liposomes for pharmaceuticals and cosmetics, structured phospholipids and structured lipids. Phospholipases of the invention can be used in oil extraction. Phospholipases of the invention can be used to process and make various soaps.

In another embodiment, provided herein is a method for obtaining a phospholipid from an edible oil. In certain embodiment, the phospholipids obtained by the methods provided herein include a variety of phospholipids, including, but not limited to phosphatidylcholine (PC), phosphatidylethanolamine (PE), phosphatidylserine (PS), phosphatidylinositol (PI), phosphatidic acid (PA), lysophosphatidylcholine (LPC), lysophosphatidylethanolamine (LPE), lysophosphatidylserine (LPS), lysophosphatidylinositol (LPI), lysophosphatidic acid (LPA), choline (C), ethanolamine (E), serine (S), and inositol (I).

Processing Edible Oils: Generation of 1, 3-Diacylglycerol (1,3 DAG)

The invention provides processes using enzyme(s) of the invention to make 1,3-diacylglycerol (1,3 DAG). In one aspect, a phospholipase C or phospholipase D plus a phosphatase generates 1,2-diacylglycerol; this improves oil yield during edible oil refining. When used in a process that includes a caustic neutralization step, for example as a caustic refining aid, as much as 70% of the 1,2-diacylglyceride (1,2-DAG) undergoes acyl migration and is converted to 1,3-DAG. 1,3-DAG possesses increased health benefits and therefore the use of PLC as a caustic refining aid produces an oil with increased nutritional value.

The invention provides processes using enzyme(s) of the invention to make and process edible oils, including generation of edible oils with increased amounts of 1,3-DAG. Diacylglycerols are naturally occurring compounds found in many edible oils. In one aspect of a method of the invention, e.g., the oil degumming process, a base (caustic) causes the isomerization of 1,2-DAG, produced by PLC, into 1,3-DAG which provides a nutritional health benefit over 1,2-DAG, e.g., the 1,3-DAG is burned as energy instead of being stored as fat (as is 1,2-DAG). By adding the PLC at the front end of caustic refining process (and the acid and caustic subsequently), the methods of the invention generate an elevated level of 1,3-DAG (decreasing 1,2-DAG). Nutritionally, 1,3-DAG is better for you than 1,2-DAG. In alternative aspects, the invention comprises an oil degumming process using a PLC of the invention, whereby the final degummed oil product contains not less than 0.5%, 1.0%, 2.0% or 3.0% or more 1,3-DAG.

Thus, the invention provides a process for making (through interesterification) a refined oil (e.g., a diacylglycerol oil), including edible oils, containing increased levels of 1,3-diacylglycerol (1,3-DAG), where a phospholipase, such as an enzyme of the invention, is "front-loaded" or added before addition of acid or caustic. The generation by enzymatic hydrolysis of a DAG from a triglyceride generates by interesterification 1,3 DAG from 1,2 DAG. The 1,3 DAG-comprising edible oil shows different metabolic effects compared to conventional edible oils. Differences in metabolic pathways between 1,3 DAG and either 1,2 DAG or triglycerides allow a greater portion of fatty acids from 1,3 diacylglycerol to be burned as energy rather than being stored as fat. Clinical studies have shown that regular consumption of DAG oil as part of a sensible diet can help individuals to manage their body weight and body fat. In addition, metabolism of 1,3 DAG reduces circulating postmeal triglycerides in the bloodstream. Since obesity and elevated blood lipids are associated as risk factors for chronic diseases including cardiovascular disease and Type II diabetes, these lifestyle-related health conditions may be impacted in a beneficial manner with regular consumption of DAG oils.

Consumption of DAG-comprising oil can take place through a variety of means. Thus, in one aspect, the invention provides a process using an enzyme of the invention for making a food, e.g., a baked good, having increased levels of 1,3-DAG diacylglycerol and baked goods comprising diacylglycerol oils. In one aspect, the baked goods are cookies, cakes and similar baked goods.

In alternative embodiments, combination of enzymes that can be used in the methods of the invention, including the processing of edible oils, include (where one, several or all of the enzymes in the combination comprise an enzyme of the instant invention):

PLC+PI-PLC+PLA (PLA added after completion of PLC reactions);

PLD+phosphatase+PI-PLC followed by PLA; or,

PLC or (PLC+PI-PLC)+PLA specific for phosphatidic acid (all enzymes added together or sequentially).

Oil Degumming and Vegetable Oil Processing

The enzymes of the invention (e.g., polypeptides of the invention having lipase, phospholipase, esterase and/or glycosidase or equivalent activity) can be used in various vegetable oil processing steps, such as in vegetable oil extraction, particularly, in the removal of "phospholipid gums" in a process called "oil degumming".

These processes of the invention can be used on a "process scale", e.g., on a scale from about 15,000; 25,000; 50,000; 75,000; or 100,000 lbs of refined oil/day up to about 1, 2, 3, 4, 5 or 6 or more million lbs refined oil/day.

In one aspect, the invention provides oil degumming processes comprising use of a phospholipase of the invention, e.g., a PLC, e.g. a PI-PLC of the invention. In one aspect, the process further comprises addition of another phospholipase (which can also be a phospholipase of the invention), e.g., another PLC, a PLA, a PLB, a PLB or a patatin of the invention, or an enzyme (which can also be an enzyme of the invention) having a lysophospholipase-transacylase (LPTA) activity or lysophospholipase (LPL) activity and lysophospholipase-transacylase (LPTA), or a combination thereof, and/or a patatin-like phospholipase (which can also be an enzyme of the invention). In one aspect, all enzymes are added together, or, alternatively, the enzymes are added in a specific order, e.g., PLC addition is followed by PLA and/or patatin addition; or, an enzyme or enzymes of the invention having PC and PE activity added first, then PI PLC added second.

In one aspect, this process provides a yield improvement as a result of the phospholipase (e.g., PLC of the invention) treatment. In one aspect, this process provides an additional decrease of the phosphorus content of the oil as a result of the phospholipase (e.g., PLA of the invention) treatment.

In one aspect, the invention provides processes comprising use of a phospholipase of the invention, e.g., a PLC or a PI-PLC of the invention, to reduce gum mass and increase neutral oil (triglyceride) gain through reduced oil entrapment. In one aspect, the invention provides processes comprising use of a phospholipase of the invention, e.g., a PLC of the invention, e.g., a PI-PLC of the invention, for increasing neutral oils and diacylglycerol (DAG) production to contribute to the oil phase. In alternative aspects, processes of the invention (e.g., degumming processes) may comprise one or more other enzymes such as a protease, an amylase, a lipase, a cutinase, another phospholipase (including, e.g., an enzyme of the invention), a carbohydrase, a cellulase, a pectinase, a mannanase, an arabinase, a galactanase, a xylanase, an oxidase, e.g., a lactase, and/or a peroxidase, or polypeptides with equivalent activity, or a combination thereof.

The phospholipases of the invention can be used in various vegetable oil processing steps, such as in vegetable oil extraction, particularly, in the removal of "phospholipid gums" in a process called "oil degumming," as described above. The invention provides methods for processing vegetable oils from various sources, such as rice bran, soybeans, rapeseed, peanuts and other nuts, sesame, sunflower, palm and corn. The methods can used in conjunction with processes based on extraction with as hexane, with subsequent refining of the crude extracts to edible oils, including use of the methods and enzymes of the invention. The first step in the refining sequence is the so-called "degumming" process, which serves to separate phosphatides by the addition of water. The material precipitated by degumming is separated and further processed to mixtures of lecithins. The commercial lecithins, such as soybean lecithin and sunflower lecithin, are semi-solid or very viscous materials. They consist of a mixture of polar lipids, mainly phospholipids, and oil, mainly triglycerides.

The phospholipases of the invention can be used in any "degumming" procedure, including water degumming, ALCON oil degumming (e.g., for soybeans), safinco degumming, "super degumming," UF degumming, TOP degumming, uni-degumming, dry degumming and ENZYMAX™ degumming. See, e.g., U.S. Pat. Nos. 6,355,693; 6,162,623; 6,103,505; 6,001,640; 5,558,781; 5,264,367. Various "degumming" procedures incorporated by the methods of the invention are described in Bockisch, M. (1998) In Fats and Oils Handbook, The extraction of Vegetable Oils (Chapter 5), 345-445, AOCS Press, Champaign, Ill. The phospholipases of the invention can be used in the industrial application of enzymatic degumming of triglyceride oils as described, e.g., in EP 513 709.

In one aspect, phospholipases of the invention are used to treat vegetable oils, e.g., crude oils, such as rice bran, soy, canola, flower and the like. In one aspect, this improves the efficiency of the degumming process. In one aspect, the invention provides methods for enzymatic degumming under conditions of low water, e.g., in the range of between about 0.1% to 20% water, or, 0.5% to 10% water. In one aspect, this results in the improved separation of a heavy phase from the oil phase during centrifugation. The improved separation of these phases can result in more efficient removal of phospholipids from the oil, including both hydratable and nonhydratable oils. In one aspect, this can produce a gum fraction that contains less entrained neutral oil (triglycerides), thereby improving the overall yield of oil during the degumming process.

In one aspect, phospholipases of the invention, e.g., a polypeptide having PLC activity, e.g., a PI-PLC activity, are used to treat oils (e.g., vegetable oils, including crude oils, such as rice bran, soy, canola, flower and the like), e.g., in degumming processes, to reduce gum mass and increase neutral oil gain through reduced oil entrapment. In one aspect, phospholipases of the invention e.g., a polypeptide having PLC activity, are used for diacylglycerol (DAG) production and to contribute to the oil phase.

The phospholipases of the invention can be used in the industrial application of enzymatic degumming as described, e.g., in CA 1102795, which describes a method of isolating polar lipids from cereal lipids by the addition of at least 50% by weight of water. This method is a modified degumming in the sense that it utilizes the principle of adding water to a crude oil mixture.

In one aspect, the invention provides enzymatic processes comprising use of phospholipases of the invention (e.g., a PLC, e.g., a PI-PLC) comprising hydrolysis of hydrated phospholipids in oil at a temperature of about 20° C. to 40° C., at an alkaline pH, e.g., a pH of about pH 8 to pH 10, using a reaction time of about 3 to 10 minutes. This can result in less than 10 ppm final oil phosphorus levels. The invention also provides enzymatic processes comprising use of phospholipases of the invention (e.g., a PI-PLC) comprising hydrolysis of hydratable and non-hydratable phospholipids in oil at a temperature of about 50° C. to 60° C., at a pH slightly below neutral, e.g., of about pH 5 to pH 6.5, using a reaction time of about 30 to 60 minutes. This can result in less than 10 ppm final oil phosphorus levels.

In one aspect, the invention provides enzymatic processes that utilize a phospholipase C enzyme to hydrolyze a glyceryl phosphoester bond and thereby enable the return of the diacylglyceride portion of phospholipids back to the oil, e.g., a vegetable, fish or algae oil (a "phospholipase C (PLC) caustic refining aid"); and, reduce the phospholipid content in a degumming step to levels low enough for high phosphorus oils to be physically refined (a "phospholipase C (PLC) degumming aid"). The two approaches can generate different values and have different target applications.

In various exemplary processes of the invention, a number of distinct steps compose the degumming process preceding the core bleaching and deodorization refining processes. These steps include heating, mixing, holding, separating and drying. Following the heating step, water and often acid are added and mixed to allow the insoluble phospholipid "gum" to agglomerate into particles which may be separated. While water separates many of the phosphatides in degumming, portions of the phospholipids are non-hydratable phosphatides (NHPs) present as calcium or magnesium salts. Degumming processes address these NHPs by the addition of acid. Following the hydration of phospholipids, the oil is mixed, held and separated by centrifugation. Finally, the oil is dried and stored, shipped or refined, as illustrated, e.g., in FIG. 1. The resulting gums are either processed further for lecithin products or added back into the meal.

In one embodiment, provided herein is a method for hydration of non hydratable phospholipids within a lipid matrix by enabling them to migrate to an oil-water interface. The non hydratable phospholipids are then reacted and/or removed from the lipids. In one embodiment, the method comprises a) mixing an aqueous acid with an edible oil to obtain an acidic mixture having pH of less than about 4; and b) mixing a base with the acidic mixture to obtain a reacted mixture having pH of about 6-9, wherein the mixing in steps a) and/or b) creates an emulsion that comprises an aqueous phase in average droplet size between about 15 µm to about 45 µm in size. In certain embodiments, mixing in steps a) and/or b) creates an emulsion that comprises at least about 60% of an aqueous phase by volume in droplet size between about 15 µm to about 45 µm in size, wherein percentage of the aqueous phase is based on the total volume of the aqueous phase. In certain embodiment, the methods provided herein allow the non hydratable phospholipids within a lipid matrix to migrate to an oil-water interface.

In certain embodiments, the mixing in steps a) and/or b) creates an emulsion that comprises an aqueous phase in average droplet size between about 15-40 µm, 15-35 µm, 17-40 µm, 20-40 µm, 20-30 µm, 25-30 µm, 25-40 µm, or 25-35 µm. In certain embodiments, the mixing in step a) creates an emulsion that comprises an aqueous phase in average droplet size between about 15-40 µm, 15-35 µm, 17-40 µm, 20-40 µm, 20-30 µm, 25-30 µm, 25-40 µm, or 25-35 µm. In certain embodiments, the mixing in step b) creates an emulsion that comprises an aqueous phase in average droplet size between about 15-40 µm, 15-35 µm, 17-40 µm, 20-40 µm, 20-30 µm, 25-30 µm, 25-40 µm, or 25-35 µm. In certain embodiments, the average droplet size is about 15 µm, 17 µm, 19 µm, 20 µm, 22 µm, 25 µm, 27 µm, 30 µm, 35 µm, or 40 µm. In certain embodiments, the average droplet size is about 20 µm.

In certain embodiments, the mixing in steps a) and/or b) creates an emulsion that comprises at least about 60% of the aqueous phase by volume in droplet size between about 20 µm to about 40 µm in size, wherein percentage of the aqueous phase is based on the total volume of the aqueous phase. In certain embodiments, the mixing steps creates an emulsion that comprises about 60-95%, 60-90%, 60-80%, 70-95%, 80-95% of the aqueous phase by volume in droplet size between about 20-40 µm, 20-35 µm, 25-40 µm, 30-40 µm, 35-40 µm, or 25-45 µm, wherein percentage of the aqueous phase is based on the total volume of the aqueous phase. In certain embodiments, the mixing in steps a) and/or b) creates an emulsion that comprises at least about 60, 70, 80, 90, 93, 95, 96, 97, 98, or 99% of the aqueous phase by volume in droplet size between about 15-45 µm, 20-40 µm, 20-45 µm, 25-40 µm, 20-35 µm, 30-40 µm, 35-40 µm, or 25-45 µm, wherein percentage of the aqueous phase is based on the total volume of the aqueous phase. In certain embodiments, the mixing in step a) creates an emulsion that comprises at least about 60, 70, 80, 90, 93, 95, 96, 97, 98, or 99% of the aqueous phase by volume in droplet size between about 15-45 µm, 20-40 µm, 20-45 µm, 25-40 µm, 20-35 µm, 30-40 µm, 35-40 µm, or 25-45 µm, wherein percentage of the aqueous phase is based on the total volume of the aqueous phase. In certain embodiments, the mixing in step b) creates an emulsion that comprises at least about 60, 70, 80, 90, 93, 95, 96, 97, 98, or 99% of the aqueous phase by volume in droplet size between about 15-45 µm, 20-40 µm, 20-45 µm, 25-40 µm, 20-35 µm, 30-40 µm, 35-40 µm, or 25-45 µm, wherein percentage of the aqueous phase is based on the total volume of the aqueous phase. In certain embodiments, the mixing in steps a) and/or b) creates an emulsion that comprises at least about 10-30% of the aqueous phase by volume in droplet size less than about 10 µm, wherein percentage of the aqueous phase is based on the total volume of the aqueous phase. In certain embodiments, the mixing in steps a) and/or b) creates an emulsion that comprises at least about 20-25% of the aqueous phase by volume in droplet size less than about 10 µm, wherein percentage of the aqueous phase is based on the total volume of the aqueous phase. In certain embodiments, the mixing in steps a) and/or b) creates an emulsion that comprises at least about 60-95% of the aqueous phase by volume in droplet size greater than about 10µ, wherein percentage of the aqueous phase is based on the total volume of the aqueous phase. In certain embodiments, the mixing in steps a) and/or b) creates an emulsion that comprises at least about 70-80% of the aqueous phase by volume in droplet size greater than about 10µ, wherein percentage of the aqueous phase is based on the total volume of the aqueous phase. In certain embodiments, the mixing in steps a) and/or b) creates an emulsion that comprises at least about 90% of the aqueous phase by volume in average droplet size of about 20µ, wherein percentage of the aqueous phase is based on the total volume of the aqueous phase.

Without being bound by any particular theory, it is believed that in step a), the calcium, magnesium, and iron salts of phosphatidic acid and phosphatidyl ethanolamine dissociate. The free calcium, magnesium, and iron cations react with, for example, citrate, acetate or phosphate anions from the acid, to form metal salts. In step b), the metal cations from the base, for example sodium or potassium ions, form complexes with the phosphatidic acid or the phosphatidyl ethanolamine. In the certain embodiments, the method further comprises addition of water followed by a high shear mixing to form a mechanical emulsion. The emulsified phospholipids are then removed by chemical degumming or reacted in the enzymatic degumming.

Any shearing and/or mixing device deemed suitable by one of skill in the art can be used for mixing in the methods provided herein. In certain embodiments, mixing comprises shearing and agitation. In certain embodiment, the mixing device is an overhead mixer, including an IKA RW 20 digital mixer with a flat blade paddle. In certain embodiments, the mixing device is operated at about 50 rpm, 100 rpm, 150 rpm or 200 rpm for normal agitation and about 250 rpm, 300 rpm, 350 rpm, 400 rpm or more for vigorous agitation. In certain embodiment, the shear mixing is accomplished with IKA's Ultra-Turrax homogenizer T-50 basic with a S 50 N-G 45 G dispersion element at 10,000 rpm.

In certain embodiments, the mixer is a rotor/stator high shear mixer with tip speed (radial velocity in the mixer chamber) of at least about 1400 cm/s. In certain embodiments, and the power dissipated by the mixer is at least 1.0 KW/metric ton of product/h. In certain embodiments, oil/water emulsions in industrial scale are obtained with tip speeds ranging from about 1400 cm/s to 2300 cm/s, or even higher. In certain embodiments, the tip speed is about 1400 cm/s, 1600 cm/s, 1800 cm/s, 2000 cm/s, 2100 cm/s, 2300 cm/s, 2500 cm/s, 3000 cm/s, or 3500 cm/s. In certain embodiments, the tip speed is about 2300 cm/s. In certain embodiments, and the power dissipated by the mixer is from about 1.0 to about 2.0 KW/metric ton of product/h. In certain embodiments, and the power dissipated by the mixer is about 2.0 KW/metric ton of product/h. In certain embodiments, for a continuous process, 10 KW of effective power dissipation in the high shear mixer is required for 10 metric ton of oil per hour.

In certain embodiments, mixing of acid comprises shearing for less than about 1 minute. In certain embodiments, mixing of acid comprises shearing for about 1 second, 3 seconds, 5 seconds, 8 seconds, 10 seconds, 20 seconds, 30 seconds, 40 seconds, 50 seconds or 60 seconds. In certain embodiments, mixing of acid comprises shearing for at least about 1 minute. In certain embodiments, mixing of acid comprises shearing for at least about 1 second up to about 10 minutes, at least about 1 second up to about 10 minutes, at least about 1 second up to about 7 minutes, at least about 1 second up to about 5 minutes, at least about 1 second up to about 3 minutes or at least about 1 second up to about 2 minutes. In certain embodiments, mixing of acid comprises shearing for at least about 1, 2, 3, 4, 5, 6, 7, 8, 9 or 10 minutes.

In certain embodiments, mixing of acid comprises shearing followed by agitation from about 1 minute up to about 5 hours. In certain embodiments, the acidic mixture is agitated for at least about 1 minute. In certain embodiments, agitation of acid is continued from about 10 minutes to about 5 hours or more. In certain embodiments, agitation of acid is continued from about 30 minutes to about 5 hours or more. In certain embodiments, agitation of acid is continued from about 30 minutes to about 3 hours or more. In certain embodiments, agitation of acid is continued from about 30 minute to about 2 hours or more. In certain embodiments, agitation of acid is continued for about 1, 10, 20, 30, 40, 50, 60, 70, 80, 90, 120, 150 or 180 minutes.

In certain embodiments, the acid used in step a) is selected from the group consisting of phosphoric acid, acetic acid, citric acid, tartaric acid, succinic acid, and mixtures thereof. In one embodiment, the acid is citric acid.

In certain embodiments, the pH of the acidic mixture in step a) is about 1 to about 4. In certain embodiments, the pH of the acidic mixture in step a) is about 1, 1.5, 2, 2.5, 3, 3.5 or 4.

In certain embodiments, mixing of acid is continued till the calcium, magnesium, and iron salts of phosphatidic acid and phosphatidyl ethanolamine dissociate.

In certain embodiments, the aqueous acid used in the method comprises at least about 5% by weight acid based on the combined weight of acid and water. In certain embodiments, the aqueous acid used in the method comprises at least about 5 up to about 90%, about 5 up to about 80%, about 5 up to about 70%, about 10 up to about 90%, about 20 up to about 60%, about 30 up to about 60%, or about 40 up to about 60% by weight acid based on the combined weight of acid and water. In certain embodiments, the aqueous acid used in the method comprises at least about 5, 10, 15, 20, 25, 30, 35, 40, 45, 50, 55, 60, 70, 80, 85, 90% by weight acid based on the combined weight of acid and water. In certain embodiments, the aqueous acid used in the methods comprises at least about 5% by weight citric acid based on the combined weight of citric acid and water. In certain embodiments, the aqueous acid used in the methods comprises at least about 5, 10, 15, 20, 25, 30, 35, 40, 45, 50, 55 or 60% by weight citric acid based on the combined weight of citric acid and water. In certain embodiments, the aqueous acid used in the methods comprises at least about 40, 45, 50, 55 or 60% by weight citric acid based on the combined weight of citric acid and water. In one embodiment, the aqueous acid used in the method comprises about 50% by weight citric acid based on the combined weight of citric acid and water. In certain embodiments, the aqueous acid used in the methods comprises at least about 5, 10, 15, 20, 25, 30, 35, 40, 45, 50, 55, 60, 70, 80, 85, 90% by weight phosphoric acid based on the combined weight of phosphoric acid and water.

In certain embodiments, the aqueous acid is used in at least about 0.01% by weight based on total weight of the oil. In certain embodiments, the aqueous acid is used in at least about 0.05% by weight based on total weight of the oil. In certain embodiments, the aqueous acid is used in at least about 0.01 up to about 10%, about 0.01 up to about 5%, about 0.05 up to about 5%, about 0.05 up to about 3%, about 0.05 up to about 2% or about 0.1 up to about 2% by weight based on total weight of the oil. In certain embodiments, the aqueous acid is used in about 0.01, 0.05, 0.1, 0.15, 0.2, 0.25, 0.3, 0.5, 1, 2, 5, 7 or 10% by weight based on total weight of the oil.

A base is mixed with the acidic mixture to obtain a reacted mixture having pH of about 6-9 at the aqueous phase. The mixing is continued to allow the non hydratable phospholipids within a lipid matrix to migrate to an oil-water interface. Any base deemed suitable by one of skill in the art can be used in step b). In certain embodiments, the base is selected from the group consisting of sodium hydroxide, potassium hydroxide, sodium silicate, sodium carbonate, calcium carbonate, and a combination thereof. In one embodiment, the base is sodium hydroxide. In certain embodiments, the base is added as a dilute aqueous solution such that the base does not saponify any neutral oil. In certain embodiments, the base is added as about 0.1 up to about 8 M, about 1 up to about 4 M, about 1 up to about 3 M, or about 0.5 up to about 3 M aqueous solution. In certain embodiments, the base is added as about 0.1 M, 0.5 M, 1 M, 2 M, 3 M, 4 M, 5 M, 6 M, 7 M or 8 M aqueous solution. In one embodiment, the minimum amount of base to be used for the removal of the NHPs to be effective is such that the pH of the aqueous phase is raised to at least about 6. In certain embodiments, the amount of base used is sufficient to raise the pH of the aqueous phase to about 6, 6.5, 7, 7.5 or 8. In certain embodiments, mixing of base is continued for at least about 1 minute. In certain embodiments, mixing of base is continued from about 1 minute to about 5 hours or more. In certain embodiments, mixing of base is continued for about 1, 10, 20, 30, 40, 50, 60, 70, 80, 90, 120, 150 or 180 minutes.

The methods provided herein can be conducted at any temperature deemed suitable by one of skill in the art. In certain embodiments, the temperature during the process is in the range from about 20° C. to about 100° C., about 20° C. to about 90° C., about 40° C. to about 80° C., or about 40° C. to about 70° C. In certain embodiments, the temperature during the process is about 20, 30, 40, 50 60, 70, 80, 90 or 100° C.

In certain embodiments, water is added after reaction with the base in an amount from about 0.1 to 5% or more based on the total volume of the reaction mixture followed by a high shear mixing to form a mechanical emulsion enabling either phospholipids to be emulsified in the chemical degumming or reacted in the enzymatic degumming. In certain embodiments, water is then added in about 0.1, 0.5, 1, 2, 3, 4, 5% or more based on the total volume of the reaction mixture.

In one embodiment, provided herein is a method wherein hydration of NHPs is followed by enzymatic treatment to remove various phospholipids and lecithins. Such methods can be practiced on either crude or water-degummed oils.

In certain embodiments, an oil degumming method provided herein comprises: a) mixing an aqueous acid with an edible oil to obtain an acidic mixture having pH of about 1 to 4; b) mixing a base with the acidic mixture to obtain a reacted mixture having pH of about 6-9; and c) degumming the reacted mixture with water or an enzyme to obtain a degummed oil, wherein the mixing in steps a) and/or b) is carried out with a high shear mixer.

In the embodiments where an enzyme is used in the degumming step, one or more enzymes can be added to the oil either separately or together. Enzymatic reaction parameters including temperature, pH, and enzyme concentration can be controlled to optimize the reaction for a particular enzyme combination in a particular oil system. Many varieties of enzymes and their equivalents are suitable for use in the methods provided herein, including the phospholipase A and phospholipase C families that are available commercially. Exemplary enzymes are described elsewhere herein.

In certain embodiments, the different phospholipases used together in the enzymatic degumming step are mixed together before addition to the oil to be treated. Alternatively, the enzymes are added to the oil separately, either sequentially or simultaneously.

The amount of enzyme used in the methods provided herein depends on the reaction conditions, the type of oil and the type of enzyme use. In certain embodiments, the amount is in the range from 10 to 20,000 units, from 20 to 10,000 units, from 50 to 5,000 units, or from 100 to 2,000 units, per 1 kg of the oil.

In one embodiment, provided herein is a method for removing NHPs, hydratable phospholipids, and lecithins (known collectively as "gums") from vegetable oils to produce a degummed oil or fat product that can be used for food production and/or non-food applications. In certain embodiments, the degumming methods provided herein utilize water, various acids and/or various bases or a combination thereof.

In one embodiment, methods provided herein are useful for removal of salts of phosphatidic acid and phosphatidyl ethanolamine from vegetable oils. In certain embodiments, calcium and magnesium citrate salts are formed in step a). The methods provided herein eliminate the problems associated with equipment fouling due to deposition of calcium and magnesium citrate salts on post-reaction equipments. The calcium and magnesium citrate salts are soluble at the pH at which the enzymatic reaction and further processing is carried out in the methods provided herein.

In certain embodiments, provided herein are methods for enhancing the reaction rate of a phospholipase used in an enzymatic degumming, such that the enzyme reaction has a duration of less than about six, five, four, three, two or one hour. In certain embodiments, the enhancement in the reaction rate is achieved by a high shear mixing of the reacted mixture of step b) to form a mechanical emulsion which is then reacted with the enzyme.

It is yet another aspect, provides herein is a method for degumming a vegetable oil composition in which both hydratable and non-hydratable phospholipids can be treated in a single process, wherein an enzyme reaction is completed in less than about one hour.

In certain embodiment, the oil comprises *Neochloris oleoabundans* oil, *Scenedesmus dimorphus* oil, *Euglena gracilis* oil, *Phaeodactylum tricornutum* oil, *Pleurochrysis carterae* oil, *Prymnesium parvum* oil, *Tetraselmis chui* oil, *Tetraselmis suecica* oil, *Isochrysis galbana* oil, *Nannochloropsis salina* oil, *Botryococcus braunii* oil, *Dunaliella tertiolecta* oil, *Nannochloris* species oil, *Spirulina* species oil, *Chlorophycease* oil, *Bacilliarophy* oil, acai oil, almond oil, babassu oil, blackcurrent seed oil, borage seed oil, canola oil, cashew oil, castor oil, coconut oil, coriander oil, corn oil, cottonseed oil, crambe oil, flax seed oil, grape seed oil, hazelnut oil, other nut oils, hempseed oil, jatropha oil, jojoba oil, linseed oil, macadamia nut oil, mango kernel oil, meadowfoam oil, mustard oil, neat's foot oil, olive oil, palm oil, palm kernel oil, peanut oil, pecan oil, pine nut oil, pistachio oil, poppy seed oil, rapeseed oil, rice bran oil, safflower oil, sasanqua oil, sesame oil, shea butter oil, soybean oil, sunflower seed oil, tall oil, tsubaki oil, walnut oil, varieties of "natural" oils having altered fatty acid compositions via Genetically Modified Organisms (GMO) or traditional "breading" such as high oleic, low linolenic, or low saturated oils (high oleic canola oil, low linolenic soybean oil or high stearic sunflower oils) or a blend of thereof. In one embodiment, oils that can be treated include but are not limited to the following: canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, soybean oil, sunflower seed oil, tall oil, tsubaki oil, and vegetable oil.

In certain embodiments, the methods provided herein reduce the phospholipids content of an oil to less than about 30 ppm phosphorus, less than about 20 ppm phosphorus, less than about 15 ppm phosphorus, less than about 10 ppm phosphorus, less than about 7 ppm phosphorus, less than about 5 ppm phosphorus or less than about 3 ppm phosphorus. In certain embodiments, the methods provided herein reduce the phospholipid content of an oil to about 10 ppm phosphorus, about 7 ppm phosphorus, about 5 ppm phosphorus or about 3 ppm phosphorus.

After the degumming step, the degummed oil can be separated from the gums, and subjected to further processing steps known in the art including bleaching or deodorizing, as may be necessary or desirable depending on the end use for which the degummed oil product is intended.

In certain embodiment, provided herein are methods for obtaining phospholipids comprising:
a) mixing an aqueous acid with the edible oil to obtain an acidic mixture having pH of less than about 4;
b) mixing a base with the acidic mixture to obtain a reacted mixture having pH of about 6-9, wherein the mixing in steps a) and/or b) creates an emulsion that comprises at least about 60% of an aqueous phase by volume in droplet size between about 15 µm to about 45 µm in size;
c) mixing an enzyme selected from phospholipase A, phospholipase C, phosphatidyl-inositol specific phospholipase C, or a combination thereof; and
d) isolating the phospholipids.

Figure 2:
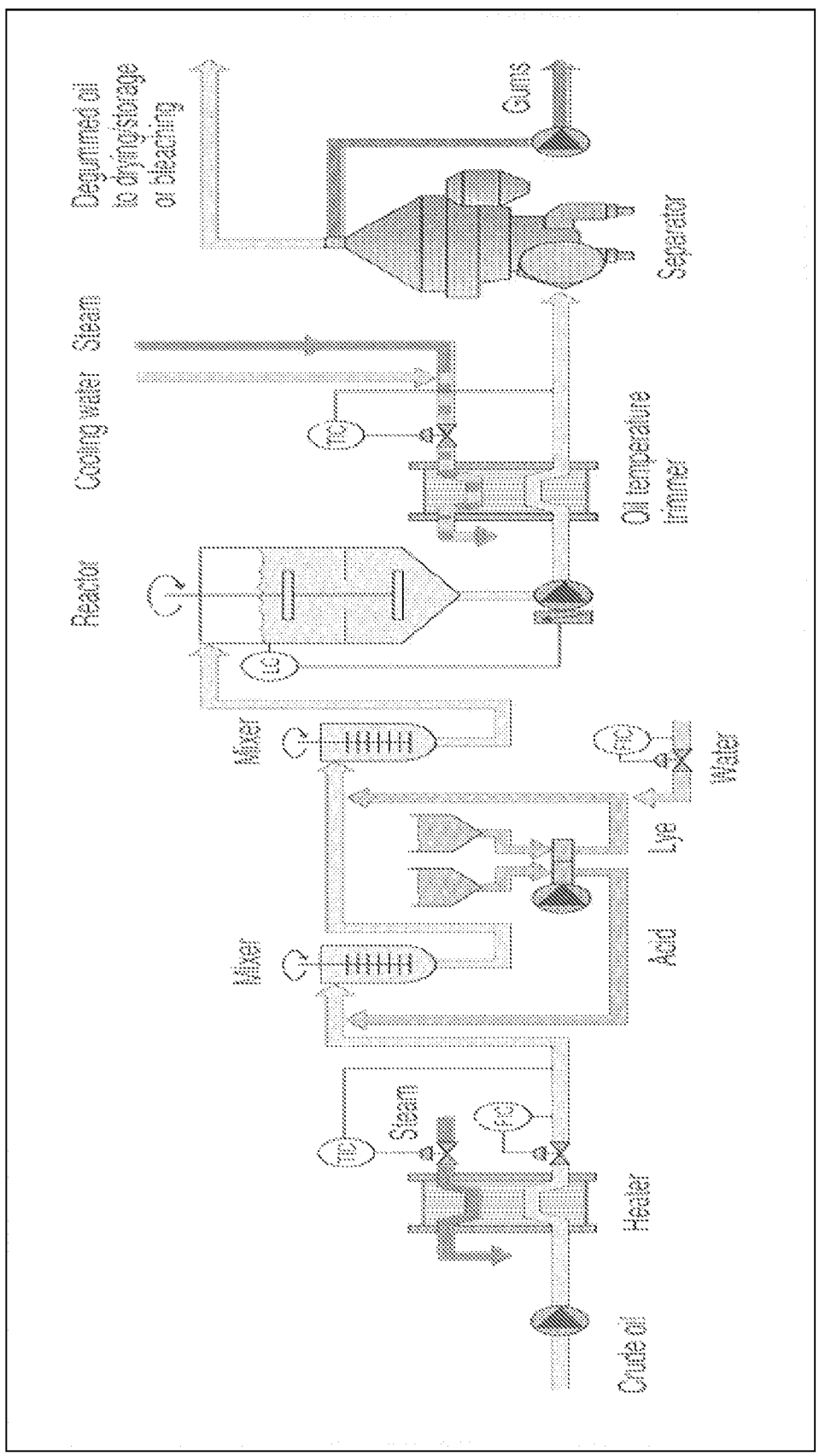
FIG. 2 schematically illustrates an exemplary degumming process of the invention for physically refined oils, as discussed in detail, below.

In various exemplary processes of the invention phosphorus levels are reduced low enough for physical refining. The separation process can result in potentially higher yield losses than caustic refining. Additionally, degumming processes may generate waste products that may not be sold as commercial lecithin, see, e.g., FIG. 2 for an exemplary degumming process for physically refined oils. Therefore, these processes have not achieved a significant share of the market and caustic refining processes continue to dominate the industry for rice bran, soy, canola and sunflower. Note however, that a phospholipase C enzyme employed in a special degumming process would decrease gum formation and return the diglyceride portion of the phospholipid back to the oil.

In one aspect, the invention provides methods using a PI-PLC of the invention in the gum fraction. In one aspect of this method, oil is added to the crude oil to create an emulsion that results in the movement of the phosphatidylcholine, phosphatidylethanolamine and phosphatidylinositol into the aqueous phase (water degumming). Following centrifugation, these phospholipids are major components of the aqueous gum fraction. The phospholipids in the gum fraction can be treated with phospholipase C or phospholipase D plus phosphatase (or other combinations, noted below) to generate diacylglycerol (DAG) and a phosphate ester. At this point, the DAG can be extracted from the other gum components and treated with a lipase under conditions suitable for the transesterification of the DAG to produce a desired triacylglycerol (structured lipid).

In another aspect, the majority of the 1,2-DAG can be converted to 1,3-DAG by increasing the pH of the gum following the PLC reaction, for example, by adding caustic. The 1,3-DAG can then be extracted from the gum and reacted with a lipase under the appropriate conditions to transesterify the 1,3-DAG at the sn2 position to create the desired structured triacylglycerol.

In alternative aspects, the fatty acids used in the transesterification reaction could come from a variety of sources including the free fatty acids found in the crude oil.

In one aspect, the phospholipids from water degumming are used in combination with a PLC of the invention to create structured lipids. The water-degummed oil can be exposed to a PLC and/or PLD (either or both can be enzymes of the invention) plus phosphatase or one of these combinations followed by PLA (can be an enzyme of the invention) to reduce the phosphorus to levels suitable for caustic or physical refining.

In alternative embodiments, combination of enzymes that can be used in the methods of the invention, including these degumming processes, include (where one, several or all of the enzymes in the combination comprise an enzyme of the instant invention):
PLC+PI-PLC+PLA (PLA added after completion of PLC reactions);
PLD+phosphatase+PI-PLC followed by PLA; or,
PLC or (PLC+PI-PLC)+PLA specific for phosphatidic acid (all enzymes added together or sequentially).

Caustic Refining

The invention provides processes using phospholipases (including enzymes of the invention) in caustic refining, where the enzymes are used as caustic refining aids. In alternative aspects, a PLC or PLD and/or a phosphatase are used in the processes as a drop-in, either before, during, or after a caustic neutralization refining process (either continuous or batch refining). The amount of enzyme added may vary according to the process. The water level used in the process can be low, e.g., about 0.5 to 5%. Alternatively, caustic is be added to the process multiple times. In addition, the process may be performed at different temperatures (25° C. to 70° C.), with different acids or caustics, and at varying pH (4-12). Concentrated solutions of caustic, e.g., more concentrated than the industrial standard of 11%, to decrease mass of gum can be used. In alternative aspects, the concentrated solution of caustic is between about 12% and 50% concentrated, e.g., about 20%, 30%, 40%, 50%, or 60% or more concentrated.

Figure 3:
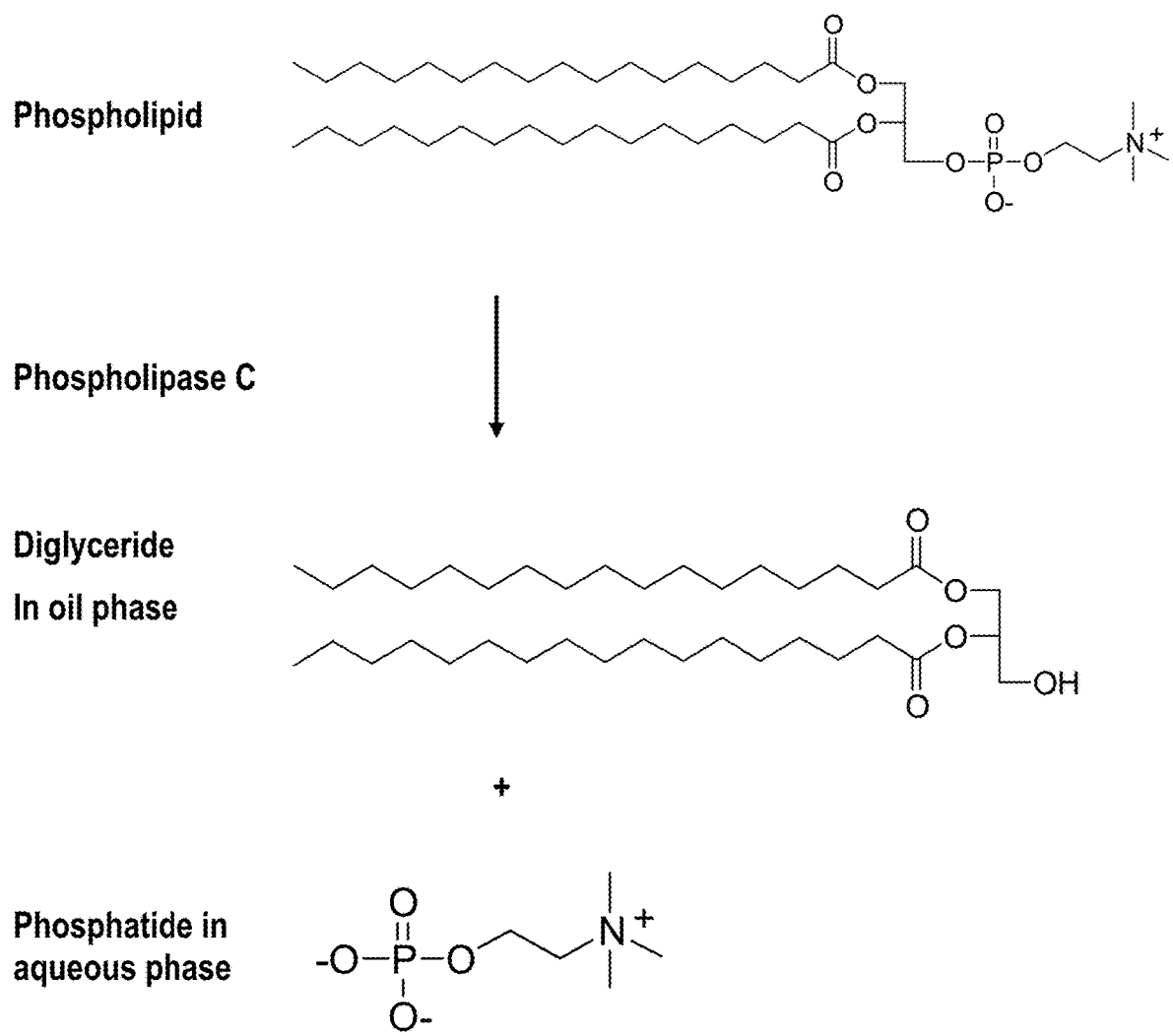
FIG. 3 schematically illustrates phosphatide hydrolysis with a phospholipase C of the invention, as discussed in detail, below.

In one aspect, a phospholipase C enzyme of the invention hydrolyzes a phosphatide at a glyceryl phosphoester bond to generate a diglyceride and water-soluble phosphate compound. The hydrolyzed phosphatide moves to the aqueous phase, leaving the diglyceride in the oil phase, as illustrated in FIG. 3. One objective of the PLC "Caustic Refining Aid" is to convert the phospholipid gums formed during neutralization into a diacylglycerol that will migrate back into the oil phase. In contrast, one objective of the "PLC Degumming Aid" is to reduce the phospholipids in crude oil to a phosphorus equivalent of less than 10 parts per million (ppm).

Acids that may be used in a caustic refining process include, but are not limited to, phosphoric, citric, ascorbic, sulfuric, fumaric, maleic, hydrochloric and/or acetic acids. Acids are used to hydrate non-hydratable phospholipids. Caustics that may be used include, but are not limited to, KOH— and NaOH. Caustics are used to neutralize free fatty acids. Alternatively, phospholipases, or more particularly a PLC or a PLD and a phosphatase, are used for purification of phytosterols from the gum/soapstock.

An alternate embodiment of the invention to add the phospholipase before caustic refining is to express the phospholipase in a plant. In another embodiment, the phospholipase is added during crushing of the plant, seeds or other plant part. Alternatively, the phospholipase is added following crushing, but prior to refining (i.e. in holding vessels). In addition, phospholipase is added as a refining pre-treatment, either with or without acid.

Another embodiment of the invention, already described, is to add the phospholipase during a caustic refining process. In this process, the levels of acid and caustic are varied depending on the level of phosphorus and the level of free fatty acids. In addition, broad temperature and pH ranges are used in the process, dependent upon the type of enzyme used.

Figure 5:
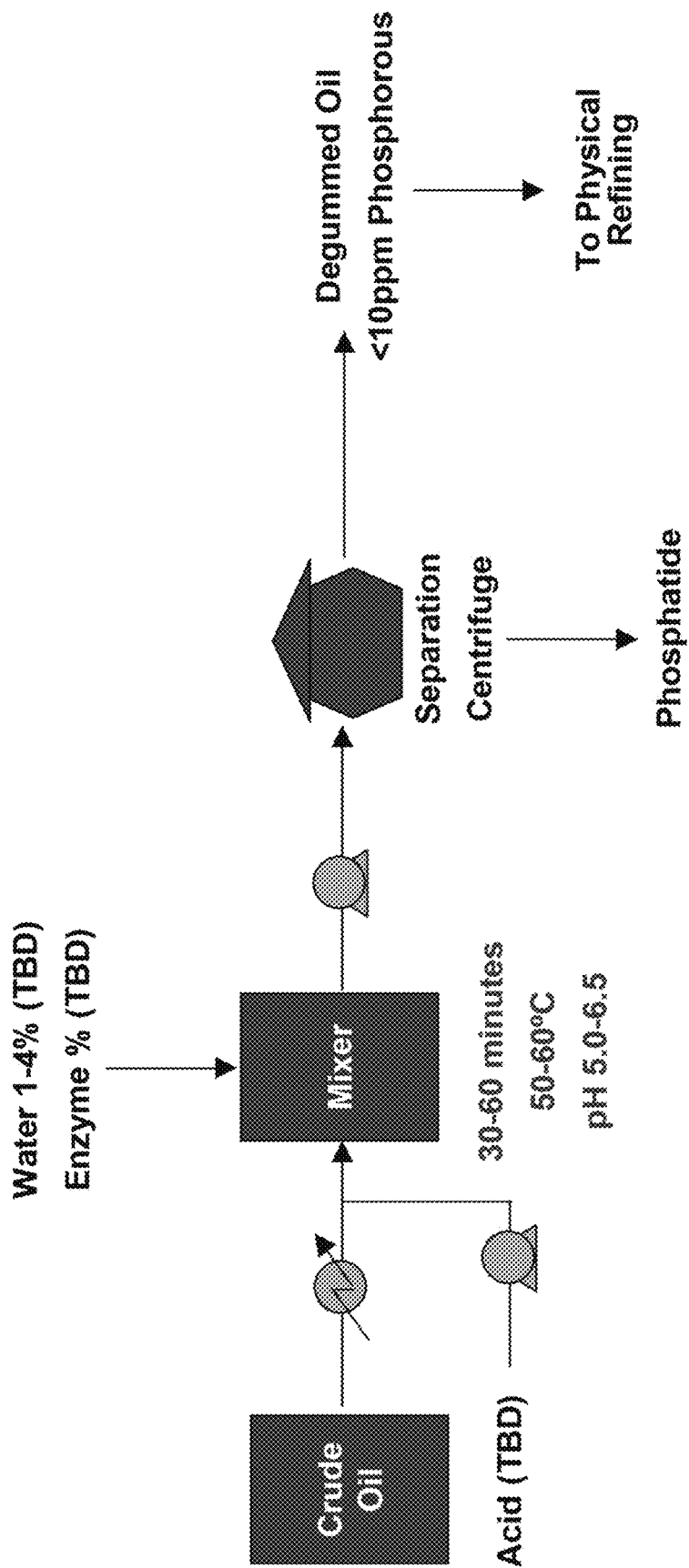
FIG. 5 schematically illustrates application of a phospholipase C of the invention as a degumming aid, as discussed in detail, below.

In another embodiment of the invention, the phospholipase is added after caustic refining (FIG. 5). In one instance, the phospholipase is added in an intense mixer or in a retention mixer, prior to separation. Alternatively, the phospholipase is added following the heat step. In another embodiment, the phospholipase is added in the centrifugation step. In an additional embodiment, the phospholipase is added to the soapstock. Alternatively, the phospholipase is added to the washwater. In another instance, the phospholipase is added during the bleaching and/or deodorizing steps.

Figure 4:
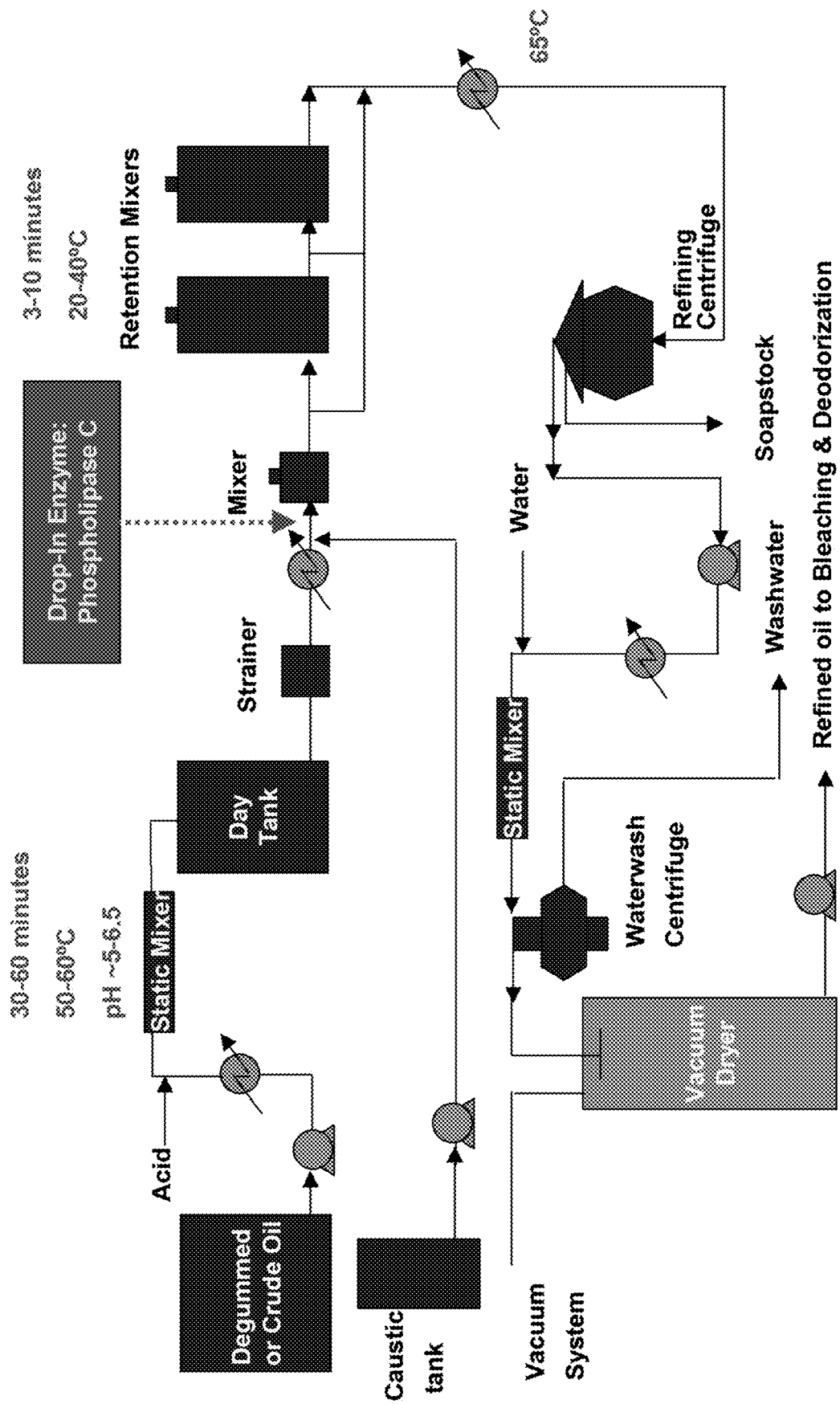
FIG. 4 schematically illustrates an exemplary caustic refining process of the invention, and illustrates an alternative embodiment comprising application of a phospholipase C of the invention as a "Caustic Refining Aid" (Long Mix Caustic Refining), as discussed in detail, below.
Figure 6:
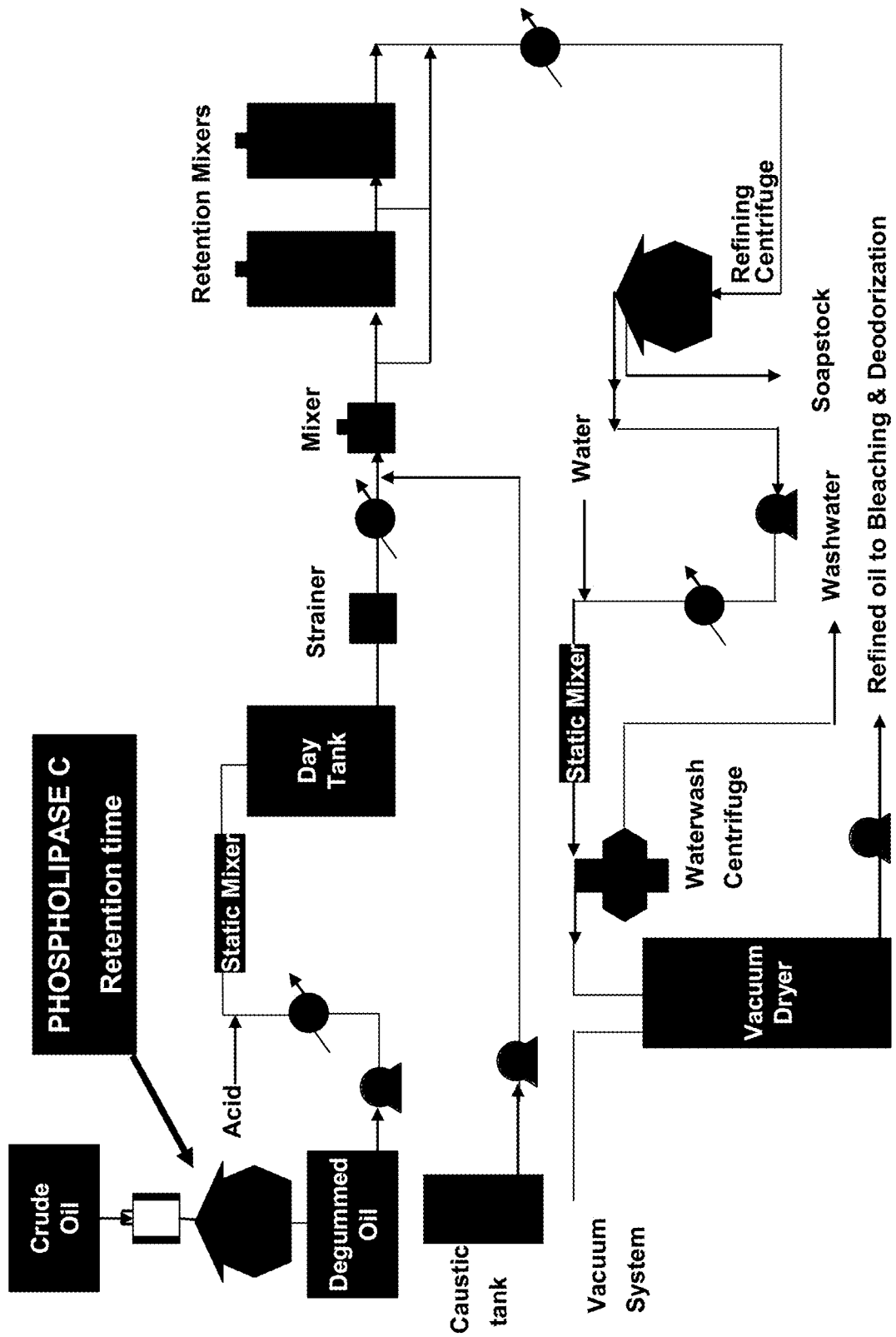
FIG. 6 schematically illustrates an exemplary caustic refining process of the invention, and illustrates an alternative embodiment comprising application of a phospholipase C of the invention as a "Caustic Refining Aid" (Long Mix Caustic Refining), as discussed in detail, below.
Figure 7:
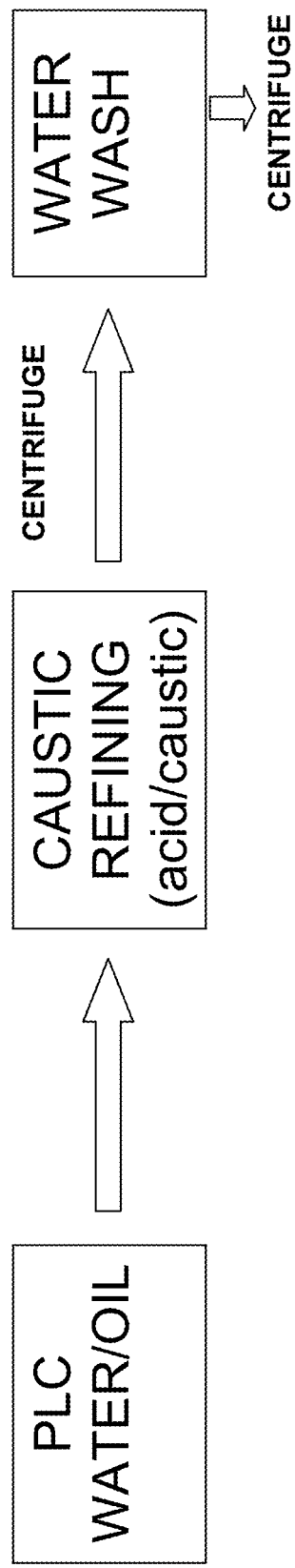
FIG. 7 illustrates another variation of methods of the invention where two centrifugation steps are used in the process, as discussed in detail, below.
Figure 8:
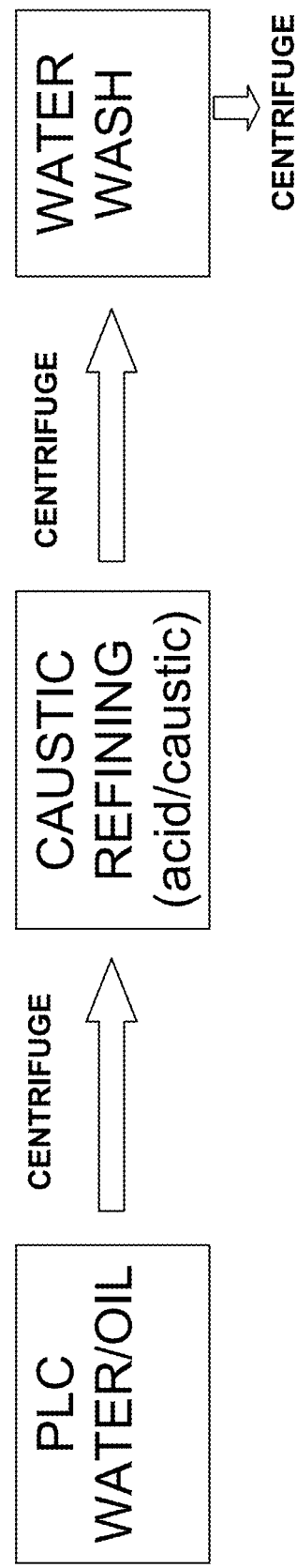
FIG. 8 illustrates another variation of methods of the invention where three centrifugation steps are used in the process, as discussed in detail, below.
Figure 9:
FIG. 9 illustrates another exemplary variation of this process using acid treatment and having a centrifugation step before a degumming step, as discussed in detail, below.

In one aspect, a phospholipase, e.g., a phospholipase C, enzyme of the invention will hydrolyze the phosphatide from both hydratable and non-hydratable phospholipids in neutralized crude and degummed oils before bleaching and deodorizing. Exemplary "caustic refining" processes of the invention are illustrated in FIG. 4 and FIG. 6. FIG. 4 includes exemplary times, temperature and pHs for static mixer (30 to 60 min, 50 to 60° C., pH 5 to 6.5) and retention mixer (3 to 10 min, 20 to 40° C.). The target enzyme can be applied as a drop-in product in the existing caustic neutralization process, as illustrated in FIG. 4. In this aspect, the enzyme will not be required to withstand extreme pH levels if it is added after the addition of caustic. As illustrated in FIG. 6 (an enzyme "front loading" exemplary process), any phospholipase, including, e.g., a phospholipase of the invention, such as a PLC, PI-PLC, PLB, PLA and/or PLC, can be used in a crude oil degumming process, as described, e.g., in Bailey's Industrial Oil & Fat Products v.4 (ed. Y. H. Hui). FIG. 7 and FIG. 8 illustrate variations of methods of the invention where two or three centrifugation steps, respectively, are used in the process, which can be used to process any oil, e.g., a vegetable oil such as crude soy oil, as shown in the figure. The exemplary method of FIG. 8 has a centrifugation step before caustic refining (in addition to a centrifugation step after caustic refining and before the water wash, and, after the water wash), while the exemplary method of FIG. 7 does not have a centrifugation step before caustic refining. FIG. 9 illustrates another exemplary variation of this process using acid treatment and having a centrifugation step before a degumming step; this exemplary process can be used to process any oil, e.g., a vegetable oil such as crude soy oil, as shown in the figure.

In one aspect, a phospholipase of the invention enables phosphorus to be removed to the low levels acceptable in physical refining. In one aspect, a PLC of the invention will hydrolyze the phosphatide from both hydratable and non-hydratable phospholipids in crude oils before bleaching and deodorizing. The target enzyme can be applied as a drop-in product in an existing degumming operation, see, e.g., FIG. 5. Given sub-optimal mixing in commercial equipment, it is likely that acid will be required to bring the non-hydratable phospholipids in contact with the enzyme at the oil/water interface. Therefore, in one aspect, an acid-stable PLC of the invention is used.

In one aspect, a PLC Degumming Aid process of the invention can eliminate losses in one, or all three, areas noted in Table 4. Losses associated in a PLC process can be estimated to be about 0.8% versus 5.2% on a mass basis due to removal of the phosphatide.

TABLE 4

Losses Addressed by PLC Products

|  | Caustic Refining Aid | Degumming Aid |
|---|---|---|
| 1) Oil lost in gum formation & separation | 2.1% | X | X |
| 2) Saponified oil in caustic addition | 3.1% |  | X |

TABLE 4-continued

Losses Addressed by PLC Products

|  | Caustic Refining Aid | Degumming Aid |
|---|---|---|
| 3) Oil trapped in clay in bleaching* | <1.0% | X | X |
| Total Yield Loss | ~5.2% | ~2.1% | ~5.2% |

Additional potential benefits of this process of the invention include the following:
  Reduced adsorbents—less adsorbents required with lower (<5 ppm) phosphorus
  Lower chemical usage—less chemical and processing costs associated with hydration of non-hydratable phospholipids
  Lower waste generation—less water required to remove phosphorus from oil Oils processed (e.g., "degummed") by the methods of the invention include plant oilseeds, e.g., soybean oil, rapeseed oil, rice bran oil and sunflower oil. In one aspect, the "PLC Caustic Refining Aid" of the invention can save 1.2% over existing caustic refining processes. The refining aid application addresses soy oil that has been degummed for lecithin and these are also excluded from the value/load calculations.

Performance targets of the processes of the invention can vary according to the applications and more specifically to the point of enzyme addition, see Table 5.

TABLE 5

Performance Targets by Application

|  | Caustic Refining Aid | Degumming Aid |
|---|---|---|
| Incoming Oil Phosphorus Levels | <200 ppm* | 600-1,400 ppm |
| Final Oil Phosphorus Levels | <10 ppm† | <10 ppm |
| Hydratable & Non-hydratable gums | Yes | Yes |
| Residence Time | 3-10 minutes | 30 minutes‡ |
| Liquid Formulation | Yes | Yes |
| Target pH | 8-10‡‡‡ | 5.0-5.5‡‡ |
| Target Temperature | 20-40° C. | ~50-60° C. |
| Water Content | <5% | 1-1.25% |
| Enzyme Formulation Purity | No lipase/protease[1] | No lipase/protease |
| Other Key Requirements | Removal of Fe | Removal of Fe |

*Water degummed oil
†Target levels achieved in upstream caustic neutralization step but must be maintained
‡1-2 hours existing
‡‡Acid degumming will require an enzyme that is stable in much more acidic conditions: pH at 2.3 for citric acid at 5%. (~Roehm USPN 6,001,640).
‡‡‡The pH of neutralized oil is NOT neutral. Testing at POS indicates that the pH will be in the alkaline range from 6.5-10 (Dec. 9, 2002). Typical pH range needs to be determined.

Other processes that can be used with a phospholipase of the invention, e.g., a phospholipase $A_1$ can convert non-hydratable native phospholipids to a hydratable form. In one aspect, the enzyme is sensitive to heat. This may be desirable, since heating the oil can destroy the enzyme. However, the degumming reaction must be adjusted to pH 4-5 and 60° C. to accommodate this enzyme. At 300 Units/kg oil saturation dosage, this exemplary process is successful at taking previously water-degummed oil phosphorus content down to ≤10 ppm P. Advantages can be decreased $H_2O$ content and resultant savings in usage, handling and waste. Table 6 lists exemplary applications for industrial uses for enzymes of the invention:

TABLE 6

| Exemplary Application | Caustic Refining Aid | Degumming Aid |
|---|---|---|
| Soy oil w/ lecithin production | X | |
| Chemical refined soy oil, Sunflower oil, Canola oil | X | X |
| Low phosphatide oils (e.g. palm) | | X |

In addition to these various "degumming" processes, the phospholipases of the invention can be used in any vegetable oil processing step. For example, phospholipase enzymes of the invention can be used in place of PLA, e.g., phospholipase A2, in any vegetable oil processing step. Oils that are "processed" or "degummed" in the methods of the invention include soybean oils, rapeseed oils, corn oils, oil from palm kernels, canola oils, sunflower oils, sesame oils, peanut oils, rice bran oil and the like. The main products from this process include triglycerides.

In one exemplary process, when the enzyme is added to and reacted with a crude oil, the amount of phospholipase employed is about 10-10,000 units, or, alternatively, about, 100-2,000 units, per 1 kg of crude oil. The enzyme treatment is conducted for 5 min to 10 hours at a temperature of 30° C. to 90° C., or, alternatively, about, 40° C. to 70° C. The conditions may vary depending on the optimum temperature of the enzyme. The amount of water added to dissolve the enzyme is 5-1,000 wt. parts per 100 wt. parts of crude oil, or, alternatively, about, 10 to 200 wt. parts per 100 wt. parts of crude oil.

Upon completion of such enzyme treatment, the enzyme liquid is separated with an appropriate means such as a centrifugal separator and the processed oil is obtained. Phosphorus-containing compounds produced by enzyme decomposition of gummy substances in such a process are practically all transferred into the aqueous phase and removed from the oil phase. Upon completion of the enzyme treatment, if necessary, the processed oil can be additionally washed with water or organic or inorganic acid such as, e.g., acetic acid, citric acid, phosphoric acid, succinic acid, and equivalent acids, or with salt solutions.

In one exemplary process for ultra-filtration degumming, the enzyme is bound to a filter or the enzyme is added to an oil prior to filtration or the enzyme is used to periodically clean filters.

In one exemplary process for a phospholipase-mediated physical refining aid, water and enzyme are added to crude oil (e.g., crude vegetable oil). In one aspect, a PLC or a PLD of the invention and a phosphatase are used in the process. In phospholipase-mediated physical refining, the water level can be low, i.e. 0.5-5% and the process time should be short (less than 2 hours, or, less than 60 minutes, or, less than 30 minutes, or, less than 15 minutes, or, less than 5 minutes). The process can be run at different temperatures (25° C. to 70° C.), using different acids and/or caustics, at different pHs (e.g., 3-10).

In alternate aspects, water degumming is performed first to collect lecithin by centrifugation and then PLC or PLC and PLA of the invention is added to remove non-hydratable phospholipids (the process should be performed under low water concentration). In another aspect, water degumming of crude oil to less than 10 ppm (edible oils) and subsequent physical refining (less than 50 ppm for biodiesel) is performed. In one aspect, an emulsifier is added and/or the crude oil is subjected to an intense mixer to promote mixing. Alternatively, an emulsion-breaker is added and/or the crude oil is heated to promote separation of the aqueous phase. In another aspect, an acid is added to promote hydration of non-hydratable phospholipids. Additionally, phospholipases can be used to mediate purification of phytosterols from the gum/soapstock.

In one aspect, the invention provides compositions and methods (which can comprise use of phospholipases of the invention) for oil degumming comprising using varying amounts of acid and base without making soapstock. Using this aspect of the invention for oil degumming, acid (including phosphoric and/or citric) can be used to hydrate non-hydratable phospholipids in high phosphorus oils (including soybean, canola, and sunflower). Once the phospholipids are hydrated, the pH of the aqueous phase can be raised using caustic addition: the amount of caustic added can create a favorable pH for enzyme activity but will not result in the formation of a significant soapstock fraction in the oil. Because a soapstock is not formed, the free fatty acids in the oil can be removed downstream, following the degumming step, during bleaching and deodorization.

Enzymes of the invention are used to improve oil extraction and oil degumming (e.g., vegetable oils). In one aspect, a PLC of the invention and at least one plant cell wall degrader (e.g., a cellulase, a hemicellulase or the like, to soften walls and increase yield at extraction) is used in a process of the invention. In this exemplary approach to using enzymes of the invention to improve oil extraction and oil degumming, a phospholipase C of the invention as well as other hydrolases (e.g., a cellulase, a hemicellulase, an esterase, a protease and/or a phosphatase) are used during the crushing steps associated with oil production (including but not limited to soybean, canola, sunflower, rice bran oil). By using enzymes prior to or in place of solvent extraction, it is possible to increase oil yield and reduce the amount of hydratable and non-hydratable phospholipids in the crude oil. The reduction in non-hydratable phospholipids may result from conversion of potentially non-hydratable phospholipids to diacylglycerol and corresponding phosphate-ester prior to complexation with calcium or magnesium. The overall reduction of phospholipids in the crude oil will result in improved yields during refining with the potential for eliminating the requirement for a separate degumming step prior to bleaching and deodorization.

In one aspect, the invention provides processes using a phospholipase of the invention (e.g., a phospholipase-specific phosphohydrolase of the invention), or another phospholipase, in a modified "organic refining process," which can comprise addition of the enzyme (e.g., a PI-PLC) in a citric acid holding tank.

The enzymes of the invention can be used in any oil processing method, e.g., degumming or equivalent processes. For example, the enzymes of the invention can be used in processes as described in U.S. Pat. Nos. 5,558,781; 5,264,367; 6,001,640. The process described in U.S. Pat. No. 5,558,781 uses either phospholipase A1, A2 or B, essentially breaking down lecithin in the oil that behaves as an emulsifier.

The enzymes and methods of the invention can be used in processes for the reduction of phosphorus-containing components in edible oils comprising a high amount of non-hydratable phosphorus by using of a phospholipase of the invention, e.g., a polypeptide having a phospholipase A and/or B activity, as described, e.g., in EP Patent Number: EP 0869167. In one aspect, the edible oil is a crude oil, a so-called "non-degummed oil." In one aspect, the method treat a non-degummed oil, including pressed oils or extracted oils, or a mixture thereof, from, e.g., rapeseed, soybean, sesame, peanut, corn, rice bran or sunflower. The phosphatide content in a crude oil can vary from 0.5 to 3% w/w corresponding to a phosphorus content in the range of 200 to 1200 ppm, or, in the range of 250 to 1200 ppm. Apart from the phosphatides, the crude oil can also contain small concentrations of carbohydrates, sugar compounds and metal/phosphatide acid complexes of Ca, Mg and Fe. In one aspect, the process comprises treatment of a phospholipid or lysophospholipid with the phospholipase of the invention so as to hydrolyze fatty acyl groups. In one aspect, the phospholipid or lysophospholipid comprises lecithin or lysolecithin. In one aspect of the process the edible oil has a phosphorus content from between about 50 to 250 ppm, and the process comprises treating the oil with a phospholipase of the invention so as to hydrolyze a major part of the phospholipid and separating an aqueous phase containing the hydrolyzed phospholipid from the oil. In one aspect, prior to the enzymatic degumming process the oil is water-degummed. In one aspect, the methods provide for the production of an animal feed comprising mixing the phospholipase of the invention with feed substances and at least one phospholipid.

The enzymes and methods of the invention can be used in processes of oil degumming as described, e.g., in WO 98/18912. The phospholipases of the invention can be used to reduce the content of phospholipid in an edible oil. The process can comprise treating the oil with a phospholipase of the invention to hydrolyze a major part of the phospholipid and separating an aqueous phase containing the hydrolyzed phospholipid from the oil. This process is applicable to the purification of any edible oil, which contains a phospholipid, e.g. vegetable oils, such as soybean oil, rice bran oil, rapeseed oil and sunflower oil, fish oils, algae and animal oils and the like. Prior to the enzymatic treatment, the vegetable oil is preferably pretreated to remove slime (mucilage), e.g. by wet refining. The oil can contain between about 50 to 250 ppm, or between 50 to about 1500 ppm, or more, of phosphorus, as phospholipid at the start of the treatment with phospholipase, and the process of the invention can reduce this value to below between about 5 to 10 ppm.

The enzymes of the invention can be used in processes as described in JP Application No.: H5-132283, filed Apr. 25, 1993, which comprises a process for the purification of oils and fats comprising a step of converting phospholipids present in the oils and fats into water-soluble substances containing phosphoric acid groups and removing them as water-soluble substances. An enzyme action is used for the conversion into water-soluble substances. An enzyme having a phospholipase C activity is preferably used as the enzyme.

The enzymes of the invention can be used in processes as described as the "Organic Refining Process," (ORP) (IPH, Omaha, Nebr.) which is a method of refining seed oils. ORP may have advantages over traditional chemical refining, including improved refined oil yield, value added co-products, reduced capital costs and lower environmental costs.

The enzymes of the invention can be used in processes for the treatment of an oil or fat, animal or vegetal, raw, semi-processed or refined, comprising adding to such oil or fat at least one enzyme of the invention that allows hydrolyzing and/or depolymerizing the non-glyceridic compounds contained in the oil, as described, e.g., in EP Application number: 82870032.8. Exemplary methods of the invention for hydrolysis and/or depolymerization of non-glyceridic compounds in oils are:

1) The addition and mixture in oils and fats of an enzyme of the invention or enzyme complexes previously dissolved in a small quantity of appropriate solvent (for example water). A certain number of solvents are possible, but a non-toxic and suitable solvent for the enzyme is chosen. This addition may be done in processes with successive loads, as well as in continuous processes. The quantity of enzyme(s) necessary to be added to oils and fats, according to this process, may range, depending on the enzymes and the products to be processed, from between about 5 to 400 ppm, or between about 20 to 400 ppm; e.g., 0.005 kg to 0.4 kg of enzyme for 1000 kg of oil or fat, and preferably from 5 to 100 ppm, i.e., from 0.005 to 0.1 kg of enzyme for 1000 kg of oil, these values being understood to be for concentrated enzymes, i.e., without diluent or solvent.

2) Passage of the oil or fat through a fixed or insoluble filtering bed of enzyme(s) of the invention on solid or semi-solid supports, preferably presenting a porous or fibrous structure. In this technique, the enzymes are trapped in the micro-cavities of the porous or fibrous structure of the supports. These consist, for example, of resins or synthetic polymers, cellulose carbonates, gels such as agarose, filaments of polymers or copolymers with porous structure, trapping small droplets of enzyme in solution in their cavities. Concerning the enzyme concentration, it is possible to go up to the saturation of the supports.

3) Dispersion of the oils and fats in the form of fine droplets, in a diluted enzymatic solution, in alternative aspects containing between about 0.05 to 4%, or containing between about 0.2 to 4%, in volume of an enzyme of the invention. This technique is described, e.g., in Belgian patent No. 595,219. A cylindrical column with a height of several meters, with conical lid, is filled with a diluted enzymatic solution. For this purpose, a solvent that is non-toxic and non-miscible in the oil or fat to be processed, preferably water, is chosen. The bottom of the column is equipped with a distribution system in which the oil or fat is continuously injected in an extremely divided form (approximately 10,000 flux per m$^2$). Thus an infinite number of droplets of oil or fat are formed, which slowly rise in the solution of enzymes and meet at the surface, to be evacuated continuously at the top of the conical lid of the reactor.

Palm oil can be pre-treated before treatment with an enzyme of the invention. For example, about 30 kg of raw palm oil is heated to +50° C. 1% solutions were prepared in distilled water with cellulases and pectinases. 600 g of each of these was added to aqueous solutions of the oil under strong agitation for a few minutes. The oil is then kept at +50° C. under moderate agitation, for a total reaction time of two hours. Then, temperature is raised to +90° C. to deactivate the enzymes and prepare the mixture for filtration and further processing. The oil is dried under vacuum and filtered with a filtering aid.

The enzymes of the invention can be used in processes as described in EP patent EP 0 513 709 B2. For example, the invention provides a process for the reduction of the content process for the reduction of the content of phosphorus-containing components in animal and vegetable oils by enzymatic decomposition using a phospholipase of the invention. In alternative aspects, predemucilaginated animal and vegetable oil with a phosphorus content of between about of 50 to 1500 ppm, or, between about 50 to 250 ppm, is agitated with an organic carboxylic acid and the pH value of the resulting mixture set to between about pH 4 to pH 6, an enzyme solution which contains phospholipase $A_1$, $A_2$, or B of the invention is added to the mixture in a mixing vessel under turbulent stirring and with the formation of fine droplets, where an emulsion with 0.5 to 5% by weight relative to the oil is formed, said emulsion being conducted through at least one subsequent reaction vessel under turbulent motion during a reaction time of 0.1 to 10 hours at temperatures in the range of 20 to 80° C. and where the treated oil, after separation of the aqueous solution, has a phosphorus content under 5 ppm.

The organic refining process is applicable to both crude and degummed oil. The process uses inline addition of an organic acid under controlled process conditions, in conjunction with conventional centrifugal separation. The water separated naturally from the vegetable oil phospholipids ("VOP") is recycled and reused. The total water usage can be substantially reduced as a result of the Organic Refining Process.

The phospholipases and methods of the invention can also be used in the enzymatic treatment of edible oils, as described, e.g., in U.S. Pat. No. 6,162,623. In this exemplary methods, the invention provides an amphiphilic enzyme. It can be immobilized, e.g., by preparing an emulsion containing a continuous hydrophobic phase and a dispersed aqueous phase containing the enzyme and a carrier for the enzyme and removing water from the dispersed phase until this phase turns into solid enzyme coated particles. The enzyme can be a lipase. The immobilized lipase can be used for reactions catalyzed by lipase such as interesterification of mono-, di- or triglycerides, de-acidification of a triglyceride oil, or removal of phospholipids from a triglyceride oil when the lipase is a phospholipase. The aqueous phase may contain a fermentation liquid, an edible triglyceride oil may be the hydrophobic phase, and carriers include sugars, starch, dextran, water soluble cellulose derivatives and fermentation residues. This exemplary method can be used to process triglycerides, diglycerides, monoglycerides, glycerol, phospholipids, glycolipids or fatty acids, which may be in the hydrophobic phase. In one aspect, the process for the removal of phospholipids from triglyceride oil comprising mixing a triglyceride oil containing phospholipids with a preparation containing a phospholipase of the invention; hydrolyzing the phospholipids to lysophospholipid; separating the hydrolyzed phospholipids from the oil, wherein the phospholipase is an immobilized phospholipase.

The phospholipases and methods of the invention can also be used in the enzymatic treatment of edible oils, as described, e.g., in U.S. Pat. No. 6,127,137. This exemplary method hydrolyzes both fatty acyl groups in intact phospholipid. The phospholipase of the invention used in this exemplary method has no lipase activity and is active at very low pH. These properties make it very suitable for use in oil degumming, as enzymatic and alkaline hydrolysis (saponification) of the oil can both be suppressed. In one aspect, the invention provides a process for hydrolyzing fatty acyl groups in a phospholipid or lysophospholipid comprising treating the phospholipid or lysophospholipid with the phospholipase that hydrolyzes both fatty acyl groups in a phospholipid and is essentially free of lipase activity. In one aspect, the phospholipase of the invention has a temperature optimum at about 50° C., measured at pH 3 to pH 4 for 10 minutes, and a pH optimum of about pH 3, measured at 40° C. for about 10 minutes. In one aspect, the phospholipid or lysophospholipid comprises lecithin or lysolecithin. In one aspect, after hydrolyzing a major part of the phospholipid, an aqueous phase containing the hydrolyzed phospholipid is separated from the oil. In one aspect, the invention provides a process for removing phospholipid from an edible oil, comprising treating the oil at pH 1.5 to 3 with a dispersion of an aqueous solution of the phospholipase of the invention, and separating an aqueous phase containing the hydrolyzed phospholipid from the oil. In one aspect, the oil is treated to remove mucilage prior to the treatment with the phospholipase. In one aspect, the oil prior to the treatment with the phospholipase contains the phospholipid in an amount corresponding to 50 to 250 ppm of phosphorus. In one aspect, the treatment with phospholipase is done at 30° C. to 45° C. for 1 to 12 hours at a phospholipase dosage of 0.1 to 10 mg/l in the presence of 0.5 to 5% of water.

The phospholipases and methods of the invention can also be used in the enzymatic treatment of edible oils, as described, e.g., in U.S. Pat. No. 6,025,171. In this exemplary methods, enzymes of the invention are immobilized by preparing an emulsion containing a continuous hydrophobic phase, such as a triglyceride oil, and a dispersed aqueous phase containing an amphiphilic enzyme, such as lipase or a phospholipase of the invention, and carrier material that is partly dissolved and partly undissolved in the aqueous phase, and removing water from the aqueous phase until the phase turns into solid enzyme coated carrier particles. The undissolved part of the carrier material may be a material that is insoluble in water and oil, or a water soluble material in undissolved form because the aqueous phase is already saturated with the water soluble material. The aqueous phase may be formed with a crude lipase fermentation liquid containing fermentation residues and biomass that can serve as carrier materials. Immobilized lipase is useful for ester re-arrangement and de-acidification in oils. After a reaction, the immobilized enzyme can be regenerated for a subsequent reaction by adding water to obtain partial dissolution of the carrier, and with the resultant enzyme and carrier-containing aqueous phase dispersed in a hydrophobic phase evaporating water to again form enzyme coated carrier particles.

The phospholipases and methods of the invention can also be used in the enzymatic treatment of edible oils, as described, e.g., in U.S. Pat. No. 6,143,545. This exemplary method is used for reducing the content of phosphorus containing components in an edible oil comprising a high amount of non-hydratable phosphorus content using a phospholipase of the invention. In one aspect, the method is used to reduce the content of phosphorus containing components in an edible oil having a non-hydratable phosphorus content of at least 50 ppm measured by pre-treating the edible oil, at 60° C., by addition of a solution comprising citric acid monohydrate in water (added water vs. oil equals 4.8% w/w; (citric acid) in water phase=106 mM, in water/oil emulsion=4.6 mM) for 30 minutes; transferring 10 ml of the pre-treated water in oil emulsion to a tube; heating the emulsion in a boiling water bath for 30 minutes; centrifuging at 5000 rpm for 10 minutes, transferring about 8 ml of the upper (oil) phase to a new tube and leaving it to settle for 24 hours; and drawing 2 g from the upper clear phase for measurement of the non-hydratable phosphorus content (ppm) in the edible oil. The method also can comprise contacting an oil at a pH from about pH 5 to 8 with an aqueous solution of a phospholipase A or B of the invention (e.g., PLA1, PLA2, or a PLB), which solution is emulsified in the oil until the phosphorus content of the oil is reduced to less than 11 ppm, and then separating the aqueous phase from the treated oil.

The phospholipases and methods of the invention can also be used in the enzymatic treatment of edible oils, as described, e.g., in U.S. Pat. No. 5,532,163. The invention provides processes for the refining of oil and fat by which phospholipids in the oil and fat to be treated can be decomposed and removed efficiently. In one aspect, the invention provides a process for the refining of oil and fat which comprises reacting, in an emulsion, the oil and fat with an enzyme of the invention, e.g., an enzyme having an activity to decompose glycerol-fatty acid ester bonds in glycerophospholipids (e.g., a PLA2 of the invention); and another process in which the enzyme-treated oil and fat is washed with water or an acidic aqueous solution. In one aspect, the acidic aqueous solution to be used in the washing step is a solution of at least one acid, e.g., citric acid, acetic acid, phosphoric acid and salts thereof. In one aspect, the emulsified condition is formed using 30 weight parts or more of water per 100 weight parts of the oil and fat. Since oil and fat can be purified without employing the conventional alkali refining step, generation of washing waste water and industrial waste can be reduced. In addition, the recovery yield of oil is improved because loss of neutral oil and fat due to their inclusion in these wastes does not occur in the inventive process. In one aspect, the invention provides a process for refining oil and fat containing about 100 to 10,000 ppm of phospholipids which comprises: reacting, in an emulsified condition, said oil and fat with an enzyme of the invention having activity to decompose glycerol-fatty acid ester bonds in glycerophospholipids. In one aspect, the invention provides processes for refining oil and fat containing about 100 to 10,000 ppm of phospholipids which comprises reacting, in an emulsified condition, oil and fat with an enzyme of the invention having activity to decompose glycerol-fatty acid ester bonds in glycerophospholipids; and subsequently washing the treated oil and fat with a washing water.

The phospholipases and methods of the invention can also be used in the enzymatic treatment of edible oils, as described, e.g., in U.S. Pat. No. 5,264,367. The content of phosphorus-containing components and the iron content of an edible vegetable or animal oil, such as an oil, e.g., soybean oil, which has been wet-refined to remove mucilage, are reduced by enzymatic decomposition by contacting the oil with an aqueous solution of an enzyme of the invention, e.g., a phospholipase A1, A2, or B, and then separating the aqueous phase from the treated oil. In one aspect, the invention provides an enzymatic method for decreasing the content of phosphorus- and iron-containing components in oils, which have been refined to remove mucilage. An oil, which has been refined to remove mucilage, can be treated with an enzyme of the invention, e.g., phospholipase C, A1, A2, or B. Phosphorus contents below 5 ppm and iron contents below 1 ppm can be achieved. The low iron content can be advantageous for the stability of the oil.

The phospholipases and methods of the invention can also be used for preparing transesterified oils, as described, e.g., in U.S. Pat. No. 5,288,619. The invention provides methods for enzymatic transesterification for preparing a margarine oil having both low trans-acid and low intermediate chain fatty acid content. The method includes the steps of providing a transesterification reaction mixture containing a stearic acid source material and an edible liquid vegetable oil, transesterifying the stearic acid source material and the vegetable oil using a 1-, 3-positionally specific lipase, and then finally hydrogenating the fatty acid mixture to provide a recycle stearic acid source material for a recyclic reaction with the vegetable oil. The invention also provides a counter-current method for preparing a transesterified oil. The method includes the steps of providing a transesterification reaction zone containing a 1-, 3-positionally specific lipase, introducing a vegetable oil into the transesterification zone, introducing a stearic acid source material, conducting a supercritical gas or subcritical liquefied gas counter-current fluid, carrying out a transesterification reaction of the triglyceride stream with the stearic acid or stearic acid monoester stream in the reaction zone, withdrawing a transesterified triglyceride margarine oil stream, withdrawing a counter-current fluid phase, hydrogenating the transesterified stearic acid or stearic acid monoester to provide a hydrogenated recycle stearic acid source material, and introducing the hydrogenated recycle stearic acid source material into the reaction zone.

In one aspect, the highly unsaturated phospholipid compound may be converted into a triglyceride by appropriate use of a phospholipase C of the invention to remove the phosphate group in the sn-3 position, followed by 1,3 lipase acyl ester synthesis. The 2-substituted phospholipid may be used as a functional food ingredient directly, or may be subsequently selectively hydrolyzed in reactor 160 using an immobilized phospholipase C of the invention to produce a 1-diglyceride, followed by enzymatic esterification as described herein to produce a triglyceride product having a 2-substituted polyunsaturated fatty acid component.

The phospholipases and methods of the invention can also be used in a vegetable oil enzymatic degumming process as described, e.g., in U.S. Pat. No. 6,001,640. This method of the invention comprises a degumming step in the production of edible oils. Vegetable oils from which hydratable phosphatides have been eliminated by a previous aqueous degumming process are freed from non-hydratable phosphatides by enzymatic treatment using a phospholipase of the invention. The process can be gentle, economical and environment-friendly. Phospholipases that only hydrolyze lysolecithin, but not lecithin, are used in this degumming process.

In one aspect, to allow the enzyme of the invention to act, both phases, the oil phase and the aqueous phase that contain the enzyme, must be intimately mixed. It may not be sufficient to merely stir them. Good dispersion of the enzyme in the oil is aided if it is dissolved in a small amount of water, e.g., 0.5-5 weight-% (relative to the oil), and emulsified in the oil in this form, to form droplets of less than 10 micrometers in diameter (weight average). The droplets can be smaller than 1 micrometer. Turbulent stirring can be done with radial velocities above 100 cm/sec. The oil also can be circulated in the reactor using an external rotary pump. The aqueous phase containing the enzyme can also be finely dispersed by means of ultrasound action. A dispersion apparatus can be used.

The enzymatic reaction probably takes place at the border surface between the oil phase and the aqueous phase. It is the goal of all these measures for mixing to create the greatest possible surface for the aqueous phase which contains the enzyme. The addition of surfactants increases the microdispersion of the aqueous phase. In some cases, therefore, surfactants with HLB values above 9, such as Na-dodecyl sulfate, are added to the enzyme solution, as described, e.g., in EP-A 0 513 709. A similar effective method for improving emulsification is the addition of lysolecithin. The amounts added can lie in the range of 0.001% to 1%, with reference to the oil. The temperature during enzyme treatment is not critical. Temperatures between 20° C. and 80° C. can be used, but the latter can only be applied for a short time. In this aspect, a phospholipase of the invention having a good temperature and/or low pH tolerance is used. Application temperatures of between 30° C. and 50° C. are optimal. The treatment period depends on the temperature and can be kept shorter with an increasing temperature. Times of 0.1 to 10 hours, or, 1 to 5 hours are generally sufficient. The reaction takes place in a degumming reactor, which can be divided into stages, as described, e.g., in DE-A 43 39 556. Therefore continuous operation is possible, along with batch operation. The reaction can be carried out in different temperature stages. For example, incubation can take place for 3 hours at 40° C., then for 1 hour at 60° C. If the reaction proceeds in stages, this also opens up the possibility of adjusting different pH values in the individual stages. For example, in the first stage the pH of the solution can be adjusted to 7, for example, and in a second stage to 2.5, by adding citric acid. In at least one stage, however, the pH of the enzyme solution must be below 4, or, below 3. If the pH was subsequently adjusted below this level, a deterioration of effect may be found. Therefore the citric acid can be added to the enzyme solution before the latter is mixed into the oil.

After completion of the enzyme treatment, the enzyme solution, together with the decomposition products of the NHP contained in it, can be separated from the oil phase, in batches or continuously, e.g., by means of centrifugation. Since the enzymes are characterized by a high level of stability and the amount of the decomposition products contained in the solution is slight (they may precipitate as sludge) the same aqueous enzyme phase can be used several times. There is also the possibility of freeing the enzyme of the sludge, see, e.g., DE-A 43 39 556, so that an enzyme solution which is essentially free of sludge can be used again. In one aspect of this degumming process, oils which contain less than 15 ppm phosphorus are obtained. One goal is phosphorus contents of less than 10 ppm; or, less than 5 ppm. With phosphorus contents below 10 ppm, further processing of the oil according to the process of distillative de-acidification is easily possible. A number of other ions, such as magnesium, calcium, zinc, as well as iron, can be removed from the oil, e.g., below 0.1 ppm. Thus, this product possesses ideal prerequisites for good oxidation resistance during further processing and storage.

The phospholipases and methods of the invention also can also be used for reducing the amount of phosphorus-containing components in vegetable and animal oils as described, e.g., in EP patent EP 0513709. In this method, the content of phosphorus-containing components, especially phosphatides, such as lecithin, and the iron content in vegetable and animal oils, which have previously been deslimed, e.g. soya oil, are reduced by enzymatic breakdown using a phospholipase A1, A2 or B of the invention.

The phospholipases and methods of the invention can also be used for refining fat or oils as described, e.g., in JP 06306386. The invention provides processes for refining a fat or oil comprising a step of converting a phospholipid in a fat or an oil into a water-soluble phosphoric-group-containing substance and removing this substance. The action of an enzyme of the invention (e.g., a PI-PLC) is utilized to convert the phospholipid into the substance. Thus, it is possible to refine a fat or oil without carrying out an alkali refining step from which industrial wastes containing alkaline waste water and a large amount of oil are produced. Improvement of yields can be accomplished because the loss of neutral fat or oil from escape with the wastes can be reduced to zero. In one aspect, gummy substances are converted into water-soluble substances and removed as water-soluble substances by adding an enzyme of the invention having a phospholipase C activity in the stage of degumming the crude oil and conducting enzymatic treatment. In one aspect, the phospholipase C of the invention has an activity that cuts ester bonds of glycerin and phosphoric acid in phospholipids. If necessary, the method can comprise washing the enzyme-treated oil with water or an acidic aqueous solution. In one aspect, the enzyme of the invention is added to and reacted with the crude oil. The amount of phospholipase C employed can be 10 to 10,000 units, or, about 100 to 2,000 units, per 1 kg of crude oil.

The phospholipases and methods of the invention can also be used for water-degumming processes as described, e.g., in Dijkstra, Albert J., et al., Oleagineux, Corps Gras, Lipides (1998), 5(5), 367-370. In this exemplary method, the water-degumming process is used for the production of lecithin and for dry degumming processes using a degumming acid and bleaching earth. This method may be economically feasible only for oils with a low phosphatide content, e.g., palm oil, lauric oils, etc. For seed oils having a high NHP-content, the acid refining process is used, whereby this process is carried out at the oil mill to allow gum disposal via the meal. In one aspect, this acid refined oil is a possible "polishing" operation to be carried out prior to physical refining.

The phospholipases and methods of the invention can also be used for degumming processes as described, e.g., in Dijkstra, et al., Res. Dev. Dep., N. V. Vandemoortele Coord. Cent., Izegem, Belg. JAOCS, J. Am. Oil Chem. Soc. (1989), 66:1002-1009. In this exemplary method, the total degumming process involves dispersing an acid such as $H_3PO_4$ or citric acid into soybean oil, allowing a contact time, and then mixing a base such as caustic soda or Na silicate into the acid-in-oil emulsion. This keeps the degree of neutralization low enough to avoid forming soaps, because that would lead to increased oil loss. Subsequently, the oil passed to a centrifugal separator where most of the gums are removed from the oil stream to yield a gum phase with minimal oil content. The oil stream is then passed to a second centrifugal separator to remove all remaining gums to yield a dilute gum phase, which is recycled. Washing and drying or in-line alkali refining complete the process. After the adoption of the total degumming process, in comparison with the classical alkali refining process, an overall yield improvement of about 0.5% is realized. The totally degummed oil can be subsequently alkali refined, bleached and deodorized, or bleached and physically refined.

The phospholipases and methods of the invention can also be used for the removal of nonhydratable phospholipids from a plant oil, e.g., soybean oil, as described, e.g., in Hvolby, et al., Sojakagefabr., Copenhagen, Den., J. Amer. Oil Chem. Soc. (1971) 48:503-509. In this exemplary method, water-degummed oil is mixed at different fixed pH values with buffer solutions with and without $Ca^{++}$, Mg/Ca-binding reagents, and surfactants. The nonhydratable phospholipids can be removed in a nonconverted state as a component of micelles or of mixed emulsifiers. Furthermore, the nonhydratable phospholipids are removable by conversion into dissociated forms, e.g., by removal of Mg and Ca from the phosphatidates, which can be accomplished by acidulation or by treatment with Mg/Ca-complexing or Mg/Ca-precipitating reagents. Removal or chemical conversion of the nonhydratable phospholipids can result in reduced emulsion formation and in improved separation of the deacidified oil from the emulsion layer and the soapstock.

The phospholipases and methods of the invention can also be used for the degumming of vegetable oils as described, e.g., Buchold, et al., Frankfurt/Main, Germany. Fett Wissenschaft Technologie (1993), 95(8), 300-304. In this exemplary process of the invention for the degumming of edible vegetable oils, aqueous suspensions of an enzyme of the invention, e.g., phospholipase A2, is used to hydrolyze the fatty acid bound at the sn2 position of the phospholipid, resulting in 1-acyl-lysophospholipids which are insoluble in oil and thus more amenable to physical separation. Even the addition of small amounts corresponding to about 700 lecitase units/kg oil results in a residual P concentration of less than 10 ppm, so that chemical refining is replaceable by physical refining, eliminating the necessity for neutralization, soapstock splitting, and wastewater treatment.

The phospholipases and methods of the invention can also be used for the degumming of vegetable oils as described, e.g., by EnzyMax, Dahlke, Klaus, Dept. G-PDO, Lurgi Ol-Gas, Chemie, GmbH, Frankfurt, Germany. Oleagineux, Corps Gras, Lipides (1997), 4(1), 55-57. This exemplary process is a degumming process for the physical refining of almost any kind of oil. By an enzymatic-catalyzed hydrolysis, phosphatides are converted to water-soluble lysophosphatides which are separated from the oil by centrifugation. The residual phosphorus content in the enzymatically degummed oil can be as low as 2 ppm P.

The phospholipases and methods of the invention can also be used for the degumming of vegetable oils as described, e.g., by Cleenewerck, et al., N. V. Vamo Mills, Izegem, Belg. Fett Wissenschaft Technologie (1992), 94:317-22; and, Clausen, Kim; Nielsen, Munk. Novozymes A/S, Den. Dansk Kemi (2002) 83(2):24-27. The phospholipases and methods of the invention can incorporate the pre-refining of vegetable oils with acids as described, e.g., by Nilsson-Johansson, et al., Fats Oils Div., Alfa-Laval Food Eng. AB, Tumba, Swed. Fett Wissenschaft Technologie (1988), 90(11), 447-51; and, Munch, Ernst W. Cereol Deutschland GmbH, Mannheim, Germany. Editor(s): Wilson, Richard F. Proceedings of the World Conference on Oilseed Processing Utilization, Cancun, MX, Nov. 12-17, (2001), Meeting Date 2000, 17-20.

The phospholipases and methods of the invention can also be used for the degumming of vegetable oils as described, e.g., by Jerzewska, et al., Inst. Przemyslu Miesnego i Tluszczowego, Warsaw, Pol., Tluszcze Jadalne (2001), 36(3/4), 97-110. In this process of the invention, enzymatic degumming of hydrated low-erucic acid rapeseed oil is by use of a phospholipase A2 of the invention. The enzyme can catalyze the hydrolysis of fatty acid ester linkages to the central carbon atom of the glycerol moiety in phospholipids. It can hydrolyze non-hydratable phospholipids to their corresponding hydratable lyso-compounds. With a nonpurified enzyme preparation, better results can be achieved with the addition of 2% preparation for 4 hours (87% P removal).

In another exemplary process of the invention for oil degumming (or an oil degumming process using an enzyme of the invention), an acidic polymer, e.g., an alginate or pectin, is added. In this oil degumming process of the invention, an acidic polymer (e.g. alginic acid or pectin or a more soluble salt form) is added to the crude oil with a low amount of water (e.g., in a range of between about 0.5 to 5%). In this aspect, the acidic polymers can reduce and/or disrupt phospholipid-metal complexes by binding calcium and/or magnesium in the crude oil, thereby improving the solubility of nonhydratable phospholipids. In alternative aspects, these phospholipids will move to the oil/water interface or enter the aqueous phase and either be converted to diacylglycerol and the corresponding side chain or the intact phospholipid will be removed by subsequent centrifugation as a component of the heavy phase. The presence of the acidic polymer in the aqueous phase can also increase the density of the aqueous phase and result in an improved separation of the heavy phase from the oil (light) phase.

One exemplary process of the invention for oil degumming (or an oil degumming process using an enzyme of the invention) alters the deodorization procedure to get a diacylglycerol (DAG) fraction. In alternative aspect, if necessary or desired, following enzyme-assisted degumming, the deodorization conditions (temperature, pressure, configuration of the distillation apparatus) can be modified with the goal of improving the separation of the free fatty acids (FFA) from the diacylglycerol/triacylglycerol fraction or further modified to separate the diacylglycerol from the triacylglycerol fraction. As a result of these modifications, using this method of the invention, it is possible to obtain food grade FFA and diacylglycerol if an enzyme of the invention (e.g., a phosphatase, or, a PLC or a combination of PLC and phosphatases) are used to degum edible oil in a physical refining process.

In various aspects, practicing the methods of the invention as described herein (or using the enzymes of the invention), have advantages such as: decrease or eliminate solvent and solvent recovery; lower capital costs; decrease downstream refining costs, decrease chemical usage, equipment, process time, energy (heat) and water usage/wastewater generation; produce higher quality oil; expeller pressed oil may be used without refining in some cooking and sautéing applications (this pressed oil may have superior stability, color and odor characteristics and high tocopherol content); produce higher quality meal; produce a lower fat content in meal (currently, meal coming out of mechanical press causes digestion problems in ruminants); produce improved nutritional attributes—reduced levels of glucosinolates, tannins, sinapine, phytic acid (as described, e.g., in Technology and Solvents for Extracting Oilseeds and Nonpetroleum Oils, AOCS 1997).

In one aspect, the invention provides methods for refining vegetable oils (e.g., soybean oil, corn oil, cottonseed oil, palm oil, peanut oil, rapeseed oil, safflower oil, sunflower seed oil, sesame seed oil, rice bran oil, coconut oil or canola oil) and their byproducts, and processes for deodorizing lecithin, for example, as described in U.S. Pat. Nos. 6,172, 248, or 6,172,247, wherein the methods comprise use of at least one enzyme of the invention, e.g., a phospholipase C of the invention. Thus, the invention provides lecithin and vegetable oils comprising at least one enzyme of the invention. In an exemplary organic acid refining process, vegetable oil is combined with a dilute aqueous organic acid solution and subjected to high shear to finely disperse the acid solution in the oil. The resulting acid-and-oil mixture is mixed at low shear for a time sufficient to sequester contaminants into a hydrated impurities phase, producing a purified vegetable oil phase. In this exemplary process, a mixer or recycle system (e.g., recycle water tank) and/or a phosphatide or lecithin storage tank can be used, e.g., as described in U.S. Pat. Nos. 4,240,972, 4,049,686, 6,172,247 or 6,172,248. These processes can be conducted as a batch or continuous process. Crude or degummed vegetable oil can be supplied from a storage tank (e.g., through a pump) and can be heated. The vegetable oil to be purified can be either crude or "degummed" oil.

In one aspect, phosphatidylinositol-PLC (PI-PLC) enzymes of the invention are used for vegetable oil degumming. PI-PLC enzymes of the invention can be used alone or in combination with other enzymes (for instance PLC, PLD, phosphatase enzymes of the invention) to improve oil yield during the degumming of vegetable oils (including soybean, canola, and sunflower). The PI-PLC may preferentially convert phosphatidylinositol to 1, 2-diacylglycerol (DAG) and phosphoinositol but it may also demonstrate activity on other phospholipids including phosphatidylcholine, phosphatidylethanolamine, phosphatidylserine, or phosphatidic acid, or a combination thereof. The improvement in yield will be realized as an increase in the amount of DAG in the enzyme-treated vegetable oil and an increase in neutral oil, due to a decrease in the amount of oil entrained in the smaller gum fraction that results from enzyme treatment of the vegetable oil.

Enzymatic Processing of Oilseeds

The invention provides compositions (e.g., enzymes) and methods for enzymatic processing of oilseeds, including soybean, canola, coconut, avocado and olive paste. In one aspect, these processes of the invention can increase the oil yield and to improve the nutritional quality of the obtained meals. In some aspects, enzymatic processing of oilseeds using the enzymes and methods of the invention will provide economical and environmental benefits, as well as alternative technologies for oil extraction and processing food for human and animal consumption. In alternative aspects, the processes of the invention comprise use of phospholipases of the invention, other phospholipases, proteases, phosphatases, phytases, xylanases, amylases (e.g., α-amylases), glucanases (e.g., β-glucanases), polygalacturonases, galactolipases, cellulases, hemicellulases, pectinases and other plant cell wall degrading enzymes, as well as mixed enzyme preparations and cell lysates.

In alternative aspects, the processes of the invention can be practiced in conjunction with other processes, e.g., enzymatic treatments, e.g., with carbohydrases, including cellulase, hemicellulase and other side degrading activities, or, chemical processes, e.g., hexane extraction of soybean oil. The enzymatic treatment can increase the oil extractability by 8-10% when the enzymatic treatment is carried out prior to the solvent extraction.

In alternative aspects, the processes of the invention can be practiced with aqueous extraction processes. The aqueous extraction methods can be environmentally cleaner alternative technologies for oil extraction. Low extraction yields of aqueous process can be overcome by using enzymes that hydrolyze the structural polysaccharides forming the cell wall of oilseeds, or that hydrolyze the proteins which form the cell and lipid body membranes, e.g., utilizing digestions comprising cellulase, hemicellulase, and/or protopectinase for extraction of oil from soybean cells. In one aspect, methods are practiced with an enzyme of the invention as described by Kasai (2003) J. Agric. Food Chem. 51:6217-6222, who reported that the most effective enzyme to digest the cell wall was cellulase.

In one aspect, proteases are used in combination with the methods of the invention. The combined effect of operational variables and enzyme activity of protease and cellulase on oil and protein extraction yields combined with other process parameters, such as enzyme concentration, time of hydrolysis, particle size and solid-to-liquid ratio has been evaluated. In one aspect, methods are practiced with an enzyme of the invention as described by Rosenthal (2001) Enzyme and Microb. Tech. 28:499-509, who reported that use of protease can result in significantly higher yields of oil and protein over the control when heat treated flour is used.

In one aspect, complete protein, pectin, and hemicellulose extraction are used in combination with the methods of the invention. The plant cell consists of a series of polysaccharides often associated with or replaced by proteins or phenolic compounds. Most of these carbohydrates are only partially digested or poorly utilized by the digestive enzymes. The disruption of these structures through processing or degrading enzymes can improve their nutrient availability. In one aspect, methods are practiced with an enzyme of the invention as described by Ouhida (2002) J. Agric. Food Chem. 50:1933-1938, who reported that a significant degradation of the soybean cell wall cellulose (up to 20%) has been achieved after complete protein, pectin, and hemicellulose extraction.

In one aspect, the methods of the invention further comprise incorporation of various enzymatic treatments in the treatment of seeds, e.g., canola seeds, these treatments comprising use of proteases, cellulases, and hemicellulases (in various combinations with each other and with one or more enzymes of the invention). For example, the methods can comprise enzymatic treatments of canola seeds at 20 to 40 moisture during the incubation with enzymes prior to a conventional process; as described, e.g., by Sosulski (1990) Proc. Can. Inst. Food Sci. Technol. 3:656. The methods of the invention can further comprise incorporation of proteases, amylases, polygalacturonases (in various combinations with each other and with one or more enzymes of the invention) to hydrolyze cellular material in coconut meal and release the coconut oil, which can be recovered by centrifugation, as described, e.g., by McGlone (1986) J. of Food Sci. 51:695-697. The methods of the invention can further comprise incorporation of pectinases, amylases, proteases, cellulases in different combinations (with each other and with one or more enzymes of the invention) to result in significant yield improvement (~70% in the best case) during enzymatic extraction of avocado oil, as described, e.g., by Buenrostro (1986) Biotech. Letters 8(7):505-506. In processes of the invention for olive oil extraction, olive paste is treated with cellulase, hemicellulase, poligalacturonase, pectin-methyltransferase, protease and their combinations (with each other and with one or more enzymes of the invention), as described, e.g., by Montedoro (1976) Acta Vitamin. Enzymol. (Milano) 30:13.

Purification of Phytosterols from Vegetable Oils

The invention provides methods for purification of phytosterols and triterpenes, or plant sterols, from vegetable oils. Phytosterols that can be purified using phospholipases and methods of the invention include β-sitosterol, campesterol, stigmasterol, stigmastanol, β-sitostanol, sitostanol, desmosterol, chalinasterol, poriferasterol, clionasterol and brassicasterol. Plant sterols are important agricultural products for health and nutritional industries. Thus, phospholipases and methods of the invention are used to make emulsifiers for cosmetic manufacturers and steroidal intermediates and precursors for the production of hormone pharmaceuticals. Phospholipases and methods of the invention are used to make (e.g., purify) analogs of phytosterols and their esters for use as cholesterol-lowering agents with cardiologic health benefits. Phospholipases and methods of the invention are used to purify plant sterols to reduce serum cholesterol levels by inhibiting cholesterol absorption in the intestinal lumen. Phospholipases and methods of the invention are used to purify plant sterols that have immunomodulating properties at extremely low concentrations, including enhanced cellular response of T lymphocytes and cytotoxic ability of natural killer cells against a cancer cell line. Phospholipases and methods of the invention are used to purify plant sterols for the treatment of pulmonary tuberculosis, rheumatoid arthritis, management of HIV-infested patients and inhibition of immune stress, e.g., in marathon runners.

Phospholipases and methods of the invention are used to purify sterol components present in the sterol fractions of commodity vegetable oils (e.g., coconut, canola, cocoa butter, corn, cottonseed, linseed, olive, palm, peanut, rice bran, safflower, sesame, soybean, sunflower oils), such as sitosterol (40.2-92.3%), campesterol (2.6-38.6%), stigmasterol (0-31%) and 5-avenasterol (1.5-29%).

Methods of the invention can incorporate isolation of plant-derived sterols in oil seeds by solvent extraction with chloroform-methanol, hexane, methylene chloride, or acetone, followed by saponification and chromatographic purification for obtaining enriched total sterols. Alternatively, the plant samples can be extracted by supercritical fluid extraction with supercritical carbon dioxide to obtain total lipid extracts from which sterols can be enriched and isolated. For subsequent characterization and quantification of sterol compounds, the crude isolate can be purified and separated by a wide variety of chromatographic techniques including column chromatography (CC), gas chromatography, thin-layer chromatography (TLC), normal phase high-performance liquid chromatography (HPLC), reversed-phase HPLC and capillary electro-chromatography. Of all chromatographic isolation and separation techniques, CC and TLC procedures employ the most accessible, affordable and suitable for sample clean up, purification, qualitative assays and preliminary estimates of the sterols in test samples.

Phytosterols are lost in the vegetable oils lost as byproducts during edible oil refining processes. Phospholipases and methods of the invention use phytosterols isolated from such byproducts to make phytosterol-enriched products isolated from such byproducts. Phytosterol isolation and purification methods of the invention can incorporate oil processing industry byproducts and can comprise operations such as molecular distillation, liquid-liquid extraction and crystallization.

Methods of the invention can incorporate processes for the extraction of lipids to extract phytosterols. For example, methods of the invention can use nonpolar solvents as hexane (commonly used to extract most types of vegetable oils) quantitatively to extract free phytosterols and phytosteryl fatty-acid esters. Steryl glycosides and fatty-acylated steryl glycosides are only partially extracted with hexane, and increasing polarity of the solvent gave higher percentage of extraction. One procedure that can be used is the Bligh and Dyer chloroform-methanol method for extraction of all sterol lipid classes, including phospholipids. One exemplary method to both qualitatively separate and quantitatively analyze phytosterol lipid classes comprises injection of the lipid extract into HPLC system.

Phospholipases and methods of the invention can be used to remove sterols from fats and oils, as described, e.g., in U.S. Pat. No. 6,303,803. This is a method for reducing sterol content of sterol-containing fats and oils. It is an efficient and cost effective process based on the affinity of cholesterol and other sterols for amphipathic molecules that form hydrophobic, fluid bilayers, such as phospholipid bilayers. Aggregates of phospholipids are contacted with, for example, a sterol-containing fat or oil in an aqueous environment and then mixed. The molecular structure of this aggregated phospholipid mixture has a high affinity for cholesterol and other sterols, and can selectively remove such molecules from fats and oils. The aqueous separation mixture is mixed for a time sufficient to selectively reduce the sterol content of the fat/oil product through partitioning of the sterol into the portion of phospholipid aggregates. The sterol-reduced fat or oil is separated from the aqueous separation mixture. Alternatively, the correspondingly sterol-enriched fraction also may be isolated from the aqueous separation mixture. These steps can be performed at ambient temperatures, costs involved in heating are minimized, as is the possibility of thermal degradation of the product. Additionally, a minimal amount of equipment is required, and since all required materials are food grade, the methods require no special precautions regarding handling, waste disposal, or contamination of the final product(s).

Phospholipases and methods of the invention can be used to remove sterols from fats and oils, as described, e.g., in U.S. Pat. No. 5,880,300. Phospholipid aggregates are contacted with, for example, a sterol-containing fat or oil in an aqueous environment and then mixed. Following adequate mixing, the sterol-reduced fat or oil is separated from the aqueous separation mixture. Alternatively, the correspondingly sterol-enriched phospholipid also may be isolated from the aqueous separation mixture. Plant (e.g., vegetable) oils contain plant sterols (phytosterols) that also may be removed using the methods of the present invention. This method is applicable to a fat/oil product at any stage of a commercial processing cycle. For example, the process of the invention may be applied to refined, bleached and deodorized oils ("RBD oils"), or to any stage of processing prior to attainment of RBD status. Although RBD oil may have an altered density compared to pre-RBD oil, the processes of the invention are readily adapted to either RBD or pre-RBD oils, or to various other fat/oil products, by variation of phospholipid content, phospholipid composition, phospholipid: water ratios, temperature, pressure, mixing conditions, and separation conditions as described below.

Alternatively, the enzymes and methods of the invention can be used to isolate phytosterols or other sterols at intermediate steps in oil processing. For example, it is known that phytosterols are lost during deodorization of plant oils. A sterol-containing distillate fraction from, for example, an intermediate stage of processing can be subjected to the sterol-extraction procedures described above. This provides a sterol-enriched lecithin or other phospholipid material that can be further processed in order to recover the extracted sterols.

Detergent Compositions

The invention provides detergent compositions comprising one or more phospholipase of the invention, and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Phospholipases of the invention can facilitate the removal of stains by means of catalytic hydrolysis of phospholipids. Phospholipases of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of phospholipase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Phospholipases of the present invention can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, as well as builders and stabilizers. The addition of phospholipases of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning or disinfecting compositions including detergent and/or disinfecting compositions for cleaning and/or disinfecting hard surfaces, detergent compositions for cleaning and/or disinfecting fabrics, dishwashing compositions, oral cleaning compositions, denture cleaning compositions, and/or contact lens cleaning solutions.

In one aspect, the invention provides a method for washing an object comprising contacting the object with a phospholipase of the invention under conditions sufficient for washing. A phospholipase of the invention may be included as a detergent additive. The detergent composition of the invention may, for example, be formulated as a hand or machine laundry detergent composition comprising a phospholipase of the invention. A laundry additive suitable for pre-treatment of stained fabrics can comprise a phospholipase of the invention. A fabric softener composition can comprise a phospholipase of the invention. Alternatively, a phospholipase of the invention can be formulated as a detergent composition for use in general household hard surface cleaning operations. In alternative aspects, detergent additives and detergent compositions of the invention may comprise one or more other enzymes such as a protease, a lipase, a cutinase, another phospholipase, a carbohydrase, a cellulase, a pectinase, a mannanase, an arabinase, a galactanase, a xylanase, an oxidase, e.g., a lactase, and/or a peroxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, phospholipase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

Waste Treatment

The phospholipases of the invention can be used in waste treatment. In one aspect, the invention provides a solid waste digestion process using phospholipases of the invention. The methods can comprise reducing the mass and volume of substantially untreated solid waste. Solid waste can be treated with an enzymatic digestive process in the presence of an enzymatic solution (including phospholipases of the invention) at a controlled temperature. The solid waste can be converted into a liquefied waste and any residual solid waste. The resulting liquefied waste can be separated from said any residual solidified waste. See e.g., U.S. Pat. No. 5,709,796.

Detoxification

The phospholipases (e.g., PI-PLCs of the invention) can be used in detoxification processes, e.g., for the detoxification of endotoxins, e.g., compositions comprising lipopolysaccharides (LPS), and, the invention provides detoxification processes using at least one enzyme of the invention, e.g., a polypeptide comprising a sequence as set forth in SEQ ID NO:6 and having one or more mutations as set forth in Tables 12 to 15, or an enzymatically active fragment thereof.

In one aspect, a phospholipase of the invention is used to detoxify a lipopolysaccharide (LPS). In one aspect, this detoxification is by deacylation of 2' and/or 3' fatty acid chains from lipid A. In one aspect, a phospholipase (e.g., a PI-PLC) of the invention is used to hydrolyze a 2'-lauroyl and/or a 3'-myristoyl chain from a lipid, e.g., a lipid A (e.g., from a bacterial endotoxin). In one aspect, the process of the invention is used to destroy an endotoxin, e.g., a toxin from a gram negative bacteria, as from $E.\ coli$. In one aspect, a phospholipase (e.g., a PI-PLC) of the invention is used to ameliorate the effects of toxin poisoning (e.g., from an on-going gram negative infection), or, to prophylactically to prevent the effects of endotoxin during an infection (e.g., an infection in an animal or a human). Accordingly, the invention provides a pharmaceutical composition comprising a phospholipase (e.g., PI-PLC) of the invention, and method using a hydrolase of the invention, for the amelioration or prevention of lipopolysaccharide (LPS) toxic effects, e.g., during sepsis.

Processing Foods

The phospholipases of the invention can be used to process foods, e.g., to change their stability, shelf-life, flavor, texture, improve on their nutritional status, and the like. For example, in one aspect, phospholipases of the invention are used to generate acidic phospholipids for controlling bitter taste in foods.

In one aspect, the invention provides cheese-making processes using phospholipases of the invention (and, thus, the invention also provides cheeses comprising phospholipases of the invention). In one aspect, the enzymes of the invention (e.g., phospholipase A, lysophospholipase or a combination thereof) are used to process cheeses for flavor enhancement, to increase yield and/or for "stabilizing" cheeses, e.g., by reducing the tendency for "oil-off," or, in one aspect, the enzymes of the invention are used to produce cheese from cheese milk. These processes of the invention can incorporate any method or protocol, e.g., as described, e.g., in U.S. Pat. Nos. 6,551,635, and 6,399,121, WO 03/070013, WO 00/054601. For example, in one aspect, the phospholipases of the invention are used to stabilize fat emulsion in milk or milk-comprising compositions, e.g. cream, and are used to stabilize milk compositions, e.g. for the manufacturing of creams or cream liquors. In one aspect, the invention provides a process for enhancing the favor of a cheese using at least one enzyme of the invention, the process comprising incubating a protein, a fat and a protease and a lipase in an aqueous medium under conditions that produce an enhanced cheese flavor (e.g., reduced bitterness), e.g., as described in WO 99/66805. In one aspect, phospholipases of the invention are used to enhance flavor in a cheese (e.g., a curd) by mixing with water, a protease, and a lipase (of the invention) at an elevated temperature, e.g., between about 75° C. to 95° C., as described, e.g., in U.S. Pat. No. 4,752,483. In one aspect, phospholipases of the invention are used to accelerate cheese aging by adding an enzyme of the invention (e.g., a lipase or a phospholipase) to a cheese (e.g., a cheese milk) before adding a coagulant to the milk, or, adding an enzyme of the invention to a curd with salt before pressing, e.g., as described, e.g., in U.S. Pat. No. 4,707,364. In one aspect, a lipase of the invention is used degrade a triglyceride in milk fat to liberate free fatty acids, resulting in flavor enhancement. A protease also can be used in any of these processes of the invention, see, e.g., Brindisi (2001) J. of Food Sci. 66:1100-1107. In another aspect, a combination of esterases, lipases, phospholipases and/or proteases can be used in these or any process of the invention.

In one aspect, a phospholipase of the invention is used to reduce the content of phosphorus components in a food, e.g., an oil, such as a vegetable oil having a high non-hydratable phosphorus content, e.g., as described in WO 98/26057.

Biomass Conversion and Production of Clean Biofuels

The invention provides polypeptides, including enzymes (phospholipases (PLs), e.g., PLAs, PLCs or PLDs of the invention) and antibodies of the invention, and methods for the conversion of a biomass or any lignocellulosic material (e.g., any composition comprising cellulose, hemicellulose and lignin), to a fuel (e.g., bioethanol, biopropanol, biobutanol, biopropanol, biomethanol, biodiesel), in addition to feeds, foods and chemicals. For example, in alternative embodiment, enzyme(s) of the invention used for biomass conversion and for the production of biofuels can have one or more phospholipase activities, including a phospholipase C (PLC) activity; a PI-PLC activity, a phospholipase A (PLA) activity, such as a phospholipase A1 or phospholipase A2 activity; a phospholipase D (PLD) activity, such as a phospholipase D1 or a phospholipase D2 activity; a phospholipase B (PLB) activity, e.g., a phospholipase and a lysophospholipase (LPL) activity or a phospholipase and a lysophospholipase-transacylase (LPTA) activity or a phospholipase and a lysophospholipase (LPL) activity and lysophospholipase-transacylase (LPTA) activity; or patatin activity, or a combination thereof.

Thus, the compositions and methods of the invention provide effective and sustainable alternatives or adjuncts to use of petroleum-based products, e.g., as a mixture of a biofuel such as biomethanol, bioethanol, biopropanol, biobutanol, and the like, to diesel fuel, gasoline, kerosene and the like. The invention provides organisms expressing enzymes of the invention for participation in chemical cycles involving natural biomass conversion. In one aspect, enzymes and methods for the conversion are used in enzyme ensembles for phospholipid processing. The invention provides methods for discovering and implementing the most effective of enzymes to enable these important new "biomass conversion" and alternative energy industrial processes.

The compositions and methods of the invention can be used to provide effective and sustainable alternatives or adjuncts to use of petroleum-based products, e.g., as a mixture of bioethanol, biopropanol, biobutanol, biopropanol, biomethanol and/or biodiesel and gasoline. The invention provides organisms expressing enzymes of the invention for participation in chemical cycles involving natural biomass conversion. The invention provides methods for discovering and implementing the most effective of enzymes to enable these important new "biomass conversion" and alternative energy industrial processes.

The invention provides methods, enzymes and mixtures of enzymes or "cocktails" of the invention, for processing a material, e.g. a biomass material, comprising a cellooligosaccharide, an arabinoxylan oligomer, a lignin, a lignocellulose, a xylan, a glucan, a cellulose and/or a fermentable sugar comprising contacting the composition with a polypeptide of the invention, or a polypeptide encoded by a nucleic acid of the invention, wherein optionally the material is derived from an agricultural crop (e.g., wheat, barley, potatoes, switchgrass, poplar wood), is a byproduct of a food or a feed production, is a lignocellulosic waste product, or is a plant residue or a waste paper or waste paper product, and optionally the plant residue comprise stems, leaves, hulls, husks, corn or corn cobs, corn stover, corn fiber, hay, straw (e.g. rice straw or wheat straw), sugarcane bagasse, sugar beet pulp, citrus pulp, and citrus peels, wood, wood thinnings, wood chips, wood pulp, pulp waste, wood waste, wood shavings and sawdust, construction and/or demolition wastes and debris (e.g. wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g. the paper fraction of municipal solid waste, municipal wood waste, and municipal green waste, along with other materials containing sugar, starch, and/or cellulose can be used. In alternative aspects, the processing of the material, e.g. the biomass material, generates a bioalcohol, e.g., a bioethanol, biomethanol, biobutanol or biopropanol.

Alternatively, the polypeptide of the invention may be expressed in the biomass plant material or feedstock itself.

The methods of the invention also include taking a processed, or "converted" (e.g., by process comprising use of an enzyme of this invention) biomass or plant material, e.g., a lipid-comprising or a lignocellulosic material (processed by, e.g., enzymes of the invention) and making it into a fuel (e.g. a bioalcohol, e.g., a bioethanol, biomethanol, biobutanol or biopropanol, or biodiesel) by fermentation (e.g., by yeast) and/or by chemical synthesis. In one aspect, the produced sugars are fermented and/or the non-fermentable products are gasified.

The methods of the invention also include converting algae, vegetable oil such as virgin vegetable oils or waste vegetable oils, animal fats and greases (e.g. tallow, lard, and yellow grease), or sewage, using enzymes of the invention, and making it into a fuel (e.g. a bioalcohol, e.g., a bioethanol, biomethanol, biobutanol or biopropanol, or biodiesel) by fermentation and/or by chemical synthesis or conversion.

The enzymes of the invention (including, for example, organisms, such as microorganisms, e.g., fungi, yeast or bacteria, making and in some aspects secreting recombinant enzymes of the invention) can be used in or included/integrated at any stage of any biomass conversion process, e.g., at any one step, several steps, or included in all of the steps, or all of the following methods of biomass conversion processes, or all of these biofuel alternatives:

Direct combustion: the burning of material by direct heat and is the simplest biomass technology; can be very economical if a biomass source is nearby.

Pyrolysis: is the thermal degradation of biomass by heat in the absence of oxygen. In one aspect, biomass is heated to a temperature between about 800 and 1400 degrees Fahrenheit, but no oxygen is introduced to support combustion resulting in the creation of gas, fuel oil and charcoal.

Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic digestion: converts organic matter to a mixture of methane, the major component of natural gas, and carbon dioxide. In one aspect, biomass such as water-waste (sewage), manure, or food processing waste, is mixed with water and fed into a digester tank without air.

Fermentation

Alcohol Fermentation: fuel alcohol is produced by converting cellulosic mass and/or starch to sugar, fermenting the sugar to alcohol, then separating the alcohol water mixture by distillation. Feedstocks such as dedicated crops (e.g., wheat, barley, potatoes, switchgrass, poplar wood), agricultural residues and wastes (e.g. rice straw, corn stover, wheat straw, sugarcane bagasse, rice hulls, corn fiber, sugar beet pulp, citrus pulp, and citrus peels), forestry wastes (e.g. hardwood and softwood thinnings, hardwood and softwood residues from timber operations, wood shavings, and sawdust), urban wastes (e.g. paper fraction of municipal solid waste, municipal wood waste, municipal green waste), wood wastes (e.g. saw mill waste, pulp mill waste, construction waste, demolition waste, wood shavings, and sawdust), and waste paper or other materials containing sugar, starch, and/or cellulose can be converted to sugars and then to alcohol by fermentation with yeast. Alternatively, materials containing sugars can be converted directly to alcohol by fermentation.

Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.

Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.

Hydrolysis: includes hydrolysis of a compound, e.g., a biomass, such as a lignocellulosic material, catalyzed using an enzyme of the instant invention.

Congeneration: is the simultaneous production of more than one form of energy using a single fuel and facility. In one aspect, biomass cogeneration has more potential growth than biomass generation alone because cogeneration produces both heat and electricity.

In one aspect, the polypeptides of the invention have hydrolase activity, e.g., phospholipase, patatin and/or other related enzymatic activity for generating a fuel (e.g. a bioalcohol, e.g., a bioethanol, biomethanol, biobutanol or biopropanol, or biodiesel) from an organic material, e.g., a biomass, such as compositions derived from plants and animals, including any agricultural crop or other renewable feedstock, an agricultural residue or an animal waste, the organic components of municipal and industrial wastes, or construction or demolition wastes or debris, or microorganisms such as algae or yeast.

In one aspect, polypeptides of the invention are used in processes for converting any biomass, e.g., an animal, algae and/or plant biomass including lipid-comprising or lignocellulosic biomass to a fuel (e.g. a bioalcohol, e.g., a bioethanol, biomethanol, biobutanol or biopropanol, or biodiesel), or otherwise are used in processes for hydrolyzing or digesting biomaterials such that they can be used as a fuel (e.g. a bioalcohol, e.g., a bioethanol, biomethanol, biobutanol or biopropanol, or biodiesel), or for making it easier for the biomass to be processed into a fuel.

Enzymes of the invention, including the mixture of enzymes or "cocktails" of the invention, can also be used in glycerin refining. The glycerin by-product contains unreacted catalyst and soaps that are neutralized with an acid. Water and alcohol are removed to produce 50% to 80% crude glycerin. The remaining contaminants include unreacted fats and oils, which can be processes using the polypeptides of the invention. In a large biodiesel plants of the invention, the glycerin can be further purified, e.g., to 99% or higher purity, for the pharmaceutical and cosmetic industries.

Fuels (including bioalcohols such as bioethanols, biomethanols, biobutanols or biopropanols, or biodiesels) made using the polypeptides of the invention, including the mixture of enzymes or "cocktails" of the invention, can be used with fuel oxygenates to improve combustion characteristics. Adding oxygen results in more complete combustion, which reduces carbon monoxide emissions. This is another environmental benefit of replacing petroleum fuels with biofuels (e.g., a fuel of the invention). A biofuel made using the compositions and/or methods of this invention can be blended with gasoline to form an E10 blend (about 5% to 10% ethanol and about 90% to 95% gasoline), but it can be used in higher concentrations such as E85 or in its pure form. A biofuel made using the compositions and/or methods of this invention can be blended with petroleum diesel to form a B20 blend (20% biodiesel and 80% petroleum diesel), although other blend levels can be used up to B100 (pure biodiesel).

The invention also provides processes for making biofuels (including bioalcohols such as bioethanols, biomethanols, biobutanols or biopropanols, or biodiesels) from compositions comprising any biomass, e.g., an animal, algae and/or plant biomass including lipid-comprising or lignocellulosic biomass. The biomass material can be obtained from agricultural crops, as a byproduct of food or feed production, or as lignocellulosic waste products, such as plant residues, waste paper or construction and/or demolition wastes or debris. Examples of suitable plant sources or plant residues for treatment with polypeptides of the invention include kelp, algae, grains, seeds, stems, leaves, hulls, husks, corn cobs, corn stover, straw, grasses (e.g., Indian grass, such as *Sorghastrum nutans*; or, switch grass, e.g., *Panicum* species, such as *Panicum virgatum*), and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials. Examples of construction and demolition wastes and debris include wood, wood scraps, wood shavings and sawdust.

In one embodiment, the enzymes, including the mixture of enzymes or "cocktails" of the invention, and methods of the invention can be used in conjunction with more "traditional" means of making ethanol, methanol, propanol, butanol, propanol and/or diesel from biomass, e.g., as methods comprising hydrolyzing lipids and/or lignocellulosic materials by subjecting dried any biomass, e.g., an animal, algae and/or plant biomass including lipid-comprising or lignocellulosic biomass material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506 and 6,423,145.

Another exemplary method that incorporated use of enzymes of the invention, including the mixture of enzymes or "cocktails" of the invention, comprises hydrolyzing any biomass, e.g., an animal, algae and/or plant biomass including lipid-comprising or lignocellulosic biomass containing hemicellulose, cellulose and lignin, or any other polysaccharide that can be hydrolyzed by an enzyme of this invention, by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention (including the invention's mixtures, or "cocktails" of enzymes) can be added at any stage of this exemplary process.

Another exemplary method that incorporated use of enzymes of the invention, including the mixture of enzymes or "cocktails" of the invention, comprises processing a any biomass, e.g., an animal, algae and/or plant biomass including lipid-comprising or lignocellulosic biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention, including the mixture of enzymes or "cocktails" of the invention, comprises prehydrolyzing any biomass, e.g., an animal, algae and/or plant biomass including lipid-comprising or lignocellulosic biomass material in a prehydrolysis reactor; adding an acidic liquid to the solid material (e.g., lignocellulosic material) to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

In one aspect, methods of the invention for the enzymatic degradation of any biomass, e.g., an animal, algae and/or plant biomass including lipid-comprising or lignocellulosic biomass, e.g., for production of biofuels (including bioalcohols such as bioethanols, biomethanols, biobutanols or biopropanols, or biodiesels) from any organic material, and can also comprise use of ultrasonic treatment of the biomass material; see, e.g., U.S. Pat. No. 6,333,181.

In another aspect, methods of the invention for producing biofuels (including bioalcohols such as bioethanols, biomethanols, biobutanols or biopropanols, or biodiesels) from a cellulosic substrate comprise providing a reaction mixture in the form of a slurry comprising cellulosic substrate, an enzyme of this invention and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260). In one aspect, experiment or theoretical calculations can determine an optimum feeding frequency. In one aspect, additional quantities of the cellulosic substrate and the enzyme are provided into the reaction vessel at an interval(s) according to the optimized feeding frequency.

One exemplary process for making biofuels (including bioalcohols such as bioethanols, biomethanols, biobutanols or biopropanols, or biodiesels) of the invention is described in U.S. Pat. App. Pub. Nos. 20050069998; 20020164730; and in one aspect comprises stages of grinding the any biomass, e.g., an animal, algae and/or plant biomass including lipid-comprising or lignocellulosic biomass (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press, introducing the solid fraction in a fermentation deposit and adding one or more enzymes of the invention, e.g., a cellulase and/or beta-glucosidase enzyme (e.g., dissolved in citrate buffer pH 4.8).

Another exemplary process for making biofuels (including bioalcohols such as bioethanols, biomethanols, biobutanols or biopropanols, or biodiesels) of the invention comprising bioethanols, biomethanols, biobutanols or biopropanols using enzymes of the invention comprises pretreating a starting material comprising any biomass, e.g., an animal, algae and/or plant biomass including lipid-comprising or lignocellulosic biomass feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for using enzymes of the invention in the hydrolysis of any biomass, e.g., an animal, algae and/or plant biomass including lipid-comprising or lignocellulosic biomass include reactions at temperatures between about 30° C. and 48° C., and/or a pH between about 4.0 and 6.0. Other exemplary conditions include a temperature between about 30° C. and 60° C. and a pH between about 4.0 and 8.0.

Glucanases, (or cellulases), mannanases, xylanases, amylases, xanthanases and/or glycosidases, e.g., cellobiohydrolases, mannanases and/or beta-glucosidases of the invention can be used in the conversion of biomass to fuels, and in the production of ethanol, e.g., as described in PCT Application Nos. WO 0043496 and WO 8100857. Glucanases (or cellulases), mannanases, xylanases, amylases, xanthanases and/or glycosidases, e.g., cellobiohydrolases, mannanases and/or beta-glucosidases of the invention can be used to produce fermentable sugars and glucan-containing biomass that can be converted into fuel ethanol.

BioDiesels—Using Enzymes of the Invention to Make them

The invention provides compositions, including enzymes of the invention, and methods, for making biodiesel fuels, including any biofuel, e.g., a biodiesel, comprising alkyl esters made from the transesterification of vegetable oils and/or animal fats.

For example, in alternative aspects, polypeptides of the invention, including the mixture of enzymes or "cocktails" of the invention, are used in processes for a transesterification process reacting an alcohol (like ethanol, propanol, butanol, propanol, methanol) with a triglyceride oil contained in a vegetable oil, animal fat or recycled greases, forming fatty acid alkyl esters—including biodiesel—and glycerin. In one aspect, biodiesel is made from soybean oil or recycled cooking oils. Animal's fats, other vegetable oils, and other recycled oils can also be used (and processed by enzymes, e.g., phospholipases, of the invention) to produce a biodiesel, depending on their costs and availability. In another aspect, blends of all kinds of fats and oils are used to produce a biodiesel fuel of the invention using enzymes of the invention.

The invention provides compositions, including enzymes of the invention, and methods, for processing "yellow grease", a term initially coined by the rendering industry. Yellow grease that can be processed using the compositions and methods of the invention include grease from frying oils, e.g., from deep fryers or restaurants' grease traps, or from various (e.g., lower-quality) grades of tallow from rendering plants. Thus, the invention also provides oils, grease, frying oils, vegetable oils, waste restaurant greases and processes grades of tallow comprising at least one enzyme of this invention.

Yellow grease processed using compositions of the invention, including enzymes, and methods of the invention, can be used to spray on roads, e.g., for dust control, or for animal feed additives or feeds, or food supplements.

In another aspect, compositions of the invention, including enzymes, and methods of the invention, can be used to process lipids, e.g., greases such as waste restaurant greases to make a biofuel, e.g., a biodiesel fuel, e.g., for cars, buses, trucks or boats. In one aspect, biodiesel made using a composition or method of the invention can be generated from any renewable plant source, e.g., soybeans, and/or from a grease, such as the "yellow grease".

Compositions of the invention, including enzymes, and methods of the invention, can be used to process "SVO", or "straight vegetable oil", including any vegetable oil that can fuel a diesel engine, e.g., wherein the processing comprises transesterification of lipids in the fuel, e.g., for use in lower temperatures.

Compositions of the invention, including enzymes, and methods of the invention, can be used to process "WVO", or waste vegetable oil, to make, e.g., a yellow grease, including the grease from restaurants; in one aspect, the grease has to be filtered to remove food particles. Yellow grease processed by compositions of the invention, including enzymes, and methods of the invention, can fall in the category of SVO/WVO, including any grease, e.g., a restaurant waste grease, that can contain beef tallow and other animal products.

Distillers Dried Grain Processing

In another aspect, the enzymes (e.g., phospholipases) of the invention can be used to treat/process "distillers dried solubles (DDS)", "distillers dried grains (DDS)", "condensed distillers solubles (CDS)", "distillers wet grains (DWG)", and "distillers dried grains with solubles (DDGS)"; distillers dried grains can be a cereal byproduct of a distillation process, and can include solubles. These processes can comprise dry-grinding plant by-products, e.g. for feed applications, e.g., for poultry, bovine, swine and other domestic animals. Thus, the enzymes of the invention can be used to treat/process grains, e.g., cereals, that are byproducts of any distillation process, including processes using any source of grain, for example, the traditional sources from brewers, or alternatively, from an ethanol-producing plant (factory, mill or the like). Enzymes of the invention can be used to treat/process drying mash from distilleries; this mash can be subsequently used for a variety of purposes, e.g., as fodder for livestock, especially ruminants; thus the invention provides methods for processing fodder for livestock such as ruminants, and enzyme-processed fodder comprising phytases of this invention.

Figure 12:
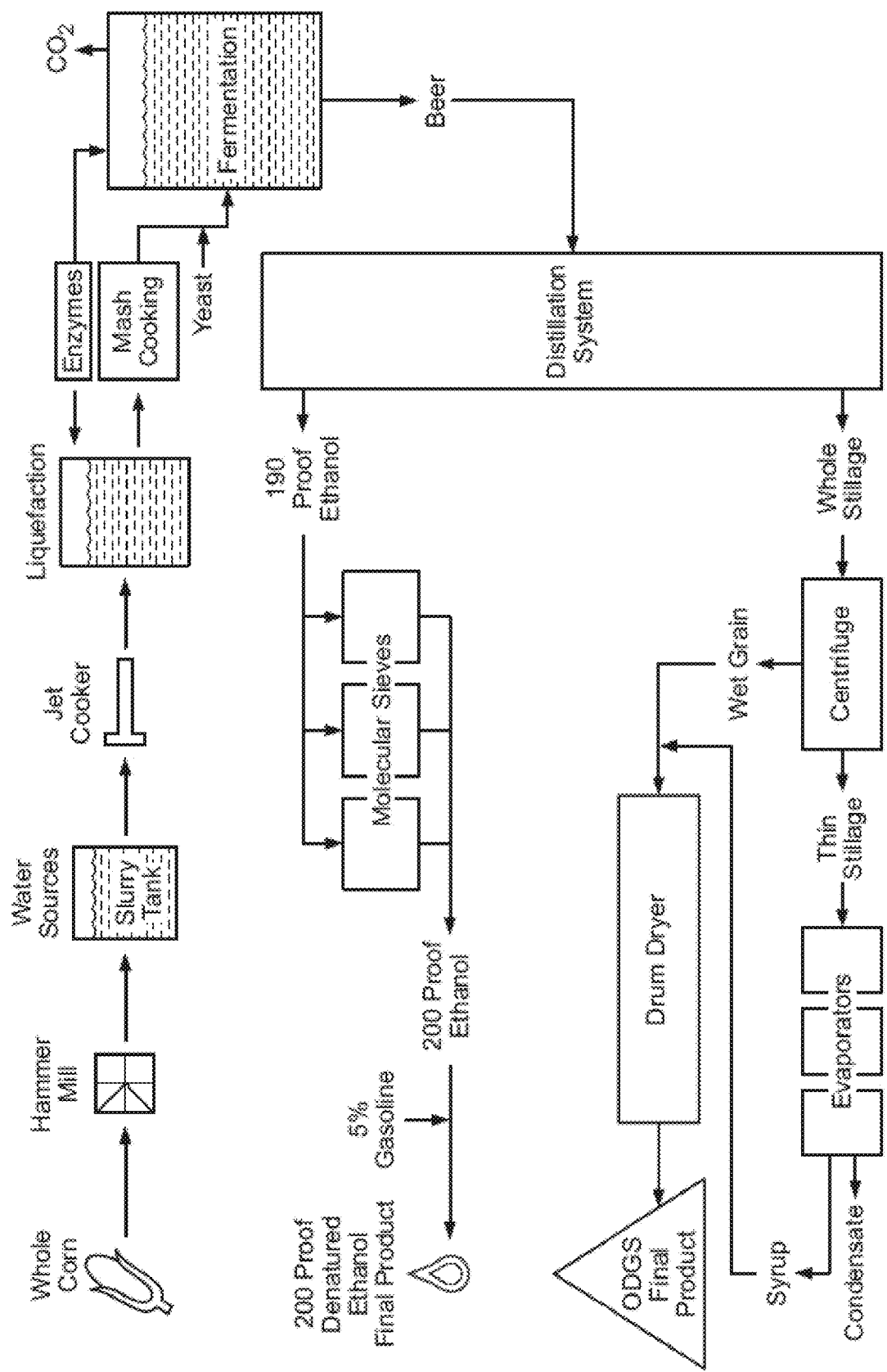
FIG. 12 illustrates an exemplary alcohol process that can incorporate use of enzymes of this invention.

Enzymes of this invention can be used alone or with other enzymes to process "distillers dried solubles (DDS)", "distillers dried grains (DDS)", "condensed distillers solubles (CDS)", "distillers wet grains (DWG)", and "distillers dried grains with solubles (DDGS)". For example, enzymes of this invention can be used in any step of an alcohol product process as illustrated in FIG. 12. Enzymes of this invention can be used to increase the bioavailability of phosphorus in any biofuel, or potential biofuel, including phosphorus found in "distillers dried solubles (DDS)", "distillers dried grains (DDS)", "condensed distillers solubles (CDS)", "distillers wet grains (DWG)", and "distillers dried grains with solubles (DDGS)" (see, e.g., C. Martinez Amezcua, 2004 Poultry Science 83:971-976).

Spirit, or Drinkable Alcohol Production

Enzymes of this invention of this invention also can be used in processing distillers dried grains for alcohol production—alcohol as in "spirits", e.g., beer or whiskey production (in addition to use in processing biomass for making biofuels). Enzymes of this invention of this invention can be used in ethanol plants, e.g. for processing grains such as corn. Distillers dried grains can be made by first grinding a grain (e.g., corn) to a coarse consistency and adding to hot water. After cooling, yeast is added and the mixture ferments for several days to a week. The solids remaining after fermentation are the distillers grains. Phytases of this invention of this invention can be used at any step of this process.

Formulations

The invention provides novel formulations comprising enzymes of this invention, and formulations for phospholipases of the invention, including formulations which include the novel enzymes of the invention. The enzymes of the invention can be used or formulated alone or as mixture of phospholipases of the invention, or other phospholipases, or other enzymes such as xylanases, cellulases, proteases, lipases, amylases, or redox enzymes such as laccases, peroxidases, catalases, oxidases, or reductases. They can be used formulated in a solid form such as a powder, a lyophilized preparation, a granule, a tablet, a bar, a crystal, a capsule, a pill, a pellet, or in a liquid form such as in an aqueous solution, an aerosol, a gel, a paste, a slurry, an aqueous/oil emulsion, a cream, a capsule, or in a vesicular or micellar suspension. The formulations of the invention can comprise any or a combination of the following ingredients: polyols such as a polyethylene glycol, a polyvinyl-alcohol, a glycerol, a sugar such as a sucrose, a sorbitol, a trehalose, a glucose, a fructose, a maltose, a mannose, a gelling agent such as a guar gum, a carageenan, an alginate, a dextrans, a cellulosic derivative, a pectin, a salt such as a sodium chloride, a sodium sulfate, an ammonium sulfate, a calcium chloride, a magnesium chloride, a zinc chloride, a zinc sulfate, a salt of a fatty acid and a fatty acid derivative, a metal chelator such as an EDTA, an EGTA, a sodium citrate, an antimicrobial agent such as a fatty acid or a fatty acid derivative, a paraben, a sorbate, a benzoate, an additional modulating compound to block the impact of an enzyme such as a protease, a bulk proteins such as a BSA, a wheat hydrolysate, a borate compound, an amino acid or a peptide, an appropriate pH or temperature modulating compound, an emulsifier such as a non-ionic and/or an ionic detergent, a redox agent such as a cystine/cysteine, a glutathione, an oxidized glutathione, a reduced or an antioxidant compound such as an ascorbic acid, or a dispersant.

Cross-linking and protein modification such as pegylation, fatty acid modification, glycosylation can also be used to improve enzyme stability.

Other Uses for the Phospholipases of the Invention

The phospholipases of the invention can also be used to study the phosphoinositide (PI) signaling system; in the diagnosis, prognosis and development of treatments for bipolar disorders (see, e.g., Pandey (2002) Neuropsychopharmacology 26:216-228); as antioxidants; as modified phospholipids; as foaming and gelation agents; to generate angiogenic lipids for vascularizing tissues; to identify phospholipase, e.g., PLA, PLB, PLC, PLD and/or patatin modulators (agonists or antagonists), e.g., inhibitors for use as anti-neoplastics, anti-inflammatory and as analgesic agents. They can be used to generate acidic phospholipids for controlling the bitter taste in food and pharmaceuticals. They can be used in fat purification. They can be used to identify peptides inhibitors for the treatment of viral, inflammatory, allergic and cardiovascular diseases. They can be used to make vaccines. They can be used to make polyunsaturated fatty acid glycerides and phosphatidylglycerols.

The phospholipases of the invention, for example PLC enzymes, are used to generate immunotoxins and various therapeutics for anti-cancer treatments.

The phospholipases of the invention can be used in conjunction with other enzymes for decoloring (i.e. chlorophyll removal) and in detergents (see above), e.g., in conjunction with other enzymes (e.g., lipases, proteases, esterases, phosphatases). For example, in any instance where a PLC is used, a PLD and a phosphatase may be used in combination, to produce the same result as a PLC alone.

The following Table 7 summaries several exemplary processes and formulations of the invention:

TABLE 7

| Exemplary Processes of the invention | Purposes |
|---|---|
| Chemical usage in PLC oil degumming | |
| No use of acid | Chemical elimination |
| No use of caustic | Chemical elimination |
| Range of acid and caustic use (no excess to excess) | Chemical reduction/degumming process alternative embodiment |
| Other types of acid and caustic | Degumming process alternative embodiments |
| Impact of water in PLC oil degumming | |
| Use of silica gel | Replacement of water wash step |
| Use of water drying agent | Elimination of water in final product |
| Impact of lower water during caustic treatment | Elimination of water in final product |
| Minimal water content (<5%) | Elimination of water in final product |
| Maximal water content (>5%) | Process alternative |
| Humidity profiles on PLC degumming | Degumming process alternative embodiment |
| Oil dependence on water content for PLC degumming | Degumming process alternative embodiment |
| In situ removal of free fatty acids, FFAs | |
| Addition of FFA chelating agent | Degumming process alternative embodiment; improves conditions in oil from spoilt beans |
| Impact of mixing regimen on PLC oil degumming | |
| PLC degumming with minimal mixing | Protection of enzyme from mixing induced denaturation, energy savings |
| PLC degumming with initial shear mixing, followed by paddle mixing | Degumming process alternative embodiment |
| Order of addition of chemicals | |
| Order of addition: enzyme-water followed by acid then caustic | Allow the PLC to work before exposure to acid and or caustic, causing potential pH or metal chelation PLC inactivation |

TABLE 7-continued

| PLC oil degumming process alternative embodiments for temperature and time | |
|---|---|
| Enzyme treatment step (time): <60 min, preferably <30 min | Degumming process alternative embodiment |
| Enzyme treatment step (temperature): 50-70° C., possibly <50° C. (e.g. RT) | Degumming process alternative embodiment |

| Benefits from PLC oil degumming | |
|---|---|
| Producing soapstock with minimized PL content and enriched in water soluble phosphate esters | Degumming process alternative embodiment |
| Reduced neutral oil in gum through use of PLC | Degumming process alternative embodiment |
| Process of generating increase of DAG in vegetable oils (for ex, 1,3-DAG) | Degumming process alternative embodiment |
| Benefits of using increased DAG vegetable oils with other oils for health benefits | Exemplary Product benefit |
| Investigate degumming process that leaves no PLC activity in oil | Degumming process alternative embodiment/ regulatory improvement |
| Investigate degumming process that leaves no detectable PLC protein in oil | Degumming process alternative embodiment/ regulatory improvement |
| Use of an enzyme to produce DAG from lecithin gum mass | Exemplary Product benefit |
| Use of PLC with specialty oils (PA, PI enriched) | Exemplary Product benefit |
| Use of PA/PI specific enzymes (e.g. 596ES2/PI specific) | Degumming process alternative embodiment |
| Use of PA/PI specific enzymes (e.g. 596ES2/PI specific) + PC/PE specific enzymes; impact of order of addition | Degumming process alternative embodiment |
| Batch or continuous process | Degumming process alternative embodiment |
| Use of resuspended PLC treated gum for further oil degumming operations | Degumming process alternative embodiment |
| Mass balance for DAG, FFA, P, metals, neutral oil in gum | Degumming process alternative embodiment |

| Miscellaneous | |
|---|---|
| Addition of PLC to flaked oil seed kernels before extrusion | Process alternative embodiment |
| Small scale degumming assay | Degumming process alternative embodiment |
| Use of other enzymes to reduce gum mass (e.g., PYROLASE ® enzyme, chlorophyllase, peroxidase, lipase, laccase, mannanase, protease, lactase, amylase, etc. or combinations thereof) | Degumming process alternative embodiment |
| Use of compound to better facilitate oil/gum separation | Degumming process alternative embodiment |
| Harden gum from PLC treated oil | Degumming process alternative embodiment |
| Glycosylated/deglycosylated variants of phospholipase | Degumming process alternative embodiment |

| Exemplary Formulations of the invention | Purpose |
|---|---|

| Exemplary Liquid formulation for stability | |
|---|---|
| Use of compounds to increase the stability of PLC at different pH and temp. ranges (polyols, salts, metals . . . ) | Stabilization of enzyme for maximum DAG production, possibly for altering substrate specificity or directing product formation towards the 1,3-DAG type |
| Use of a hydrophobic delivery system for PLC (liposomes, hydrated enzyme in refined oil droplets) | Stabilization of enzyme for maximum DAG production, possibly for altering substrate specificity or directing product formation towards the 1,3-DAG type |

| Solid formulation for stability | |
|---|---|
| Use of different PLC, phospholipase carrier systems (immobilization resins, porous matrices, gels, granules, powders, tablets, vesicles/micelles, encapsulates, structured liquids, etc) to stabilize phospholipase and co-enzymes | Stabilization of the enzyme(s) and ease of separation of the enzyme from the oil or gum phase after degumming; recyclability of the enzyme preparation; physical separation of the enzyme phase during oil processing; attack of PI/PA by PLC |
| Use of degumming waste materials (gum components, seed hulls) for PLC formulation | Cost reduction of formulation ingredient, better miscibility of enzyme with oil, thermostabilization of enzyme |

TABLE 7-continued

Exemplary Formulation and processes for activity boost

| | |
|---|---|
| Use of chemical or enzyme to help disperse the enzyme better in oil (e.g. effervescent matrix, etc) | Faster reaction time/degumming process/reduction of chemical usage |
| Re-use of gums/enzyme for further degumming reactions | Recyclability of enzyme |
| Use of formulations that enhance the segregation or enzyme capture of PLs for hydrolysis | Faster reaction time/degumming process/reduction of chemical usage |
| Use of multiple formulations to accommodate PLCs with different PL specificities | Versatility of process; different enzymes may require different formulations or may be added at different stages in the process |
| Use of multiple formulations to prevent inactivation of one PLC by a component in the prep of another PLC with a different substrate specificity | Protection of PLC activities in a multi-enzyme format embodiment |
| Use of multiple formulations to prevent inactivation of one PLC by a component in the prep of another enzyme (hydrolase, oxidase) | Protection of PLC activity in a multi-enzyme format embodiment |
| Use of intermittent caustic additions as in time released caustic addition formulation | Protection of enzyme from mixing induced denaturation, energy savings |

Inactivating and Modulating Activity of Enzymes by Glycosylation

This invention provides methods comprising use of recombinant technology to make and expressing enzymes or other proteins with biological activity, e.g., noxious or toxic enzymes, (wherein the enzymes or other proteins are not normally glycosylated) in an inactive or less active, but re-activatable, form. The method comprises adding one or more glycosylation sites (e.g., N-linked or O-linked glycosylation) into the enzymes or other proteins with biological activity (e.g., an enzyme of the present invention) by engineering a coding sequence incorporating the new glycosylation site(s); expressing the variant coding sequences in eukaryotic cells or an equivalent engineered or in vitro system capable of post-translational glycosylation. For example, the 3 amino acid sequence NXS/T is the site for glycosylation in eukaryotic cells, prokaryotic cells do not do this. Thus, the invention comprises adding at least one 3 amino acid sequence NXS/T to the protein such that its activity is decreased or inactivated because of post-translational glycosylation.

The glycosylation can result in 2 molecules of N-acetyl glucosamine (NGlucNac) being added to the N residue. Subsequent additions can be organism specific. In most species mannose (Mann) sugars are then added onto the NGlucNac, with the number Mann residues ranging from 10 to 100. Sialic acid can also be added in some species. In *Pichia* after the NGlucNac is added, 10 to 25 Mann residues can be added.

These methods comprise using any deglycosylating enzyme or set of enzymes, many of which can have been identified and/or are commercially available. For example, the endoglycosidase H enzyme cleaves at the last NGlucNac leaving one NGlucNac still attached to the N residue. The PNGaseF enzyme cleaves off all of the sugars and converts the amino side chain of the N residue into a hydroxyl group resulting in the N amino acid becoming an aspartate (D) amino acid in the enzyme. Thus, the methods comprise using endoglycosidase H and/or PNGaseF or equivalent enzymes in vivo or in vitro to re-activate partially or completely the engineered "temporarily inactivated" proteins.

The method comprises targeting the enzymes or other polypeptides to the host secretory pathway so that the enzymes will be glycosylated. The new glycosylation sites are designed such that glycosylation inactivates the enzyme or modifies its activity, e.g., decreases it activity or other otherwise modifies activity, such as blocks a substrate binding site. Because the enzyme is inactive or less active, noxious or toxic enzymes could be expressed at higher levels since the negative effects of their activity are no longer a limitation to how much of the protein can accumulate in the host cells. The inactive, glycosylated enzyme can be re-activated (partially or completely) by removing the sugars, e.g., using commercially available deglycosylating enzymes, for example, by removing the sugars in vitro, or removing the sugars in vivo using whole cell engineering approaches.

In one aspect, a eukaryotic glycosylation target site such as NXS/T is added to any protein, for example, an enzyme of the invention. This enables one skilled in the art to add glycosylation sites to a protein of interest with the expectation of converting that protein into one that is temporarily inactive when that protein is glycosylated by expressing that protein in a eukaryotic host cell and targeting the protein to the host cell's secretory pathway.

Thus, the invention provides methods for the production of enzymes that normally are too noxious or toxic to be tolerated in large amounts by a host cell. The effect can temporary as it is possible to regenerate the active enzyme (by deglycosylation, e.g., by post-translational modification/deglycosylation) for future work requiring an active enzyme.

In one aspect, the invention provides methods for making and expressing a protein having a biological activity whose activity is temporarily inactivated by glycosylation comprising: (a) providing a nucleic acid encoding a protein having a biological activity, wherein the protein is not naturally glycosylated; (b) inserting at least one glycosylation motif coding sequence into the protein-encoding nucleic acid, wherein the glycosylated form of the protein is inactive; (c) inserting a targeting sequence into the protein such that it is directed to a host cell's secretory pathway, wherein the host cell is capable of recognizing the glycosylation motif and glycosylating the protein; and (d) expressing the modified nucleic acid in the host cell. In one aspect, the method further comprises deglycosylating the expressed the protein, thereby re-activating the activity of the protein, e.g., an enzyme, such as an enzyme of the invention. In one aspect, the host cell is a eukaryotic cell. In one aspect, the inactivated expressed recombinant protein is re-activated in vitro by deglycosylation, either chemical or enzymatic.

Determining the placement of one or more glycosylation motifs to temporarily inactivate a protein involves only routine methods of making variant protein-encoding nucleic acids, e.g., by GSSM, and routine screening protocols, e.g., activity or binding assays.

An enzyme whose activity was detrimental to the host cell was rendered inactive because of glycosylation. Because it was inactive it could accumulate in much higher levels in the eukaryotic host cells. Because it was no longer active it could no longer able to exert its negative effects. The inactivation of the toxic enzyme was temporary because deglycosylating the enzyme using EndoH or PNGase F resulted in a complete restoration of normal activity to the enzyme. A large amount of the glycosylated, inactive enzyme accumulated in the medium suggesting that it was tolerated well by the host as the inactive form.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the methods of use provided herein, may be made without departing from the spirit and scope thereof. Patents, patent publications, and other publications referenced herein are incorporated by reference.

The invention will be further described with reference to the following examples; however, it is to be understood that the invention is not limited to such examples.

EXAMPLES

Example 1: Blast Program Used for Sequence Identify Profiling

This example describes an exemplary sequence identity program to determine if a nucleic acid is within the scope of the invention. An NCBI BLAST 2.2.2 program is used, default options to blastp. All default values were used except for the default filtering setting (i.e., all parameters set to default except filtering which is set to OFF); in its place a "–F F" setting is used, which disables filtering. Use of default filtering often results in Karlin-Altschul violations due to short length of sequence. The default values used in this example:

```
"Filter for low complexity: ON
> Word Size: 3
> Matrix: Blosum62
> Gap Costs: Existence:11
>    Extension:1"
```

Other default settings were: filter for low complexity OFF, word size of 3 for protein, BLOSUM62 matrix, gap existence penalty of –11 and a gap extension penalty of –1. The "–W" option was set to default to 0. This means that, if not set, the word size defaults to 3 for proteins and 11 for nucleotides. The settings read:

```
<<README.bls.txt>>
> ------------------------------------------------------------------------
> blastall arguments:
>
>          -p Program Name [String]
>          -d Database [String]
>             default = nr
>          -i Query File [File In]
>             default = stdin
>          -e Expectation value (E) [Real]
>             default = 10.0
>          -m alignment view options:
> 0 = pairwise,
> 1 = query-anchored showing identities,
> 2 = query-anchored no identities,
> 3 = flat query-anchored, show identities,
> 4 = flat query-anchored, no identities,
> 5 = query-anchored no identities and blunt ends,
> 6 = flat query-anchored, no identities and blunt ends,
> 7 = XML Blast output,
> 8 = tabular,
> 9 tabular with comment lines [Integer]
>             default = 0
>          -o BLAST report Output File [File Out] Optional
>             default = stdout
>          -F Filter query sequence (DUST with blastn, SEG with others) [String]
>             default = T
>          -G Cost to open a gap (zero invokes default behavior) [Integer]
>             default = 0
>          -E Cost to extend a gap (zero invokes default behavior) [Integer]
>             default = 0
>          -X X dropoff value for gapped alignment (in bits) (zero invokes default
> behavior) [Integer]
>             default = 0
>          -I Show GI's in deflines [T/F]
>             default = F
>          -q Penalty for a nucleotide mismatch (blastn only) [Integer]
>             default = -3
>          -r Reward for a nucleotide match (blastn only) [Integer]
>             default = 1
```

-continued

```
>         -v Number of database sequences to show one-line descriptions for (V)
> [Integer]
>             default = 500
>         -b Number of database sequence to show alignments for (B) [Integer]
>             default = 250
>         -f Threshold for extending hits, default if zero [Integer]
>             default = 0
>         -g Perform gapped alignment (not available with tblastx) [T/F]
>             default = T
>         -Q Query Genetic code to use [Integer]
>             default = 1
>         -D DB Genetic code (for tblast[nx] only) [Integer]
>             default = 1
>         -a Number of processors to use [Integer]
>             default = 1
>         -O SeqAlign file [File Out] Optional
>         -J Believe the query defline [T/F]
>             default = F
>         -M Matrix [String]
>             default = BLOSUM62
>         -W Word size, default if zero [Integer]
>             default = 0
>         -z Effective length of the database (use zero for the real size)
> [String]
>             default = 0
>         -K Number of best hits from a region to keep (off by default, if used a
> value of 100 is recommended) [Integer]
>             default = 0
>         -P 0 for multiple hits 1-pass, 1 for single hit 1-pass, 2 for 2-pass
> [Integer]
>             default = 0
>         -Y Effective length of the search space (use zero for the real size)
> [Real]
>             default = 0
>         -S Query strands to search against database (for blast[nx], and
> tblastx). 3 is both, 1 is top, 2 is bottom [Integer]
>             default = 3
>         -T Produce HTML output [T/F]
>             default = F
>         -l Restrict search of database to list of GI's [String] Optional
>         -U Use lower case filtering of FASTA sequence [T/F] Optional
>             default = F
>         -y Dropoff (X) for blast extensions in bits (0.0 invokes default
> behavior) [Real]
>             default = 0.0
>         -Z X dropoff value for final gapped alignment (in bits) [Integer]
>             default = 0
>         -R PSI-TBLASTN checkpoint file [File In] Optional
>         -n MegaBlast search [T/F]
>             default = F
>         -L Location on query sequence [String] Optional
>         -A Multiple Hits window size (zero for single hit algorithm) [Integer]
>             default = 40
```

Example 2: Modifications to a PLC Enzyme (ePLC)

This example describes exemplary protocols for making PLC enzymes of this invention, including PI-PLC enzymes of this invention. This example describes enzymes that can be used to practice this invention, e.g., used in combination with PLC enzymes of this invention (e.g., an enzyme having a sequence as set forth in SEQ ID NO:8, or as described in Table 12 to 15). Enzymes that can be used to practice this invention, e.g., in combinations or mixtures comprising PLC enzymes of this invention, include any phospholipase enzyme, including an enzyme having a sequence as set forth in Table 8 or Table 9, or described in WO 2008/036863. In alternative embodiments, enzymes that can be used to practice this invention include polypeptides having a sequence as set forth in SEQ ID NO:2 and/or SEQ ID NO:4, and variants thereof as described in Tables 8 and 9, below.

Phospholipase C enzyme having a sequence as set forth in SEQ ID NO:2 (encoded e.g. by SEQ ID NO:1) is an enzymatically active subsequence of the longer sequence SEQ ID NO:4 (encoded e.g. by SEQ ID NO:3). SEQ ID NO:4 has a leader sequence of residues 1 to 37 (bolded) of SEQ ID NO:2. SEQ ID NO:4, as encoded by SEQ ID NO:3, was used as a template for further modification using GSSM technology. Positions are numbered starting with the N-terminal Methionine. Mutations are underlined and in bold (numbered here as N100D, N168S and N171D).

(SEQ ID NO: 4)
MKKKVLALAA MVALAAPVQS VVFAQTNNSE SPAPILRWSA

EDKHNEGINS HLWIVNRAID IMSRNTTIVN PNETALLNEW

RADLENGIYS ADYENPYYDD STYASHFYDP DTGTTYIPFA

KHAKETGAKY FNLAGQAYQN QDMQQAFFYL GLSLHYLGDV

NQPMHAASFT DLSYPMGFHS KYENFVDTIK NNYIVSDSNG

-continued
YWNWKGANPE DWIEGAAVAA KQDYPGVVND TTKDWFVKAA

VSQEYADKWR AEVTPVTGKR LMEAQRVTAG YIHLWFDTYV NR (SEQ ID NO: 2)
WSA

EDKHNEGINS HLWIVNRAID IMSRNTTIVN PNETALLNEW

RADLENGIYS ADYENPYYDD STYASHFYDP DTGTTYIPFA

KHAKETGAKY FNLAGQAYQN QDMQQAFFYL GLSLHYLGDV

NQPMHAASFT DLSYPMGFHS KYENFVDTIK NNYIVSDSNG

YWNWKGANPE DWIEGAAVAA KQDYPGVVND TTKDWFVKAA

VSQEYADKWR AEVTPVTGKR LMEAQRVTAG YIHLWFDTYV NR (SEQ ID NO: 3)
ATGAAAAAGAAAGTATTAGCACTAGCAGCTATGGTTGCTTTAGCTGCGCC

AGTTCAAAGTGTAGTATTTGCACAAACAAATAATAGTGAAAGTCCTGCAC

CGATTTTAAGATGGTCAGCTGAGGATAAGCATAATGAGGGGATTAACTCT

CATTTGTGGATTGTAAATCGTGCAATTGACATCATGTCTCGTAATACAAC

GATTGTGAATCCGAATGAAACTGCATTATTAAATGAGTGGCGTGCTGATT

TAGAAAATGGTATTTATTCTGCTGATTACGAGAATCCTTATTATGATGAT

AGTACATATGCTTCTCACTTTTATGATCCGGATACTGGAACAACATATAT

TCCTTTTGCGAAACATGCAAAAGAAACAGGCGCAAAATATTTTAACCTTG

CTGGTCAAGCATACCAAAATCAAGATATGCAGCAAGCATTCTTCTACTTA

GGATTATCGCTTCATTATTTAGGAGATGTGAATCAGCCAATGCATGCAGC

ATCTTTTACGGATCTTTCTTATCCAATGGGTTTCCATTCTAAATACGAAA

ATTTTGTTGATACAATAAAAAATAACTATATTGTTTCAGATAGCAATGGA

TATTGGAATTGGAAAGGAGCAAACCCAGAAGATTGGATTGAAGGAGCAGC

GGTAGCAGCTAAACAAGATTATCCTGGCGTTGTGAACGATACGACAAAAG

ATTGGTTTGTAAAAGCAGCCGTATCTCAAGAATATGCAGATAAATGGCGT

GCGGAAGTAACACCGGTGACAGGAAAGCGTTTAATGGAAGCGCAGCGCGT

TACAGCTGGTTATATTCATTTGTGGTTTGATACGTATGTAAATCGCTAA (SEQ ID NO: 1)
TGGTCAGCTGAGGATAAGCATAATGAGGGGATTAACTCTCATTTGTGGAT

TGTAAATCGTGCAATTGACATCATGTCTCGTAATACAACGATTGTGAATC

CGAATGAAACTGCATTATTAAATGAGTGGCGTGCTGATTTAGAAAATGGT

ATTTATTCTGCTGATTACGAGAATCCTTATTATGATGATAGTACATATGC

TTCTCACTTTTATGATCCGGATACTGGAACAACATATATTCCTTTTGCGA

AACATGCAAAAGAAACAGGCGCAAAATATTTTAACCTTGCTGGTCAAGCA

TACCAAAATCAAGATATGCAGCAAGCATTCTTCTACTTAGGATTATCGCT

TCATTATTTAGGAGATGTGAATCAGCCAATGCATGCAGCATCTTTTACGG

ATCTTTCTTATCCAATGGGTTTCCATTCTAAATACGAAAATTTTGTTGAT

ACAATAAAAAATAACTATATTGTTTCAGATAGCAATGGATATTGGAATTG

GAAAGGAGCAAACCCAGAAGATTGGATTGAAGGAGCAGCGGTAGCAGCTA

AACAAGATTATCCTGGCGTTGTGAACGATACGACAAAAGATTGGTTTGTA

AAAGCAGCCGTATCTCAAGAATATGCAGATAAATGGCGTGCGGAAGTAAC

ACCGGTGACAGGAAAGCGTTTAATGGAAGCGCAGCGCGTTACAGCTGGTT

ATATTCATTTGTGGTTTGATACGTATGTAAATCGCTAA

Single-residue mutations were made using Gene Site Saturation Mutagenesis (GSSM) methods described above and assayed for phospholipase activity. For screening purposes, the expression vector was pASK in *E. coli* host Top10. GSSM hits were selected from a primary screen for which a PA/PI emulsion was used as the substrate and the samples were analyzed by LCMS. These primary hits were then confirmed on soybean oil and analyzed by $^{31}$P NMR and HPLC.

The soybean oil assay and procedure for preparing the samples for analysis by NMR is as follows:

NMR Detergent was made by dissolving 25 g Deoxycholic acid, 5.84 g EDTA, 5.45 g Tris base in 900 mL of water, then adjust the pH to 10.5 using KOH pellets. The internal NMR standard was 50 mM TIP and 12.5 mM TBP in HPLC-grade isopropanol. Deuterium oxide (D, 99.9%) low paramagnetic was from Cambridge Isotope Laboratories Inc. (DLM-11-100). The NMR control was Avanti Lecithin (International Lecithin & Phospholipids Society mixed soy phospholipids reference Standard oil), Avanti Polar Lipids Inc, #95309.

The standards and samples were prepared as follows:
Thoroughly mix a batch of Crude Soybean Oil
Dispense 1 mL of oil into a 2 mL tube. Add 60 µL of purified enzyme (for controls, 18 Units) or pure cell lysate (for screening mutants); mix for 15 seconds.
Units are defined as hydrolysis of 1 µmol PC per minute at 37° C. at pH 7.3.
Incubate at 60° C. for 48 hours in thermomixer shaking at 14000 rpm, vortexing intermittently.
After incubation, mix the samples thoroughly using a vortex
Weigh out 250 mg (+/−0.2 mg) of each sample into a 2 mL tube and weigh out a NMR control of 10 mg (+/−0.1 mg) of Avanti Lecithin.
Add 900 µL of NMR Detergent then add 100 µL of D$_2$O to each sample.
Mix the samples thoroughly by vortexing and shaking in Eppendorf Thermomixer, at 30-37° C. and 14000 rpm for 30 minutes
Centrifuge at 13,000 RPM for 10 minutes
Carefully remove the top oily layer
Add 750 µL of hexane to each sample and vortex gently*
Centrifuge at 13,000 RPM for 10 minutes
Carefully remove 600 µL of bottom aqueous layer and transfer to a new tube
Add 25 µL of Internal Standard, mix well
Transfer 500 µL to a 5 mm NMR tube.
Release of DAG was measured by quantitative HPLC according to the following protocol:
The sample solution was approximately 50 µl oil samples and 950 ul hexane/isopropanol (9:1) to make 1 ml. The standard solutions were, for example 0.25 mg/ml, 0.5 mg/ml, 1 mg/ml, 2 mg/ml, and 4 mg/ml of ENOVA™ oil (Kao Corporation, Itasca, Ill.). Enova oil is high-DAG oil that has a fatty acids distribution similar to regular vegetable oil (1,3-DAG and 1,2-DAG).
HPLC Settings:
Column: Chromegasphere™ SI-60, 15 cm×4.6 mm
Temperature: 40° C.
Flow Rate: 2 mL/min
Injection volume: 20 ul Mobile phase A: Hexane
Mobile phase B: Hexane/Isopropanol/Ethyl Acetate/Formic acid=800:100:100:1
Gradient elution:

| Time (min) | 0 | 8 | 8.5 | 15 | 15.1 | 19 |
|---|---|---|---|---|---|---|
| % B | 2 | 35 | 98 | 98 | 2 | 2 |

Evaporative Light Scattering Detector (ELSD) Settings:
A exemplary setting was temperature 40° C., gain 5, and nitrogen gas 3.5 bars. The DAG peak was identified by comparison of retention time with that of standard. Quantification was based on the relationship between the detector's response (peak area) and the analyte's concentration.

Table 8 describes sequences that can be used to practice this invention, e.g., in combination with polypeptides of this invention (see, e.g., Tables 12 to 15), e.g., as mixtures or combinations of enzymes.

Based on: NMR and HPLC data, the mutations shown in Table 8, below, were selected. Table 8, below, indicates the starting amino acid, the position number of the amino acid change and the changed amino acid (for SEQ ID NO:4). Table 8 also indicates the original codon, the replacement codon and other codons for the same changed to amino acid. For example, the second row, "E41A", indicates that the amino acid in position 41 was originally "E" (glutamic acid), but was changed to "A" (alanine). The original codon for change E41A was "GAG", but was changed to "GCA". However, codons "GCG", "GCC" or "GCT" could also have been used. The codon variants as set forth in Table 8 that produced variants (of SEQ ID NO:4) with the best variation or "improvement" over "wild type" (SEQ ID NO:4) for PA hydrolysis. The invention provides nucleic acids, and the polypeptides that encode them, comprising one, several or all or the variations, or the equivalent of all the variations, set forth in Table 8.

In FIG. 10, the weight-fraction of individual phospholipid (PL) species is given relative to the total PL remaining after the reaction, reflecting the specificity of the mutants to particular species. Here, the species were phosphatidic acid (PA), phosphatidylethanolamine (PE), phosphatidylinositol (PI), phosphatidylcholine (PC). "TIP" refers to the internal NMR standard. "DAG released" was measured by HPLC and reflects relative values between samples and controls of total 1,3-DAG and 1,2-DAG. The positive control was a purified sample of E41A mutant previously described in Tan et al., *Biochemistry* 37:4275-4279 (1998). The results indicate that the mutants release DAG well and have good activity on various species, including phosphatidylcholine (PC) and phosphatidylethanolamine (PE), comparable or better than the template (SEQ ID NO:4). For example D100L and D100M show particular activity on PA. Q265R shows particular activity on PI. These mutations can be combined to provide enzymes having desired activities on various substrates.

TABLE 8

| PLC GSSM Hits | Original Codon | Changed To | Other codons encoding the same "changed to" AA | Original AA | AA Changed To | Codon Mutation Location |
|---|---|---|---|---|---|---|
| E41A | GAG | GCA | GCG, GCC, GCT | E | A | 41 |
| E41W | GAG | TGG | — | E | W | 41 |
| E41F | GAG | TTC | TTT | E | F | 41 |
| E41Y | GAG | TAC | TAT | E | Y | 41 |
| E41R | GAG | CGT | CGC, CGA, CGG, AGA, AGG | E | R | 41 |
| E94R | GAG | CGG | CGC, CGA, CGT, AGA, AGG | E | R | 94 |
| D100L | GAT | TTG | CTC, TTA, CTT, CTA, CTG | D | L | 100 |
| D100M | GAT | ATG | — | D | M | 100 |
| D100Y | GAT | TAT | TAC | D | Y | 100 |
| D100F | GAT | TTT | TTC | D | F | 100 |
| D100W | GAT | TGG | — | D | W | 100 |
| A104L | GCT | CTT | CTC, TTA, TTG, CTA, CTG | A | L | 104 |
| D111R | GAT | AGG | CGC, CGA, CGT, AGA, CGG | D | R | 111 |
| T112R | ACT | CGG | CGC, CGA, CGT, AGA, AGG | T | R | 112 |
| Y116W | TAT | TGG | — | Y | W | 116 |
| I117W | ATT | TGG | — | I | W | 117 |
| P118W | CCT | TGG | — | P | W | 118 |
| E125K | GAA | AAG | AAA | E | K | 125 |
| S168N | TCT | AAC | AAT | N | S | 168 |

TABLE 8-continued

GSSM hits

| PLC GSSM Hits | Original Codon | Changed To | Other codons encoding the same "changed to" AA | Original AA | AA Changed To | Codon Mutation Location |
|---|---|---|---|---|---|---|
| D171V | GAT | GTG | GTT, GTC, GTA | D | V | 171 |
| D171E | GAT | GAG | GAA | D | E | 171 |
| M176W | ATG | TGG | — | M | W | 176 |
| D230H | GAT | CAT | CAC | D | H | 230 |
| D230R | GAT | CGT | CGC, CGA, CGG, AGA, AGG | D | R | 230 |
| D234W | GAT | TGG | — | D | W | 234 |
| D234V | GAT | GTG | GTT, GTC, GTA | D | V | 234 |
| D234G | GAT | GGT | GGC, GGA, GGG | D | G | 234 |
| D234R | GAT | CGG | CGC, CGA, CGT, AGA, AGG | D | R | 234 |
| D234K | GAT | AAG | AAA | D | K | 234 |
| Q265R | CAG | CGT | CGC, CGA, CGG, AGA, AGG | Q | R | 265 |

In alternative embodiments, the invention provides combinations (mixtures) of PLC enzymes, or the nucleic acids that encode them, comprising the nucleic acid sequence SEQ ID NO:3 (encoding the polypeptide SEQ ID NO:4) and/or the nucleic acid sequence SEQ ID NO:1 (encoding the polypeptide SEQ ID NO:2); or combinations (mixtures) of PLC enzymes comprising SEQ ID NO:2 and/or SEQ ID NO:4.

In alternative embodiments, the invention provides combinations (mixtures) of PLC enzymes, or the nucleic acids that encode them, comprising the nucleic acid sequence SEQ ID NO:3 (encoding the polypeptide SEQ ID NO:4) and/or the nucleic acid sequence SEQ ID NO:1 (encoding the polypeptide SEQ ID NO:2) having one, two, or more or all of nucleic-acid (mutations) that encode the amino-acid mutations listed above in Table 8, including e.g. the codon changes described herein. In alternative embodiments, the invention provides combinations (mixtures) of PLC enzymes encoded by these nucleic acids, e.g., combinations (mixtures) of PLC enzymes encoded by one, several or all of the nucleic acid sequence variations of SEQ ID NO:3 and/or SEQ ID NO:1, as described in Table 8.

Figure 11:
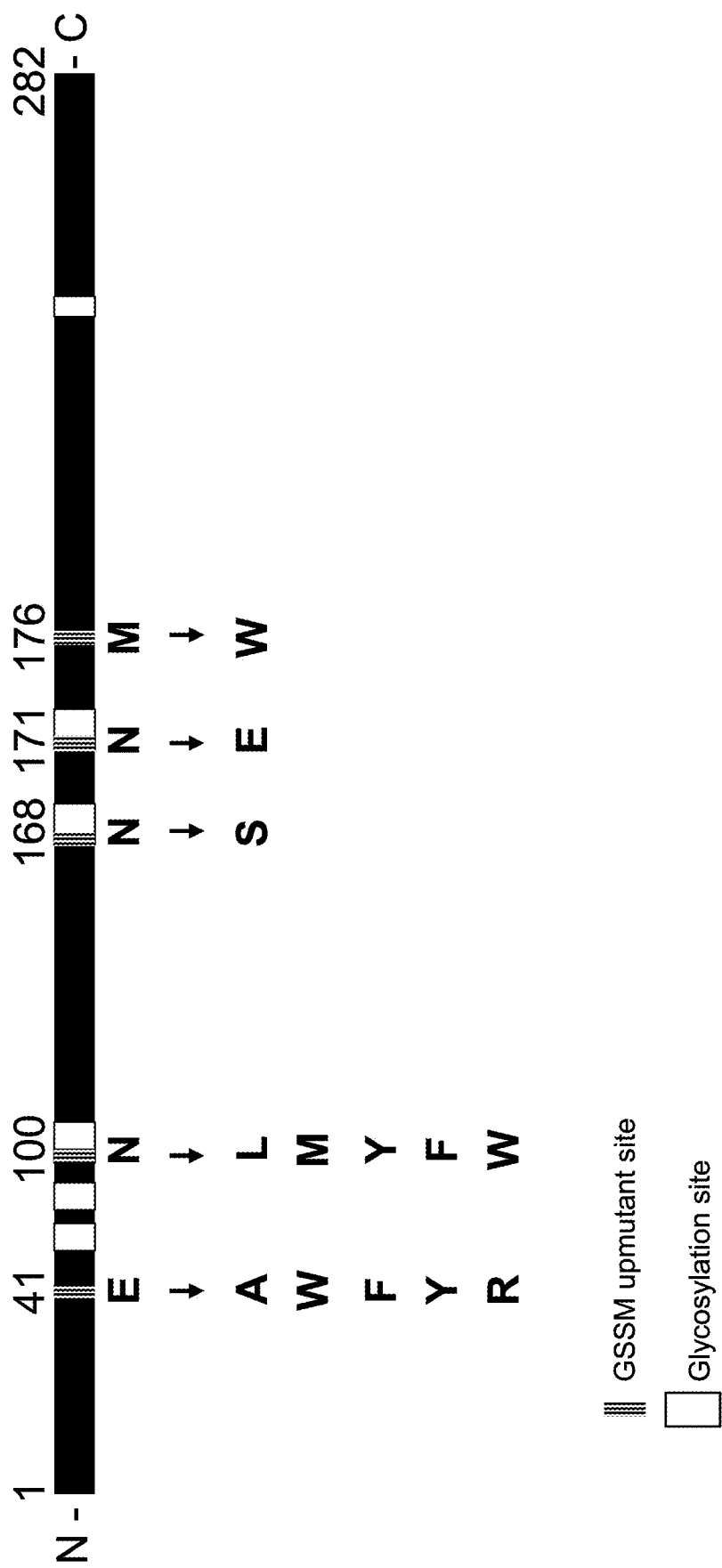
FIG. 11 illustrates the "Gene Site Saturation Mutagenesis" or "GSSM" upmutants selected for inclusion in the GeneReassembly Library, which includes exemplary phospholipases of the invention.

After GSSM hits were screened and the top hits selected (see Table 8, above), further characterization assays on eggyolk plates were performed in order to narrow down the number of single GSSM mutants carried forth for combination using GeneReassembly technology. Table 10 shows the eggyolk assay data (eggyolk assay described below), along with the results of oil assays and thermal tolerance residual activity determination. FIG. 11 illustrates the single GSSM upmutants that were selected for inclusion in the GeneReassembly process. GeneReassembly was performed as described herein.

Table 9, below, lists 288 polypeptide sequences that can be used to practice this invention, e.g., in combination with polypeptides of this invention (see, e.g., Tables 12 to 15), e.g., as mixtures or combinations of enzymes. The Table 9 sequences were created by GeneReassembly combination of the selected single GSSM upmutants. All are variants of the starting amino acid sequence SEQ ID NO:4 (the "wild type" or "WT" sequence).

To aid in reading Table 9, for example, for the phospholipase characterized as "evolved" phospholipase 1 (second row of table):
- the wild-type amino acid residue "E", or glutamic acid (glu) at residue position 41 (of SEQ ID NO:4) is modified to a "Y", or tyrosine (tyr) residue;
- the wild-type amino acid residue "N", or asparagine (asp) at residue position 100 (of SEQ ID NO:4) is modified to a "M", or methionine (met) residue;
- the wild-type amino acid residue "N", or asparagine (asp) at residue position 168 (of SEQ ID NO:4) is modified to an "S" or serine (ser) residue;
- the wild-type amino acid residue "N", or asparagine (asp) at residue position 171 (of SEQ ID NO:4) remains an "N"; and,
- the wild-type amino acid residue "M", or methionine (met) at residue position 176 (of SEQ ID NO:4) remains an "M".

TABLE 9

Phospholipase Library Resulting from GeneReassembly Combination of Single GSSM Upmutants

| "Evolved" Phospholipase | E41 | N100 | N168 | N171 | M176 |
|---|---|---|---|---|---|
| 1 | Y | M | S | N | M |
| 2 | F | W | S | E | M |
| 3 | A | M | N | E | W |
| 4 | Y | F | S | E | M |
| 5 | Y | Y | S | N | M |
| 6 | R | F | N | E | M |
| 7 | E | Y | N | E | M |
| 8 | E | F | N | N | W |
| 9 | A | W | S | E | M |
| 10 | Y | Y | S | N | W |
| 11 | E | L | S | N | W |
| 12 | A | F | N | N | M |
| 13 | W | M | N | N | M |
| 14 | W | Y | S | E | M |
| 15 | R | L | N | E | W |
| 16 | W | W | S | E | W |
| 17 | W | N | S | N | M |
| 18 | W | L | N | E | M |

TABLE 9-continued

Phospholipase Library Resulting from GeneReassembly Combination of Single GSSM Upmutants

| "Evolved" Phospholipase | E41 | N100 | N168 | N171 | M176 |
|---|---|---|---|---|---|
| 19 | R | N | N | E | M |
| 20 | F | N | N | N | W |
| 21 | Y | N | S | E | M |
| 22 | R | N | S | N | W |
| 23 | F | Y | S | N | W |
| 24 | F | L | N | E | W |
| 25 | A | N | N | E | M |
| 26 | A | W | N | N | M |
| 27 | W | M | N | E | W |
| 28 | F | L | S | E | W |
| 29 | Y | F | S | N | M |
| 30 | F | F | N | N | M |
| 31 | E | W | N | E | M |
| 32 | E | W | N | N | W |
| 33 | E | W | S | E | M |
| 34 | E | Y | S | N | M |
| 35 | E | N | S | N | M |
| 36 | E | L | N | E | W |
| 37 | Y | M | N | E | M |
| 38 | F | N | S | N | W |
| 39 | W | N | N | E | W |
| 40 | E | M | S | N | M |
| 41 | Y | N | S | N | M |
| 42 | Y | Y | N | E | M |
| 43 | Y | L | N | E | M |
| 44 | F | M | N | N | W |
| 45 | F | N | S | E | M |
| 46 | F | M | S | N | W |
| 47 | E | F | S | N | W |
| 48 | W | Y | N | E | W |
| 49 | F | F | N | E | M |
| 50 | R | M | S | N | W |
| 51 | A | N | N | E | W |
| 52 | R | W | S | N | M |
| 53 | R | L | S | N | M |
| 54 | R | W | N | E | M |
| 55 | F | W | N | N | M |
| 56 | E | L | N | N | W |
| 57 | E | L | S | E | M |
| 58 | A | Y | S | N | W |
| 59 | E | Y | S | N | W |
| 60 | W | N | N | E | M |
| 61 | W | N | N | N | W |
| 62 | A | F | S | N | M |
| 63 | Y | M | S | E | W |
| 64 | R | F | S | N | M |
| 65 | A | M | N | N | M |
| 66 | F | N | N | E | M |
| 67 | E | M | N | E | M |
| 68 | E | Y | S | E | M |
| 69 | E | F | S | E | M |
| 70 | E | W | S | N | M |
| 71 | F | W | S | N | W |
| 72 | E | W | N | E | W |
| 73 | Y | L | N | N | W |
| 74 | Y | N | S | N | W |
| 75 | A | Y | S | E | W |
| 76 | E | F | S | N | M |
| 77 | W | L | S | N | M |
| 78 | Y | N | N | E | M |
| 79 | E | F | N | E | M |
| 80 | W | N | S | E | M |
| 81 | E | M | S | E | M |
| 82 | W | N | S | N | W |
| 83 | E | W | S | N | W |
| 84 | Y | M | N | E | W |
| 85 | E | Y | N | N | W |
| 86 | F | M | N | E | W |
| 87 | R | L | S | E | W |
| 88 | W | F | S | N | M |
| 89 | E | L | S | N | M |
| 90 | E | L | N | E | M |
| 91 | Y | F | N | N | W |
| 92 | Y | L | S | E | M |
| 93 | A | N | S | N | W |
| 94 | E | N | N | N | W |
| 95 | E | M | S | N | W |
| 96 | R | N | N | E | W |
| 97 | E | M | N | E | W |
| 98 | F | W | S | E | W |
| 99 | W | W | N | N | M |
| 100 | W | N | N | N | M |
| 101 | E | N | S | E | W |
| 102 | R | W | S | E | W |
| 103 | A | W | S | E | W |
| 104 | A | Y | S | E | M |
| 105 | F | Y | S | E | W |
| 106 | A | Y | N | N | W |
| 107 | R | N | S | N | M |
| 108 | F | F | N | N | W |
| 109 | Y | N | N | E | W |
| 110 | E | W | S | E | W |
| 111 | R | N | S | E | M |
| 112 | E | L | N | N | M |
| 113 | E | N | S | N | W |
| 114 | R | W | S | N | W |
| 115 | F | W | N | E | M |
| 116 | Y | Y | N | E | W |
| 117 | F | Y | N | N | W |
| 118 | W | Y | S | N | W |
| 119 | A | N | S | N | M |
| 120 | A | L | S | N | W |
| 121 | E | Y | N | E | W |
| 122 | E | Y | S | E | W |
| 123 | W | N | S | E | W |
| 124 | E | M | N | N | M |
| 125 | E | N | N | E | M |
| 126 | Y | W | N | E | W |
| 127 | A | W | N | N | W |
| 128 | Y | Y | S | E | M |
| 129 | W | Y | N | N | W |
| 130 | F | Y | N | E | M |
| 131 | A | N | S | E | W |
| 132 | A | L | S | E | W |
| 133 | E | F | N | E | W |
| 134 | R | N | S | E | W |
| 135 | F | N | S | E | W |
| 136 | E | W | N | N | M |
| 137 | E | N | N | E | W |
| 138 | W | W | N | E | W |
| 139 | Y | W | S | N | W |
| 140 | W | Y | N | E | M |
| 141 | R | Y | S | N | W |
| 142 | F | Y | S | N | M |
| 143 | Y | F | S | N | W |
| 144 | R | L | N | E | M |
| 145 | F | N | N | E | W |
| 146 | Y | N | S | E | W |
| 147 | R | N | N | N | M |
| 148 | E | Y | N | N | M |
| 149 | R | W | S | E | M |
| 150 | Y | W | N | N | W |
| 151 | A | W | S | N | W |
| 152 | R | Y | S | E | W |
| 153 | R | Y | N | E | M |
| 154 | W | Y | S | E | W |
| 155 | A | Y | N | E | W |
| 156 | Y | M | N | N | W |
| 157 | Y | F | N | N | M |
| 158 | A | N | S | N | W |
| 159 | Y | N | N | N | M |
| 160 | E | F | N | N | M |
| 161 | Y | W | S | E | M |
| 162 | Y | W | N | E | M |
| 163 | W | w | N | N | W |
| 164 | F | Y | N | E | W |
| 165 | W | Y | S | N | M |
| 166 | A | Y | N | E | M |
| 167 | F | F | S | E | W |
| 168 | W | L | S | E | M |

TABLE 9-continued

Phospholipase Library Resulting from GeneReassembly Combination of Single GSSM Upmutants

| "Evolved" Phospholipase | E41 | N100 | N168 | N171 | M176 |
|---|---|---|---|---|---|
| 169 | Y | Y | S | E | W |
| 170 | E | L | S | E | W |
| 171 | F | N | N | N | M |
| 172 | E | N | N | N | M |
| 173 | W | W | S | E | M |
| 174 | A | W | N | E | M |
| 175 | R | Y | N | N | W |
| 176 | A | Y | S | N | M |
| 177 | R | Y | S | N | M |
| 178 | R | Y | S | E | W |
| 179 | R | M | N | E | W |
| 180 | W | F | N | E | M |
| 181 | E | F | S | E | W |
| 182 | E | M | S | E | W |
| 183 | A | N | N | N | M |
| 184 | E | N | S | E | M |
| 185 | F | W | N | N | W |
| 186 | F | W | S | N | M |
| 187 | R | Y | N | E | W |
| 188 | Y | Y | N | N | W |
| 189 | F | Y | S | E | M |
| 190 | F | N | S | N | M |
| 191 | R | F | S | E | W |
| 192 | F | L | S | N | W |
| 193 | W | Y | N | N | M |
| 194 | A | L | N | N | M |
| 195 | F | L | N | N | M |
| 196 | A | F | S | E | W |
| 197 | W | F | S | E | W |
| 198 | A | F | N | E | W |
| 199 | R | L | S | N | W |
| 200 | W | L | N | E | W |
| 201 | Y | L | S | N | W |
| 202 | R | M | N | E | M |
| 203 | A | M | S | E | W |
| 204 | Y | W | S | N | M |
| 205 | R | Y | N | N | M |
| 206 | Y | M | N | N | M |
| 207 | W | M | N | N | W |
| 208 | F | F | S | E | M |
| 209 | Y | F | S | E | W |
| 210 | W | F | S | E | M |
| 211 | W | L | S | N | W |
| 212 | R | L | N | N | W |
| 213 | W | L | N | N | W |
| 214 | W | M | S | N | W |
| 215 | W | M | S | E | W |
| 216 | R | W | N | E | W |
| 217 | R | L | N | N | M |
| 218 | R | F | N | N | M |
| 219 | A | N | N | N | W |
| 220 | Y | F | N | E | M |
| 221 | W | F | N | N | W |
| 222 | R | F | S | E | M |
| 223 | F | L | S | N | M |
| 224 | F | L | S | E | M |
| 225 | A | M | S | E | M |
| 226 | A | M | S | N | M |
| 227 | R | M | S | E | M |
| 228 | R | W | N | N | W |
| 229 | A | Y | N | N | M |
| 230 | Y | W | N | N | M |
| 231 | E | M | N | N | W |
| 232 | A | F | S | E | M |
| 233 | W | F | N | E | W |
| 234 | W | F | S | N | W |
| 235 | A | L | S | E | M |
| 236 | Y | L | N | E | W |
| 237 | F | M | S | E | M |
| 238 | W | M | S | E | M |
| 239 | F | M | S | E | W |
| 240 | Y | W | S | E | W |
| 241 | W | F | N | N | M |
| 242 | W | L | N | N | M |
| 243 | R | M | N | N | W |
| 244 | R | F | N | N | W |
| 245 | A | F | N | N | W |
| 246 | F | F | N | E | W |
| 247 | A | L | N | E | W |
| 248 | Y | L | S | N | M |
| 249 | F | M | S | N | M |
| 250 | Y | M | S | E | M |
| 251 | F | M | N | E | M |
| 252 | F | W | N | E | W |
| 253 | Y | L | N | N | M |
| 254 | R | W | N | N | M |
| 255 | Y | N | N | N | W |
| 256 | R | F | S | N | W |
| 257 | A | F | S | N | W |
| 258 | A | F | N | E | M |
| 259 | A | L | N | N | W |
| 260 | A | L | N | E | M |
| 261 | R | M | S | E | W |
| 262 | W | M | S | N | M |
| 263 | R | M | S | N | M |
| 264 | A | W | S | N | M |
| 265 | R | M | N | N | M |
| 266 | F | Y | N | N | M |
| 267 | A | M | N | N | W |
| 268 | F | F | S | N | M |
| 269 | Y | F | N | E | W |
| 270 | F | L | N | E | M |
| 271 | Y | L | S | E | W |
| 272 | F | L | N | N | W |
| 273 | Y | M | S | N | W |
| 274 | A | M | N | E | M |
| 275 | A | W | N | E | W |
| 276 | W | W | S | N | W |
| 277 | F | M | N | N | M |
| 278 | Y | Y | N | N | M |
| 279 | R | N | N | N | W |
| 280 | F | F | S | N | W |
| 281 | R | F | N | E | W |
| 282 | A | L | S | N | M |
| 283 | W | L | S | E | W |
| 284 | R | L | S | E | M |
| 285 | W | M | N | E | M |
| 286 | A | M | S | N | W |
| 287 | W | W | N | E | M |
| 288 | W | W | S | N | M |

Table 10 summarizes the results of assays analyzing various enzymatic activity, and expression system behavior, of exemplary enzymes of the invention (and in the case of the *Pichia Pastoris* Expression system—the expression activity of the nucleic acids that encode them), all of the polypeptides of the invention being sequence variants of starting phospholipase sequence SEQ ID NO:4 (encoded, e.g., by the nucleic acid sequence SEQ ID NO:3).

TABLE 10

ACTIVITY ANALYSIS AND SUMMARY

| PLC GSSM Upmutants | GSSM Upmutant Amino acid residue # | GSSM Amino Acid change | Oil Assay % PA Hydrolysis at 24 hrs | Pichia Pastoris Expression Activity on eggyolk plates | Thermal Tolerance Percent Residual activity | |
|---|---|---|---|---|---|---|
| | | | | | E. coli Expressed protein | Pichia pastoris Expressed protein |
| Crude oil | | | 0 | | | |
| E41E | 41 | Wild type | 20 | Active | 81% | 100% |
| E41A | 41 | A | 29 | Active | 83% | 99% |
| E41W | 41 | W | 31 | Active | 94% | N/A |
| E41F | 41 | F | 68 | Inactive | 80% | N/A |
| E41Y | 41 | Y | 69 | Inactive | 89% | N/A |
| E41R | 41 | R | 66 | Active | 78% | 104% |
| E94R | 94 | R | 23 | Active | N/A | N/A |
| D100L | 100 | L | 45 | Active | N/A | 87% |
| D100M | 100 | M | 48 | Active | N/A | 104% |
| D100Y | 100 | Y | 57 | Active | N/A | 105% |
| D100F | 100 | F | 59 | Active | 43% | 92% |
| D100W | 100 | W | 61 | Active | N/A | 91% |
| A104L | 104 | L | 26 | Active | 115% | 86% |
| D111R | 111 | R | 27 | Active | N/A | 99% |
| T112R | 112 | R | 23 | Active | 107% | 92% |
| Y116W | 116 | W | 23 | Active | 118% | 102% |
| I117W | 117 | W | 15 | Active | 109% | 102% |
| P118W | 118 | W | 17 | Active | N/A | N/A |
| E125K | 125 | K | 15 | Active | 99% | 86% |
| D171V | 171 | V | 29 | Active | N/A | 106% |
| D171E | 171 | E | 44 | Active | N/A | 110% |
| M176W | 176 | W | 42 | Active | 101% | 101% |
| D230H | 230 | H | 21 | Active | N/A | 97% |
| D230R | 230 | R | 14 | Active | 107% | 104% |
| D234W | 234 | W | 10 | Active | 101% | 98% |
| D234V | 234 | V | 0 | Active | 109% | 102% |
| D234G | 234 | G | 3 | Active | 109% | 114% |
| D234R | 234 | R | 27 | Active | 114% | 90% |
| D234K | 234 | K | 23 | Active | N/A | 101% |
| Q265R | 265 | R | 0 | Inactive | N/A | N/A |
| E41A NNN | 41, 100, 168, 171 | A, N, N, N | 72 | | 63% | |
| E41A NKN | 41, 100, 168, 171 | A, N, K, N | 75 | | 65% | |
| E41A NRN | 41, 100, 168, 171 | A, N, R, N | 79 | | 75% | |
| E41A NSN | 41, 100, 168, 171 | A, N, S, N | 72 | | 85% | |

Egg Yolk Assay

The egg yolk assay is performed as follows:

Egg yolk agar plates are prepared by adding 0.5% (by wt.) egg yolk phosphatidylcholine to media prior to autoclaving. The plates are more uniform if the phosphatidylcholine is dispersed with a high shear mixer prior to autoclaving the media.

Wells are punched in the agar and equal volumes (for example, 2 ml) of serial dilutions of samples, including positive control, are loaded in the wells.

The plates are left for 3-12 hours at 37° C., during which time the enzyme diffuses out of the wells, hydrolyses the egg yolk lecithin and forms precipitation zones due to the formation of diacylglycerol.

The area within the precipitation ring, measured as ring diameter or integrated density value (IDV) is plotted against the standard curve for the positive control to determine the activity of the sample phospholipase. The whole process can be used to determine the unknown PLC activity of a sample. The method is semi-quantitative.

Phosphatidylcholine (PC): From Sigma, Catalog No. P 5394

PC from Dried Egg Yolk, Type X-E, approx. 60% PC by TLC.

In alternative embodiments, the invention provides combinations or mixtures of enzymes of the invention and enzymes as described in Example 2, including e.g., all of the enzyme variants described in Table 8 and Table 9, and in WO 2008/036863.

Example 3: Making Exemplary Phosphatidylinositol-Specific Phospholipase C (PI-PLC) Enzymes of the Invention This example describes exemplary phosphatidylinositol-specific phospholipase C (PI-PLC) enzymes of the invention, including the polypeptide having the sequence as set forth in SEQ ID NO:8, and the polypeptides having a PI-PLC activity as described in Tables 12 to 15; and exemplary methods for making and using them, and assays for determining their phospholipase activity.

In alternative embodiments, the invention provides polypeptides having a PI-PLC enzyme activity. In some embodiments, these polypeptides were constructed by the following methods:

For this series of embodiments, the polypeptide having the amino acid sequence of SEQ ID NO:6 (encoded e.g., by SEQ ID NO:5) was selected as the "parent" or "wild-type" sequence for further modification (or "evolution"); in particular, the underlined (see below) subsequence of SEQ ID NO:6 (or SEQ ID NO:5) was used with the addition of a starting Methionine (e.g. MASSINV . . . ), as the "parent" or starting sequence for "evolution" or sequence changes to make enzyme variants. Note the "parent" or starting sequence for "evolution" lacks the first 30 amino acids, which includes the signal sequence (italics), or

*MNNKKFILKLFICSMVLSAFVF*, encoded e.g., by:
*ATGAACAATAAGAAGTTTATTTTGAAGTTATTCATATGTAGTATGGTACT*

*TAGCGCCTTTGTATTT*

The "parent" or starting sequence for "evolution" also lacks a predicted cleavage site (bold italics) GCTTTC (nucleic acid) or AF (amino acid residues).

"Evolution" (sequence change, or "mutation") was performed using "Gene Site Saturation Mutagenesis" (GSSM) and GeneReassembly (see above for description of GSSM and GeneReassembly) on SEQ ID NO:5 using the underlined sequences, below, with the addition of nucleic acid encoding a starting "M" or methionine (e.g., for the encoded amino acid sequence, MASSINV . . . ), as the parent or starting sequence for "evolution":

SEQ ID NO: 5:
ATGAACAATAAGAAGTTTATTTTGAAGTTATTCATATGTAGTATGGTACT

TAGCGCCTTTGTATTTGCTTTAATGATAAGAAAACCGTT<u>GCAGCTAGC</u>

<u>TCTATTAATGTGCTTGAAAATTGGTCTAGATGGATGAAACCTATAAATGA</u>

<u>TGACATACCGTTAGCACGAATTTCAATTCCAGGAACACATGATAGTGGAA</u>

<u>CGTTCAAGTTGCAAAATCCGATAAAGCAAGTGTGGGGAATGACGCAAGAA</u>

<u>TATGATTTTCGTTATCAAATGGATCATGGAGCTAGAATTTTTGATATAAG</u>

<u>AGGGCGTTTAACAGATGATAATACGATAGTTCTTCATCATGGGCCATTAT</u>

<u>ATCTTTATGTAACACTGCACGAATTTATAAACGAAGCGAAACAATTTTTA</u>

<u>AAAGATAATCCAAGTGAAACGATTATTATGTCTTTAAAAAAAGAGTATGA</u>

<u>GGATATGAAAGGGGCGGAAAGCTCATTTAGTAGTACGTTTGAGAAAAATT</u>

<u>ATTTTCGTGATCCAATCTTTTTAAAAACAGAAGGGAATATAAAGCTTGGA</u>

<u>GATGCTCGTGGGAAAATTGTATTACTAAAAAGATATAGTGGTAGTAATGA</u>

<u>ATCTGGGGATATAATAATTTCTATTGGCCAGACAATGAGACGTTTACCT</u>

<u>CAACTATAAATCAAAATGTAAATGTAACAGTACAAGATAAATATAAAGTG</u>

<u>AGTTATGATGAGAAAATAAACGCTATTAAAGATACATTAAATGAAACGAT</u>

<u>TAACAATAGTGAAGATGTTAATCATCTATATATTAATTTTACAAGCTTGT</u>

<u>CTTCTGGTGGTACAGCATGGAATAGTCCATATTATTATGCGTCCTACATA</u>

<u>AATCCTGAAATTGCAAATTATATGAAGCAAAAGAATCCTACGAGAGTGGG</u>

<u>CTGGATAATACAAGATTATATAAATGAAAAATGGTCACCATTACTTTATC</u>

<u>AAGAAGTTATAAGAGCGAATAAGTCACTTGTAAAATAG</u>

SEQ ID NO: 6:
*MNNKKFILKLFICSMVLSAFVF*AFNDKKTVA<u>ASSINVLENWSRWMK</u>

<u>PINDDIPLARISIPGTHDSGTFKLQNPIKQVWGMTQEYDFRYQMDHGARI</u>

<u>FDIRGRLTDDNTIVLHHGPLYLYVTLHEFINEAKQFLKDNPSETIIMSLK</u>

<u>KEYEDMKGAESSFSSTFEKNYFRDPIFLKTEGNIKLGDARGKIVLLKRYS</u>

<u>GSNESGGYNNFYWPDNETFTSTINQNVNVTVQDKYKVSYDEKINAIKDTL</u>

<u>NETINNSEDVNHLYINFTSLSSGGTAWNSPYYYASYINPEIANYMKQKNP</u>

<u>TRVGWIIQDYINEKWSPLLYQEVIRANKSLVK</u>

Thus, the starting sequence for GSSM was a nucleic acid encoding:

MASSINVLENWSRWMKPINDDIPLARISIPGTHDSGTFKLQNPIKQVWGM

TQEYDFRYQMDHGARIFDIRGRLTDDNTIVLHHGPLYLYVTLHEFINEAK

QFLKDNPSETIIMSLKKEYEDMKGAESSFSSTFEKNYFRDPIFLKTEGNI

KLGDARGKIVLLKRYSGSNESGGYNNFYWPDNETFTSTINQNVNVTVQDK

YKVSYDEKINAIKDTLNETINNSEDVNHLYINFTSLSSGGTAWNSPYYYA

SYINPEIANYMKQKNPTRVGWIIQDYINEKWSPLLYQEVIRANKSLVK

"Evolved" nucleic acid variants (the new nucleic acid sequences made by subjecting SEQ ID NO:5 to GSSM) were subcloned for expression in either *E. coli* (for the GSSM phase) or in *P. fluorescens* (for the GeneReassembly phase).

GSSM was performed as described in e.g. U.S. Pat. Nos. 6,171,820; 6,238,884 (see also explanation herein). See also WO 2008/036863.

Resulting new "variant" or "evolved" nucleic acid and polypeptide sequences were assayed using a high throughput assay as follows:

SOP for High Throughput Thermal Stability Assay

The GSSM screens used the *E. coli* host, XL1Blue (Stratagene, San Diego, Calif.), with the pASK vector (IBA GmbH, Gottingen, Germany). The GeneReassembly screens used the *Pseudomonas fluorescens* host (Dow Global Technologies Inc., US Patent PUB. APP. NO. 20050130160, US Patent PUB. APP. NO. 20050186666 and US Patent PUB. APP. NO. 20060110747) with the pDOW1169 vector (Dow Global Technologies Inc., US Patent PUB. APP. NO. 20080058262) and were selected by growth in M9 minimal medium (Dow Global Technologies Inc., US Patent PUB. APP. NO. 20050186666).

Master Plates

1. The Master Plates were created by colony picking GSSM or GeneReassembly variants into a 384 well plate containing 50 μL of media per well.
   a. The media used for growing the GSSM variants was LB and the GeneReassembly variants used M9 (-uracil).
2. Master plates were grown overnight at 30° C. in a humidified incubator. Followed by the addition of 20% glycerol before storing the plates at −80° C.

Expression Plates

1. Master Plates were thawed at room temperature or 30° C. prior to replication.
2. Master Plates were replicated using a 384 well pintool to inoculate the Expression Plates containing 60 μL of media. The same media was used for the Expression Plates as the Master Plates.
3. Expression Plates were grown overnight (approximately 16 hrs) at 30° C. in a humidified incubator.
4. Expression Plates for the GSSM screen were induced with 200 ng/mL of anhydrous tetracycline (AHT) and the GeneReassembly plates were induced a final concentration of 0.3 mM IPTG.
5. Expression Plates were grown overnight at 30° C. in a humidified incubator.
6. Expression Plates were then stored at −20° C. until frozen, usually overnight, to lyse the host cells.
7. Prior to assaying the Expression Plates they were thawed at room temperature or 30° C.

Robotic Thermal Tolerance Screen
1. The robot was programmed to transfer 10 µL from the Expression Plates to an Assay RT Plate and an Assay Heat Plate.
2. The Assay RT Plate remained at room temperature while the Assay Heat Plate was incubated at elevated temperature for 1 hour. During heat treatment the Assay Heat Plates were covered with a foam top. Temperatures for the heat treatment are listed in the following Table 11:

TABLE 11

Temperatures for primary and secondary robotic screens.

| Screen | Temperature Treatment of GSSM Variants | Temperature Treatment of GeneReassembly Variants |
|---|---|---|
| Primary | 50° C., 55° C. | 65° C. |
| Secondary | 57° C., 60° C. | 70° C. |

3. After the heat treatment 40 µL of the substrate, methylumbelliferyl myo-inositol phosphate (MUPI), was added using a titertek. The substrate was prepared at a concentration of 3 mM so that the final concentration in the Assay Plates is 2.5 mM.
4. The Assay Plates were incubated at room temperature for 5 min. The fluorescence was then measured as relative fluorescent units (RFU) on a fluorescence reader at an excitation wavelength of 360 nm and an emission of 465 nm.

Calculation of % Residual Activity
1. Each Assay plate contained 12 positive and 12 negative controls. The positive controls contained the wild type enzyme and the negative controls contained the vector only within the host organism.
2. The fluorescence from the negative controls was averaged for each 384 well plate and subtracted from the fluorescence of the GSSM or GeneReassembly variants for the Assay RT and Assay Heat plates.
3. Each well of the Assay Heat Plate was then divided by the corresponding well from the Assay RT Plate to get a percent residual activity (% RA) for each variant.
4. The % RA was used to rank the most thermal tolerant variants from the high throughput robotic screen. These hits were confirmed in additional assays Secondary Screen
1. Improved thermal tolerance was confirmed using secondary screens on selected hits. The hits were cherry picked from the primary screen Master Plates into new Master Plates and assayed at elevated temperatures listed in Table 11. The assay protocol was the same as the protocol detailed above for the primary screen.

TABLE 12

Summarizes the sequences and percent (%) residual activity of the top thermal tolerant GSSM variants selected for the construction of the GeneReassembly library.

| | | | % Residual Activity | | |
|---|---|---|---|---|---|
| AA Site | Original AA | New AA | 55° C. | 57° C. | 60° C. |
| 105 | D | G | 81.0% | 58.8% | 3.5% |
| 175 | N | P | 119.9% | 75.7% | 2.1% |
| 176 | N | F | 136.7% | 103.8% | 10.1% |
| 176 | N | L | 102.2% | 97.2% | 9.8% |
| 176 | N | W | 131.9% | 61.7% | 3.2% |
| 176 | N | Y | 180.0% | 106.0% | 4.1% |
| 191 | Q | G | 124.6% | 77.6% | 2.3% |
| 205 | Y | L | 174.3% | 114.2% | 0.0% |
| 244 | N | T | 174.6% | 95.7% | 5.0% |
| 252 | Y | L | 148.4% | 62.0% | 22.2% |
| 252 | Y | R | 149.3% | 187.2% | 15.4% |
| 276 | Y | F | 161.6% | 112.1% | 1.1% |
| 282 | S | C | 161.6% | 116.4% | 8.9% |
| 282 | S | H | 256.8% | 142.0% | 0.7% |
| 282 | S | L | 143.6% | 97.8% | 0.1% |
| 282 | S | P | 147.6% | 96.8% | 1.0% |
| 282 | S | R | 101.6% | 72.5% | 4.9% |
| 284 | L | F | 85.9% | 72% | 0% |
| 291 | R | N | 86.4% | 75.5% | 5.6% |

Point-mutants and associated data for Table 12 are shown immediately below as Table 13. Note, in Table 13, the numbering of amino acid positions begins with the added starting Methionine (e.g. amino acid "M" is position 1, amino acid "A" is position 2, amino acid "S" is position 3, amino acid "S" is position 4, amino acid "I" is position 5, amino acid "N" is position 6, and so on). This is important to make clear: for the variants of SEQ ID NO:6, the numbering of the amino acid changes begins with amino acid 31 of SEQ ID NO:6, were amino acid 31 ("A") is replaced with methionine ("M").

TABLE 13

| Amino Acid Position | Original Amino Acid | New Amino Acid | 50° C. | 55° C. | 57° C. | 60° C. | RT plate (data in relative fluorescence units, RFUs) |
|---|---|---|---|---|---|---|---|
| 5 | I | R | 109.5% | −72.4% | −27.7% | −83.3% | 119213 |
| 10 | N | P | 142.6% | −97.8% | −167.1% | −149.5% | 47737 |
| 12 | S | C | 98.6% | 37.8% | 19.6% | −1.6% | 3926817 |
| 17 | P | R | 105.9% | 70.7% | 50.6% | 0.6% | 2834413 |
| 20 | D | R | 168.8% | 56.2% | 9.5% | −37.7% | 243024 |
| 22 | I | R | 164.2% | −56.3% | −8.8% | −67.9% | 501992 |
| 30 | P | Q | 69.1% | 134.8% | 119.4% | 56.4% | −98428 |
| 31 | G | L | 59.7% | 321.6% | 52.3% | 66.5% | −89982 |
| 32 | T | R | 112.1% | 234.3% | 158.3% | 141.4% | −32840 |
| 32 | T | P | −12.9% | −39.0% | 5.5% | 56.1% | 506296 |
| 32 | T | N | −41.5% | 25.5% | −6.8% | 15.2% | 215696 |
| 34 | D | G | 111.4% | 105.7% | 112.3% | 17.0% | 292094 |
| 34 | D | V | 98.0% | −39.1% | 19.5% | −8.2% | 623943 |
| 34 | D | S | 108.0% | 118.4% | 67.9% | −18.3% | 400778 |
| 48 | W | C | | 0.7% | −88% | 48% | 279831 |

TABLE 13-continued

| Amino Acid Position | Original Amino Acid | New Amino Acid | 50° C. | 55° C. | 57° C. | 60° C. | RT plate (data in relative fluorescence units, RFUs) |
|---|---|---|---|---|---|---|---|
| 52 | Q | G | −19.0% | −31.2% | 45.1% | −11.0% | 440078 |
| 52 | Q | L | −24.5% | −18.9% | −17.5% | −15.0% | 243731 |
| 52 | Q | R | −13.8% | −103.8% | −45.8% | −357.5% | 64939 |
| 56 | F | P | −19.0% | −41.0% | −17.8% | −14.6% | 528700 |
| 57 | R | P |  | 36.5% | −5% | 6% | 673072 |
| 57 | R | H | 196.2% | 54.8% | 11.4% | −2.7% | 1766819 |
| 57 | R | W |  | 94.5% | 32% | −4% | 888544 |
| 58 | Y | G |  | 87.4% | 8% | 0% | 2203075 |
| 59 | Q | P |  | 125.1% | −1003% | 211% | 30707 |
| 64 | A | P |  | −17.1% | −38% | 21% | 298218 |
| 67 | F | A |  | −84.1% | −167% | −46% | 132639 |
| 68 | D | G |  | 859.6% | 2454% | 113% | −5565 |
| 69 | I | R | 550.5% | 219.2% | 283.9% | 123.1% | −39813 |
| 69 | I | S |  | −26.7% | 4% | −2% | 837975 |
| 79 | I | R | 111.4% | 216.0% | 308.4% | 539.6% | −47241 |
| 79 | I | C |  | −9.4% | 18% | −19% | 901719 |
| 79 | I | S |  | 242.7% | −642% | −145% | −33068 |
| 103 | L | E |  | 391.0% | −504% | 492% | 26863 |
| 103 | L | G | 312.7% | 333.5% | 394.9% | 317.6% | −14442 |
| 103 | L | R |  | 135.6% | 279% | 238% | −42440 |
| 103 | L | A |  | 13.2% | −7% | 38% | 520801 |
| 103 | L | S | 105.0% | 48.7% | −162.4% | −90.0% | 53552 |
| 103 | L | N |  | −331.1% | −381% | −229% | 51581 |
| 104 | K | P |  | −1319.4% | 1845% | 4021% | −7815 |
| 105 | D | G | 106.9% | 81.0% | 58.8% | 3.5% | 1739646 |
| 107 | P | H |  | 30.7% | 7% | −3% | 2397754 |
| 107 | P | R |  | 21.4% | 4% | −3% | 3155286 |
| 107 | P | L | 65.8% | 55.2% | 34.4% | −4.7% | 447512 |
| 108 | S | G | 95.5% | 65.1% | 49.6% | −4.3% | 307147 |
| 110 | T | F |  | −10.5% | −7% | 2% | 875451 |
| 110 | T | K | 126.1% | 52.7% | 18.9% | −49.3% | 134884 |
| 112 | I | A |  | −23.7% | −20% | −4% | 453446 |
| 112 | I | K | 55.2% | 95.2% | 15.4% | −46.1% | 59053 |
| 115 | L | E |  | −102.6% | −89% | 103% | 48860 |
| 115 | L | N |  | −12.4% | −15% | −10% | 1025328 |
| 115 | L | S | −5.3% | −8.9% | −10.3% | −10.1% | 556124 |
| 115 | L | G | −21.1% | −36.4% | −10.3% | −41.2% | 644336 |
| 115 | L | R |  | 106.0% | −28% | −215% | −55337 |
| 116 | K | T |  | 18.1% | 7% | 18% | 230855 |
| 116 | K | V | 45.1% | −4.6% | −19.7% | −14.4% | 235560 |
| 116 | K | L | 78.8% | −0.9% | −37.9% | −19.2% | 343119 |
| 116 | K | P | 97.5% | 16.1% | −20.9% | −32.3% | 182525 |
| 116 | K | C |  | −26.1% | −64% | −81% | 226865 |
| 116 | K | F |  | −560.3% | −780% | −126% | 49518 |
| 116 | K | Y |  | −245.0% | −488% | −141% | 39189 |
| 117 | K | G |  | 10.2% | −26% | −21% | 387561 |
| 117 | K | S |  | −31.6% | −25% | −23% | 548036 |
| 118 | E | K |  | 167.4% | 409% | 163% | −44595 |
| 118 | E | Y |  | 106.8% | −57% | 40% | 132171 |
| 118 | E | G | 45.4% | −7.5% | −11.7% | −10.8% | 408480 |
| 118 | E | P | 100.9% | −77.5% | −82.4% | −11.7% | 227778 |
| 118 | E | W |  | −140.1% | −30% | −49% | 115308 |
| 118 | E | A |  | −61.4% | −217% | −58% | 106520 |
| 118 | E | V |  | −112.9% | 57% | −89% | 54418 |
| 118 | E | S | −111.6% | −294.0% | −83.6% | −172.0% | 84511 |
| 118 | E | L | −615.3% | −772.3% | −540.2% | −764.3% | 6410 |
| 127 | S | G |  | 167.2% | 24% | −2% | 2332741 |
| 129 | F | S | −103.1% | −140.8% | −135.6% | −138.6% | 38893 |
| 129 | F | K |  | 166.2% | 46% | −224% | −32568 |
| 130 | S | A |  | 209.1% | 13% | −3% | 2817649 |
| 133 | F | S |  | −96.6% | 245% | 124% | 68055 |
| 134 | E | G |  | −11.5% | −6% | −6% | 1437969 |
| 134 | E | P | −50.2% | −179.6% | −112.4% | −71.5% | 107620 |
| 136 | N | P |  | −7.0% | −9% | −7% | 967546 |
| 139 | R | S |  | 95.2% | 9% | 7% | 3316801 |
| 139 | R | M |  | 65.5% | 3% | −2% | 3452962 |
| 139 | R | P |  | 176.0% | 53% | −3% | 2170436 |
| 140 | D | T |  | 7.5% | −4% | 0% | 3067537 |
| 141 | P | L |  | 12.2% | −3% | −1% | 3026938 |
| 142 | I | P | 105.3% | 42.2% | 15.3% | −4.4% | 1571795 |
| 142 | I | R |  | −9.6% | −5% | −5% | 2239061 |
| 142 | I | G |  | −2.2% | −7% | −7% | 1821775 |
| 143 | F | G |  | 84.3% | −10% | 14% | 547682 |
| 143 | F | V | 7.9% | −5.3% | −3.4% | −3.4% | 2475003 |
| 143 | F | S | 27.1% | −10.3% | −12.1% | −11.6% | 492372 |
| 143 | F | T |  | 7.0% | −22% | −15% | 1395343 |
| 144 | L | R |  | −3.1% | −8% | 3% | 3104379 |

TABLE 13-continued

| Amino Acid Position | Original Amino Acid | New Amino Acid | 50° C. | 55° C. | 57° C. | 60° C. | RT plate (data in relative fluorescence units, RFUs) |
|---|---|---|---|---|---|---|---|
| 144 | L | P |  | 7.8% | −2% | 0% | 1673141 |
| 151 | K | T |  | 112.2% | 6% | 0% | 3537421 |
| 153 | G | M |  | 103.8% | 1% | −7% | 2086156 |
| 153 | G | V |  | 97.6% | −8% | −13% | 1534593 |
| 154 | D | R |  | −4.6% | −3% | −3% | 1464648 |
| 155 | A | R | 101.5% | 149.6% | 225.5% | 159.3% | −37404 |
| 155 | A | P |  | 505.6% | 86% | 111% | −84103 |
| 159 | I | T | 80.3% | 9.4% | −3.2% | −4.9% | 1414669 |
| 160 | V | R |  | −72.5% | −8% | −88% | 360024 |
| 162 | L | S | 77.9% | −1.3% | −0.7% | 9.5% | 653562 |
| 162 | L | F |  | 126.7% | 11% | 5% | 2305681 |
| 162 | L | G | 84.3% | 14.3% | −14.4% | −24.4% | 822742 |
| 162 | L | E | −8.9% | −25.7% | −27.5% | −99.2% | 255160 |
| 162 | L | D |  | −252.6% | −180% | −107% | 41739 |
| 162 | L | R | 8.6% | 10.3% | −856.1% | −184.2% | −45546 |
| 163 | K | E |  | −6.9% | −10% | 10% | 1257238 |
| 163 | K | W |  | −6.8% | −25% | −11% | 935455 |
| 164 | R | L |  | 684.4% | 2692% | 890% | −11232 |
| 164 | R | T |  | −267.9% | −259% | −276% | 35611 |
| 165 | Y | E | 4.2% | −3.1% | −3.5% | −3.1% | 1330418 |
| 165 | Y | S | −0.6% | −4.5% | −5.0% | −4.5% | 1204269 |
| 165 | Y | D |  | −9.9% | −26% | −8% | 849532 |
| 165 | Y | G |  | −21.0% | −9% | −12% | 703657 |
| 174 | Y | R | −27.9% | −10.0% | −12.8% | −11.4% | 478910 |
| 175 | N | P | 186.8% | 119.9% | 75.7% | 2.1% | 3423684 |
| 176 | N | F | 151.7% | 136.7% | 103.8% | 10.1% | 3166873 |
| 176 | N | L | 159.0% | 102.2% | 97.2% | 9.8% | 1973048 |
| 176 | N | Y | 215.1% | 180.0% | 106.0% | 4.1% | 2686812 |
| 176 | N | W | 153.3% | 131.9% | 61.7% | 3.2% | 3375824 |
| 179 | W | V |  | 654.7% | −2109% | 736% | 21624 |
| 179 | W | L |  | 211.2% | −87% | −107% | 66095 |
| 187 | S | V |  | 81.7% | 20% | 9% | 3668103 |
| 191 | Q | G | 141.5% | 124.6% | 77.6% | 2.3% | 4030462 |
| 193 | V | L | 229.3% | 177.3% | 85.1% | −0.3% | 2339956 |
| 196 | T | P | 253.8% | 195.0% | 122.7% | 363.7% | −81049 |
| 197 | V | R | 84.1% | 159.2% | 43.9% | 67.0% | −67056 |
| 201 | Y | R |  | 97.6% | 244% | 571% | −94821 |
| 201 | Y | A |  | 105.4% | 168% | 262% | −79800 |
| 201 | Y | L | 114.7% | 108.5% | 94.5% | 111.0% | −69345 |
| 201 | Y | P |  | 99.5% | 87% | 109% | −77061 |
| 201 | Y | Q | 103.9% | 100.2% | 114.2% | 100.9% | −78259 |
| 201 | Y | E | 98.4% | 196.7% | 94.8% | 22.0% | −75564 |
| 201 | Y | S | 93.7% | 276.0% | −294.6% | −67.2% | −89008 |
| 201 | Y | H |  | −469.7% | −450% | −233% | 38056 |
| 205 | Y | L | 176.2% | 174.3% | 114.2% | −0.4% | 6193145 |
| 206 | D | C |  | 68.6% | 7% | 2% | 2578407 |
| 208 | K | S |  | −95.6% | −56% | −50% | 101991 |
| 215 | T | L | 241.1% | 100.4% | 42.5% | −2.6% | 2276174 |
| 216 | L | A |  | 2.1% | −22% | 9% | 739181 |
| 222 | N | P |  | −1.8% | −27% | 16% | 605972 |
| 238 | S | G | 188.7% | 120.1% | 64.7% | −8.5% | 1960740 |
| 244 | N | T | 147.2% | 174.6% | 95.7% | 5.0% | 3312364 |
| 244 | N | S | 144.6% | 234.0% | 148.4% | 1.1% | 2624829 |
| 252 | Y | L | 131.0% | 148.4% | 62.0% | 22.2% | 6033264 |
| 252 | Y | R | 220.0% | 149.3% | 187.2% | 15.4% | 3753916 |
| 252 | Y | I |  | 96.9% | 41.4% | 3.9% | 10341043 |
| 261 | M | I | 129.8% | 117.8% | 90.7% | −1.0% | 3413811 |
| 268 | R | S |  | −22.2% | −19% | −23% | 353376 |
| 268 | R | L |  | −513.9% | −333% | −149% | 49591 |
| 272 | I | S | 163.2% | 519.8% | 300.9% | 1188.1% | −42385 |
| 272 | I | R | 4.9% | 485.2% | 277.9% | 404.0% | −76173 |
| 272 | I | G |  | 20.2% | 161% | 102% | −85289 |
| 272 | I | E | 199.6% | 142.4% | 163.1% | 97.2% | −65592 |
| 272 | I | N |  | −91.2% | −208% | −77% | 99735 |
| 272 | I | P | 92.7% | −130.0% | −142.8% | −113.3% | 73365 |
| 276 | Y | F | 193.7% | 161.6% | 112.1% | 1.1% | 2536481 |
| 282 | S | C | 153.5% | 161.6% | 116.4% | 8.9% | 1804086 |
| 282 | S | R | 108.4% | 101.6% | 72.5% | 4.9% | 3108844 |
| 282 | S | P | 158.8% | 147.6% | 96.8% | 1.0% | 3082327 |
| 282 | S | H | 193.9% | 256.8% | 142.0% | 0.7% | 1966076 |
| 282 | S | L | 164.4% | 143.6% | 97.8% | 0.1% | 2208563 |
| 282 | S | E | 159.0% | 199.7% | 77.4% | −1.0% | 2499129 |
| 282 | S | W |  | 116.8% | 6% | −3% | 2625324 |
| 282 | S | K | 180.0% | 181.2% | 93.1% | −5.0% | 1412699 |
| 282 | S | F | 144.9% | 113.1% | 28.7% | −5.1% | 1668567 |
| 284 | L | F |  | 85.9% | 72% | −1% | 3744515 |
| 287 | Q | L | 106.5% | 68.1% | 34.0% | −7.2% | 2032181 |

TABLE 13-continued

| Amino Acid Position | Original Amino Acid | New Amino Acid | 50° C. | 55° C. | 57° C. | 60° C. | RT plate (data in relative fluorescence units, RFUs) |
|---|---|---|---|---|---|---|---|
| 291 | R | N | 143.8% | 86.4% | 75.5% | 5.6% | 3463258 |
| 296 | L | E | | −169.4% | 20% | 31% | 188612 |
| | Negative control | | | 103.5% | 130% | 182% | −60543 |
| | Negative control | | 161.4% | 136.6% | 156.0% | 157.1% | −47900 |
| | Negative control | | | 450.3% | 69% | 156% | −63840 |
| | Negative control | | | 125.1% | 267% | 137% | −67530 |
| | Negative control | | 483.8% | 140.8% | 138.9% | 135.3% | −33533 |
| | Negative control | | 508.5% | 123.0% | 138.5% | 116.6% | −44840 |
| | Negative control | | | 104.3% | 119% | 114% | −58308 |
| | Negative control | | 150.3% | 96.9% | 96.4% | 89.8% | −57605 |
| | Positive control | | | 106.8% | 12% | 6% | 3745053 |
| | Positive control | | | 122.1% | 3% | 6% | 2931573 |
| | Positive control | | | 106.6% | 8% | 6% | 3418796 |
| | Positive control | | 92.3% | 70.7% | 55.1% | 3.9% | 5793014 |
| | Positive control | | | 55.1% | 7% | 2% | 3312736 |
| | Positive control | | 153.4% | 89.3% | 51.6% | 1.3% | 4765881 |
| | Positive control | | 132.9% | 70.0% | 34.0% | 0.4% | 5520616 |
| | Positive control | | 154.3% | 80.7% | 17.6% | −0.7% | 4018936 |

GeneReassembly was performed on nucleic acids as described herein using the top thermostable mutants from the GSSM phase; and assay conditions for the GeneReassembly variants described above in section entitled "SOP for High Throughput Thermal Stability Assay", of this example, above. (To reiterate: the nucleic acids encoding the thirty one (31) amino acids of SEQ ID NO:6 (encoded e.g., by SEQ ID NO:5) were removed and a nucleotides encoding a starting methionine were added for the nucleic acid that was "evolved" in the GSSM and GeneReassembly).

The best combination of enzyme variants after GeneReassembly (on the thermostable mutants from the GSSM phase) are set forth in Table 14, below. The invention provides enzymes, and the nucleic acids that encode them, comprising any one, several or all of the amino acid changes described in Table 14. For example, from the first row of Table 14, one exemplary enzyme of the invention is an enzyme comprising an amino acid sequence as set forth in SEQ ID NO:6, but with amino acid changes as follows: N176F, Q191G, Y205L, N244T, Y252R, Y276F, S282H, L284F and/or R291N. Activity data for these exemplary enzymes of the invention is set forth in Table 15, below.

TABLE 14 best combination of enzyme variants after GeneReassembly

| | | | Amino Acid Change | | | | | | | | |
|---|---|---|---|---|---|---|---|---|---|---|---|
| ID | N175 | N176 | | Q191 | Y205 | N244 | Y252 | | Y276 | S282 | L284 | R291 |
| A1 | | F | | G | L | T | R | | F | H | F | N |
| B1 | P | Y | Y178H | G | L | T | R | | F | H | | N |
| 3 | P | Y | | G | L | T | R | | F | H | F | N |
| 4 | P | L | | G | L | T | R | | F | L | F | N |
| 5 | | F | | G | | T | | | F | H | | N |
| 6 | P | Y | | G | L | | R | M261I | F | R | | N |
| 8 | P | Y | | G | L | T | R | | F | R | | N |
| B2 | P | F | | G | L | T | L | | F | H | | N |
| 11 | | F | | G | | T | R | | F | H | | N |
| 12 | | Y | | G | L | T | | | F | H | F | N |
| 14 | P | F | | G | L | T | R | | F | L | F | N |
| G2 | | F | | G | L | T | R | M261I | F | H | | N |
| 17 | P | Y | | G | L | T | R | | F | L | F | N |
| 18 | | F | | G | | T | R | | F | H | F | |
| 20 | | F | | G | L | T | R | | F | H | F | N |
| 21 | | L | | G | L | T | L | | F | H | F | |
| 22 | P | Y | | G | L | T | | | F | H | | N |
| 23 | | F | | G | | T | R | | F | R | F | |
| 24 | P | Y | | G | L | T | L | | F | R | F | |
| A4 | | F | | G | L | T | L | | F | R | F | |
| 26 | | F | | G | L | T | L | | F | R | | |
| 27 | | Y | | G | L | T | R | | F | H | F | N |
| 28 | P | | | G | L | | R | | F | H | F | N |
| 29 | P | F | | G | L | T | L | | F | H | F | N |
| 30 | P | L | | | L | T | R | | F | P | F | |
| 32 | P | W | | G | L | T | R | | F | R | F | |
| 33 | P | Y | | | L | T | R | | F | H | F | N |
| 34 | P | Y | | G | | T | L | | F | R | F | N |
| 35 | | F | | G | L | T | R | | F | R | F | N |
| 36 | P | W | | G | L | T | L | | F | R | | N |
| 37 | | F | | G | L | T | L | | F | P | | |
| 39 | | F | | G | | T | L | | F | H | F | N |

TABLE 14-continued best combination of enzyme variants after GeneReassembly

Amino Acid Change

| ID | N175 | N176 | Q191 | Y205 | N244 | Y252 | Y276 | S282 | L284 | R291 |
|---|---|---|---|---|---|---|---|---|---|---|
| 40 | P | Y | G |   |   | T | R | F | R | F | N |
| 41 |   | F | G | L |   | T |   | F | R | F | N |
| 42 | P | Y | G |   |   | T | R | F | R | F | N |
| 43 | P | Y | G | L |   |   | L |   | H | F | N |
| 44 | P | W | G | L |   | T | R | F | R | F |   |
| 45 | P | Y | G |   |   | T | R |   |   | F | N |
| 46 | P | W | G | L |   | T | L | F | R |   |   |
| 47 | P | Y | G | L |   |   | L | F | R | F | N |
| 48 | P | Y | G | L |   |   | L |   | H | F |   |
| 49 | P |   | G |   |   | T | R | F | H |   | N |
| 50 |   | L | G | L |   | T | L | F | H |   |   |
| 51 | P | F | G | L |   |   | R |   | H | F | N |
| 52 | P | Y | G |   |   | T | L | F | L | F |   |
| 53 |   | Y | G | L | N210N |   | R | F | H | F | N |
| 54 |   | F | G | L |   |   | R |   | H |   | N |
| 55 | P | W | G | L |   |   | R | F | P | F |   |
| 57 | P | Y | G | L |   | T | R |   | R | F |   |
| 58 | P | F | G | L |   | T | L | F | H |   |   |
| 59 | P | F |   | L |   | T | R | F | H |   | N |
| 60 | P | W | G | L |   | T | L | F | R | F |   |
| 61 | P |   | G | L |   | T | L |   | H | F | N |

Data for the GeneReassembly variants is:

TABLE 15

| Name | 65C Residual Activity | 70C Residual Activity | N175 | N176 | Q191 | Y205 | N244 | Y252 | Y276 | S282 | L284 | R291 | Additional mutation |
|---|---|---|---|---|---|---|---|---|---|---|---|---|---|
| A1 | 106.24 | 37.14 |   | F | G | L | T | R | F | H | F | N |   |
| B1 | 111.5 | 23.4 | P | Y | G | L | T | R | F | H |   | N | Y178H |
| 3 | 106.77 | 25.48 | P | Y | G | L | T | R | F | H | F | N |   |
| 4 | 105.4 | 15.89 | P | L | G | L | T | R | F | L | F | N |   |
| 5 | 88.84 | 16.39 |   | F | G |   | T | R | F | H |   | N |   |
| 6 | 100.71 | 20.78 | P | Y | G | L |   | R | F | R |   | N | M261I |
| 8 | 105.64 | 16.94 | P | Y | G | L | T | R | F | R |   | N |   |
| B2 | 101.44 | 22.03 | P | F | G | L | T | L | F | H |   | N |   |
| 11 | 93.96 | 22.8 |   | F | G |   | T | R | F | H |   | N |   |
| 12 | 95.32 | 18.59 |   | Y | G | L | T |   | F | H | F | N |   |
| 14 | 83.24 | 22.83 | P | F | G | L | T | R | F | L | F | N |   |
| G2 | 97.66 | 83.7 |   | F | G | L | T | R | F | H |   | N | M261I |
| 17 | 95.46 | 40.92 | P | Y | G | L | T | R | F | L | F | N |   |
| 18 | 95.98 | 16.72 |   | F | G |   | T | R | F | H | F |   |   |
| 20 | 93.48 | 28.26 |   | F | G | L | T | R | F | H | F | N |   |
| 21 | 93.52 | 15.54 |   | L | G | L | T | L | F | H | F |   |   |
| 22 | 82.46 | 17.4 | P | Y | G | L | T |   | F | H |   | N |   |
| 23 | 86.13 | 17.28 |   | F | G |   | T | R | F | R | F |   |   |
| 24 | 121.7 | 44 | P | Y | G | L | T | L | F | R | F |   |   |
| A4 | 148.28 | 35.27 |   | F | G | L | T | L | F | R | F |   |   |
| 26 | 108.03 | 18.92 |   | F | G | L | T | L | F | R |   |   |   |
| 27 | 85.02 | 16.09 |   | Y | G | L | T | R | F | H | F | N |   |
| 28 | 86.9 | 16.52 | P |   | G | L |   | R | F | H | F | N |   |
| 29 | 157.32 | 22.71 | P | F | G | L | T | L | F | H | F | N |   |
| 30 | 86.49 | 15.47 | P | L |   | L | T | R | F | P | F |   |   |
| 32 | 112.42 | 18.88 | P | W | G | L | T | R | F | R | F |   |   |
| 33 | 121.27 | 15.74 | P | Y |   | L | T | R | F | H | F | N |   |
| 34 | 88.4 | 30.67 | P | Y | G |   | T | L | F | R | F | N |   |
| 35 | 109.4 | 58.72 |   | F | G | L | T | R | F | R | F | N |   |
| 36 | 90.24 | 18.57 | P | W | G | L | T | L | F | R |   | N |   |
| 37 | 92.94 | 16 |   | F | G | L | T | L | F | P |   |   |   |
| 39 | 104.51 | 19.07 |   | F | G |   | T | L | F | H | F | N |   |
| 40 | 102.54 | 57.09 | P | Y | G |   | T | R | F | R | F | N |   |
| 41 | 94.23 | 27.83 |   | F | G | L | T |   | F | R | F | N |   |
| 42 | 112.91 | 16.34 | P | Y | G |   | T | R | F | R | F | N |   |
| 43 | 168.76 | 15.56 | P | Y | G | L |   | L |   | H | F | N |   |
| 44 | 254.08 | 28.87 | P | W | G | L | T | R | F | R | F |   |   |
| 45 | 141.67 | 15.51 | P | Y | G |   | T | R |   |   | F | N |   |
| 46 | 175.31 | 23.58 | P | W | G | L | T | L | F | R |   |   |   |
| 47 | 172.6 | 35.64 | P | Y | G | L |   | L | F | R | F | N |   |
| 48 | 109.25 | 15.12 | P | Y | G | L |   | L |   | H | F |   |   |
| 49 | 95.01 | 15.33 | P |   | G |   | T | R | F | H |   | N |   |

TABLE 15-continued

| Name | 65C Residual Activity | 70C Residual Activity | N175 | N176 | Q191 | Y205 | N244 | Y252 | Y276 | S282 | L284 | R291 | Additional mutation |
|---|---|---|---|---|---|---|---|---|---|---|---|---|---|
| 50 | 81.01 | 16.01 |  | L | G | L |  | T | L | F | H |  |  |  |
| 51 | 109.05 | 15.06 | P | F | G | L |  |  | R |  | H | F | N |  |
| 52 | 84.83 | 15.32 | P | Y | G |  | T | L | F |  | L | F |  |  |
| 53 | 97.17 | 16.81 |  | Y | G | L |  | R | F | H | F |  | N | N210N |
| 54 | 127.34 | 15.05 |  | F | G | L |  | R |  | H |  |  | N |  |
| 55 | 97.32 | 15.11 | P | W | G | L |  | R | F | P | F |  |  |  |
| 57 | 149.08 | 19.49 | P | Y | G | L | T | R |  | R | F |  |  |  |
| 58 | 106.56 | 17.47 | P | F | G | L | T | L | F | H |  |  |  |  |
| 59 | 89.33 | 15.06 | P | F |  | L | T | R | F | H |  |  | N |  |
| 60 | 89.94 | 17.85 | P | W | G | L | T | L | F | R | F |  |  |  |
| 61 | 108.91 | 17.96 | P |  | G | L | T | L |  | H | F |  | N |  |

Lead GeneReassembly hit="G2", or SEQ ID NO:8 encoded by SEQ ID NO:7:

SEQ ID NO: 7:
ATGGCTAGCTCTATTAATGTGCTTGAAAATTGGTCTAGATGGATGAAACC

TATAAATGATGACATACCGTTAGCACGAATTTCAATTCCAGGAACACATG

ATAGTGGAACGTTCAAGTTGCAAAATCCGATAAAGCAAGTGTGGGAATG

ACGCAAGAATATGATTTTCGTTATCAAATGGATCATGGAGCTAGAATTTT

TGATATAAGAGGGCGTTTAACAGATGATAATACGATAGTTCTTCATCATG

GGCCATTATATCTTTATGTAACACTGCACGAATTTATAAACGAAGCGAAA

CAATTTTTAAAAGATAATCCAAGTGAAACGATTATTATGTCTTTAAAAAA

AGAGTATGAGGATATGAAAGGGCGGAAAGCTCATTTAGTAGTACGTTTG

AGAAAAATTATTTTCGTGATCCAATCTTTTTAAAAACAGAAGGAAATATA

AAGCTTGGAGATGCTCGTGGGAAAATTGTATTACTAAAAAGATATAGTGG

TAGTAATGAATCTGGGGATATAATTTTTTCTATTGGCCAGACAATGAGA

CGTTTACCTCAACTATAAATGGTAATGTAAATGTAACAGTACAAGATAAA

TATAAAGTGAGTTTGGATGAGAAAATAAACGCTATTAAAGATACATTAAA

TGAAACGATTAACAATAGTGAAGATGTTAATCATCTATATATTAATTTTA

CAAGCTTGTCTTCTGGTGGTACAGCATGGACGAGTCCATATTATTATGCG

TCCAGGATAAATCCTGAAATTGCAAATTATATTAAGCAAAAGAATCCTAC

GAGAGTGGGCTGGATAATACAAGATTTTATAAATGAAAAATGGCATCCAT

TACTTTATCAAGAAGTTATAAATGCGAATAAGTCACTTGTAAAATGA

SEQ ID NO: 8:
MASSINVLENWSRWMKPINDDIPLARISIPGTHDSGTFKLQNPIKQVWGM

TQEYDFRYQMDHGARIFDIRGRLTDDNTIVLHHGPLYLYVTLHEFINEAK

QFLKDNPSETIIMSLKKEYEDMKGAESSFSSTFEKNYFRDPIFLKTEGNI

KLGDARGKIVLLKRYSGSNESGGYNFFYWPDNETFTSTINGNVNVTVQDK

YKVSLDEKINAIKDTLNETINNSEDVNHLYINFTSLSSGGTAWTSPYYYA

SRINPEIANYIKQKNPTRVGWIIQDFINEKWHPLLYQEVINANKSLVK

Oil screen data: small scale screening for phospholipid content for GeneReassembly hits is summarized in the table below. Oils were treated (or not treated, in the case of the control) with enzyme as described in the protocol entitled "Small scale oil procedure", below. Samples were then analyzed for phospholipid content using NMR using the following protocol:

Small Scale Oil Procedure

Objective: To examine the activity of ePLC and PI-PLC in crude soybean oil at timepoints during the enzyme reaction.

Oil:
Crude Soybean oil
FFA: 0.24%
pH: 6.97
DAG: 0.27% 1,2+0.24% 1,3=0.51% total DAG
PLs: 0.21% PA, 0.43% PE, 0.25% PI, 0.44% PC (1.34% total PLs); No LPA, 0.01% LPE, No LPI, 0.02% LPC, No 1-LPLs; 0.01% A, No E, I or C; 661 ppm total phosphorus of which 628.6 ppm is from PLs
CP: 742 ppm P, 73.8 ppm Ca, 69.8 ppm Mg, 0.0 ppm Fe
Enzymes:
Evolved phospholipase 8 (Example 2, Table 9)~11.5 Units/mg
Want 5.5 units×15 samples=82.5 units total/11.5 Units/mg~7 mg
Weighted out 12.1 mg×11.5 U/mg=139.15 Units resuspended in 120 uL 20 mM Hepes pH 7.4, 1 mM ZnSO4=1.16 units/uL
Want 5.5 units in 10 uL
5.5 units/(1.16 units/uL)=4.7 uL+5.3 uL=10 uL
Prepare stock 94 uL of 1.16 Units/uL and 106 uL 20 mM Hepes pH 7.4, 1 mM ZnSO4.
Add 10 uL to reaction
SEQ ID NO:8—4.2 Units/mg
Want 0.02 units×15 samples=0.3 units total/4.2 Units/mg~1 mg
Weighted out 4.2 mg×4.2 U/mg=17.64 Units resuspended in 120 uL 20 mM Hepes pH 7.4, 1 mM ZnSO4=0.147 units/uL
Want 0.02 units in 10 uL
0.02 units/(0.147 units/uL)=0.14 uL+9.86 uL=10 uL
Prepare stock 3 uL of 0.147 Units/uL and 197 uL 20 mM Hepes pH 7.4, 1 mM ZnSO4.
Add 10 uL to reaction
Reaction Conditions:
1 mL of oil was aliquoted into 2 mL tubes using a Glison distriman.
Oil was preheated at 60 C shaking at 1400 rpm in thermomixer for ~30 minutes before addition of enzyme.
Enzyme was added to each sample then polytroned for 30 seconds and incubated at 60 C with continuous shaking.
Samples were removed at timepoints.
Immediately after removal of samples at timepoints, samples were prepared for NMR analysis. The addition of NMR detergent pH10.5 which should stop enzyme reaction.

Preparation of Reagents, Standards, and Samples for $^{31}$P NMR Determination of Phospholipids and Products:

Two internal $^{31}$P standards of either TMP (2,2,6,6-Tetramethylpiperidine)/tributylphosphate (TBP) or TMP/trimethylpsoralen (TIP) at pH 10.5, were used. The TIP is most immune from spectral overlap but it does have a longer relaxation time (2.76 sec) compared with 1.02 sec for TBP. TBP matches the Ti values of PC, PE and PI whereas TIP matches more with PA. Saturation factors have been calculated from data obtained with normal recycle delay of 1.74 sec vs. a 21.6 second recycle using a 58 degree tip angle for optimum S/N per unit time using TIP. This is probably the preferred method. TBP though more efficient because of the shorter Ti has a chemical shift intermediate between PI and PC and is highly temperature dependent and suffers from overlap.

This provides the following advantages:
(i) pH 10.5 cleanly separates LPI from PE (they are overlapped at pH 8.6, and 9.5),
(ii) TBP and TIP internal standards allows more rapid recycling NMR delays with approximately 2.8 improvement in S/N per unit time,
(iii) Provides an internal check of both 2 mM TBP/TIP and 2 mM TMP references,
(iv) Allows different NMR conditions to be selected based on needs (PL's or products, for example).

Preparation of Reagents
1. 5% Deoxycholic acid (DOC): dissolve 5.0 g of Deoxycholic acid Na salt into 100 ml of HPLC grade water.
2. 50 mM EDTA/112.5 mM TRIS: add 1.46 g of EDTA acid and 1.3624 g of TRIS base to 100 ml of HPLC grade water.
3. 5:4 DOC/(EDTA/TRIS), pH 10.5 Detergent: mix 50 ml of DOC Na and 40 ml of EDTA/TRIS. Add pellet wise KOH until pH is 10.5 (a few pellets). This detergent contains 50 mM TRIS for pH buffering.
4. In summary, to make 900 ml detergent: 25 g DOC, 5.84 g EDTA, 5.45 g Tris base, 900 ml $H_2O$, adjust the pH to 10.5 using KOH pellets.
5. 50 mM TMP and 50 mM TBP Internal Standard in HPLC grade isopropanol (IPA): first prepare 100 mM TMP (MW 140.08) and 100 mM TBP (MW 266.32) in IPA respectively, and then mix them at the ratio of 1:1. Prepare a fresh stock each week of analysis and store it at 4° C. to maintain stability.

Preparation of Standards and Samples
6. PL Calibration solution: accurately weigh (+/−0.1 mg) approximately 10 mg of Avanti lecithin (PA 5.9%, PE 10.4%, PI 8.3%, PC 14.0%, LPC 0.5%) into a 2 ml vial. Add 40 µl of 50 mM TMP/50 mM TBP internal standard, 100 µl $D_2O$, and 860 µl Detergent and mix thoroughly by vortexing for half an hour, and take 500 µl clear aqueous solution into a standard 5 mm NMR tube after spinning for a while*. The concentration of TMP and TBP are 2000 µM and 2000 µM respectively; the molecular weights of PA, PE, PI, PC, and PLC are approximately 697, 716, 857, 758, and 496 respectively, so for 10.0 mg/ml Avanti lecithin, PA is 0.846 mM, PE is 1.453 mM, PI is 0.968 mM, PC is 1.847 mM, and LPC 0.101 mM.
7. Crude soy oil sample solution: vortex the oil and accurately weigh (+/−0.2 mg) approximately 100 mg oil into a 2 ml vial. Add 100 ul $D_2O$, and 900 µl Detergent and mix thoroughly by vortexing for half an hour. After spinning for a while, take 600 µl clear aqueous solution into a vial* and add 24 µl of 50 mM TMP/50 mM TBP internal standard and mix thoroughly, then take 500 µl clear aqueous solution into a standard 5 mm NMR tube.
8. De-gummed oil sample solution: vortex the oil and accurately weigh (+/−0.2 mg) approximately 250 mg oil into a 2 ml vial. Add 100 µl $D_2O$, and 900 µl detergent and mix thoroughly by vortexing for half an hour. After spinning for a while, take 600 µl clear aqueous solution into a vial* and add 24 µl of 50 mM TMP/50 mM TBP internal standard and mix thoroughly, then take 500 µl clear aqueous solution into a standard 5 mm NMR tube.
9. Gum sample solution: weigh approximately 10 mg gum (+/−0.1 mg) (no more than 11 mg) into a 2 ml vial. Add 40 ul of 50 mM TMP/12.5 mM TBP internal standard, 100 ul $D_2O$, and 860 ul Detergent and mix thoroughly by vortexing for half an hour, and take 500 ul clear aqueous solution into a standard 5 mm NMR tube after spinning for a while*.

*The sample solution becomes two layers after spinning. A needle syringe is used to transfer the lower layer of the clear aqueous solution into the NMR tube. Use caution not to disturb the top layer.

10. Crude canola oil sample solution: vortex the oil and accurately weigh (+/−0.2 mg) approximately 250 mg oil into a 2 ml vial. Add 100 ul $D_2O$, and 900 µl Detergent and mix thoroughly by vortexing for half an hour. After spinning for a while, take 600 µl clear aqueous solution into a vial* and add 24 ul of 50 mM TMP/50 mM TBP internal standard and mix thoroughly, then take 500 µl clear aqueous solution into a standard 5 mm NMR tube.
11. Water Wastes sample solution: give an estimation of the % v of the oil in the water waste. Vortex the water waste and take 0.5 ml into a 2 ml vial and accurately weigh it (approximately 500 mg). Add 100 µl D20 and approximately 400 µl of detergent to make a 1 ml solution (excluding the oil entrained in the water wastes) and mix thoroughly by vortexing. After spinning for a while, take 600 ul clear aqueous solution into a vial* and add 24 µl of 50 mM TMP/50 mM TBP internal standard and mix thoroughly, then take 500 µl clear aqueous solution into a standard 5 mm NMR tube.

*The sample solution becomes two layers after spinning. A needle syringe is used to transfer the lower layer of the clear aqueous solution into the NMR tube. Use caution not to disturb the top layer.

Data Collection for $^{31}$P NMR Determination of Phospholipids and Products

Data parameter sets have been set up for automated ICONNMR™ (Bruker BioSpin Corporation, Fremont, Calif.) operation with a 58 degree tip angle coded for the default high power. Insert sample into probe with "ej"/"ij" commands. Check edte=300.0. In TopSpin use the "rpar" operation first and read in the parameter set P31_TBP_TMP_std. Go to the acquisition window with "acqu" and tune the QNP probe for both 31P and 1H using the "wobb" command. "ej" sample and then proceed with IconNMR automation using the same parameter table. In automation samples are queued and run in turn with shimming beforehand. Editable parameters are NS and DI. For allocated time NS=512-2048 provide adequate S/N. Scaling factors to account for the different relaxation times have been accumulated and should be checked on an Avanti lecithin sample run with any samples.

TABLE 16

Oil screen data (small scale, phospholipid content) for GeneReassembly hits:

| Oil | Enzyme Treatment | Oil: Mix | Weight of oil (mg) | PA(%) | PE(%) | PI(%) | PC(%) | Total PL(%) | LPA(%) |
|---|---|---|---|---|---|---|---|---|---|
| Crude Soy Oil | PI-PLC A1 | 200 mgs | 210.8 | 0.24 | 0.42 | 0.07 | 0.40 | 1.13 | 0.00 |
| Crude Soy Oil | PI-PLC A1 | 200 mgs | 214.7 | 0.23 | 0.42 | 0.06 | 0.39 | 1.09 | 0.00 |
| Crude Soy Oil | PI-PLC B1 | 200 mgs | 211.4 | 0.24 | 0.47 | 0.05 | 0.44 | 1.20 | 0.00 |
| Crude Soy Oil | PI-PLC B1 | 200 mgs | 214.5 | 0.24 | 0.44 | 0.18 | 0.43 | 1.28 | 0.00 |
| Crude Soy Oil | PI-PLC B2 | 200 mgs | 210.9 | 0.26 | 0.48 | 0.07 | 0.47 | 1.28 | 0.00 |
| Crude Soy Oil | PI-PLC B2 | 200 mgs | 211.4 | 0.26 | 0.48 | 0.06 | 0.47 | 1.26 | 0.00 |
| Crude Soy Oil | PI-PLC G2 | 200 mgs | 211.6 | 0.25 | 0.47 | 0.05 | 0.45 | 1.22 | 0.00 |
| Crude Soy Oil | PI-PLC G2 | 200 mgs | 210 | 0.24 | 0.45 | 0.05 | 0.43 | 1.18 | 0.00 |
| Crude Soy Oil | PI-PLC A4 | 200 mgs | 209.9 | 0.24 | 0.43 | 0.15 | 0.41 | 1.23 | 0.01 |
| Crude Soy Oil | PI-PLC A4 | 200 mgs | 208.5 | 0.25 | 0.46 | 0.10 | 0.43 | 1.24 | 0.00 |
| Crude Soy Oil | PI-PLC WT (SEQ ID NO: 6) | 200 mgs | 212 | 0.22 | 0.41 | 0.20 | 0.41 | 1.24 | 0.00 |
| Crude Soy Oil | PI-PLC WT (SEQ ID NO: 6) | 200 mgs | 209.4 | 0.24 | 0.46 | 0.16 | 0.43 | 1.29 | 0.02 |
| Crude Soy Oil | No Enzyme | 200 mgs | 211.3 | 0.21 | 0.39 | 0.22 | 0.38 | 1.20 | 0.00 |
| Crude Soy Oil | No Enzyme | 200 mgs | 209.9 | 0.26 | 0.44 | 0.26 | 0.41 | 1.37 | 0.00 |
| Crude Canola Oil | No Enzyme | 200 mgs | 194.7 | 0.17 | 0.13 | 0.20 | 0.34 | 0.85 | 0.00 |
| Crude Canola Oil | No Enzyme | 200 mgs | 194.9 | 0.17 | 0.14 | 0.21 | 0.34 | 0.85 | 0.00 |
| Crude Canola Oil | No Enzyme | 200 mgs | 196.1 | 0.18 | 0.14 | 0.22 | 0.35 | 0.89 | 0.00 |

TABLE 17

| Oil | LPE(%) | LPI(%) | LPC(%) | 1-LPA(%) | 1-LPE(%) | 1-LPI(%) | 1-LPC(%) | A(%) | E(%) | I(%) | C(%) | Total P (ppm) | Total P from PLs (ppm) |
|---|---|---|---|---|---|---|---|---|---|---|---|---|---|
| Crude Soy Oil | 0.01 | 0.00 | 0.02 | 0.00 | 0.00 | 0.01 | 0.00 | 0.01 | 0.00 | 0.02 | 0.00 | 644 | 478 |
| Crude Soy Oil | 0.01 | 0.00 | 0.02 | 0.00 | 0.00 | 0.01 | 0.00 | 0.01 | 0.00 | 0.02 | 0.00 | 646 | 462 |
| Crude Soy Oil | 0.01 | 0.00 | 0.02 | 0.00 | 0.00 | 0.02 | 0.00 | 0.01 | 0.00 | 0.02 | 0.00 | 725 | 510 |
| Crude Soy Oil | 0.01 | 0.00 | 0.02 | 0.00 | 0.00 | 0.00 | 0.00 | 0.01 | 0.00 | 0.00 | 0.00 | 640 | 535 |
| Crude Soy Oil | 0.01 | 0.00 | 0.02 | 0.00 | 0.00 | 0.00 | 0.00 | 0.01 | 0.00 | 0.03 | 0.00 | 729 | 540 |
| Crude Soy Oil | 0.01 | 0.00 | 0.02 | 0.00 | 0.00 | 0.02 | 0.00 | 0.01 | 0.00 | 0.03 | 0.00 | 755 | 534 |
| Crude Soy Oil | 0.02 | 0.00 | 0.02 | 0.00 | 0.00 | 0.03 | 0.00 | 0.01 | 0.00 | 0.03 | 0.00 | 729 | 516 |
| Crude Soy Oil | 0.01 | 0.00 | 0.03 | 0.00 | 0.00 | 0.01 | 0.00 | 0.01 | 0.00 | 0.03 | 0.00 | 733 | 498 |
| Crude Soy Oil | 0.02 | 0.01 | 0.03 | 0.00 | 0.00 | 0.02 | 0.00 | 0.01 | 0.00 | 0.02 | 0.00 | 701 | 515 |
| Crude Soy Oil | 0.01 | 0.00 | 0.02 | 0.00 | 0.00 | 0.02 | 0.00 | 0.01 | 0.00 | 0.03 | 0.00 | 700 | 522 |
| Crude Soy Oil | 0.01 | 0.01 | 0.02 | 0.00 | 0.00 | 0.02 | 0.00 | 0.01 | 0.00 | 0.00 | 0.01 | 657 | 518 |
| Crude Soy Oil | 0.01 | 0.00 | 0.02 | 0.00 | 0.00 | 0.03 | 0.00 | 0.01 | 0.00 | 0.00 | 0.00 | 737 | 540 |
| Crude Soy Oil | 0.01 | 0.02 | 0.02 | 0.00 | 0.00 | 0.02 | 0.00 | 0.01 | 0.00 | 0.00 | 0.00 | 608 | 499 |
| Crude Soy Oil | 0.01 | 0.01 | 0.02 | 0.00 | 0.00 | 0.02 | 0.00 | 0.01 | 0.01 | 0.00 | 0.02 | 759 | 569 |
| Crude Canola Oil | 0.02 | 0.02 | 0.04 | 0.00 | 0.00 | 0.02 | 0.00 | 0.02 | 0.00 | 0.00 | 0.00 | 480 | 348 |
| Crude Canola Oil | 0.01 | 0.01 | 0.04 | 0.00 | 0.00 | 0.01 | 0.00 | 0.01 | 0.00 | 0.00 | 0.00 | 474 | 349 |
| Crude Canola Oil | 0.01 | 0.01 | 0.04 | 0.00 | 0.00 | 0.01 | 0.00 | 0.01 | 0.00 | 0.00 | 0.00 | 484 | 365 |

TABLE 18

AVERAGED DATA

| Oil | Enzyme Treatment | PA(%) | PE(%) | PI(%) | PC(%) | Total PL(%) | LPA(%) | LPE(%) | LPI(%) | LPC(%) |
|---|---|---|---|---|---|---|---|---|---|---|
| Crude Soy Oil | PI-PLC A1 | 0.24 | 0.42 | 0.06 | 0.39 | 1.11 | 0.00 | 0.01 | 0.00 | 0.02 |
| Crude Soy Oil | PI-PLC B1 | 0.24 | 0.45 | 0.12 | 0.43 | 1.24 | 0.00 | 0.01 | 0.00 | 0.02 |
| Crude Soy Oil | PI-PLC B2 | 0.26 | 0.48 | 0.06 | 0.47 | 1.27 | 0.00 | 0.01 | 0.00 | 0.02 |
| Crude Soy Oil | PI-PLC G2 | 0.24 | 0.46 | 0.05 | 0.44 | 1.20 | 0.00 | 0.01 | 0.00 | 0.03 |
| Crude Soy Oil | PI-PLC A4 | 0.24 | 0.45 | 0.13 | 0.42 | 1.24 | 0.01 | 0.01 | 0.00 | 0.02 |
| Crude Soy Oil | PI-PLC WT (SEQ ID NO: 6) | 0.23 | 0.44 | 0.18 | 0.42 | 1.27 | 0.01 | 0.01 | 0.01 | 0.02 |
| Crude Soy Oil | No Enzyme | 0.23 | 0.42 | 0.24 | 0.40 | 1.29 | 0.00 | 0.01 | 0.01 | 0.02 |
| Crude Canola Oil | No Enzyme | 0.17 | 0.14 | 0.21 | 0.34 | 0.87 | 0.00 | 0.01 | 0.01 | 0.04 |

TABLE 19

AVERAGED DATA

| Oil | 1-LPA(%) | 1-LPE(%) | 1-LPI(%) | 1-LPC(%) | A(%) | E(%) | I(%) | C(%) | Total P (ppm) | Total P from PLs (ppm) |
|---|---|---|---|---|---|---|---|---|---|---|
| Crude Soy Oil | 0.00 | 0.00 | 0.01 | 0.00 | 0.01 | 0.00 | 0.02 | 0.00 | 645.40 | 470.17 |
| Crude Soy Oil | 0.00 | 0.00 | 0.01 | 0.00 | 0.01 | 0.00 | 0.01 | 0.00 | 682.44 | 522.47 |
| Crude Soy Oil | 0.00 | 0.00 | 0.01 | 0.00 | 0.01 | 0.00 | 0.03 | 0.00 | 741.94 | 536.72 |
| Crude Soy Oil | 0.00 | 0.00 | 0.02 | 0.00 | 0.01 | 0.00 | 0.03 | 0.00 | 730.76 | 506.92 |
| Crude Soy Oil | 0.00 | 0.00 | 0.02 | 0.00 | 0.01 | 0.00 | 0.02 | 0.00 | 700.48 | 518.82 |
| Crude Soy Oil | 0.00 | 0.00 | 0.02 | 0.00 | 0.01 | 0.00 | 0.00 | 0.00 | 697.17 | 528.75 |
| Crude Soy Oil | 0.00 | 0.00 | 0.02 | 0.00 | 0.01 | 0.00 | 0.00 | 0.01 | 683.32 | 533.87 |
| Crude Canola Oil | 0.00 | 0.00 | 0.01 | 0.00 | 0.02 | 0.00 | 0.00 | 0.00 | 479.51 | 354.10 |

Large scale degumming with PI-PLC and ePLC or PI-PLC with PLC (SEQ ID NO: 2), with the results summarized in the Tables 20, 21 and 22, below. Oils were treated (or not treated, in the case of the control) with enzyme using this "Large Scale Oil Procedure":

Large Scale Oil Procedure

Objective:

To compare the activity of PLC, PI-PLC, "Evolved" PLCs (or "ePLCs") of Example 2, above, in 2 k g of crude soybean oil.

Oil:

Crude Soybean oil

FFA: 0.24% pH: 6.97

DAG: 0.27% 1,2+0.24% 1,3=0.51% total DAG

PLs: 0.21% PA, 0.43% PE, 0.25% PI, 0.44% PC (1.34% total PLs); No LPA, 0.01% LPE, No LPI, 0.02% LPC, No 1-LPLs; 0.01% A, No E, I or C; 661 ppm total phosphorus of which 628.6 ppm is from PLs CP: 742 ppm P, 73.8 ppm Ca, 69.8 ppm Mg, 0.0 ppm Fe Enzymes:

PLC (SEQ ID NO:2)

Want 5.5 units=200 ppm=0.4 g/2000 g oil

Preheat oil to 60° C. with continuous mixing 200 rpm.

Move preheated oil to high shear mixer.

Start mixing at low speed.

Add 0.4 g PLC (SEQ ID NO:2)+60 g room temperature water to preheated oil while mixing.

Adjust high shear mixer to 6 (highest speed) for 1 minute. Move sample back to paddlemixer and continuously stir at 200 rpm at 60° C. for 2 hours.

Adjust temperature to 80° C. Collect noncentrifuged oil sample and store at RT for analysis Once temperature of oil reaches 80 C, centrifuge using Gyro tester centrifuge.

Evolved phospholipase 8 (Example 2, Table 9)-11.5 U/mg

Want 5.5 units/g oil, reaction 2 kg or 2000 g=11 000 units total

Want 11,000 units/11.5 U/mg=957 mg

Crude Oil:

Weighted out 958.6 mg×11.5 U/mg=11,024 Units. Resuspended samples in 60 g water immediately before addition to crude oil.

Evolved phospholipase 156 (Example 2, Table 9)-17.2 U/mg

Want 5.5 units/g oil, reaction 2 kg or 2000 g=11 000 units total

Want 11,000 units/17.2 U/mg=640 mg

Crude Oil:

Weighted out 642.49 mg×17.2 U/mg=11,049 Units. Resuspended samples in 60 g water immediately before addition to crude oil.

SEQ ID NO:8—4.2 U/mg

Want 0.02 units/g oil, reaction 2 kg or 2000 g=40 units total

Want 40 units/4.2 U/mg=9.5 mg

Crude Oil:

Weighted out 9.6 mg×4.2 U/mg=40.32 Units. Resuspended samples in 60 g water immediately before addition to crude oil.

Evolved phospholipase 8+SEQ ID NO:8—2 hrs: Weighted out 959.2 mg Evolved phospholipase 8 PH045× 11.5 U/mg=11,031 Units. Weighted out 9.8 mg SEQ ID NO:8×4.2 U/mg=41.16 Units Evolved phospholipase 8+SEQ ID NO:8—4 hrs: Weighted out 959.1 mg Evolved phospholipase 8 PH045× 11.5 U/mg=11,030 Units. Weighted out 9.8 mg SEQ ID NO:8×4.2 U/mg=41.16 Units Resuspended samples in 60 g water immediately before addition to crude oil and Evolved phospholipase 8+SEQ ID NO:8 at same time.

Reaction Conditions:

2000 g of oil was weighted into a 4 L beaker. The oil was preheated to 60 C on hotplate with feedback temperature control (Barnstead/Themolyne mirak)

Oil was preheated at 60 C with continuous stirring at ~200 rpm before addition of enzyme.

Samples were moved to high speed mixer, enzyme+60 g room temperature water to preheated oil while mixing at low speed then immediately high shear mixed (max speed) for 1 minute.

Move sample back to paddlemixer and continuously stir at 200 rpm at 60 C for 2 hours.

Adjust temperature to 80 C. Collect noncentrifuged oil sample and store at −20 C for analysis Once temperature of oil reaches 80 C, centrifuge using high speed centrifuge.

TABLE 20

| Description of oil assay | Average % 1,2-DAG | Average % 1,3-DAG | Sum 1,3 & 1,2 DAG | Net DAG | % Theoretical max DAG obtained | Free Fatty Acid (titration) |
|---|---|---|---|---|---|---|
| crude soybean oil | 0.36 | 0.32 | 0.68 | 0.00 | | 0.47 |
| SEQ ID NO: 2 treated precentrifuged oil * | 1.11 | 0.33 | 1.44 | 0.76 | 80 | 0.47 |
| SEQ ID NO: 2 treated centrifuged oil * | 0.98 | 0.33 | 1.32 | 0.64 | 68 | 0.24 |
| Evolved phosopholipase 8 treated precentrifuged oil * | 1.56 | 0.33 | 1.88 | 1.20 | 128 | 0.48 |
| Evolved phosopholipase 8 treated centrifuged oil * | 1.78 | 0.39 | 2.16 | 1.48 | 158 | 0.24 |
| Evolved phosopholipase 156 treated precentrifuged oil * | 1.44 | 0.32 | 1.76 | 1.08 | 114 | 0.49 |
| Evolved phosopholipase 156 treated centrifuged oil * | 1.48 | 0.34 | 1.82 | 1.14 | 121 | 0.25 |
| SEQ ID NO: 8 treated precentrifuged oil ** | 0.66 | 0.32 | 0.98 | 0.30 | 157 | 0.48 |
| SEQ ID NO: 8 treated centrifuged oil ** | 0.55 | 0.34 | 0.90 | 0.22 | 112 | 0.21 |
| Evolved phosopholipase 8 + SEQ ID NO: 8 treated 2 hrs precentrifuged oil *** | 1.71 | 0.33 | 2.04 | 1.36 | 119 | 0.71 |
| Evolved phosopholipase 8 + SEQ ID NO: 8 treated 2 hrs centrifuged oil *** | 1.87 | 0.37 | 2.23 | 1.55 | 136 | 0.24 |
| Evolved phosopholipase 8 + SEQ ID NO: 8 treated 4 hrs precentrifuged oil *** | 1.99 | 0.38 | 2.37 | 1.69 | 148 | 0.72 |
| Evolved phosopholipase 8 + SEQ ID NO: 8 treated 4 hrs centrifuged oil *** | 1.92 | 0.38 | 2.30 | 1.62 | 142 | 0.21 |

Net DAG = Sum 1,3 & 1,2 DAG Generated − Endogenous DAG
% Theoretical max DAG obtained = (Net DAG/Theoretical Max DAG)*100
crude soybean oil 06 17 08: PC = 0.47, PE = 0.46, PA = 0.22, PI = 0.27
* Theoretical max DAG from NMR PL PC, PE & PA values = (% PC*0.78) + (% PE*0.83) + (% PA*0.89) = 0.94
** Theoretical max DAG from NMR PL PI value = (% PI*0.72) = 0.194
*** Theoretical max DAG from NMR PL PC, PE, PA & PI values = (% PC*0.78) + (% PE*0.83) + (% PA*0.89) + (% PI*0.72) = 1.14

TABLE 21

| Description of oil assays | PA(%) | PI(%) | PE(%) | PC(%) | PA(%) SD | PI(%) SD | PE(%) SD | PC(%) SD | % PA Removal |
|---|---|---|---|---|---|---|---|---|---|
| crude soybean oil | 0.21 | 0.26 | 0.43 | 0.45 | 0.01 | 0.01 | 0.01 | 0.02 | 0 |
| SEQ ID NO: 2 treated precentrifuged oil | 0.20 | 0.25 | 0.18 | 0.06 | 0.00 | 0.00 | 0.00 | 0.01 | 7 |
| SEQ ID NO: 2 treated centrifuged oil | 0.05 | 0.00 | 0.00 | 0.00 | 0.00 | 0.01 | 0.00 | 0.00 | 77 |
| Evolved phosopholipase 8 treated precentrifuged oil | 0.04 | 0.22 | 0.00 | 0.00 | 0.00 | 0.01 | 0.00 | 0.00 | 80 |
| Evolved phosopholipase 8 treated centrifuged oil | 0.03 | 0.02 | 0.00 | 0.00 | 0.00 | 0.00 | 0.00 | 0.00 | 85 |
| Evolved phosopholipase 156 treated precentrifuged oil | 0.05 | 0.08 | 0.01 | 0.00 | 0.01 | 0.01 | 0.01 | 0.00 | 75 |
| Evolved phosopholipase 156 treated centrifuged oil | 0.04 | 0.00 | 0.00 | 0.00 | 0.00 | 0.00 | 0.00 | 0.00 | 83 |
| SEQ ID NO: 8 treated precentrifuged oil | 0.20 | 0.00 | 0.42 | 0.41 | 0.01 | 0.00 | 0.01 | 0.00 | 0 |
| SEQ ID NO: 8 treated centrifuged oil | 0.07 | 0.00 | 0.05 | 0.02 | 0.01 | 0.00 | 0.01 | 0.00 | 65 |
| Evolved phosopholipase 8 + SEQ ID NO: 8 treated 2 hrs precentrifuged oil | 0.07 | 0.00 | 0.03 | 0.00 | 0.01 | 0.00 | 0.01 | 0.00 | 67 |
| Evolved phosopholipase 8 + SEQ ID NO: 8 treated 2 hrs centrifuged oil | 0.04 | 0.00 | 0.00 | 0.00 | 0.00 | 0.00 | 0.00 | 0.00 | 82 |
| Evolved phosopholipase 8 + SEQ ID NO: 8 treated 4 hrs precentrifuged oil | 0.05 | 0.00 | 0.01 | 0.00 | 0.00 | 0.00 | 0.00 | 0.00 | 74 |
| Evolved phosopholipase 8 + SEQ ID NO: 8 treated 4 hrs centrifuged oil | 0.03 | 0.00 | 0.00 | 0.00 | 0.00 | 0.00 | 0.00 | 0.00 | 86 |

TABLE 22

| Description of oil assays | PA(%) | PI(%) | PE(%) | PC(%) | PA(%) SD | PI(%) SD | PE(%) SD | PC(%) SD | A(%) | I(%) | E(%) | C(%) |
|---|---|---|---|---|---|---|---|---|---|---|---|---|
| SEQ ID NO: 2 treated gums | 3.60 | 5.21 | 5.19 | 2.96 | 0.10 | 0.26 | 0.28 | 0.14 | 0.14 | 0.00 | 1.17 | 2.54 |
| Evolved phosopholipase 8 treated gums | 0.49 | 6.28 | 0.04 | 0.00 | 0.06 | 0.40 | 0.07 | 0.00 | 1.22 | 0.00 | 3.25 | 4.41 |
| Evolved phosopholipase 156 treated gums | 1.32 | 6.67 | 0.56 | 0.00 | 0.06 | 0.24 | 0.06 | 0.00 | 0.84 | 0.00 | 2.85 | 4.02 |
| SEQ ID NO: 8 treated gums | 2.65 | 0.63 | 7.20 | 7.15 | 0.10 | 0.04 | 0.34 | 0.24 | 0.09 | 0.86 | 0.03 | 0.12 |
| Evolved phosopholipase 8 + SEQ ID NO: 8 treated 2 hrs gums | 1.35 | 0.90 | 0.85 | 0.28 | 0.06 | 0.13 | 0.05 | 0.26 | 1.23 | 2.98 | 3.50 | 4.90 |
| Evolved phosopholipase 8 + SEQ ID NO: 8 treated 4 hrs gums | 0.95 | 0.31 | 0.39 | 0.08 | 0.11 | 0.06 | 0.03 | 0.13 | 1.34 | 4.50 | 3.57 | 4.83 |

TABLE 23

| Description of oil assays | LPA(%) | LPE(%) | LPI(%) | LPC(%) | 1-LPA(%) | 1-LPE(%) | 1-LPI(%) | 1-LPC(%) | X(uM) 12.9 ppm |
|---|---|---|---|---|---|---|---|---|---|
| crude soybean oil | 0.00 | 0.01 | 0.01 | 0.03 | 0.00 | 0.00 | 0.00 | 0.00 | 0 |
| SEQ ID NO: 2 treated gums | 0.23 | 0.40 | 0.58 | 0.46 | 0.05 | 0.00 | 0.10 | 0.00 | 0 |
| Evolved phosopholipase 8 treated gums | 0.33 | 0.00 | 0.29 | 0.28 | 0.55 | 0.00 | 0.00 | 0.00 | 60.9 |
| Evolved phosopholipase 156 treated gums | 0.00 | 0.03 | 0.36 | 0.55 | 0.46 | 0.00 | 0.00 | 0.00 | 0 |
| SEQ ID NO: 8 treated gums | 0.00 | 0.28 | 0.00 | 0.54 | 0.00 | 0.00 | 0.00 | 0.00 | 439.5 |
| Evolved phosopholipase 8 + SEQ ID NO: 8 treated 2 hrs gums | 0.26 | 0.20 | 0.00 | 0.62 | 0.60 | 0.00 | 0.00 | 0.00 | 526.9 |
| Evolved phosopholipase 8 + SEQ ID NO: 8 treated 4 hrs gums | 0.16 | 0.07 | 0.00 | 0.34 | 0.63 | 0.00 | 0.00 | 0.00 | 265.5 |

Samples were then analyzed for phopsholipid content (PL data) using NMR, as described above. Samples were also analyzed for DAG content (DAG FFA) using the following HPLC protocols:

Determination of Diacylglycerol in Vegetable Oil by High Performance Liquid Chromatography with Evaporative Light Scattering Detector This method is based on AOCS method Cd 11d-96, as described in Mono- and Diglycerides Determination by HPLC-ELSD (AOCS Official Method Cd 11d-96), with some modifications. One significant change is the adoption of ENOVA™ oil as the standard for quantification purpose. The AOCS method uses dipalmitin (C16:0) as standard. However, in vegetable oil, C16:0 only accounts for ~10%, while C18:0, C18:1, and C18:2 stand for nearly 90%. In HPLC chromatogram, not only is the peak shape of dipalmitin different from that of the actual diacylglycerols (DAG) in the vegetable oil, the detector's response to dipalmitin is also different from C18 DAG. Both factors affect the quantification result because evaporative light scattering detector (ELSD) is a non-linear detector. ENOVA™ oil is high-DAG oil produced through a patented process by ADM using soybean oil and canola oil as raw material, which has a fatty acids distribution similar to regular vegetable oil and hence a better standard for quantification of the DAG in vegetable oil. The amount of DAG in ENOVA™ oil can be determined using AOCS Official Method Cd 11b-91 (2) and $^{31}$P NMR method (3, 4).

Preparation of Sample and Standard Solutions:
1. Sample solution: accurately weight approximately 50 μl oil samples and add 950 ul hexane/isopropanol=9:1 to make 1 ml solution.
2. Standard solutions: the range of 1,2-DAG and 1,3-DAG in standard solutions shall cover the actual DAG concentration in sample solution. One example is 5 ENOVA™ oil solutions with concentration of 0.25 mg/ml, 0.5 mg/ml, 1 mg/ml, 2 mg/ml, and 4 mg/ml respectively.

HPLC Settings:
Column: Chromegasphere SI-60, 15 cm×4.6 mm
Temperature: 40° C.
Flow Rate: 2 mL/min
Injection volume: 20 ul
Mobile phase A: Hexane
Mobile phase B: Hexane/Isopropanol/Ethyl Acetate/Formic acid=800:100:100:1
Gradient elution:

| Time (min) | 0 | 8 | 8.5 | 15 | 15.1 | 19 |
|---|---|---|---|---|---|---|
| % B | 2 | 35 | 98 | 98 | 2 | 2 |

ELSD Settings:
The parameters of Sedex 75 ELSD shall be optimized to maximize the sensitivity. These include temperature, gain, nebulizer gas pressure, and the position of glass cell. A typical example is temperature 40° C., gain 5, and nitrogen gas 3.5 bars.

Peak Identification and Quantification
Identify DAG peak by comparison of retention time with that of standard. Quantification is based on the relationship between the detector's response I (Peak Area) and the analyte's concentration C: $I=K*C^M$, here K and M are experimental conditions related constants.

REFERENCES

1. Mono- and Diglycerides Determination by HPLC-ELSD (AOCS Official Method Cd 11 d-96).

2. Determination of Mono- and Diglycerides by Capillary Gas Chromatography (AOCS Official Method Cd 11b-91).
3. Spyros, A.; Dais, P. Application of $^{31}$P NMR Spectroscopy in Food Analysis. 1. Quantitative Determination of the Mono- and Diglyceride Composition of Olive Oils, *J. Agric. Food Chem.* 2000, 48, 802-805.
4. Vigli, G.; Philippids, A.; Spyros, A.; Dais, P. Classification of Edible Oils by Employing $^{31}$P and $^{1}$H NMR Spectroscopy in Combination with Multivariate Statistical Analysis. A Proposal for the Detection of Seed Oil Adulteration in Virgin Olive Oils, *J. Agric. Food Chem.* 2003, 51, 5715-5722.

Lead GR Hit "G2" was Codon Optimized:

Codon optimization was attempted two different ways on the subcloned ORF (G2 codon opt V1 and G2 codon opt V2) and with the second method providing a much more highly expressable variant. For G2 codon opt V1, original codons whose in the subcloned ORF usage fell below 15-25% for *P. fluorescens* were changed to codons in *P. fluorescens* with usage >30%. Additionally two TGA stop codons were used at the 3' end of the ORF.

G2 codon opt V1 (SEQ ID NO: 9):
ATGGCCAGCAGCATCAACGTCCTCGAAAACTGGTCGCGCTGGATGAAGCC

GATCAACGACGACATCCCGCTGGCCCGCATCAGCATCCCGGGCACCCACG

ACAGCGGCACCTTCAAGCTGCAGAACCCGATCAAGCAGGTCTGGGGCATG

ACCCAGGAATACGACTTCCGCTACCAGATGGACCACGGCGCCCGCATCTT

CGACATCCGCGGCCGCCTGACCGACGACAACACCATCGTGCTGCACCACG

GCCCGCTGTACCTGTACGTGACCCTGCACGAATTCATCAACGAAGCCAAG

CAGTTCCTGAAGGACAACCCGAGCGAAACCATCATCATGAGCCTGAAGAA

AGAATACGAAGACATGAAGGGCGCCGAAAGCAGCTTCAGCAGCACCTTCG

AAAAGAACTACTTCCGCGACCCGATCTTCCTGAAGACCGAAGGCAACATC

AAGCTGGGCGACGCCCGCGGCAAGATCGTCCTCCTGAAGCGCTACAGCGG

CAGCAACGAAAGCGGCGGCTACAACTTCTTCTACTGGCCGGACAACGAAA

CCTTCACCAGCACCATCAACGGCAACGTGAACGTGACCGTGCAGGACAAG

TACAAGGTGAGCCTGGACGAAAAGATCAACGCCATCAAGGACACCCTGAA

CGAAACCATCAACAACAGCGAAGACGTGAACCACCTGTACATCAACTTCA

CCAGCCTGAGCAGCGGCGGCACCGCCTGGACCAGCCCGTACTACTACGCC

AGCCGCATCAACCCGGAAATCGCCAACTACATCAAGCAGAAGAACCCGAC

CCGCGTGGGCTGGATCATCCAGGACTTCATCAACGAAAAGTGGCACCCGC

TGCTGTACCAGGAAGTGATCAACGCGAACAAGAGCCTGGTCAAGTGATGA

For G2 codon opt V2, *P. fluorescens* codons were chosen so that their usage (%) most closely matched the usage (%) of each codon as found in the original ORF. This is a process we call Codon Usage Transfer. Additionally the predicted mRNA secondary structure of the transcript was minimized to prevent stem loops and hairpins at the translation start (a window of nucleotides in the mRNA from −65 to +65, where translation starts at +1 with the "A" nucleotide of "ATG" which is codes for the first methionine of the protein). In this minimization, synonymous codons with similar usage (%) were used to reduce unwanted nucleotide-nucleotide pairings. As before, two TGA stop codons were used at the 3' end of the ORF.

G2 codon opt V2 (SEQ ID NO: 10):
ATGGCGAGCAGCATCAACGTCTTGGAGAACTGGTCCCGGTGGATGAAGCC

CATCAACGACGATATCCCACTGGCCCGTATCTCGATCCCGGGCACCCACG

ACAGCGGCACCTTTAAACTCCAGAACCCAATCAAACAGGTCTGGGGCATG

ACCCAGGAGTACGACTTCCGCTACCAGATGGACCACGGCGCCCGGATCTT

CGACATCCGGGGGCGCCTGACCGACGACAACACCATCGTGCTGCACCACG

GGCCGCTGTACCTGTACGTGACCTTGCATGAGTTCATCAATGAGGCGAAG

CAGTTCCTGAAGGACAACCCGAGCGAAACCATCATCATGTCCCTGAAGAA

AGAATACGAAGACATGAAGGGGGCGGAGAGTTCGTTCAGCAGCACCTTCG

AAAAGAACTACTTCCGCGACCCGATTTTCCTGAAGACCGAGGGCAACATC

AAACTGGGCGACGCCCGCGGCAAGATCGTGCTGTTGAAGCGGTACAGCGG

CAGCAACGAGTCCGGGGGCTACAACTTCTTTTACTGGCCGGATAACGAAA

CCTTCACTTCGACGATCAACGGCAACGTGAACGTGACCGTGCAGGACAAG

TACAAGGTCAGCCTCGACGAAAAGATCAATGCCATCAAGGACACCCTGAA

CGAGACCATCAATAACAGCGAGGACGTGAACCACTTGTACATCAACTTCA

CCAGTCTCTCCTCCGGCGGCACCGCCTGGACCAGCCCGTACTACTACGCG

AGTCGTATCAACCCCGAGATCGCCAACTACATCAAACAGAAAAACCCCAC

CCGGGTCGGTTGGATCATCCAGGACTTCATCAACGAGAAGTGGCACCCGC

TGCTGTACCAGGAGGTGATCAACGCGAACAAATCGCTGGTGAAGTGATGA

Data comparing 30 L fermentations of G2 (SEQ ID NO:8) and its codon optimized versions (SEQ ID NO:9 and SEQ ID NO:10) is summarized in Table 24. Fermentations were in *P. fluorescence* system described earlier. Data comparing thermotolerance between codon optimized SEQ ID NO:10 vs. SEQ ID NO:8 is summarized in Table 25. Thermotolerance was measured as described earlier.

TABLE 24

| Time | SEQ ID NO: 8 | SEQ ID NO: 9 | SEQ ID NO: 10 |
|---|---|---|---|
| 24 | | 1.90E+06 | |
| 28 | | 3.31E+06 | |
| 29 | 8.98E+05 | | |
| 32 | | 3.82E+06 | |
| 33 | 1.62E+06 | | |
| 36 | | 4.94E+06 | |
| 37 | 2.47E+06 | | |
| 40 | | 4.81E+06 | |
| 41 | 3.82E+06 | | |
| 44 | | 5.46E+06 | |
| 45 | 5.28E+06 | | |
| 46 | | | 4.38E+06 |
| 48 | | 5.26E+06 | |
| 49 | 6.04E+06 | | |
| 50 | | | 9.02E+06 |
| 52 | | 5.64E+06 | |
| 53 | 5.27E+06 | | |
| 54 | | | 1.14E+07 |
| 56 | | 1.19E+07 | |
| 58 | | | 2.02E+07 |
| 60 | | 6.22E+06 | |
| 62 | | | 1.93E+07 |
| 66 | | | 1.88E+07 |
| 70 | | | 1.53E+07 |
| 75 | | | 1.22E+07 |

TABLE 25

|  | SEQ ID NO: 8 | SEQ ID NO: 10 |
|---|---|---|
| Room Temp ° C. | 100.00% | 100.00% |
| 55° C. | 99.12% | 134.05% |
| 60° C. | 116.64% | 108.53% |
| 65° C. | 107.96% | 108.16% |
| 70° C. | 49.12% | 56.78% |

Data comparing activity of G2 (SEQ ID NO:8) and its codon optimized version (SEQ ID NO:10) is summarized in Table 26. The assays were performed using the Small scale oil procedure as described above.

TABLE 26

AVERAGED DATA

| Sample # | Experiment | PA(%) | PE(%) | PI(%) | PC(%) | Total PL(%) | LPA(%) | LPE(%) | LPI(%) | LPC(%) | 1-LPA(%) |
|---|---|---|---|---|---|---|---|---|---|---|---|
| 1 | SEQ ID NO: 8 - 0.4 U/g | 0.18 | 0.48 | 0.02 | 0.47 | 1.14 | 0.00 | 0.02 | 0.00 | 0.03 | 0.00 |
| 2 | SEQ ID NO: 8 - 0.2 U/g | 0.16 | 0.43 | 0.00 | 0.43 | 1.01 | 0.00 | 0.01 | 0.00 | 0.02 | 0.00 |
| 3 | SEQ ID NO: 8 - 0.1 U/g | 0.18 | 0.46 | 0.05 | 0.50 | 1.19 | 0.01 | 0.01 | 0.00 | 0.03 | 0.00 |
| 4 | SEQ ID NO: 8 - 0.05 U/g | 0.16 | 0.43 | 0.05 | 0.44 | 1.08 | 0.01 | 0.02 | 0.00 | 0.03 | 0.00 |
| 5 | SEQ ID NO: 10 - 0.4 U/g | 0.19 | 0.51 | 0.00 | 0.53 | 1.23 | 0.01 | 0.02 | 0.00 | 0.03 | 0.00 |
| 6 | SEQ ID NO: 10 - 0.2 U/g | 0.15 | 0.41 | 0.00 | 0.44 | 1.00 | 0.01 | 0.02 | 0.00 | 0.03 | 0.00 |
| 7 | SEQ ID NO: 10 - 0.1 U/g | 0.15 | 0.41 | 0.07 | 0.41 | 1.05 | 0.00 | 0.02 | 0.00 | 0.02 | 0.00 |
| 8 | SEQ ID NO: 10 - 0.05 U/g | 0.16 | 0.45 | 0.07 | 0.45 | 1.13 | 0.00 | 0.02 | 0.00 | 0.03 | 0.00 |
| 9 | No Enzyme (Control) | 0.17 | 0.46 | 0.23 | 0.47 | 1.33 | 0.00 | 0.02 | 0.02 | 0.03 | 0.00 |

| Sample # | Experiment | 1-LPE(%) | 1-LPI(%) | 1-LPC(%) | A(%) | E(%) | I(%) | C(%) | Total P (ppm) | Total P from PLs (ppm) |
|---|---|---|---|---|---|---|---|---|---|---|
| 1 | SEQ ID NO: 8 - 0.4 U/g | 0.00 | 0.00 | 0.00 | 0.01 | 0.00 | 0.16 | 0.00 | 804.49 | 485.05 |
| 2 | SEQ ID NO: 8 - 0.2 U/g | 0.00 | 0.00 | 0.00 | 0.01 | 0.00 | 0.16 | 0.00 | 743.13 | 429.86 |
| 3 | SEQ ID NO: 8 - 0.1 U/g | 0.00 | 0.00 | 0.00 | 0.01 | 0.00 | 0.10 | 0.00 | 794.03 | 500.55 |
| 4 | SEQ ID NO: 8 - 0.05 U/g | 0.00 | 0.00 | 0.00 | 0.01 | 0.00 | 0.08 | 0.00 | 710.86 | 453.40 |
| 5 | SEQ ID NO: 10 - 0.4 U/g | 0.00 | 0.00 | 0.00 | 0.01 | 0.00 | 0.24 | 0.00 | 943.30 | 523.00 |
| 6 | SEQ ID NO: 10 - 0.2 U/g | 0.00 | 0.00 | 0.00 | 0.01 | 0.00 | 0.16 | 0.00 | 731.12 | 423.97 |
| 7 | SEQ ID NO: 10 - 0.1 U/g | 0.00 | 0.00 | 0.00 | 0.01 | 0.00 | 0.04 | 0.00 | 632.84 | 440.85 |
| 8 | SEQ ID NO: 10 - 0.05 U/g | 0.00 | 0.00 | 0.00 | 0.01 | 0.00 | 0.05 | 0.00 | 681.24 | 476.04 |
| 9 | No Enzyme (Control) | 0.00 | 0.00 | 0.00 | 0.01 | 0.00 | 0.00 | 0.00 | 711.84 | 551.23 |

Dosage

Dosage of enzyme may be defined by the number of "units" of enzyme to be added per gram of oil to be treated, where one unit (U) is defined as the quantity of enzyme required to liberate 1 umole of 4-methylumbelliferone from 4.5 mM 4-Methylumbelliferyl myo-inositol-1-phosphate, N-methyl-morpholine salt in one minute at pH 7.5 and 30° C. In one embodiment, dosage of PLC (e.g. using SEQ ID NO:2) or ePLC ranges from 1-50 U/g of oil, while dosage of PI_PLC ranges from 0.05-20 U/g of oil. In another embodiment, dosages in the range of 1-20 U/g of oil of PLC or ePLC and 0.05-2 U/g of oil of PI-PLC are used. In another embodiment, dosages in the range of 2-10 U/g of oil of PLC or ePLC and 0.1-1 U/g of oil of PI-PLC are used. In an alternative embodiment, dosage of PLC (e.g., using SEQ ID NO:2) or ePLC is 5.5 U/g of oil and for PI-PLC is 0.2 U/g of oil.

Alternatively, dosage may be determined by using the specific activity of the enzyme to convert the number of units of enzyme required per gram of oil to the weight of enzyme (ug) required per gram of oil. Specifically, the number of units required is divided by the specific activity (U/mg) of the enzyme to arrive at the required ug of enzyme. For example, a dose of 0.2 U enzyme/gram of oil divided by a specific activity of 90.1 U/mg, results in a dose of 2.22 ug of enzyme/g of oil. Therefore, in one embodiment, the dose of PI_PLC ranges from 0.55-222 ug of enzyme/g of oil. In another embodiment, dosages in the range of 0.55-22.2 ug of enzyme/g of oil of PI-PLC are used. In another embodiment, dosages in the range of 1.11-11.1 ug of enzyme/g of oil of PI-PLC are used. In an alternative embodiment, dosage of PI-PLC is 2.22 ug of enzyme/g of oil.

In alternative embodiments, the invention also provides combinations or mixtures of enzymes comprising a PI-PLC of the invention and at least one other enzyme, e.g., a phospholipase enzyme, e.g., a described in Table 8, or Table 9, or in WO 2008/036863. For example, in alternative embodiments, the invention also provides combinations or mixtures of enzymes comprising a PI-PLC of the invention and SEQ ID NO:2, not having a signal sequence, encoded e.g., by SEQ ID NO:1; or SEQ ID NO:4, having a signal sequence (equivalent to SEQ ID NO:2 with a signal sequence), encoded e.g., by SEQ ID NO:3; or including any of the ePLC enzymes described in Example 2 (e.g., see Tables 8 and 9), and in WO 2008/036863, which describe variants of SEQ ID NO:4 (encoded e.g. by SEQ ID NO:3). In alternative embodiments, the invention also provides combinations or mixtures of enzymes comprising a PI-PLC of the invention, e.g., variants of SEQ ID NO:6 (encoded e.g. by SEQ ID NO:5) as described herein, or variants of SEQ ID NO:8 (encoded e.g. by SEQ ID NO:7, and the codon optimized SEQ ID NO:9 and SEQ ID NO:10).

Examples 4-9 are Control Examples

Examples 10-16 Describe Exemplary Methods Provided Herein

In each of the examples below, the overhead mixer was IKA's RW 20 digital with a flat blade paddle; operated at 200 rpm for normal agitation and 350 rpm for vigorous agitation. The centrifuge was a De Laval Gyro—Tester installed with "The Bowl Unit" for continuous separation. The centrifuge bowl was closed with the plug screws installed. Shear mixing was accomplished with IKA's Ultra-Turrax homogenizer T-50 basic with a S 50 N-G 45 G dispersion element at 10,000 rpm. The PLA1 enzyme was Lecitase® Ultra (lot number LYN05015A containing 11.7 Units/mg) sold by Novozymes A/S of Denmark. The PLC enzyme was Purifine® PLC (lot number 90BU006A1 or 190DU001A1 containing 26.0 or 28.6 Units/mg respectively) and the PI-PLC (SEQ ID NO:8) containing 4 Units/mg were provided by Verenium Corporation of San Diego, Calif. The reaction took place in a 4 liter beaker and was covered with a plastic wrap to reduce or eliminate any loss of water. The amount of phospholipids remaining in the treated oil was measured as ppm P in accordance with the method of American Oil Chemists' Society Official Method Ca 20-99, "Analysis of Phosphorus in Oil by Inductively Coupled Plasma Optical Emission Spectroscopy." The Free Fatty Acid (FFA) was measured utilizing the American Oil Chemists' Society Official Method Ca 5a-40. Moisture was measured using American Oil Chemists' Society Official Method Ca 2c-25. Neutral oil was measured using the method set forth in the Appendix below. Acetone-insoluble mater including phospholipids was measured using American Oil Chemists' Society Official Method Ja 4-46. Acid Value was measured using American Oil Chemists' Society Official Method Ja 6-55. The P-31 NMR procedures and the Diacylglycerol (DAG) measurements by High Performance Liquid Chromatography with Evaporative Light Scattering Detector (HPLC-ELSD), were performed by the procedures as reported by Verenium Corporation (then known as Diversa Corporation), "Analytical Profiling of Small Scale Reactions of phospholipase-C mediated Vegetable Oil Degumming," at the American Oil Chemists Society 2007 meeting.

Example 4: Control—Water Degumming at a Neutral pH 2001.2 grams of crude soybean oil containing 696.3 ppm of phosphorus was heated to 70-74° C. under normal agitation utilizing an overhead mixer. To the warm oil, 60.0 grams of de-ionized water was added. The oil/water mixture was agitated at 450 rpm for 1 minute. The agitator was slowed to 100 rpm for 30 minutes to flocculate and hydrate the gums. The water treated oil was then centrifuged; and the separated oil and wet gums were collected. The residual phosphorus in the water degummed oil was 80.0 ppm, FFA was 0.22%, and the DAG was 0.34%. The collected wet gums weighed 108.5 grams.

Example 5: Control—PLC Degumming at a Neutral pH 2003.8 grams of crude soybean oil containing 696.3 ppm of phosphorus was heated to 60° C. under normal agitation utilizing an overhead mixer. With the temperature maintained at 60° C., 0.50 grams of Verenium's Purifine® PLC lipase (lot number 90BU006A1) was added followed by 60 grams of de-ionized water and the entire mixture was shear mixed for 60 seconds. The oil mixture was agitated at normal speed for 120 minutes at a temperature of 60° C. The enzyme treated oil was then centrifuged; and the separated oil and wet gums were collected. The residual phosphorus in the neutral pH PLC treated oil produced a degummed oil with a residual phosphorus of 47.0 ppm. The FFA was 0.20% and DAG was 0.61%. The collected wet gums weighed 85.5 grams.

Example 6: Control—PI-PLC (SEQ ID NO:8) Degumming at a Neutral pH 2001.8 grams of crude soybean oil containing 696.3 ppm of phosphorus was heated to 60° C. under normal agitation utilizing an overhead mixer. With the temperature maintained at 60° C., 0.0110 grams of a PI-PLC (SEQ ID NO:8) provided by Verenium was added to a 10 ml beaker and dissolved into 1 ml of de-ionized water. Once the protein had dissolved in the water, the enzyme solution was added to the oil. The beaker was rinsed three times with approximately 1 ml of water in order to insure that all of the enzyme was added. The remainder of the water was added for a total amount of water added was 60 grams. The oil enzyme water mixture was shear mixed for 60 seconds. The oil mixture was agitated at normal speed for 120 minutes at a temperature of 60° C. The enzyme treated oil was then centrifuged; and the separated oil and wet gums were collected. The residual phosphorus in the neutral pH PI-PLC treated reaction produced a degummed oil was 50.3 ppm. The FFA was found to be 0.18% and the DAG was 0.49%. The collected wet gums weighed 102.5 grams.

Example 7: Control—PLC Plus PI-PLC (SEQ ID NO:8) Degumming at a Neutral pH 2000.2 grams of crude soybean oil containing 696.3 ppm of phosphorus was heated to 60° C. under normal agitation utilizing an overhead mixer. With the temperature maintained at 60, 0.50 grams of Verenium's Purifine® PLC lipase (lot number 90BU006A1) was added to the oil flowed by 0.0104 grams of a PI-PLC (SEQ ID NO:8) provided by Verenium was added to a 10 ml beaker and dissolved into 1 ml of de-ionized water. Once the protein had dissolved, the enzyme solution was added to the oil. The beaker was rinsed three times with approximately 1 ml of water in order to insure that all of the enzyme was added to the oil. The remainder of the water was added for a total volume of water added was 60 grams. The oil mixture was agitated at normal speed for 120 minutes at a temperature of 45° C. The enzyme treated oil was then centrifuged; and the separated oil and wet gums were collected. The residual phosphorus in the PLA1-PI-PLC at neutral pH treated reaction produced degummed oil with a residual phosphorus of 50.0 ppm. The FFA was 0.24% and DAG was 0.85%. The collected wet gums weighed 84.2 grams.

Example 8: Control—PLA1 Degumming at a Neutral pH 2000.6 grams of crude soybean oil containing 694.1 ppm of phosphorus was heated to 45° C. under normal agitation utilizing an overhead mixer. With the temperature maintained at 45° C., 0.10 grams of Novozymes' Lecitase® Ultra (PLA1 lipase lot number LYN05015) was added followed by 60 grams of de-ionized water and the entire mixture was shear mixed for 60 seconds. The oil mixture was agitated at normal speed for 240 minutes at a temperature of 45° C. The enzyme treated oil was then centrifuged; and the separated oil and wet gums were collected. The residual phosphorus in the PLA1 at neutral pH treated reaction produced a degummed oil with a residual phosphorus of 27.2 ppm. The FFA was 0.60% and DAG was 0.33%. The collected wet gums weighed 90.0 grams.

Example 9: Control—$PLA_1$ Degumming at pH 4.5

2001.2 grams of crude soybean oil containing 641.6 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 45° C., then 1.8 milliliters of 4 molar sodium hydroxide solution was added to the oil and mixed. 0.10 grams of Novozymes' Lecitase® Ultra (PLA1 lipase lot number LYN05015) was added followed by a total of 60 grams of de-ionized water and the entire mixture was shear mixed for 60 seconds. The oil mixture was agitated at normal speed for 240 minutes at a temperature of 45° C. The enzyme treated oil was then centrifuged; and the separated oil and wet gums were collected. The residual phosphorus in the PLA1 at a pH of 4.5 treated oil produced a degummed oil with a residual phosphorus of 0.5 ppm. The FFA was 0.54% and DAG was 0.33%. The collected wet gums weighed 91.4 grams.

The degumming processes described in Examples 4-10 failed to remove and/or react all of the phospholipids present in the crude oil as is evident by the residual phosphorus, except for experiment 6. Experiment 6 was depicts degumming at normal reaction conditions for Lecitase® Ultra enzyme. In Table 27, the phospholipid profiles of the collect wet gums are listed.

TABLE 27

Analytical results from the neutral control examples.

| Run | Enzyme Addition | pH | Water (g) | Temp (C.) | Reaction Time (minutes) | Phos (ppm) | FFA (%) | DAG (%) | Wet Gums (g) |
|---|---|---|---|---|---|---|---|---|---|
|   | Starting Material | Neutral | — | — | — | 668.0 | 0.53 | 0.32 | — |
| 1 | None | Neutral | 60 | 70 | 30 | 80.0 | 0.22 | 0.34 | 108.5 |
| 2 | PLC | Neutral | 60 | 60 | 120 | 47.0 | 0.20 | 0.61 | 85.5 |
| 3 | PI-PLC | Neutral | 60 | 60 | 120 | 50.3 | 0.18 | 0.49 | 102.5 |
| 4 | PLC + PI-PLC | Neutral | 60 | 60 | 120 | 50.0 | 0.24 | 0.85 | 84.2 |
| 5 | PLA1 | Neutral | 60 | 45 | 240 | 27.2 | 0.60 | 0.33 | 90.0 |
| 6 | PLA1 | 4.5 | 60 | 45 | 240 | 0.5 | 0.54 | 0.33 | 91.4 |

As seen in Table 29, water degumming, demonstrates the emulsification ability of the hydratable phospholipids enabling the removal all species of phospholipids, even some of the non-hydratable species. However, a large portion of the NHPs remained in the oil as evident by the residual phosphorus, calcium, magnesium and iron in the degummed oil (see Table 29). Degumming utilizing a phospholipase C, was able to react essentially all of the phosphatidylcholine and a significant amount of the phosphatidylethanolamine. Phosphatidylinositol and phosphatidic acid were unreacted. The amount of collected gums, was significantly lower than the water degumming example (85.5 grams versus 108.5 grams), but a large amount of the NHPs remained in the oil as evident by the residual phosphorus of near 50 ppm and the remaining Ca, Mg, and Fe left in the oil. As seen in Table 29, degumming with a phosphatidylinositol specific phospholipase, produced a wet gum with the highest amount of PC and PE of all of the control examples. Phospholipid composition of the recovered wet gums in the Examples 4-10 is also provided in FIG. 13.

All of the PI was reacted with the phospholipase C producing phosphoinositol. Like examples 4 and 5, large amounts of NHPs remained in the oil as is evident by the trace metal analysis reported in Table 29.

TABLE 29

Elemental results from the neutral control examples.

| Run | Enzyme Addition | pH | Phosphorus (ppm) | Calcium (ppm) | Magnesium (ppm) | Iron (ppm) |
|---|---|---|---|---|---|---|
| Average Crude | Starting Material | Neutral | 668.0 | 61.67 | 69.92 | 0.95 |
| 1 | None | Neutral | 80.0 | 34.97 | 18.79 | 0.44 |
| 2 | PLC | Neutral | 47.0 | 21.25 | 10.14 | 0.19 |

TABLE 29-continued

Elemental results from the neutral control examples.

| Run | Enzyme Addition | pH | Phosphorus (ppm) | Calcium (ppm) | Magnesium (ppm) | Iron (ppm) |
|---|---|---|---|---|---|---|
| 3 | PI-PLC | Neutral | 50.3 | 25.33 | 12.33 | 0.20 |
| 4 | PLC + PI-PLC | Neutral | 50.0 | 22.49 | 9.62 | 0.20 |
| 5 | PLA1 | Neutral | 27.2 | 15.14 | 7.73 | 0.13 |
| 6 | PLA1 | 4.5 | 0.5 | 0.19 | 0.12 | b.d. |

Moisture and neutral oil present in the recovered gums oil is reported in Table 29a.

TABLE 28

Phospholipid Composition of the recovered gums.

| Run | PC (%) | PE (%) | PI (%) | PA (%) | lyso-PC (%) | lyso-PE (%) | Lyso-PI (%) | lyso-PA (%) | C (%) | E (%) | I (%) | A (%) |
|---|---|---|---|---|---|---|---|---|---|---|---|---|
| 1 | 9.62 | 7.35 | 4.02 | 2.04 | 0.58 | 0.35 | 0.33 | b.d. | b.d. | b.d. | b.d. | 0.07 |
| 2 | 0.19 | 2.05 | 5.29 | 2.88 | 0.44 | 0.09 | 0.39 | 0.28 | 3.92 | 2.42 | b.d. | 0.19 |
| 3 | 11.01 | 7.78 | 0.00 | 2.33 | 0.59 | 0.36 | b.d. | b.d. | 0.05 | 0.02 | 4.29 | 0.12 |
| 4 | 2.39 | 3.09 | 1.68 | 2.77 | 0.44 | 0.17 | b.d. | 0.35 | 3.25 | 1.97 | 1.26 | 0.18 |
| 5 | 0.24 | 0.41 | 0.67 | 0.26 | 8.05 | 7.33 | 4.32 | 3.52 | b.d. | b.d. | b.d. | 0.19 |
| 6 | 0.62 | 0.74 | 0.90 | 0.13 | 7.98 | 7.40 | 4.30 | 4.28 | b.d. | b.d. | b.d. | 0.25 | b.d. = below detection limits

TABLE 29a

Moisture and Neutral Oil present in the recovered gums

| Run | Moisture (%) | Oil "as is" (%) | Oil "dry" (%) | Oil Lost (g) |
|---|---|---|---|---|
| 1 | 43.31 | 20.40 | 36.05 | 22.13 |
| 2 | 49.62 | 17.04 | 33.82 | 14.57 |
| 3 | 40.70 | 23.97 | 40.42 | 24.57 |
| 4 | 46.80 | 20.44 | 38.42 | 17.21 |
| 5 | 44.33 | 11.63 | 20.89 | 10.47 |
| 6 | 45.00 | 14.52 | 26.40 | 13.27 |

In Example 7, degumming with both PLC and PI-PLC demonstrated significant enzymatic hydrolysis of PC, PE, and PI (Table 27 and FIG. 13), but not as good as the single enzyme added alone in either Example 5 or 6. Additionally, the residual phosphorus in the oil remained at approximately 50 ppm due to the inability of the process to hydrolyze the salts of phosphatidic acid and phosphatidylethanolamine. In lowered from 4.5 to, for example, a range of 3.5 to 4.2 after the enzymatic reaction is completed dissociating the citrate salts, thereby eliminating the fouling of the equipment, particularly the heat exchangers and the separating centrifuge, that would have resulted from precipitation of calcium and magnesium salts at the optimum pH required for the enzyme activity.

As demonstrated by the following examples, the processes provided herein comprise treating an oil with an acid to lower the pH to less than three, allowing the salts of phosphatidic acid and phosphatidyl ethanolamine (the NHPs) to dissociate, then adjusting the pH of the water phase back to a neutral pH of 7, before hydrating the phospholipids in water degumming or reacting the phospholipids with a phospholipase allows the NHPs to migrate to the oil water interface allowing for better hydration and better substrate availability (NHPs) for the phospholipases. Table 30 below provides a summary of examples of the processes conducted as described below.

TABLE 30

Analytical results from the pH adjusted examples.

| Run | Enzyme Addition | Adjusted pH | Water (g) | Temp (C.) | Reaction Time (minutes) | Phos (ppm) | FFA (%) | DAG (%) | Wet Gums (g) |
|---|---|---|---|---|---|---|---|---|---|
| 7 | None | 7.0 | 60 | 70 | 30 | 26.9 | 0.24 | 0.39 | 112.0 |
| 8 | PLC | 7.0 | 60 | 60 | 120 | 14.4 | 0.21 | 1.11 | 80.0 |
| 9 | PI-PLC | 7.0 | 60 | 60 | 120 | 13.5 | 0.22 | 0.61 | 100.8 |
| 10 | PLC + PI-PLC | 7.0 | 60 | 60 | 120 | 18.7 | 0.21 | 1.04 | 84.4 |
| 11 | PLA1 | 5.5 | 60 | 45 | 240 | 1.6 | 0.54 | 0.33 | 91.7 |
| 12 | PLA1 | 6.5 | 60 | 45 | 240 | 3.4 | 0.51 | 0.33 | 88.7 |
| 13 | PLA1 | 7.0 | 60 | 45 | 240 | 3.4 | 0.52 | 0.39 | 93.1 |

Figure 13:
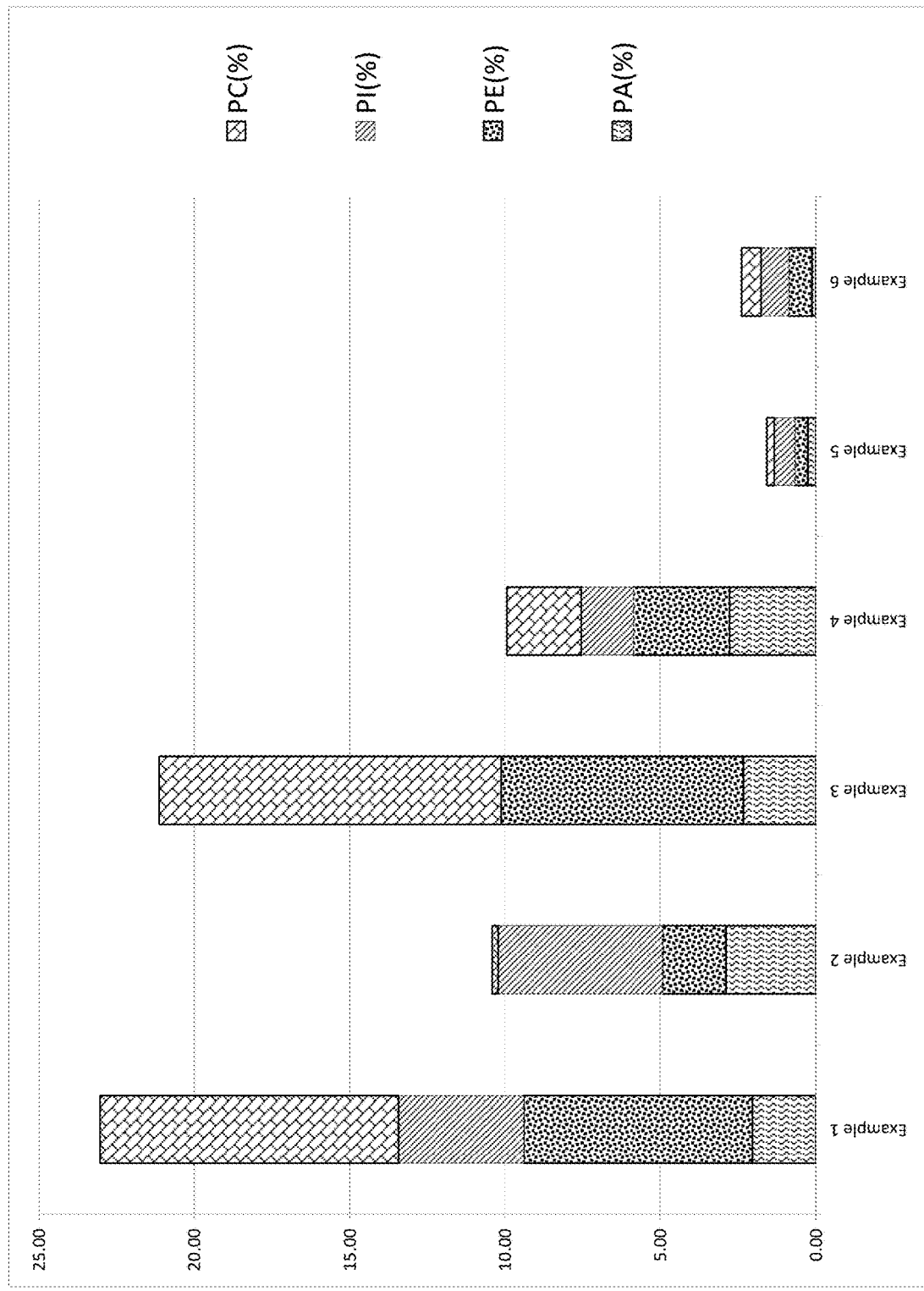
FIG. 13 provides phospholipid composition of the recovered wet gums in the control examples.

Example 8, degumming with PLA1 hydrolyzed almost all for the phospholipids present in the wet gums into their lyso-forms as seen in FIG. 13 and as is evident by the significant amount of lyso-phospholipids present (Table 28). However, even after 4 hours, significant amounts of PA remained in the oil because the NHPs were not accessible to the enzyme.

In the control experiment 6, PLA1 treated oil at pH 4.5 demonstrates the ability of the phospholipase A1 to react with all of the phospholipid species producing a degummed oil with less than 1 ppm residual phosphorus and essentially all of the gums have been converted to their water soluble lyso-species as is evident in FIG. 13 and Tables 30 and 31. The calcium, magnesium, and iron cations are no longer attached to the NHPs, but are now in the water phase. The calcium, magnesium, and iron cations are dissociated from the salts of phosphatidic acid and phosphatidylethanolamine. As a consequence, the divalent elements may now react with the citric acid present in the water phase forming a calcium, magnesium, or iron citrate that are insoluble in the water phase at the reacted pH of the water phase. These insoluble salts precipitate out of solution forming a "hard water" coating on all of the piping, heat exchangers, and even the centrifuge until the heavy phase comprising mixture of reacted gums, water, and salts is removed via the centrifugation process. Dayton et al. in U.S. 2007/0134777 disclose an improved enzymatic degumming process wherein the pH of the weakly buffered enzymatic reaction is

Example 10: Water Degumming at an Adjusted pH of 7.0

2002.2 grams of crude soybean oil containing 640.1 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. 3.65 milliliters of 4 molar sodium hydroxide solution was added to the oil and mixed. To the warm oil, 56.0 grams of de-ionized water was added (a total of 60 grams of water including the citric acid and sodium hydroxide). The oil/water mixture was agitated at 450 rpm for 1 minute. The agitator was slowed to 100 rpm for 30 minutes to flocculate and hydrate the gums. The water treated oil was then centrifuged; and the separated oil and wet gums were collected. The residual phosphorus in the water degummed oil was 26.9 ppm, FFA was 0.24%, and the DAG was 0.39%. The collected wet gums weighed 112.0 grams.

The residual phosphorus in example 10 where the pH was adjusted to 7 (26.9 ppm P) compared to the original neutral pH example (80.0 ppm P) demonstrated that more of the phospholipids were available for either hydration or mechanical entrapment. Additionally, the concentrations of both phosphatidic acid and phosphatidylethanolamine (NHPs) were increased in the recovered gums as seen in Table 31.

TABLE 31

Phospholipid composition of the recovered gums from examples 10-16.

| Run | PC (%) | PE (%) | PI (%) | PA (%) | lyso-PC (%) | lyso-PE (%) | Lyso-PI (%) | lyso-PA (%) | C (%) | E (%) | I (%) | A (%) |
|---|---|---|---|---|---|---|---|---|---|---|---|---|
| 7 | 7.62 | 7.78 | 4.19 | 2.81 | 0.59 | 0.48 | 0.34 | 0.26 | b.d. | b.d. | b.d. | 0.18 |
| 8 | 0.30 | 0.88 | 6.15 | 3.84 | 0.67 | 0.22 | 0.51 | 0.67 | 3.91 | 2.79 | 0.06 | 0.31 |
| 9 | 8.29 | 8.31 | b.d. | 3.11 | 0.71 | 0.56 | b.d. | 0.48 | 0.42 | 0.20 | 4.63 | 0.23 |
| 10 | 1.12 | 1.74 | 0.74 | 3.34 | 0.36 | 0.09 | b.d. | 0.59 | 3.87 | 2.62 | 1.85 | 0.30 |
| 11 | 0.40 | 0.51 | 0.42 | 0.18 | 7.78 | 7.06 | 4.40 | 3.83 | b.d. | b.d. | b.d. | 0.24 |
| 12 | 0.30 | 0.50 | 0.50 | 0.09 | 8.47 | 7.72 | 4.66 | 4.10 | b.d. | b.d. | b.d. | 0.24 |
| 13 | 0.14 | 0.43 | 0.07 | b.d. | 7.65 | 7.31 | 3.97 | 3.26 | 0.06 | b.d. | 0.10 | 0.24 | b.d. = below detection limits

Moisture and neutral oil present in the recovered gums from examples 10-16 is reported in Table 31a.

TABLE 31a

Moisture and Neutral Oil present in the recovered gums.

| Run | Moisture (%) | Oil "as is" (%) | Oil "dry" (%) | Oil Lost (g) |
|---|---|---|---|---|
| 7 | 45.53 | 17.44 | 32.02 | 19.53 |
| 8 | 51.58 | 13.23 | 27.32 | 10.53 |
| 9 | 43.19 | 18.29 | 32.20 | 18.44 |
| 10 | 50.33 | 17.64 | 35.51 | 14.89 |
| 11 | 44.71 | 12.43 | 22.48 | 11.40 |
| 12 | 44.44 | 11.07 | 19.92 | 9.82 |
| 13 | 43.25 | 10.37 | 18.27 | 9.65 |

Example 11: PLC Degumming at an Adjusted pH of 7.0

2002.0 grams of crude soybean oil containing 640.1 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool to 60° C. where 3.65 milliliters of 4 molar sodium hydroxide solution was added to the oil and mixed. With the temperature maintained at 60° C., 0.50 grams of Verenium's Purifine® PLC lipase (lot number 190DU001A1) was added followed by the remainder of the 60 grams of de-ionized water and the entire mixture was shear mixed for 60 seconds. The oil mixture was agitated at normal speed for 120 minutes at a temperature of 60° C. The enzyme treated oil was then centrifuged; and the separated oil and wet gums were collected. The residual phosphorus in the acid/base pH 7.0 adjusted PLC treated oil produced a degummed oil with a residual phosphorus of 14.4 ppm. The FFA was 0.21% and DAG was 1.11%. The collected wet gums weighed 80.0 grams.

Results from this experiment demonstrate both the removal of the phospholipids from the oil and the phospholipase's ability to convert phospholipids into diacylglycerols or oil. The diacylglycerols were increased from the starting oil (0.31%) or 0.34% in the control water degumming experiment to 1 to 1.11% in the enzyme degumming experiment at an adjusted pH of 7.0. The residual phosphorus in the oil was reduced from 47.0 ppm in the control experiment to 14.4 ppm in the pH adjusted experiment. The other trace metals were also significantly reduced as demonstrated in Table 32.

TABLE 32

Elemental results from examples 10-16

| Run | Enzyme Addition | Adjusted pH | Phosphorus (ppm) | Calcium (ppm) | Magnesium (ppm) | Iron (ppm) |
|---|---|---|---|---|---|---|
| 7 | None | 7.0 | 26.9 | 7.80 | 2.71 | 0.35 |
| 8 | PLC | 7.0 | 14.4 | 4.70 | 0.96 | 0.34 |
| 9 | PI-PLC | 7.0 | 13.5 | 5.30 | 1.99 | b.d. |
| 10 | PLC + PI-PLC | 7.0 | 18.7 | 4.60 | 2.14 | b.d. |
| 11 | PLA1 | 5.5 | 1.6 | 0.82 | 0.34 | 0.01 |
| 12 | PLA1 | 6.5 | 3.4 | 2.56 | 0.95 | b.d. |
| 13 | PLA1 | 7.0 | 3.4 | 2.75 | 1.03 | b.d. |

It is important to recognize that the collected gums were reduced to the lowest level in all of the experiments in the application (80.0 grams). The phospholipid composition shows that nearly all of the PC and PE were converted to the phospho-choline and phospho-ethanolamine (Table 31) forming the diacylglycerols found in the recovered oil. The amount of phosphatidic acid was also increased in the collected gums further demonstrating the increased availability of the substrate to either be hydrated/mechanically "trapped" or available to be enzymatically reacted.

Example 12: PI-PLC Degumming at an Adjusted pH of 7.0

2000.0 grams of crude soybean oil containing 694.1 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool to 60° C. where 3.65 milliliters of 4 molar sodium hydroxide solution was added to the oil and mixed. With the temperature maintained at 60° C., 0.0108 grams of a PI-PLC (SEQ ID NO:8) provided by Verenium was added to a 10 ml beaker and dissolved into 1 ml of de-ionized water. Once the protein had dissolved in the water, the enzyme solution was added to the oil. The beaker was rinsed three times with approximately 1 ml of water in order to insure that all of the enzyme was added. The remainder of the water was added for a total amount of water added was 60 grams. The entire mixture was shear mixed for 60 seconds. The oil mixture was agitated at normal speed for 120 minutes at a temperature of 60° C. The enzyme treated oil was then centrifuged; and the separated oil and wet gums were collected. The residual phosphorus in the acid/base pH 7.0 adjusted PI-PLC treated oil produced a degummed oil with a residual phosphorus of 13.5 ppm. The FFA was 0.22% and DAG was 0.61%. The collected wet gums weighed 100.8 grams.

As in the two previous examples, the amount of PA present in the collected gums was increased in the pH adjusted experiments versus the control experiments. Additionally, the greatest amount of PC, and PE were present in the collected gums, hence the 100.8 grams of wet gums. Since the phosphatidylinositol specific phospholipase predominately only reacts with PI, the increase in DAG was less than the phospholipase reaction in experiment 8 and the phospho-inositol was the predominant phospho-compound present in the collected gums (Table 31).

Example 13: PLC Plus PI-PLC Degumming at an Adjusted pH of 7.0

2003.8 grams of crude soybean oil containing 641.6 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool to 60° C. where 3.65 milliliters of 4 molar sodium hydroxide solution was added to the oil and mixed. With the temperature maintained at 60° C., 0.50 grams of Verenium's Purifine® PLC lipase (lot number 190DU001A1) was added to the oil flowed by 0.0094 grams of a PI-PLC (SEQ ID NO:8) provided by Verenium was added to a 10 ml beaker and dissolved into 1 ml of de-ionized water. Once the protein had dissolved, the enzyme solution was added to the oil. The beaker was rinsed three times with approximately 1 ml of water in order to insure that all of the enzyme was added to the oil. The remainder of the water was added for a total volume of water added to 60 grams. The entire mixture was then shear mixed for 1 minute. The oil mixture was then agitated at normal speed for 120 minutes at a temperature of 60° C. The enzyme treated oil was then centrifuged; and the separated oil and wet gums were collected. The residual phosphorus in the PLC-PI-PLC at an adjusted pH of 7.0 treated oil produced degummed oil with a residual phosphorus of 18.7 ppm. The FFA was 0.21% and DAG was 1.04%. The collected wet gums weighed 84.4 grams.

The limited amounts of PC, PE and PI collected in the gums (Table 31); the large amount of phospho-choline, phospho-ethanolamine, and phospho-inositol in the gums (Table 31); and the high level of diacylglycerol present in the recovered oil clearly demonstrates the enzymatic reaction of both the PLC and the PI-PLC in the crude oil. The PA recovered in the gums was also greater than the control combination of enzymes found in Example 7.

Example 14: $PLA_1$ Degumming at an Adjusted pH of 5.5

2001.2 grams of crude soybean oil containing 641.6 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 45° C., then 2.55 milliliters of 4 molar sodium hydroxide solution was added to the oil and mixed. 0.10 grams of Novozymes' Lecitase® Ultra (PLA1 lipase lot number LYN05015) was added followed by a total of 60 grams of de-ionized water and the entire mixture was shear mixed for 60 seconds. The oil mixture was agitated at normal speed for 240 minutes at a temperature of 45° C. The enzyme treated oil was then centrifuged; and the separated oil and wet gums were collected. The residual phosphorus in the PLA1 at a pH of 5.5 treated oil produced a degummed oil with a residual phosphorus of 1.6 ppm. The FFA was 0.54% and DAG was 0.33%. The collected wet gums weighed 91.7 grams.

Example 15: $PLA_1$ Degumming at an Adjusted pH of 6.5

2001.6 grams of crude soybean oil containing 641.6 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 45° C., then 3.31 milliliters of 4 molar sodium hydroxide solution was added to the oil and mixed. 0.10 grams of Novozymes' Lecitase® Ultra (PLA1 lipase lot number LYN05015) was added followed by a total of 60 grams of de-ionized water and the entire mixture was shear mixed for 60 seconds. The oil mixture was agitated at normal speed for 240 minutes at a temperature of 45° C. The enzyme treated oil was then centrifuged; and the separated oil and wet gums were collected. The residual phosphorus in the PLA1 at a pH of 6.5 treated oil produced a degummed oil with a residual phosphorus of 3.4 ppm. The FFA was 0.51% and DAG was 0.33%. The collected wet gums weighed 88.7 grams.

Example 16: $PLA_1$ Degumming at an Adjusted pH of 7.0

2001.6 grams of crude soybean oil containing 641.6 ppm of phosphorus was heated to 70° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 45° C., then 3.31 milliliters of 4 molar sodium hydroxide solution was added to the oil and mixed. 0.10 grams of Novozymes' Lecitase® Ultra (PLA1 lipase lot number LYN05015) was added followed by a total of 60 grams of de-ionized water and the entire mixture was shear mixed for 60 seconds. The oil mixture was agitated at normal speed for 240 minutes at a temperature of 45° C. The enzyme treated oil was then centrifuged; and the separated oil and wet gums were collected. The residual phosphorus in the PLA1 at a pH of 7.0 treated oil produced a degummed oil with a residual phosphorus of 3.4 ppm. The FFA was 0.52% and DAG was 0.39%. The collected wet gums weighed 93.1 grams.

Examples 14, 15, and 16 demonstrate the effect of increasing the pH from the optimum condition for the enzyme of 4.5 to an adjusted pH from 5.5, 6.5, and 7.0 respectively for the phospholipase A enzyme. The ability to operate the reaction at a neutral pH of 7.0, instead of 4.5, would increase the economical viability of the industrial process due to materials of construction and the cost of lowering the pH to 3.5 to 4.2 in order to prevent the fouling of the industrial equipment. In summary, experiment 13 clearly shows that a low residual phosphorus in the oil may be obtained, while still being able to react all of the phospholipids present in the gums to their lyso-forms therefore maximizing the oil yield for this type of enzymatic reaction.

Figure 14:
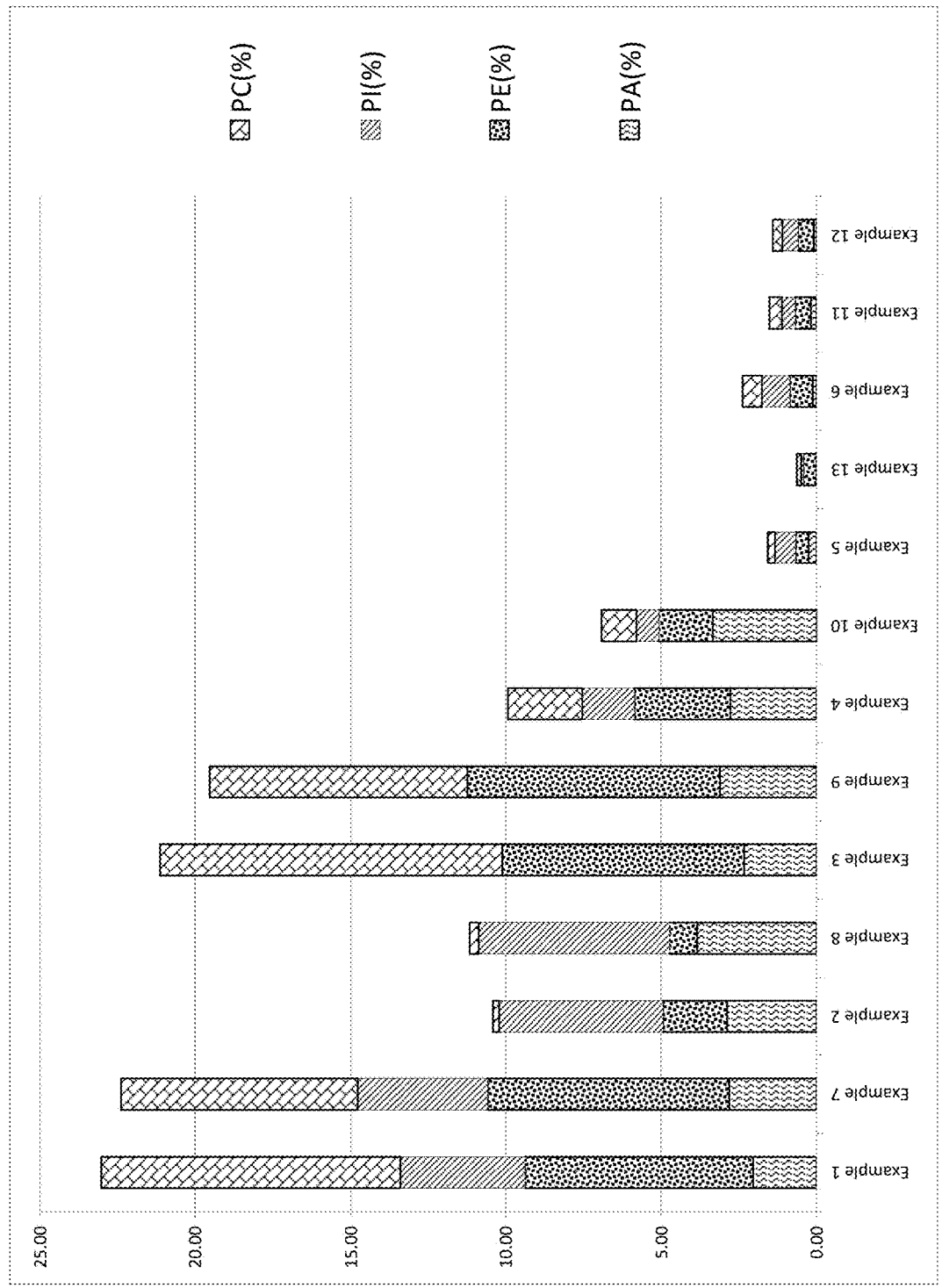
FIG. 14 provides phospholipid comparisons for the control examples versus the examples using the methods provided herein where pH in step b) is adjusted to pH 7.0.

FIG. 14 compares the phospholipid compositions of the control neutral pH reactions versus the pH adjusted reactions at a pH of 7.0, side-by-side. It can be clearly seen that in all of the reactions where an acid treatment followed by a dilute caustic treatment in order to bring the water phase to a neutral pH increases the level of NHPs in the collected gums and/or allows these NHPs to be converted to either lyso- or phospho-forms thereby increase the overall yield and minimizing any waste products generated from the process.

Figure 15:
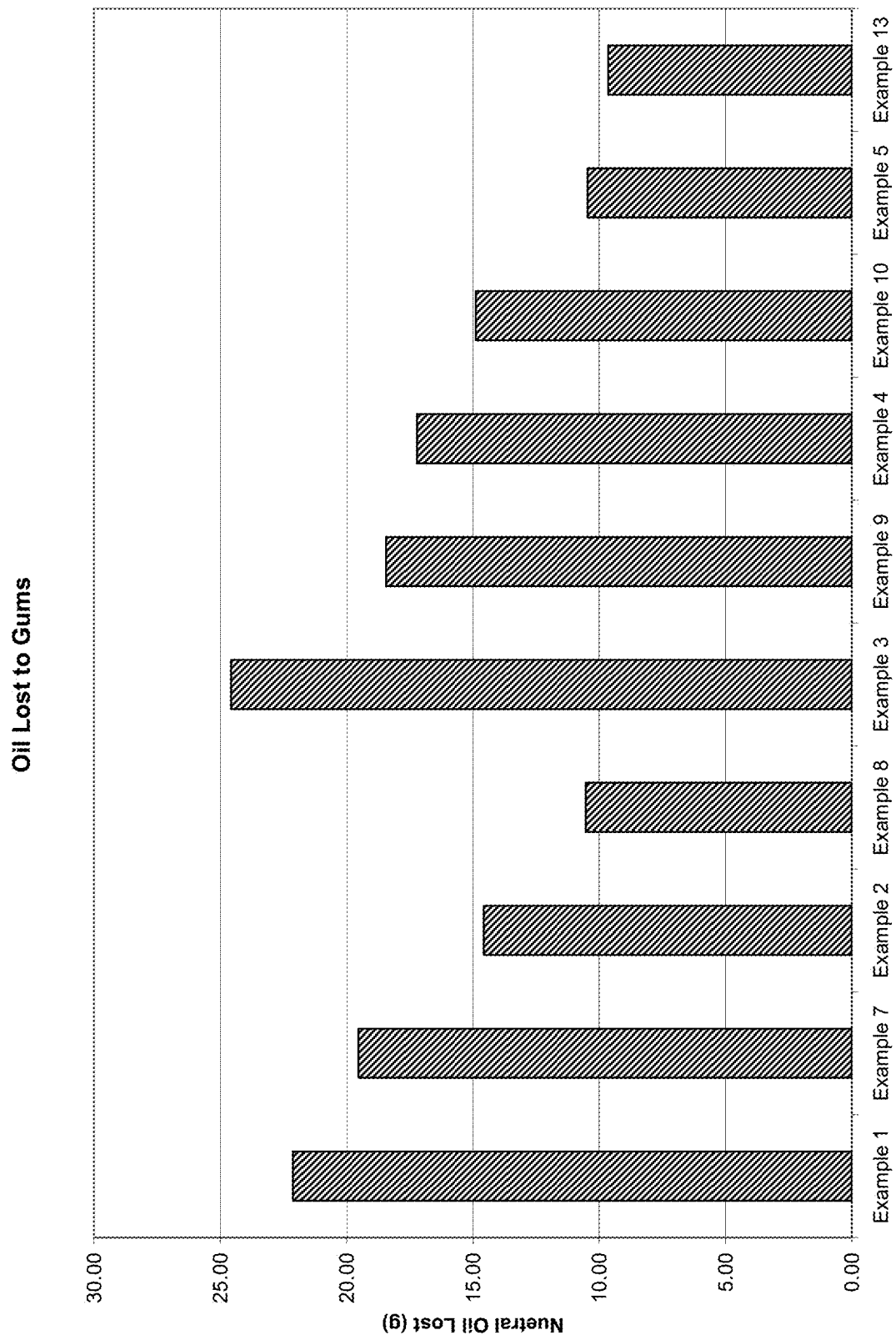
FIG. 15 compares the neutral oil lost to the gum phase in the control neutral pH reactions versus the pH adjusted reactions at a pH of 7.0, side-by-side.

FIG. 15 compares the neutral oil lost to the gum phase in the control neutral pH reactions versus the pH adjusted reactions at a pH of 7.0, side-by-side. It can clearly be seen that in all of the reactions where an acid treatment was followed by a dilute caustic treatment in order to bring the water phase to a neutral pH, the amount of neutral oil lost to the gum phase decreased.

Figure 16:
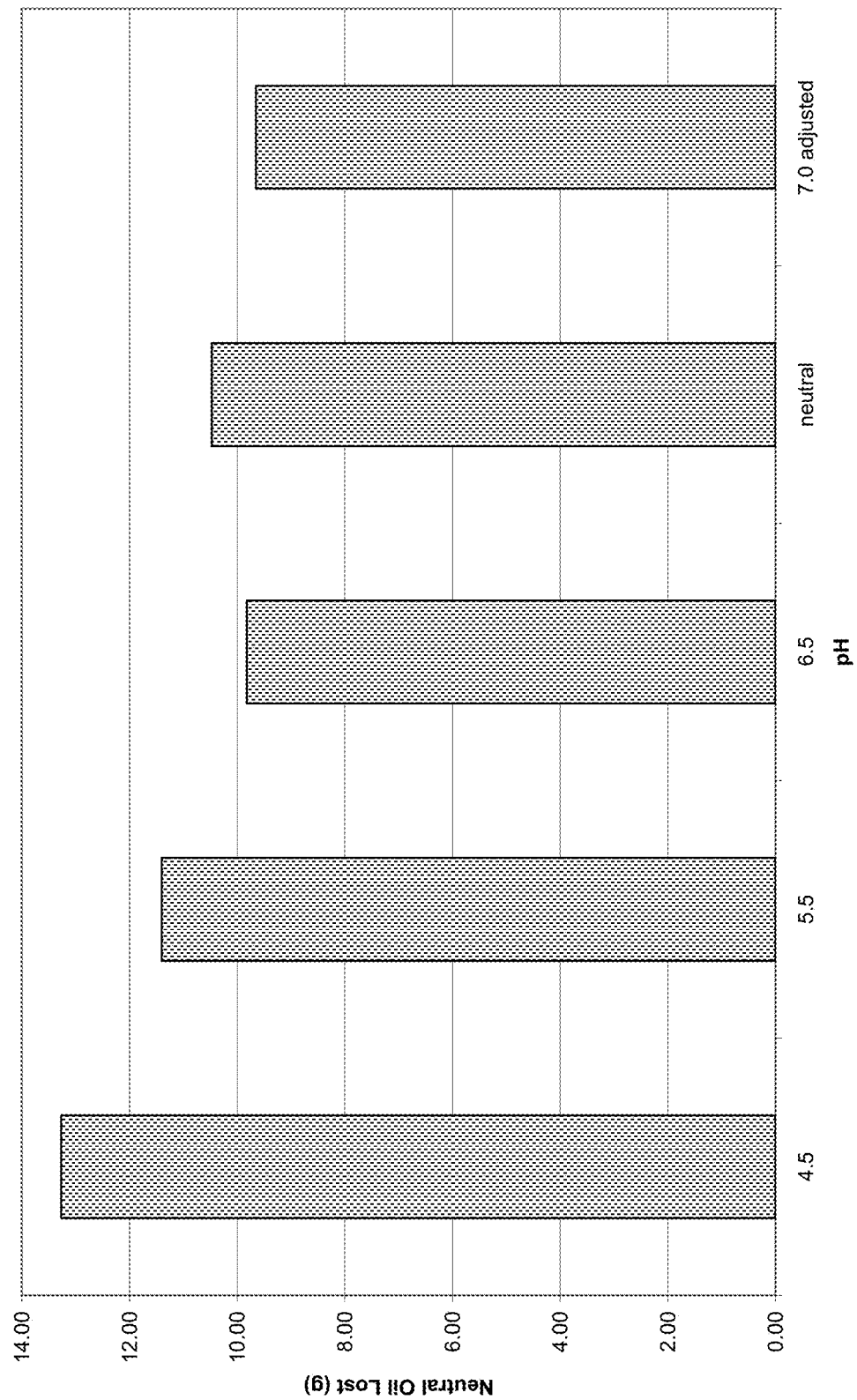
FIG. 16 compares the neutral oil lost to the gum phase of various pH conditions where a phospholipase A1 is utilized.

FIG. 16 compares the neutral oil lost to the gum phase of various pH conditions where a phospholipase A 1 is utilized. All of the reactions have an adjusted pH except the "neutral" reaction. It is demonstrated that the amount of neutral oil is lowest when the pH has been adjusted to 7.0 versus even the neutral unadjusted reaction without any acid or base added to aid in the availability of the NHP to the degumming process.

Example 17A 300 g of degummed soybean oil was heated to 90° C. in a 600 ml beaker under normal agitation utilizing a magnetic stirrer. To this was added 1.8 g of deionized water, followed by 0.565 g of phosphoric acid 85%. The mixture was then sheared for 30 seconds using a Ultra-Turrax homogenizer T-50 basic with a S 50 N-G 45 G dispersion element at 10,000 (this homogenizer is believed by the supplier to be equivalent to the Ultra Turrax T-45 used in U.S. Pat. No. 4,698,185).

Figure 17:
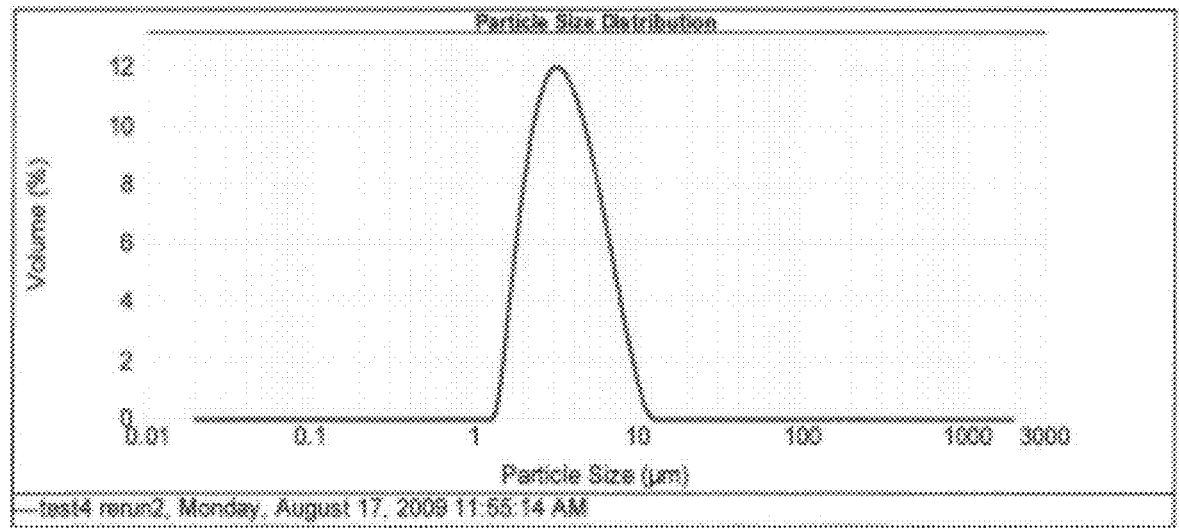
FIG. 17 depicts droplet distribution for aqueous phase obtained according to the process of Example 17A.

A sample of the emulsion formed was then analyzed in the Malvern 2000. The average droplet size for the aqueous phase was 3.963 μm and 90% of the aqueous phase appeared in droplets with diameter less than 6.675 μm (Table 33). The droplet distribution is shown in FIG. 17.

TABLE 33

| Droplet Size (μm) | volume distribution (%) | | | | accumulated volume distribution (%) | | | |
|---|---|---|---|---|---|---|---|---|
| | Example 17A | Example 17B | Example 17D | Example 17C | Example 17A | Example 17B | Example 17D | Example 17C |
| 1.259 | 0.00 | 0.00 | 0.00 | 0.00 | 0.00 | 0.00 | 0.00 | 0.00 |
| 1.445 | 0.13 | 0.00 | 0.01 | 0.00 | 0.13 | 0.00 | 0.01 | 0.00 |
| 1.660 | 2.38 | 0.91 | 0.09 | 0.01 | 2.51 | 0.91 | 0.10 | 0.01 |
| 1.905 | 5.25 | 4.62 | 0.10 | 0.10 | 7.76 | 5.53 | 0.20 | 0.11 |
| 2.188 | 7.63 | 7.51 | 0.09 | 0.23 | 15.39 | 13.04 | 0.29 | 0.34 |
| 2.512 | 9.37 | 9.76 | 0.08 | 0.35 | 24.76 | 22.80 | 0.37 | 0.69 |
| 2.884 | 10.44 | 11.18 | 0.15 | 0.49 | 35.20 | 33.98 | 0.52 | 1.18 |
| 3.311 | 10.84 | 11.71 | 0.37 | 0.67 | 46.04 | 45.69 | 0.89 | 1.85 |
| 3.802 | 10.62 | 11.45 | 0.87 | 0.90 | 56.66 | 57.14 | 1.76 | 2.75 |
| 4.365 | 9.95 | 10.60 | 1.73 | 1.20 | 66.61 | 67.74 | 3.49 | 3.95 |
| 5.012 | 8.95 | 9.35 | 2.98 | 1.60 | 75.56 | 77.09 | 6.47 | 5.55 |
| 5.754 | 7.72 | 7.89 | 4.62 | 2.12 | 83.28 | 84.98 | 11.09 | 7.67 |
| 6.607 | 6.30 | 6.27 | 6.50 | 2.77 | 89.58 | 91.25 | 17.59 | 10.44 |
| 7.586 | 4.78 | 4.58 | 8.49 | 3.56 | 94.36 | 95.83 | 26.08 | 14.00 |
| 8.710 | 3.21 | 2.92 | 10.26 | 4.46 | 97.57 | 98.75 | 36.34 | 18.46 |
| 10.000 | 1.80 | 1.23 | 11.51 | 5.46 | 99.37 | 99.98 | 47.85 | 23.92 |
| 11.482 | 0.62 | 0.00 | 11.94 | 6.45 | 99.99 | 100.00 | 59.79 | 30.37 |
| 13.183 | 0.01 | 0.00 | 11.41 | 7.30 | 100.00 | 100.00 | 71.20 | 37.67 |
| 15.136 | 0.00 | 0.00 | 9.99 | 7.97 | 100.00 | 100.00 | 81.19 | 45.64 |
| 17.378 | 0.00 | 0.00 | 7.90 | 8.27 | 100.00 | 100.00 | 89.09 | 53.91 |
| 19.953 | 0.00 | 0.00 | 5.57 | 8.23 | 100.00 | 100.00 | 94.66 | 62.14 |
| 22.909 | 0.00 | 0.00 | 3.34 | 7.81 | 100.00 | 100.00 | 98.00 | 69.95 |
| 26.303 | 0.00 | 0.00 | 1.61 | 7.06 | 100.00 | 100.00 | 99.61 | 77.01 |
| 30.200 | 0.00 | 0.00 | 0.39 | 6.08 | 100.00 | 100.00 | 100.00 | 83.09 |
| 34.674 | 0.00 | 0.00 | 0.00 | 4.97 | 100.00 | 100.00 | 100.00 | 88.06 |
| 39.811 | 0.00 | 0.00 | 0.00 | 3.85 | 100.00 | 100.00 | 100.00 | 91.91 |
| 45.709 | 0.00 | 0.00 | 0.00 | 2.82 | 100.00 | 100.00 | 100.00 | 94.73 |
| 52.481 | 0.00 | 0.00 | 0.00 | 1.96 | 100.00 | 100.00 | 100.00 | 96.69 |
| 60.256 | 0.00 | 0.00 | 0.00 | 1.28 | 100.00 | 100.00 | 100.00 | 97.97 |
| 69.183 | 0.00 | 0.00 | 0.00 | 0.79 | 100.00 | 100.00 | 100.00 | 98.76 |
| 79.433 | 0.00 | 0.00 | 0.00 | 0.47 | 100.00 | 100.00 | 100.00 | 99.23 |
| 91.201 | 0.00 | 0.00 | 0.00 | 0.27 | 100.00 | 100.00 | 100.00 | 99.50 |
| 104.713 | 0.00 | 0.00 | 0.00 | 0.17 | 100.00 | 100.00 | 100.00 | 99.67 |
| 120.226 | 0.00 | 0.00 | 0.00 | 0.11 | 100.00 | 100.00 | 100.00 | 99.78 |

Example 17: Particle Size Distribution Studies

In this example, droplet size average distribution and prevalent droplet size of the shear treatment applied in the methods provided herein and methods available in the art (for example, U.S. Pat. Nos. 4,698,185 and 6,103,505) were studied.

The particle size in this study was analyzed using the Malvern Mastersizer particle (droplet) size analyzer model 2000, with particle and volume distribution calculated by the software that accompanies the equipment.

Example 17B 2000 g of degummed soybean oil was heated to 90° C. in a 4000 ml beaker under normal agitation utilizing a magnetic stirrer. 12 g of deionized water was added to the oil, followed by 3.767 g of phosphoric acid 85%. The mixture was then sheared for 30 seconds using a Ultra-Turrax homogenizer T-50 basic with a S 50 N-G 45 G dispersion element at 10,000.

Figure 18:
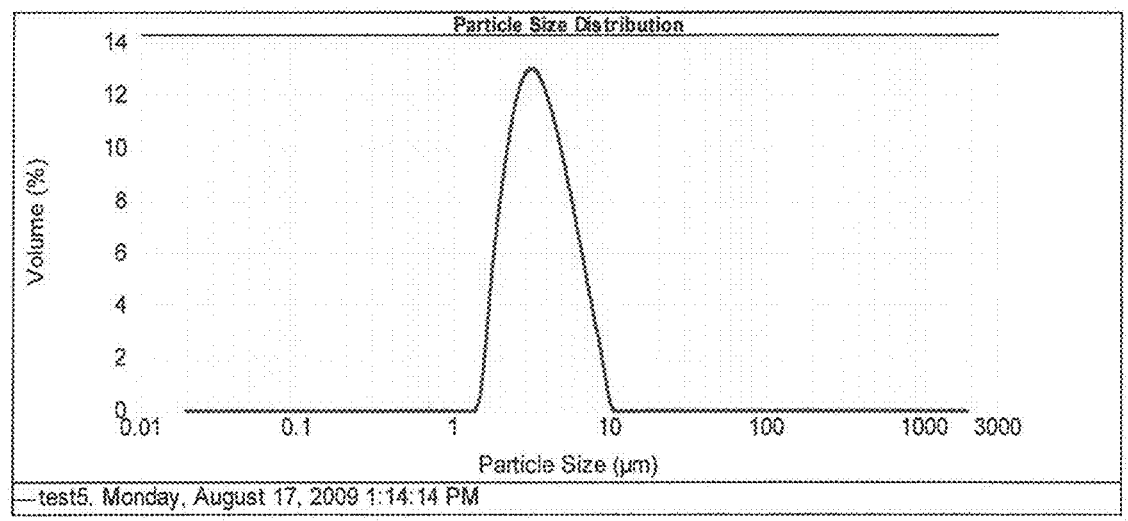
FIG. 18 depicts droplet distribution for aqueous phase obtained according to the process of Example 17B.

A sample of the emulsion formed was then analyzed in the Malvern 2000. The average droplet size for the aqueous phase was 3.905 μm and 90% of the aqueous phase appeared in droplets with diameter less than 6.405 μm (Table 33). The droplet distribution is shown in FIG. 18.

Example 17C 2000.3 g of crude soybean oil was heated to 60° C. in a 4000 ml beaker under normal agitation utilizing a magnetic stirrer. 2.0 grams of 50% w/w solution of citric acid was added and sheared for 1 minute. 3.650 milliliters of 4 molar sodium hydroxide solution was added to the oil and mixed. 0.50 grams of Purifine PLC enzyme was added followed by a total of 60 grams of de-ionized water and the entire mixture was shear mixed for 30 seconds using a Ultra-Turrax homogenizer T-50 basic with a S 50 N-G 45 G dispersion element at 10,000 rpm.

Figure 19:
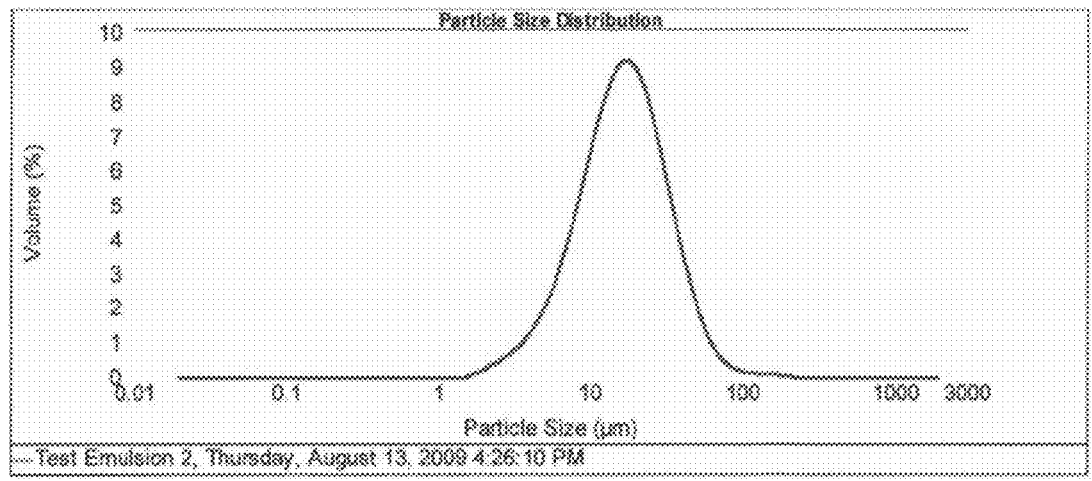
FIG. 19 depicts droplet distribution for aqueous phase obtained according to the process of Example 17C.

A sample of the emulsion formed was then analyzed in the Malvern 2000. The average droplet size for the aqueous phase was 19.957 μm and 90% of the aqueous phase appeared in droplets with diameter less than 36.998 μm (Table 33). The droplet distribution is shown in FIG. 19.

Example 17D 0.6 L (approximately 560 g) of degummed soybean oil was heated to 40° C. in a 600 ml beaker under recirculation through the Silverson mixer. The mixer was cooled in a water bath, to avoid temperature increase during the experiment. 0.6 g of 50% w/w solution of citric acid was added, followed by 1.095 milliliters of 4 molar sodium hydroxide solution. 0.028 g (50 ppm) of Lecitase Ultra PLA enzyme was added followed by a total of 16.8 g of de-ionized water.

Figure 20:
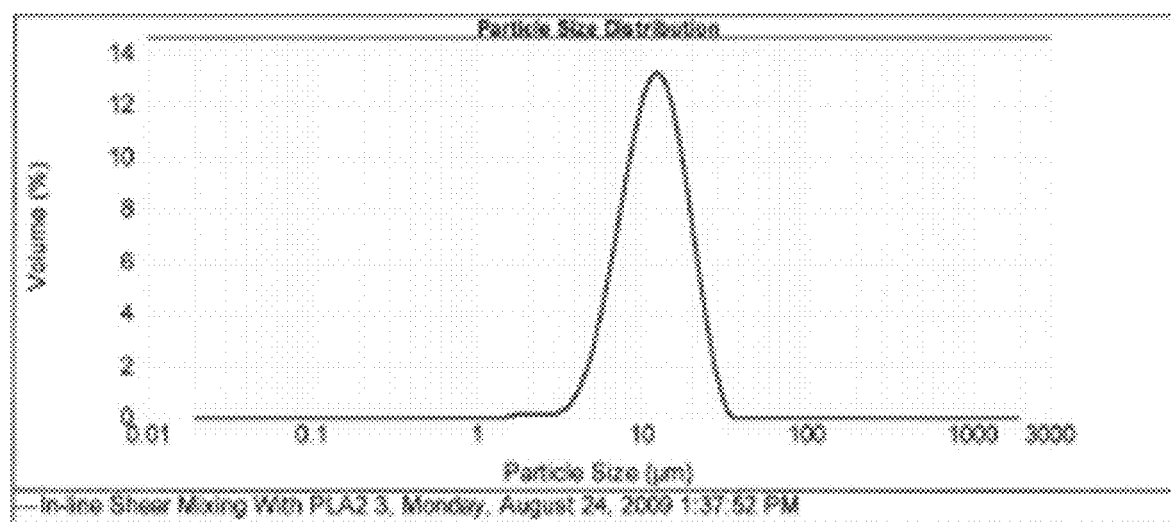
FIG. 20 depicts droplet distribution for aqueous phase obtained according to the process of Example 17D.

A sample of the emulsion formed was then collected after 15 min, in order to allow for the system equilibrium. The sample was then analyzed in the Malvern 2000. The average droplet size for the aqueous phase was 12.691 μm and 90% of the aqueous phase appeared in droplets with diameter less than 20.333 μm (Table 33). The droplet distribution is shown in FIG. 20. Being an in-line mixer, the Silverson continued to reduce droplet sizes, eventually achieving average particle size of 9 μm.

Figure 21:
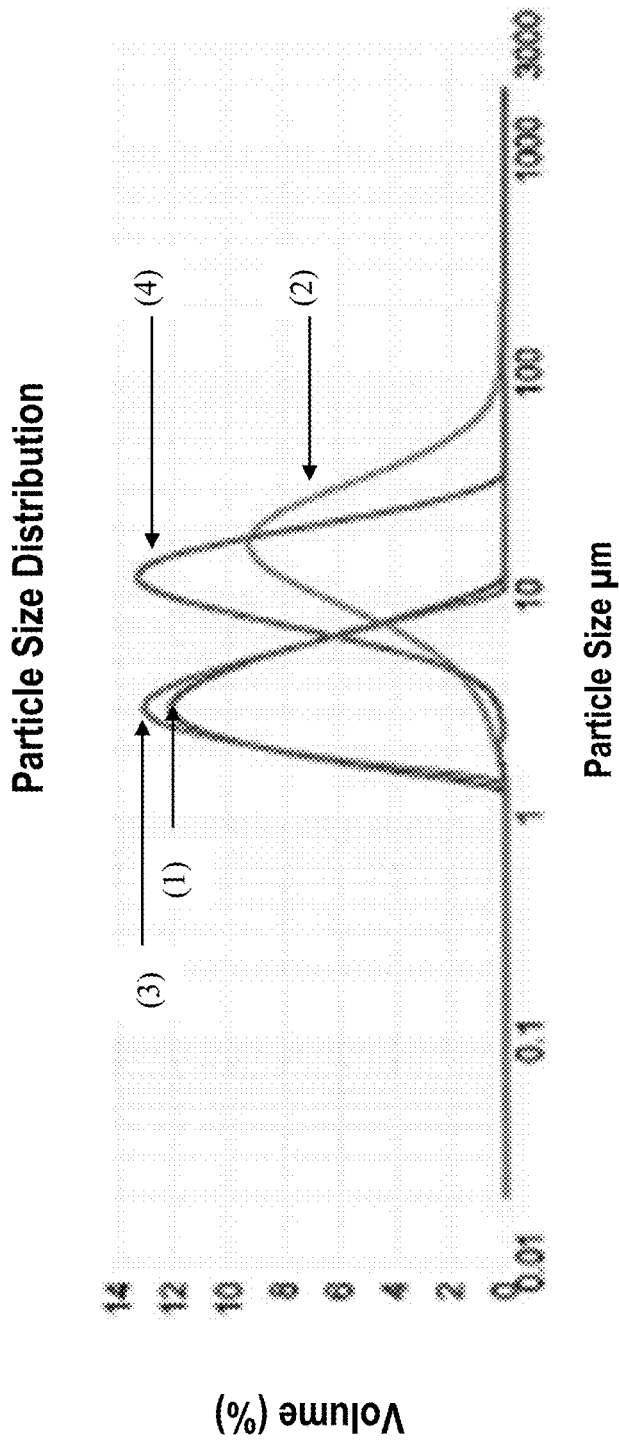
FIG. 21 depicts comparative droplet distribution for aqueous phase obtained according to the processes of Examples 17A, 17B, 17C and 17D.

FIG. 21 depicts superimposition of the droplet (particle) size distribution resulting from Examples 17A, 17B, 17C, and 17B.

Table 34 provides data for comparative particle size for Examples 17A, 17B, 17C and 17D.

TABLE 34

| | Example 17A | Example 17B | Example 17D | Example 17C |
|---|---|---|---|---|
| Average particle size (μm) | 3.963 | 3.905 | 12.691 | 19.975 |
| particle size for accumulated water volume of 90% (μm) | 6.675 | 6.405 | 20.333 | 36.998 |
| water phase in droplets <=10 μm (%) | 99.37 | 99.98 | 47.85 | 23.92 |
| water phase in droplets >10 μm (%) | 0.63 | 0.02 | 52.15 | 76.08 |

As seen from the data, Example 17C produced a very distinctive droplet distribution profile, with higher average particle size. The average particle size of Example 17C was found to be approximately 5 times bigger than Example 17A and 17B, and 1.6 times bigger than Example 17D.

As seen from the data, for Example 17C, more than 76% of the water phase is found in droplets with diameter bigger than 10 μm, while for Example 17A 52% of the water phase is found in droplets with diameter bigger than 10 μm, and less than 0.65% of the water phase is found in droplets with diameter bigger than 10 μm in Example 17D.

Example 18: Comparative Study of Gums Obtained by Various Methods

In this example, comparative data is provided for oil treated according to processes reported in U.S. Pat. No. 4,698,185 and process described in Examples 4-16 above.

Various oils (listed in Table 35) are treated according to the following protocol as described in U.S. Pat. No. 4,698,185:

oil heated to greater than 75° C.
water added to raise concentration to 0.6% wt
about 20-60 wt % phosphoric acid added into water degummed oil
acid dispersed for 30 seconds
mixing continued for three minutes
caustic solution added in about 2% by volume
the mixture centrifuged for 30 minutes at 5,000 rpm
the oil phase separated and washed with 2 wt % demineralized water
washing water removed by centrifugation for 30 minutes at 5,000 rpm
gums in the oil analyzed Table 35 below provides data for composition of gums separated from the treated oil samples:

| | Oil Type | | | | |
|---|---|---|---|---|---|
| Phospholipids | Soybean | Sunflower | Corn Germ | Rapeseed | Groundnut |
| PA | 55 | 49 | 37 | 72 | 53 |
| LPA | 6 | 20 | — | 6 | — |
| PC | 4 | 8 | 26 | <1 | 15 |
| LPC | <1 | — | — | | |
| PE | 17 | 9 | 13 | 13 | 7 |
| LPE | <1 | 5 | | 2 | |
| Cardiolipin | | | | | |
| N-acylphosphatidyl Ethanolamine | 13 | 9 | 19 | 7 | 24 |
| PI | 4 | — | 5 | — | |
| Not Identified | — | — | — | | |

Table 36 provides below provides data for phospholipids in oil samples treated according to Examples 10, 11, 12, 13, and 16 above:

TABLE 36

| Phospho-lipids | Example 10 | Example 11 | Example 12 | Example 13 | Example 16 |
|---|---|---|---|---|---|
| PA | 11.6 | 18.9 | 11.6 | 20.1 | 0.0 |
| LPA | 1.1 | 3.3 | 1.8 | 3.6 | 14.1 |
| "A" | 0.7 | 1.5 | 0.9 | 1.8 | 1.0 |
| PC | 31.4 | 1.5 | 31.0 | 6.7 | 0.6 |
| LPC | 2.4 | 3.3 | 2.7 | 2.2 | 32.9 |
| "C" | b.d. | 19.3 | 1.6 | 23.3 | 0.3 |
| PE | 32.1 | 4.3 | 30.4 | 10.5 | 1.9 |
| LPE | 2.0 | 1.1 | 1.0 | 0.5 | 31.5 |
| "E" | b.d. | 13.7 | 11.2 | 15.8 | b.d. |
| PI | 17.3 | 30.3 | 9.6 | 4.4 | 0.3 |
| LPI | 1.4 | 2.5 | b.d. | b.d. | 17.1 |
| "I" | b.d. | 0.3 | 17.3 | 11.2 | 0.4 |

Table 37 below provides summary of enzymes used, pH of the reaction and data for phospholipids in oil samples treated according to Examples 4, 5, 6, 7, 8, 10, 11, 12, 13 and 16 above.

TABLE 37

| | PC | PE | PI | PA | LPC | LPE | LPI | LPA | C | E | I | A | Enzyme | pH |
|---|---|---|---|---|---|---|---|---|---|---|---|---|---|---|
| 1 | 39.5 | 30.2 | 16.5 | 8.4 | 2.4 | 1.4 | 1.4 | 0.0 | 0.0 | 0.0 | 0.0 | 0.3 | None | Neutral |
| 7 | 31.4 | 32.1 | 17.3 | 11.6 | 2.4 | 2.0 | 1.4 | 1.1 | 0.0 | 0.0 | 0.0 | 0.7 | None | 7.0 |
| 2 | 1.1 | 11.3 | 29.1 | 15.9 | 2.4 | 0.5 | 2.2 | 1.6 | 21.6 | 13.3 | 0.0 | 1.1 | PLC | Neutral |
| 8 | 1.5 | 4.3 | 30.3 | 18.9 | 3.3 | 1.1 | 2.5 | 3.3 | 19.3 | 13.7 | 0.3 | 1.5 | PLC | 7.0 |
| 3 | 41.5 | 29.3 | 0.0 | 8.8 | 2.2 | 1.3 | 0.0 | 0.0 | 0.2 | 0.1 | 16.2 | 0.5 | PI-PLC | Neutral |
| 9 | 31.0 | 30.4 | 0.0 | 11.6 | 2.7 | 2.1 | 0.0 | 1.8 | 1.6 | 0.7 | 17.3 | 0.9 | PI-PLC | 7.0 |
| 4 | 13.6 | 17.6 | 9.6 | 15.8 | 2.5 | 1.0 | 0.0 | 2.0 | 18.5 | 11.2 | 7.2 | 1.0 | PLC + PI-PLC | Neutral |
| 10 | 6.7 | 10.5 | 4.4 | 20.1 | 2.2 | 0.5 | 0.0 | 3.6 | 23.3 | 15.8 | 11.2 | 1.8 | PLC + PI-PLC | 7.0 |
| 5 | 0.9 | 1.6 | 2.7 | 1.1 | 32.2 | 29.3 | 17.3 | 14.1 | 0.0 | 0.0 | 0.0 | 0.7 | PLA1 | Neutral |
| 13 | 0.6 | 1.9 | 0.3 | 0.0 | 32.9 | 31.5 | 17.1 | 14.1 | 0.3 | 0.0 | 0.4 | 1.0 | PLA1 | 7.0 |

As seen from the data, phospholipids obtained by the processes described herein have a unique composition.

The embodiments of the claimed subject matter described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

While the invention has been described in detail with reference to certain exemplary aspects thereof, it will be understood that modifications and variations are within the spirit and scope of that which is described and claimed.

---

What is claimed is:

1. A synthetic or recombinant polypeptide having phosphatidylinositol-specific phospholipase C (PI-PLC) enzyme activity, and
   (a) comprising an amino acid sequence
      (i) having at least 95% sequence identity to SEQ ID NO:6, and having at least one amino acid substitution selected from the group consisting of N176F, Q191G, Y205L, N244T, Y252R, M261I, Y276F, S282H, L284F, and R291N, equivalent amino acid substitutions thereof, and any combination thereof, wherein the numbering of the amino acid substitutions begins with amino acid 31 of SEQ ID NO:6, or
      (ii) the amino acid sequence of SEQ ID NO:8
   (b) the polypeptide of (a) but lacking a native signal sequence or proprotein sequence;
   (c) the polypeptide of (a) or (b) further comprising a heterologous amino acid sequence or a heterologous moiety;
   (d) the polypeptide of (c), wherein the heterologous amino acid sequence or heterologous moiety comprises, or consists of, a heterologous leader signal sequence, a tag, a detectable label an epitope, or a combination thereof;
   (e) the polypeptide of (d), wherein the heterologous leader signal sequence comprises, or consists of, an N-terminal and/or C-terminal extension for targeting to an endoplasmic reticulum (ER) or endomembrane, or to a plant endoplasmic reticulum (ER) or endomembrane system;
   (f) the polypeptide of any one of (a) to (e), wherein the PI-PLC catalyzes a reaction comprising
      1-phosphatidyl-1 D-myo-inositol 4,5-bisphosphate (also called $PIP_2$, phosphatidylinositol bisphosphate)+$H_2O$↔1D-myo-inositol 1,4,5-trisphosphate (also called $IP_3$, inositol triphosphate)+diacylglycerol;
   (g) the polypeptide of any one of (a) to (f), wherein the PI-PLC activity is thermostable;
   (h) the polypeptide of any one of (a) to (f), wherein the PI-PLC activity is thermotolerant; or
   (i) the polypeptide of any one of (a) to (h), wherein
      (i) the polypeptide is glycosylated, or the polypeptide comprises at least one glycosylation site,
      (ii) the polypeptide of (i)(i) wherein the glycosylation is an N-linked glycosylation or an O-linked glycosylation,
      (iii) the polypeptide of (i)(i) or (i)(ii) wherein the polypeptide is glycosylated after being expressed in a yeast cell, or
      (iv) the polypeptide of (i)(iii) wherein the yeast cell is a *P. pastoris* or a *S. pombe*.

2. A protein preparation comprising the polypeptide of claim 1, wherein the protein preparation comprises a liquid, a solid or a gel.

3. A heterodimer
   (a) comprising the polypeptide of claim 1 and a second domain; or
   (b) the heterodimer of (a), wherein the second domain is a polypeptide and the heterodimer is a fusion protein, or the second domain is an epitope or a tag.

4. A homodimer comprising the polypeptide of claim 1.

5. An immobilized polypeptide
   (a) wherein the polypeptide comprises the polypeptide of claim 1; or
   (b) the immobilized polypeptide of (a), wherein the polypeptide is immobilized on a cell, a metal, a resin, a polymer, a ceramic, a glass, a microelectrode, a graphitic particle, a bead, a gel, a plate, an array or a capillary tube.

6. A method of making an anti-phospholipase antibody comprising administering to a non-human animal the polypeptide of claim 1 in an amount sufficient to generate a humoral immune response, thereby making an anti-phospholipase antibody.

7. A method for identifying a polypeptide having a phospholipase activity comprising
   (a) providing the polypeptide of claim 1;
   (b) providing a phospholipase substrate;
   (c) contacting the polypeptide with the substrate of step (b); and
   (d) detecting a decrease in the amount of substrate or an increase in the amount of a reaction product, wherein a decrease in the amount of the substrate or an increase in the amount of the reaction product detects a polypeptide having a phospholipase activity.

8. A method for identifying a phospholipase substrate comprising
   (a) providing the polypeptide of claim 1;
   (b) providing a test substrate;
   (c) contacting the polypeptide of step (a) with the test substrate of step (b); and
   (d) detecting a decrease in the amount of substrate or an increase in the amount of reaction product, wherein a decrease in the amount of the substrate or an increase in the amount of a reaction product identifies the test substrate as a phospholipase substrate.

9. A method of determining whether a test compound specifically binds to a polypeptide comprising
   (a) providing the polypeptide of claim 1;
   (b) providing a test compound;
   (c) contacting the polypeptide with the test compound; and
   (d) determining whether the test compound of step (b) specifically binds to the polypeptide.

10. A method of increasing thermotolerance or thermostability of a phospholipase polypeptide, the method comprising glycosylating a phospholipase, wherein the polypeptide comprises at least thirty contiguous amino acids of the polypeptide of claim 1, thereby increasing the thermotolerance or thermostability of the phospholipase.

11. A method for washing an object comprising
    (a) providing a composition comprising the phospholipase polypeptide of claim 1;
    (b) providing an object; and
    (c) contacting the polypeptide of step (a) and the object of step (b) under conditions wherein the composition can wash the object.

12. A composition comprising the phospholipase polypeptide of claim 1.

13. A pharmaceutical composition comprising the polypeptide of claim 1.

14. A method for preventing, treating or ameliorating lipopolysaccharide (LPS)-mediated toxicity, detoxifying an endotoxin, or deacylating a 2' or a 3' fatty acid chain from a lipid A, the method comprising providing a pharmaceutical composition comprising the polypeptide of claim 1 to a subject in need thereof.

15. A composition comprising a mixture of phospholipase enzymes comprising
    (a) (i) at least one phospholipase polypeptide of claim 1 and (ii) at least one second enzyme; or
(b) the composition of (a), wherein the at least one second enzyme is a phospholipase enzyme; or
(c) the composition of (b), wherein the at least one second phospholipase enzyme comprises a polypeptide as set forth in SEQ ID NO:2 and/or SEQ ID NO:4, or at least one of the variant PLC enzymes as described in Tables 8 and 9.

16. A fuel comprising
(i) at least one polypeptide having the phospholipase activity of claim 1;
(ii) a composition comprising the phospholipase polypeptide of claim 1; or
(iii) a composition comprising a mixture of phospholipase enzymes, which mixture comprises
  (a) (i) at least one phospholipase polypeptide of claim 1 and (ii) at least one second enzyme; or
  (b) the composition of (a), wherein the at least one second enzyme is a phospholipase enzyme; or
  (c) the composition of (b), wherein the at least one second phospholipase enzyme comprises a polypeptide as set forth in SEQ ID NO:2 and/or SEQ ID NO:4, or at least one of the variant PLC enzymes as described in Tables 8 and 9.

17. A distillers dried soluble (DDS), a distillers dried grain (DDS), a condensed distillers soluble (CDS), a distillers wet grain (DWG) or a distillers dried grain with solubles (DDGS), comprising
(i) at least one polypeptide having the phospholipase activity of claim 1;
(ii) a composition comprising the phospholipase polypeptide of claim 1; or
(iii) a composition comprising a mixture of phospholipase enzymes, which mixture comprises
  (a) (i) at least one phospholipase polypeptide of claim 1 and
    (ii) at least one second enzyme; or
  (b) the composition of (a), wherein the at least one second enzyme is a phospholipase enzyme; or
  (c) the composition of (b), wherein the at least one second phospholipase enzyme comprises a polypeptide as set forth in SEQ ID NO:2 and/or SEQ ID NO:4, or at least one of the variant PLC enzymes as described in Tables 8 and 9.

18. A biomass comprising
(i) at least one polypeptide having the phospholipase activity of claim 1; or
(ii) a composition comprising the phospholipase polypeptide of claim 1; or
(iii) a composition comprising a mixture of phospholipase, which mixture comprises
  (a) (i) at least one phospholipase polypeptide of claim 1; and
    (ii) at least one second enzyme; or
  (b) the composition of (a), wherein the at least one second enzyme is a phospholipase enzyme; or
  (c) the composition of (b), wherein the at least one second phospholipase enzyme comprises a polypeptide as set forth in SEQ ID NO:2 and/or SEQ ID NO:4, or at least one of the variant PLC enzymes as described in Tables 8 and 9.

19. The polypeptide of claim 1 (a) to (i), further comprising or contained in a composition comprising at least one second enzyme, or at least one second phospholipase enzyme.

20. The polypeptide of claim 19, wherein the at least one second phospholipase enzyme comprises a polypeptide having a sequence as set forth in SEQ ID NO:2 and/or SEQ ID NO:4, or at least one of their variant PLC enzymes as described in Tables 8 and 9A.

21. A synthetic or recombinant polypeptide having phosphatidylinositol-specific phospholipase C (PI-PLC) enzyme activity comprising the amino acid sequence of SEQ ID NO: 8.

22. The biomass of claim 18 wherein the biomass is, or comprises, an animal, algae or plant biomass, or combinations thereof, a lipid-comprising or lignocellulosic biomass, or a waste material.

\* \* \* \* \*

SEQUENCE LISTING

<160> NUMBER OF SEQ ID NOS: 10

<210> SEQ ID NO 1
<211> LENGTH: 738
<212> TYPE: DNA
<213> ORGANISM: Artificial Sequence
<220> FEATURE:
<223> OTHER INFORMATION: Synthetically generated

<400> SEQUENCE: 1

```
tggtcagctg aggataagca taatgagggg attaactctc atttgtggat tgtaaatcgt      60
gcaattgaca tcatgtctcg taatacaacg attgtgaatc cgaatgaaac tgcattatta     120
aatgagtggc gtgctgattt agaaaatggt atttattctc ctgattacga gaatccttat     180
tatgatgata gtacatatgc ttctcacttt tatgatccgg atactggaac aacatatatt     240 cctttttgcga aacatgcaaa agaaacaggc gcaaaatatt ttaaccttgc tggtcaagca     300
taccaaaatc aagatatgca gcaagcattc ttctacttag gattatcgct tcattattta     360
ggagatgtga atcagccaat gcatgcagca tcttttacgg atctttctta tccaatgggt     420
ttccattcta aatacgaaaa ttttgttgat acaataaaaa ataactatat tgtttcagat     480
agcaatggat attggaattg gaaaggagca aacccagaag attggattga aggagcagcg     540
gtagcagcta aacaagatta tcctggcgtt gtgaacgata cgacaaaaga ttggttttgta     600 aaagcagccg tatctcaaga atatgcagat aaatggcgtg cggaagtaac accggtgaca     660
ggaaagcgtt taatggaagc gcagcgcgtt acagctggtt atattcattt gtggtttgat     720
acgtatgtaa atcgctaa                                                    738
```

<210> SEQ ID NO 2
<211> LENGTH: 245
<212> TYPE: PRT
<213> ORGANISM: Artificial Sequence
<220> FEATURE:
<223> OTHER INFORMATION: Synthetically generated

<400> SEQUENCE: 2

```
Trp Ser Ala Glu Asp Lys His Asn Glu Gly Ile Asn Ser His Leu Trp
 1               5                  10                  15
```

Ile Val Asn Arg Ala Ile Asp Ile Met Ser Arg Asn Thr Thr Ile Val
 20                  25                  30

Asn Pro Asn Glu Thr Ala Leu Leu Asn Glu Trp Arg Ala Asp Leu Glu
         35                  40                  45

Asn Gly Ile Tyr Ser Ala Asp Tyr Glu Asn Pro Tyr Tyr Asp Asp Ser
     50                  55                  60

Thr Tyr Ala Ser His Phe Tyr Asp Pro Asp Thr Gly Thr Thr Tyr Ile
 65                  70                  75                  80

Pro Phe Ala Lys His Ala Lys Glu Thr Gly Ala Lys Tyr Phe Asn Leu
                 85                  90                  95

Ala Gly Gln Ala Tyr Gln Asn Gln Asp Met Gln Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Met Gly Phe His Ser Lys
130                 135                 140

Tyr Glu Asn Phe Val Asp Thr Ile Lys Asn Asn Tyr Ile Val Ser Asp
145                 150                 155                 160

Ser Asn Gly Tyr Trp Asn Trp Lys Gly Ala Asn Pro Glu Asp Trp Ile
                165                 170                 175

Glu Gly Ala Ala Val Ala Ala Lys Gln Asp Tyr Pro Gly Val Val Asn
            180                 185                 190

Asp Thr Thr Lys Asp Trp Phe Val Lys Ala Val Ser Gln Glu Tyr
        195                 200                 205

Ala Asp Lys Trp Arg Ala Glu Val Thr Pro Val Thr Gly Lys Arg Leu
210                 215                 220

Met Glu Ala Gln Arg Val Thr Ala Gly Tyr Ile His Leu Trp Phe Asp
225                 230                 235                 240

Thr Tyr Val Asn Arg
            245

<210> SEQ ID NO 3
<211> LENGTH: 849
<212> TYPE: DNA
<213> ORGANISM: Artificial Sequence
<220> FEATURE:
<223> OTHER INFORMATION: Synthetically generated

<400> SEQUENCE: 3
atgaaaaaga aagtattagc actagcagct atggttgctt tagctgcgcc agttcaaagt      60
gtagtatttg cacaaacaaa taatagtgaa agtcctgcac cgattttaag atggtcagct     120
gaggataagc ataatgaggg gattaactct catttgtgga ttgtaaatcg tgcaattgac     180
atcatgtctc gtaatacaac gattgtgaat ccgaatgaaa ctgcattatt aaatgagtgg     240
cgtgctgatt tagaaaatgg tatttattct gctgattacg agaatcctta ttatgatgat     300
agtacatatg cttctcactt ttatgatccg gatactggaa caacatatat tccttttgcg     360
aaacatgcaa agaaacagg cgcaaaatat tttaaccttg ctggtcaagc ataccaaaat     420
caagatatgc agcaagcatt cttctactta ggattatcgc ttcattattt aggagatgtg     480
aatcagccaa tgcatgcagc atcttttacg gatctttctt atccaatggg tttccattct     540
aaatacgaaa attttgttga tacaataaaa aataactata ttgtttcaga tagcaatgga     600
tattggaatt ggaaaggagc aaacccagaa gattggattg aaggagcagc ggtagcagct     660
aaacaagatt atcctggcgt tgtgaacgat acgacaaaag attggtttgt aaaagcagcc     720

```
gtatctcaag aatatgcaga taaatggcgt gcggaagtaa caccggtgac aggaaagcgt      780
ttaatggaag cgcagcgcgt tacagctggt tatattcatt tgtggtttga tacgtatgta      840
aatcgctaa                                                              849
```

<210> SEQ ID NO 4
<211> LENGTH: 282
<212> TYPE: PRT
<213> ORGANISM: Artificial Sequence
<220> FEATURE:
<223> OTHER INFORMATION: Synthetically generated
<220> FEATURE:
<221> NAME/KEY: SIGNAL
<222> LOCATION: (1)..(37)

<400> SEQUENCE: 4

```
Met Lys Lys Val Leu Ala Leu Ala Ala Met Val Ala Leu Ala Ala
1               5                   10                  15

Pro Val Gln Ser Val Val Phe Ala Gln Thr Asn Asn Ser Glu Ser Pro
            20                  25                  30

Ala Pro Ile Leu Arg Trp Ser Ala Glu Asp Lys His Asn Glu Gly Ile
        35                  40                  45

Asn Ser His Leu Trp Ile Val Asn Arg Ala Ile Asp Ile Met Ser Arg
    50                  55                  60

Asn Thr Thr Ile Val Asn Pro Asn Glu Thr Ala Leu Leu Asn Glu Trp
65                  70                  75                  80

Arg Ala Asp Leu Glu Asn Gly Ile Tyr Ser Ala Asp Tyr Glu Asn Pro
                85                  90                  95

Tyr Tyr Asp Asp Ser Thr Tyr Ala Ser His Phe Tyr Asp Pro Asp Thr
            100                 105                 110

Gly Thr Thr Tyr Ile Pro Phe Ala Lys His Ala Lys Glu Thr Gly Ala
        115                 120                 125

Lys Tyr Phe Asn Leu Ala Gly Gln Ala Tyr Gln Asn Gln Asp Met Gln
    130                 135                 140

Gln Ala Phe Phe Tyr Leu Gly Leu Ser Leu His Tyr Leu Gly Asp Val
145                 150                 155                 160

Asn Gln Pro Met His Ala Ala Ser Phe Thr Asp Leu Ser Tyr Pro Met
                165                 170                 175

Gly Phe His Ser Lys Tyr Glu Asn Phe Val Asp Thr Ile Lys Asn Asn
            180                 185                 190

Tyr Ile Val Ser Asp Ser Asn Gly Tyr Trp Asn Trp Lys Gly Ala Asn
        195                 200                 205

Pro Glu Asp Trp Ile Glu Gly Ala Val Ala Ala Lys Gln Asp Tyr
    210                 215                 220

Pro Gly Val Val Asn Asp Thr Thr Lys Asp Trp Phe Val Lys Ala Ala
225                 230                 235                 240

Val Ser Gln Glu Tyr Ala Asp Lys Trp Arg Ala Glu Val Thr Pro Val
                245                 250                 255

Thr Gly Lys Arg Leu Met Glu Ala Gln Arg Val Thr Ala Gly Tyr Ile
            260                 265                 270

His Leu Trp Phe Asp Thr Tyr Val Asn Arg
        275                 280
```

<210> SEQ ID NO 5
<211> LENGTH: 987
<212> TYPE: DNA
<213> ORGANISM: Unknown

<220> FEATURE:
<223> OTHER INFORMATION: DNA obtained from an environmental sample

<400> SEQUENCE: 5

```
atgaacaata agaagtttat tttgaagtta ttcatatgta gtatggtact tagcgccttt      60
gtatttgctt tcaatgataa gaaaaccgtt gcagctagct ctattaatgt gcttgaaaat     120
tggtctagat ggatgaaacc tataaatgat gacataccgt tagcacgaat tcaattcca     180
ggaacacatg atagtggaac gttcaagttg caaaatccga taaagcaagt gtggggaatg     240
acgcaagaat atgattttcg ttatcaaatg gatcatggag ctagaatttt tgatataaga     300
gggcgtttaa cagatgataa tacgatagtt cttcatcatg gccattata tctttatgta     360
acactgcacg aatttataaa cgaagcgaaa caattttaa aagataatcc aagtgaaacg     420
attattatgt ctttaaaaaa agagtatgag gatatgaaag gggcggaaag ctcatttagt     480
agtacgtttg agaaaaatta ttttcgtgat ccaatctttt taaaaacaga agggaatata     540
aagcttggag atgctcgtgg gaaaattgta ttactaaaaa gatatagtgg tagtaatgaa     600
tctgggggat ataataattt ctattggcca gacaatgaga cgtttacctc aactataaat     660
caaaatgtaa atgtaacagt acaagataaa tataaagtga gttatgatga aaaataaac     720
gctattaaag atacattaaa tgaaacgatt aacaatagtg aagatgttaa tcatctatat     780
attaatttta caagcttgtc ttctggtggt acagcatgga atagtccata ttattatgcg     840
tcctacataa atcctgaaat tgcaaattat atgaagcaaa gaatcctac gagagtgggc     900
tggataatac aagattatat aaatgaaaaa tggtcaccat tactttatca agaagttata     960
agagcgaata agtcacttgt aaaatag                                         987
```

<210> SEQ ID NO 6
<211> LENGTH: 328
<212> TYPE: PRT
<213> ORGANISM: Unknown
<220> FEATURE:
<223> OTHER INFORMATION: Protein obtained from an environmental sample
<220> FEATURE:
<221> NAME/KEY: SIGNAL
<222> LOCATION: (1)..(23)
<220> FEATURE:
<221> NAME/KEY: DOMAIN
<222> LOCATION: (56)..(195)
<223> OTHER INFORMATION: Phosphatidylinositol-specific phospholipase C, X domain

<400> SEQUENCE: 6

```
Met Asn Asn Lys Lys Phe Ile Leu Lys Leu Phe Ile Cys Ser Met Val
1               5                   10                  15

Leu Ser Ala Phe Val Phe Ala Phe Asn Asp Lys Lys Thr Val Ala Ala
            20                  25                  30

Ser Ser Ile Asn Val Leu Glu Asn Trp Ser Arg Trp Met Lys Pro Ile
        35                  40                  45

Asn Asp Asp Ile Pro Leu Ala Arg Ile Ser Ile Pro Gly Thr His Asp
    50                  55                  60

Ser Gly Thr Phe Lys Leu Gln Asn Pro Ile Lys Gln Val Trp Gly Met
65                  70                  75                  80

Thr Gln Glu Tyr Asp Phe Arg Tyr Gln Met Asp His Gly Ala Arg Ile
                85                  90                  95

Phe Asp Ile Arg Gly Arg Leu Thr Asp Asp Asn Thr Ile Val Leu His
            100                 105                 110

His Gly Pro Leu Tyr Leu Tyr Val Thr Leu His Glu Phe Ile Asn Glu
```

```
            115                 120                 125
Ala Lys Gln Phe Leu Lys Asp Asn Pro Ser Glu Thr Ile Ile Met Ser
130                 135                 140

Leu Lys Lys Glu Tyr Glu Asp Met Lys Gly Ala Glu Ser Ser Phe Ser
145                 150                 155                 160

Ser Thr Phe Glu Lys Asn Tyr Phe Arg Asp Pro Ile Phe Leu Lys Thr
                165                 170                 175

Glu Gly Asn Ile Lys Leu Gly Asp Ala Arg Gly Lys Ile Val Leu Leu
            180                 185                 190

Lys Arg Tyr Ser Gly Ser Asn Glu Ser Gly Gly Tyr Asn Asn Phe Tyr
        195                 200                 205

Trp Pro Asp Asn Glu Thr Phe Thr Ser Thr Ile Asn Gln Asn Val Asn
    210                 215                 220

Val Thr Val Gln Asp Lys Tyr Lys Val Ser Tyr Asp Glu Lys Ile Asn
225                 230                 235                 240

Ala Ile Lys Asp Thr Leu Asn Glu Thr Ile Asn Asn Ser Glu Asp Val
                245                 250                 255

Asn His Leu Tyr Ile Asn Phe Thr Ser Leu Ser Ser Gly Gly Thr Ala
            260                 265                 270

Trp Asn Ser Pro Tyr Tyr Tyr Ala Ser Tyr Ile Asn Pro Glu Ile Ala
        275                 280                 285

Asn Tyr Met Lys Gln Lys Asn Pro Thr Arg Val Gly Trp Ile Ile Gln
    290                 295                 300

Asp Tyr Ile Asn Glu Lys Trp Ser Pro Leu Leu Tyr Gln Glu Val Ile
305                 310                 315                 320

Arg Ala Asn Lys Ser Leu Val Lys
                325

<210> SEQ ID NO 7
<211> LENGTH: 897
<212> TYPE: DNA
<213> ORGANISM: Artificial Sequence
<220> FEATURE:
<223> OTHER INFORMATION: Synthetically generated

<400> SEQUENCE: 7
atggctagct ctattaatgt gcttgaaaat tggtctagat ggatgaaacc tataaatgat     60
gacataccgt tagcacgaat ttcaattcca ggaacacatg atagtggaac gttcaagttg    120
caaaatccga taaagcaagt gtggggaatg acgcaagaat atgattttcg ttatcaaatg    180
gatcatggag ctagaatttt tgatataaga gggcgtttaa cagatgataa tacgatagtt    240
cttcatcatg ggccattata tctttatgta acactgcacg aatttataaa cgaagcgaaa    300
caattttttaa aagataatcc aagtgaaacg attattatgt cttttaaaaa agagtatgag    360
gatatgaaag gggcggaaag ctcatttagt agtacgtttg agaaaaatta ttttcgtgat    420
ccaatctttt taaaaacaga aggaaatata aagcttggag atgctcgtgg gaaaattgta    480
ttactaaaaa gatatagtgg tagtaatgaa tctgggggat ataattttttt ctattggcca    540
gacaatgaga cgtttacctc aactataaat ggtaatgtaa atgtaacagt acaagataaa    600
tataaagtga gtttggatga gaaaataaac gctattaaag atacattaaa tgaaacgatt    660
aacaatagtg aagatgttaa tcatctatat attaattttta caagcttgtc ttctggtggt    720
acagcatgga cgagtccata ttattatgcg tccaggataa atcctgaaat tgcaaattat    780
attaagcaaa agaatcctac gagagtgggc tggataatac aagattttat aaatgaaaaa    840
```
tggcatccat tactttatca agaagttata aatgcgaata agtcacttgt aaaatga      897

<210> SEQ ID NO 8
<211> LENGTH: 298
<212> TYPE: PRT
<213> ORGANISM: Artificial Sequence
<220> FEATURE:
<223> OTHER INFORMATION: Synthetically generated

<400> SEQUENCE: 8

```
Met Ala Ser Ser Ile Asn Val Leu Glu Asn Trp Ser Arg Trp Met Lys
1               5                   10                  15

Pro Ile Asn Asp Asp Ile Pro Leu Ala Arg Ile Ser Ile Pro Gly Thr
            20                  25                  30

His Asp Ser Gly Thr Phe Lys Leu Gln Asn Pro Ile Lys Gln Val Trp
        35                  40                  45

Gly Met Thr Gln Glu Tyr Asp Phe Arg Tyr Gln Met Asp His Gly Ala
    50                  55                  60

Arg Ile Phe Asp Ile Arg Gly Arg Leu Thr Asp Asn Thr Ile Val
65                  70                  75                  80

Leu His His Gly Pro Leu Tyr Leu Tyr Val Thr Leu His Glu Phe Ile
                85                  90                  95

Asn Glu Ala Lys Gln Phe Leu Lys Asp Asn Pro Ser Glu Thr Ile Ile
            100                 105                 110

Met Ser Leu Lys Lys Glu Tyr Glu Asp Met Lys Gly Ala Glu Ser Ser
        115                 120                 125

Phe Ser Ser Thr Phe Glu Lys Asn Tyr Phe Arg Asp Pro Ile Phe Leu
    130                 135                 140

Lys Thr Glu Gly Asn Ile Lys Leu Gly Asp Ala Arg Gly Lys Ile Val
145                 150                 155                 160

Leu Leu Lys Arg Tyr Ser Gly Ser Asn Glu Ser Gly Tyr Asn Phe
                165                 170                 175

Phe Tyr Trp Pro Asp Asn Glu Thr Phe Thr Ser Thr Ile Asn Gly Asn
            180                 185                 190

Val Asn Val Thr Val Gln Asp Lys Tyr Lys Val Ser Leu Asp Glu Lys
        195                 200                 205

Ile Asn Ala Ile Lys Asp Thr Leu Asn Glu Thr Ile Asn Asn Ser Glu
    210                 215                 220

Asp Val Asn His Leu Tyr Ile Asn Phe Thr Ser Leu Ser Ser Gly Gly
225                 230                 235                 240

Thr Ala Trp Thr Ser Pro Tyr Tyr Ala Ser Arg Ile Asn Pro Glu
                245                 250                 255

Ile Ala Asn Tyr Ile Lys Gln Lys Asn Pro Thr Arg Val Gly Trp Ile
            260                 265                 270

Ile Gln Asp Phe Ile Asn Glu Lys Trp His Pro Leu Leu Tyr Gln Glu
        275                 280                 285

Val Ile Asn Ala Asn Lys Ser Leu Val Lys
    290                 295
```

<210> SEQ ID NO 9
<211> LENGTH: 900
<212> TYPE: DNA
<213> ORGANISM: Artificial Sequence
<220> FEATURE:
<223> OTHER INFORMATION: Synthetically generated

<400> SEQUENCE: 9

```
atggccagca gcatcaacgt cctcgaaaac tggtcgcgct ggatgaagcc gatcaacgac      60
gacatcccgc tggcccgcat cagcatcccg ggcacccacg acagcggcac cttcaagctg     120
cagaacccga tcaagcaggt ctggggcatg acccaggaat cgacttccg ctaccagatg      180 gaccacggcg cccgcatctt cgacatccgc ggccgcctga ccgacgacaa caccatcgtg     240
ctgcaccacg gcccgctgta cctgtacgtg accctgcacg aattcatcaa cgaagccaag     300
cagttcctga aggacaaccc gagcgaaacc atcatcatga gcctgaagaa agaatacgaa     360
gacatgaagg gcgccgaaag cagcttcagc agcaccttcg aaaagaacta cttccgcgac     420
ccgatcttcc tgaagaccga aggcaacatc aagctgggcg acgcccgcgg caagatcgtc     480
ctcctgaagc gctacagcgg cagcaacgaa agcggcggct acaacttctt ctactggccg     540
gacaacgaaa ccttcaccag caccatcaac ggcaacgtga acgtgaccgt gcaggacaag     600
tacaaggtga gcctggacga aaagatcaac gccatcaagg acaccctgaa cgaaaccatc     660
aacaacagcg aagacgtgaa ccacctgtac atcaacttca ccagcctgag cagcggcggc     720
accgcctgga ccagcccgta ctactacgcc agccgcatca cccggaaat cgccaactac      780 atcaagcaga gaaccccgac ccgcgtgggc tggatcatcc aggacttcat caacgaaaag     840
tggcacccgc tgctgtacca ggaagtgatc aacgcgaaca gagcctggt caagtgatga      900
```

<210> SEQ ID NO 10
<211> LENGTH: 900
<212> TYPE: DNA
<213> ORGANISM: Artificial Sequence
<220> FEATURE:
<223> OTHER INFORMATION: Synthetically generated

<400> SEQUENCE: 10

```
atggcgagca gcatcaacgt cttggagaac tggtcccggt ggatgaagcc catcaacgac      60
gatatcccac tggcccgtat ctcgatcccg ggcacccacg acagcggcac ctttaaactc     120
cagaacccaa tcaaacaggt ctggggcatg acccaggagt cgacttccg ctaccagatg      180 gaccacggcg cccggatctt cgacatccgg ggcgcctga ccgacgacaa caccatcgtg      240
ctgcaccacg ggccgctgta cctgtacgtg accttgcatg agttcatcaa tgaggcgaag     300
cagttcctga aggacaaccc gagcgaaacc atcatcatgt ccctgaagaa agaatacgaa     360
gacatgaagg gggcggagag ttcgttcagc agcaccttcg aaaagaacta cttccgcgac     420
ccgattttcc tgaagaccga gggcaacatc aaactgggcg acgcccgcgg caagatcgtg     480
ctgttgaagc ggtacagcgg cagcaacgag tccggggggct acaacttctt ttactggccg    540
gataacgaaa ccttcacttc gacgatcaac ggcaacgtga acgtgaccgt gcaggacaag     600
tacaaggtca gcctcgacga aaagatcaat gccatcaagg acaccctgaa cgagaccatc     660
aataacagcg aggacgtgaa ccacttgtac atcaacttca ccagtctctc ctccggcggc     720
accgcctgga ccagcccgta ctactacgcg agtcgtatca accccgagat cgccaactac     780
atcaaacaga aaaccccgac ccgggtcggt tggatcatcc aggacttcat caacgagaag     840
tggcacccgc tgctgtacca ggaggtgatc aacgcgaaca atcgctggt gaagtgatga      900
```